(12) United States Patent
Ranga et al.

(10) Patent No.: US 9,862,713 B2
(45) Date of Patent: Jan. 9, 2018

(54) SUBSTITUTED BICYCLIC HETEROARYL COMPOUNDS AS RXR AGONISTS

(71) Applicant: CONNEXIOS LIFE SCIENCES PVT. LTD., Bangalore (IN)

(72) Inventors: Madhavan Gurram Ranga, Bangalore (IN); Jagannath Rao, Bangalore (IN); Chandra Sekhar Gudla, Bangalore (IN)

(73) Assignee: CONNEXIOS LIFE SCIENCES PVT. LTD., Bangalore (IN)

( * ) Notice: Subject to any disclaimer, the term of this patent is extended or adjusted under 35 U.S.C. 154(b) by 0 days.

(21) Appl. No.: 15/111,585

(22) PCT Filed: Jan. 9, 2015

(86) PCT No.: PCT/IN2015/000010
§ 371 (c)(1),
(2) Date: Jul. 14, 2016

(87) PCT Pub. No.: WO2015/107549
PCT Pub. Date: Jul. 23, 2015

(65) Prior Publication Data
US 2016/0333004 A1   Nov. 17, 2016

(30) Foreign Application Priority Data
Jan. 14, 2014   (IN) .............................. 161/CHE/2014

(51) Int. Cl.
| C07D 417/12 | (2006.01) |
| C07D 235/16 | (2006.01) |
| C07D 409/04 | (2006.01) |
| C07D 409/06 | (2006.01) |
| C07D 409/08 | (2006.01) |
| C07D 409/12 | (2006.01) |
| C07D 417/04 | (2006.01) |
| C07D 417/06 | (2006.01) |
| C07D 277/60 | (2006.01) |
| C07D 333/58 | (2006.01) |
| C07D 333/60 | (2006.01) |

(52) U.S. Cl.
CPC ......... *C07D 417/12* (2013.01); *C07D 235/16* (2013.01); *C07D 277/60* (2013.01); *C07D 333/58* (2013.01); *C07D 333/60* (2013.01); *C07D 409/04* (2013.01); *C07D 409/06* (2013.01); *C07D 409/08* (2013.01); *C07D 409/12* (2013.01); *C07D 417/04* (2013.01); *C07D 417/06* (2013.01)

(58) Field of Classification Search
CPC ........................... C07D 417/12; C07D 709/04
See application file for complete search history.

(56) References Cited

U.S. PATENT DOCUMENTS 4,931,458 A   6/1990   Klaus et al.

FOREIGN PATENT DOCUMENTS

| EP | 0098591 A1 | 1/1984 |
| WO | 2008/030618 A1 | 3/2008 |

OTHER PUBLICATIONS

Danail Bonchev et al., "Modeling the anticarcinogenic action of retinoids by making use of the OASIS method. 3. Inhibition of the induction of ornithine decarboxylase by arotinoids," Journal of Medicinal Chemistry, Jan. 1994, pp. 2,300-2,307, vol. 37, No. 15.
Wan-Ru Chao et al., "Comparison of the inhibitory effects of retinoids on 12-O-tetradecanoylphorbol-13-acetate-induced epidermal ornithine decarboxylase activities in CD-1 and Sencar mice," Cancer Letters, Oct. 1985, pp. 13-48, vol. 29, Elsevier Scientific Publishers Ireland Ltd.
Niu Huang et al., "3D-QSAR Studies on Retinoids of Anticarcinogenic Activity," Journal of Chinese Pharmaceutical Sciences, Jan. 1996, pp. 121-127, vol. 5, No. 3.
International Search Report and Written Opinion for PCT/IN2015/000010, dated Jun. 8, 2015.

*Primary Examiner* — Craig Ricci
*Assistant Examiner* — Christopher R Stone
(74) *Attorney, Agent, or Firm* — Hauptman Ham, LLP; Sean A. Passino

(57) ABSTRACT

The present invention relates to certain substituted bicyclic compounds that are agonists of RXR and which are therefore useful in the treatment of certain disorders that can be prevented or treated by activation of this receptor. In addition the invention relates to the compounds, methods for their preparation, pharmaceutical compositions containing the compounds and the uses of these compounds in the treatment of certain disorders.

12 Claims, 39 Drawing Sheets

FIG 5A
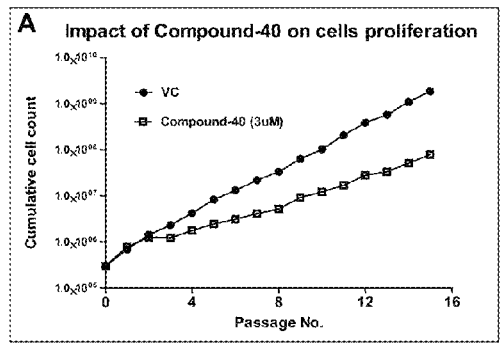
FIG 5B
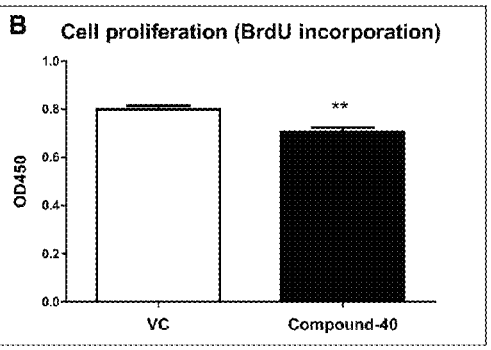
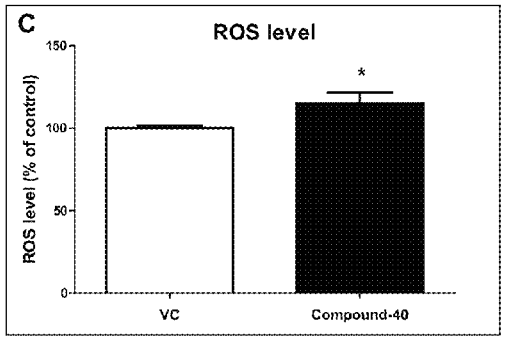
FIG 5C
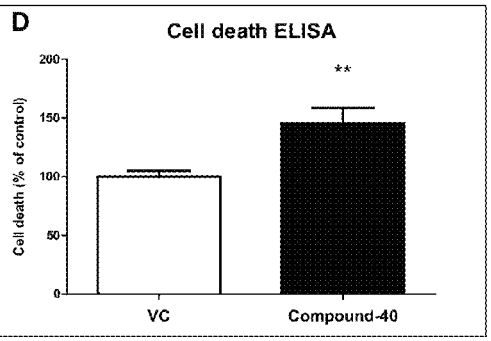
FIG 5D

▨ Lean ▨ HFD ▨ HFD+B-2 (5 mg/kg) ▨ Compound40 (10 mg/kg) ▨ Compound40 (20 mg/kg)

Normal Control      ZDF Control      ZDF + Compound 40 (10mpk)

Fasting glucose

SUBSTITUTED BICYCLIC HETEROARYL COMPOUNDS AS RXR AGONISTS

CROSS REFERENCES TO RELATED APPLICATIONS

The present application is a national phase application of international application number PCT/IN2015/000010, filed on 9 Jan. 2015 which claims priority from, IN Application Number 161/CHE/2014, filed on 14 Jan. 2014, the disclosure of which is hereby incorporated by reference herein.

FIELD OF THE INVENTION

The present invention relates to substituted bicyclic compounds that are agonists of rexinoid receptors (RXR's) and which are therefore useful in the treatment of certain disorders that can be prevented or treated by activation of these receptors. In addition the invention relates to the compounds, methods for their preparation, pharmaceutical compositions containing the compounds and the uses of these compounds in the treatment of certain disorders. It is expected that the compounds of the invention will find application in the treatment of conditions such as non-insulin dependent type 2 diabetes mellitus (NIDDM), insulin resistance, obesity, impaired fasting glucose, impaired glucose tolerance, lipid disorders such as dyslipidemia, hypertension and as well as other diseases and conditions.

BACKGROUND OF THE INVENTION

Retinoic acid (RA) which is the carboxylic acid form of vitamin A is a nutrient derivative that has been shown to have remarkable biological effects in regulating glucose, fatty acid, cholesterol and amino acid metabolism as well as adipose tissue biology and the energy balance control system. For example studies have shown that in mice, treatment with all trans RA (ATRA) reduces body weight and adiposity independent of changes in food intake and improves glucose tolerance. Additionally, it has also been shown that the ATRA induced body fat loss correlates with an activation of brown adipose tissue along with increased oxidative metabolism and thermogenesis in white adipose tissue. This is also known to be accompanied by an increased level of circulating nonesterified fatty acids which has been interpreted as meaning that fatty acids mobilized from fat stores undergo oxidation either within the adipocytes themselves or in other tissues.

It is thought that RA regulates gene expression predominantly though activation of either the RA receptors (RAR's) which have been found to be activated by ATRA and 9-cis RA or the rexinoid receptors (RXR's). Unline RAR's, RXR is part of a nuclear receptor superfamily that functions as ligand-activated transcription factors. RXR's are heterodimeric partners of many nuclear receptors such as retinoic acid receptors (RAR's), thyroid hormone receptors (T3R's), liver receptors (LXR's) peroxisome proliferator activated receptors (PPAR's) and also forms a homodimer with RXR's themselves. As such activation of these receptors should have a significant impact on gene expression.

By modulating a multitude of transcription factors, retinoic acids regulate several aspects of metabolic diseases such as hyperglycemia, hypertriglyceridemia, hypercholesterolemia, hypertension, muscle fatigue, haemostasis and managing body weight as well as visceral obesity that makes it an attractive target for obesity and diabetes as well as its related indications.

In addition to metabolic homeostasis, retinoic acid plays a vital role in regulating tissue health and regulates inflammatory responses. Indeed RXR agonists have been shown to have a large number of potential biological activities ranging from the treatment of cancer, skin disorders, metabolic diseases, fibrosis, neuro-degenerative diseases, vascular diseases, eye conditions and inflammatory diseases.

The evidence therefore strongly suggests that compounds that are agonists of RXR's would be useful in the treatment of a number of clinical conditions and therefore the search for suitable agonists of RXR is ongoing.

It would be desirable to provide compounds that are agonists of RXR's. These compounds would be expected to be useful in the treatment of conditions that can be treated by activation of these receptors.

It would also be desirable to provide a pharmaceutical composition containing a compound that is an agonist of RXR and a pharmaceutically acceptable excipient, diluent or carrier.

It would yet even further be desirable to provide a method of prevention or treatment of a condition that can be treated by activation of RXR in a mammal

STATEMENT OF INVENTION

The present invention provides a compound of formula (I):

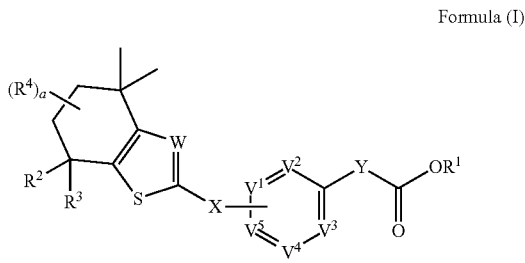

Formula (I)

wherein:

$R^1$ is selected from the group consisting of H, $C_1$-$C_6$alkyl and a carboxylic acid protecting group;

$R^2$ and $R^3$ are independently selected from the group consisting of H and $C_1$-$C_6$alkyl;

each $R^4$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^5$, $SO_3H$, $SO_2NR^5R^5$, $SO_2R^5$, $SONR^5R^5$, $SOR^5$, $COR^5$, COOH, $COOR^5$, $CONR^5R^5$, $NR^5COR^5$, $NR^5COOR^5$, $NR^5SO_2R^5$, $NR^5CONR^5R^5$, $NR^5R^5$, and acyl, or two $R^4$ on the same carbon atom when taken together form a =O substituent or a group of formula =NOH, or two $R^4$ on adjacent carbon atoms when taken together form a double bond;

each $R^5$ is independently selected from the group consisting of H, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl;

a is an integer selected from the group consisting of 0, 1, 2, 3, and 4;

X is a bond or a linking group;

$V^2$, $V^3$ and $V^4$ are each independently selected from the group consisting of N and $CR^6$;

each $R^6$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^5$, $SO_3H$, $SO_2NR^5R^5$, $SO_2R^5$, $SONR^5R^5$, $SOR^5$, $COR^5$, COOH, $COOR^5$, $CONR^5R^5$, $NR^5COR^5$, $NR^5COOR^5$, $NR^5SO_2R^5$, $NR^5CONR^5R^5$, $NR^5R^5$, and acyl;

$V^1$ and $V^5$ are selected from the group consisting of N, $CR^7$ and $CR^8$ such that one of $V^1$ and $V^5$ is $CR^8$ and the other is N or $CR^7$;

$R^7$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^5$, $SO_3H$, $SO_2NR^5R^5$, $SO_2R^5$, $SONR^5R^5$, $SOR^5$, $COR^5$, COOH, $COOR^5$, $CONR^5R^5$, $NR^5COR^5$, $NR^5COOR^5$, $NR^5SO_2R^5$, $NR^5CONR^5R^5$, $NR^5R^5$, and acyl, or $R^7$ when taken together with the carbon atom to which it is attached forms a cyclic moiety with a substituent on X;

$R^8$ is a bond to X,

Y is a bond or a linking group;

W is selected from the group consisting of N and $CR^9$;

$R^9$ is selected from H and $C_1$-$C_6$alkyl;

or a pharmaceutically acceptable salt thereof.

In a further aspect the invention relates to a pharmaceutical composition containing a compound of the invention and a pharmaceutically acceptable diluent, excipient or carrier.

In yet an even further aspect the invention relates to a method of prevention or treatment of a condition in a mammal comprising administration of an effective amount of a compound of the invention. In one embodiment the condition is a condition that can be prevented or treated by activation of RXR.

In yet an even further aspect the invention relates to the use of a compound of the invention in the preparation of a medicament for the treatment of a condition in a mammal. In one embodiment the condition is a condition that can be prevented or treated by activation of RXR.

In yet an even further aspect still the invention relates to the use of a compound of the invention for the treatment of a condition in a mammal. In one embodiment the condition is a condition that can be prevented or treated by activation of RXR.

Examples of conditions that may be treated include cancers, dermatological disorders, respiratory and pulmonary system disorders, metabolic disorders, inflammatory diseases, renal diseases, autoimmune diseases and neurodegenerative diseases.

Examples of cancers include Breast Cancer, pancreatic cancer, Cutaneous T-cell lymphoma (relapsed or refractory cutaneous T-cell lymphoma), Lung cancer, Liver cancer (hepatocellular carcinoma), Kaposi's Sarcoma (AIDS related Kaposi's sarcoma), Cutaneous T-cell lymphoma, promyelocytic leukemia, Skin cancer (basal cell carcinoma), Non-small cell Lung Cancer, Kidney cancer (advanced renal cell cancer), Gastrointestinal (stomach) cancer (advanced aerodigestive tract cancer), Mesothelioma, and Non-small-cell lung cancer.

Examples of dermatological disorders include Dermatitis (severe chronic hand eczema in adults), Psoriasis (Severe Plaque Psoriasis), Psoriasis (moderate to severe psoriasis) and alopecia.

Examples of respiratory and pulmonary system disorders include Bronchial Metaplasia and Pulmonary Fibrosis (Fibrosis).

Examples of metabolic diseases include Pre diabetes, Type 2 diabetes, Obesity, Hypercholesteriolemia, Hypertriglyceridemia, Hypertension, Dyslipidemia, hyperinsulinaemia, Liver diseases, NASH, and Atherosclerosis.

Examples of inflammatory disorders include oxidative stress, Renal fibrosis, Hepatic diseases such as steatosis, steatohepatitis (alcoholic and non alcoholic), Hepatic fibrosis and cirrhosis, autoimmune diseases and Experimental autoimmune encephalomyelitis.

An example of a neurodegenerative disorder is alzheimers disease.

Examples of other conditions that may be treated include obesity and cardiovascular disease.

The compounds of the invention may also be used to provide a number of beneficial effects to a mammal. Examples of beneficial effects that may be provided include increasing muscle endurance, improving cardiac function and achieving an exercise mimetic effect.

Accordingly in another aspect the invention provides a method of increasing muscle endurance in a mammal, the method comprising administering an effective amount of a compound of the invention.

Accordingly in another aspect the invention provides a method of improving cardiac function in a mammal, the method comprising administering an effective amount of a compound of the invention. Examples of cardiac function that may be improved include stroke work, stroke volume, ejection fraction and ventricular refilling.

Accordingly in another aspect the invention provides a method of achieving an exercise mimetic effect in a mammal, the method comprising administering an effective amount of a compound of the invention.

These and other teachings of the invention are set forth herein.

BRIEF DESCRIPTION OF THE DRAWINGS

FIG. 5A shows impact of compound 40 on cell proliferation of MCF7 cells.

FIG. 5B shows impact of compound 40 on cell proliferation of MCF7 cells (BrdU incorporation).

FIG. 5C shows reduced oxidative stress (ROS) levels in MCF7 cells treated with compound 40.

FIG. 5D shows a cell death ELISA in MCF7 cells treated with compound 40.

DETAILED DESCRIPTION OF THE INVENTION

Figure 1A:
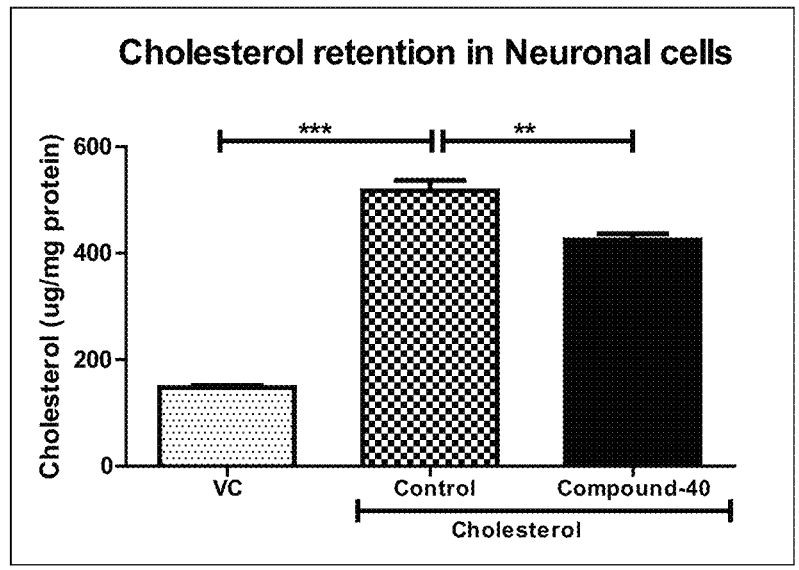
FIG. 1A shows cholesterol retention in neuronal cells treated with compound 40.
Figure 1B:
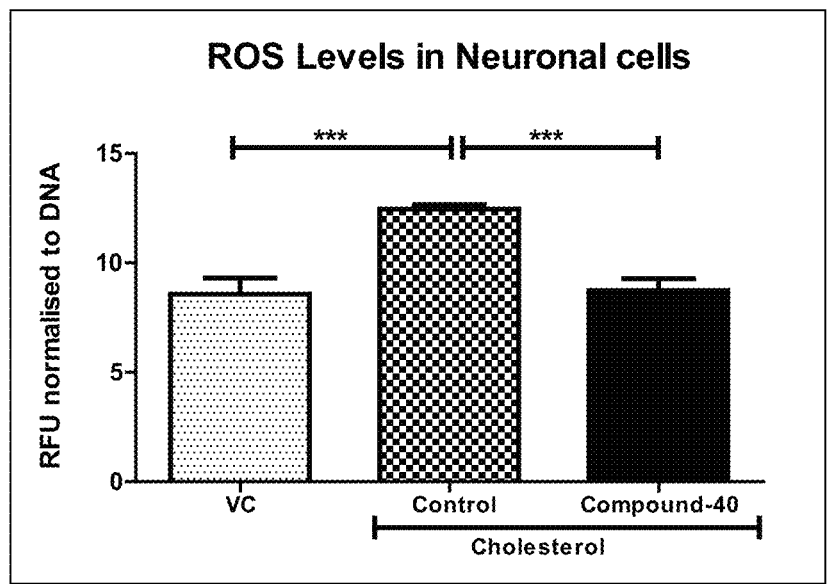
FIG. 1B shows reduced oxidative stress (ROS) levels in neuronal cells treated with compound 40.
Figure 1C:
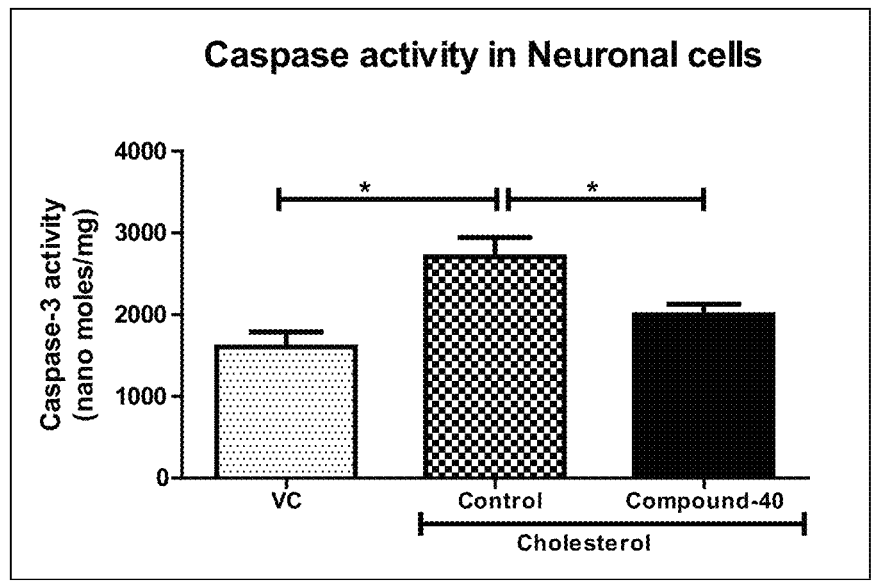
FIG. 1C shows caspase activity in neuronal cells treated with compound 40.
Figure 1D:
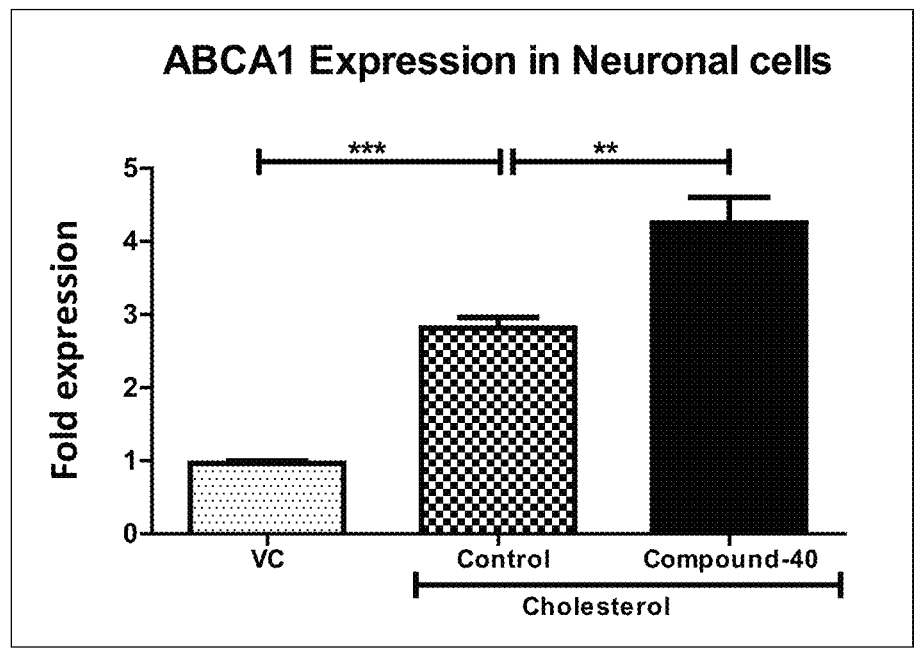
FIG. 1D shows ABCA1 expression in neuronal cells treated with compound 40.
Figure 1E:
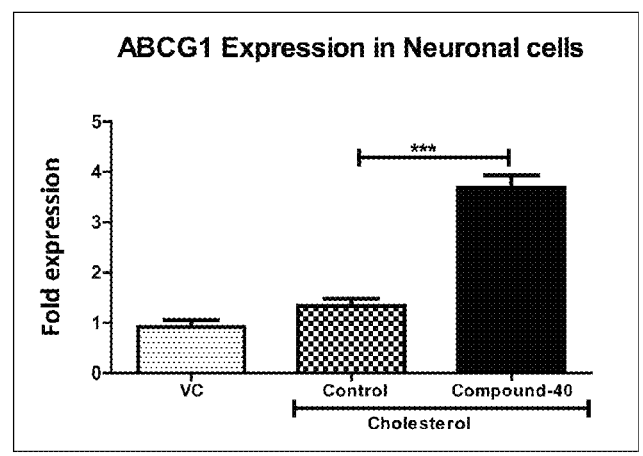
FIG. 1E shows ABCG1 expression in neuronal cells treated with compound 40.
Figure 2A:
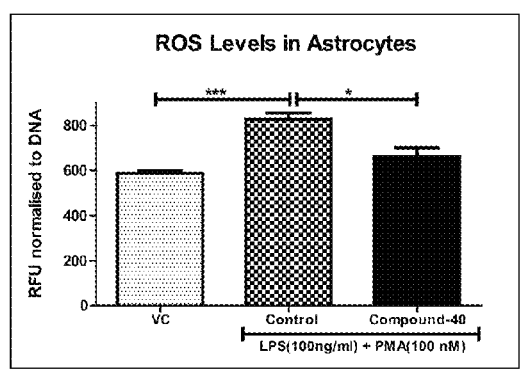
FIG. 2A shows reduced oxidative stress (ROS) levels in astrocytes treated with compound 40.
Figure 2B:
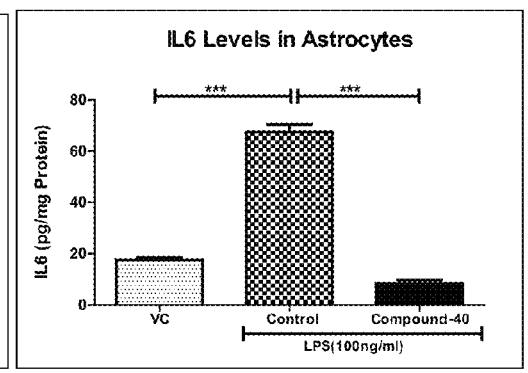
FIG. 2B shows IL6 levels in astrocytes treated with compound 40.
Figure 2C:
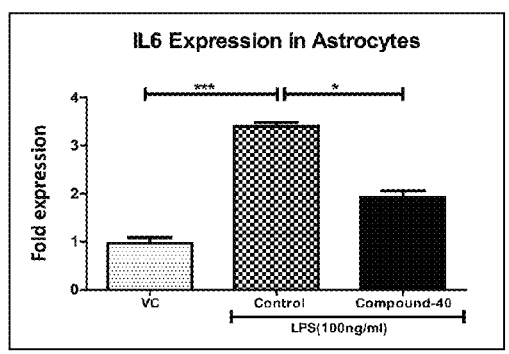
FIG. 2C shows IL6 expression in astrocytes treated with compound 40.
Figure 2D:
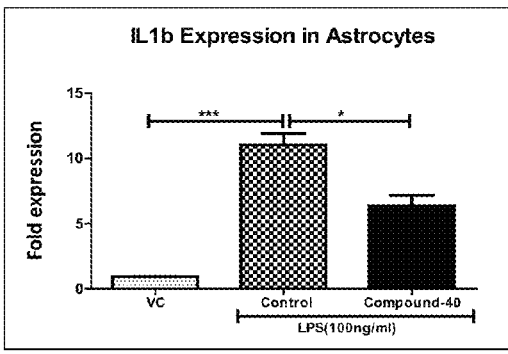
FIG. 2D shows IL1B expression in astrocytes treated with compound 40.
Figure 2E:
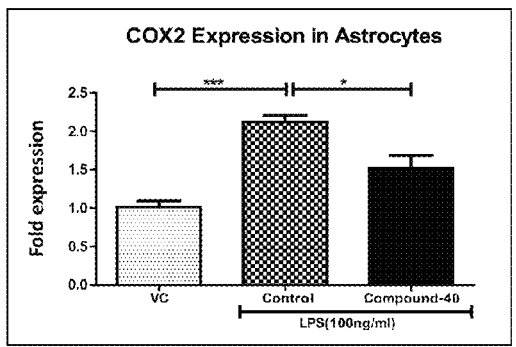
FIG. 2E shows COX2 expression in astrocytes treated with compound 40.
Figure 2F:
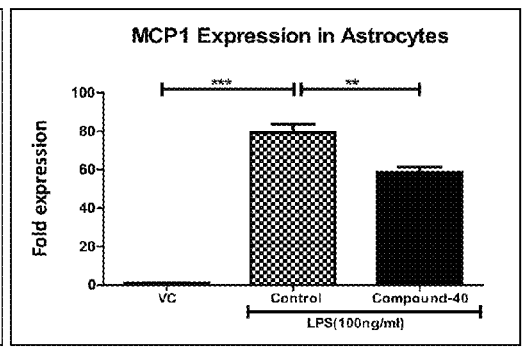
FIG. 2F shows MCP1 expression in astrocytes treated with compound 40.

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^e$, —C(=O)OR$^e$, C(=O)NR$^e$R$^f$, C(=NOH)R$^e$, C(=NR$^e$)NR$^f$R$^g$, NR$^e$R$^f$, NR$^e$C(=O)R$^f$, NR$^e$C(=O)OR$^f$, NR$^e$C(=O)NR$^f$R$^g$, NR$^e$C(=NR$^f$)NR$^g$R$^h$, NR$^e$SO$_2$R$^f$, —SR$^e$, SO$_2$NR$^e$R$^f$, —OR$^e$, OC(=O)NR$^e$R$^f$, OC(=O)R$^e$ and acyl, wherein R$^e$, R$^f$, R$^g$ and R$^h$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, C$_1$-C$_{10}$heteroalkyl, C$_3$-C$_{12}$cycloalkyl, C$_3$-C$_{12}$cycloalkenyl, C$_1$-C$_{12}$heterocycloalkyl, C$_1$-C$_{12}$heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. The alkenyl group is preferably a 1-alkenyl group. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are C$_1$-C$_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a C$_1$-C$_{12}$ alkyl, more preferably a C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means an Alkyl-NH— group, in which alkyl is as defined herein. "Dialkylamino" means a (alkyl)$_2$N— group, in which each alkyl may be the same or different and are each as defined herein for alkyl. The alkyl group is preferably a C$_1$-C$_6$alkyl group. The group may be a terminal group or a bridging group. If the group is a terminal group it is bonded to the remainder of the molecule through the nitrogen atom.

"Alkylaminocarbonyl" refers to a group of the formula $(Alkyl)_x(H)_yNC(=O)$— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl-group in which the alkyloxy and alkyl moieties are as defined herein. The group may be a terminal group or a bridging group. If the group is a terminal group it is bonded to the remainder of the molecule through the alkyl group.

"Alkyloxyaryl" refers to an alkyloxy-aryl-group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl-group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl-group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl-group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but are not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group it is bonded to the remainder of the molecule through the oxygen atom.

"Aminoalkyl" means an NH$_2$-alkyl-group in which the alkyl group is as defined herein. The group may be a terminal group or a bridging group. If the group is a terminal group it is bonded to the remainder of the molecule through the alkyl group.

"Aminosulfonyl" means an NH$_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$cycloalkyl or $C_{5-7}$cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl-group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl-group in which the aryl and alkyl moieties are as defined herein. Preferred arylalkyl groups contain a $C_{1-5}$alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. Di-arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl-group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl-group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl-group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to a heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. The group may be a monocyclic or bicyclic heteroaryl group. Examples of heteroaryl include thiophene, benzothiophene, benzofuran, benzimidazole, benzoxazole, benzothiazole, benzisothiazole, naphtho [2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$heteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl-group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl group as defined herein but containing at least one double bond. A heterocycloalkenyl group typically is a $C_2$-$C_{12}$heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$heterocycloalkyl group. The group may be a terminal group or a bridging group.

"Heterocycloalkylalkyl" refers to a heterocycloalkyl-alkyl-group in which the heterocycloalkyl and alkyl moieties are as defined herein. Exemplary heterocycloalkylalkyl groups include (2-tetrahydrofuryl)methyl, (2-tetrahydrothiofuranyl)methyl. The group may be a terminal group or a bridging group. If the group is a terminal group it is bonded to the remainder of the molecule through the alkyl group.

"Heterocycloalkylalkenyl" refers to a heterocycloalkyl-alkenyl-group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl-group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$ Heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art. For those compounds where there is the possibility of geometric isomerism the applicant has drawn the isomer that the compound is thought to be although it will be appreciated that the other isomer may be the correct structural assignment.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, arylsulfonic. In a similar vein base addition salts may be prepared by ways well known in the art using organic or inorganic bases. Example of suitable organic bases include simple amines such as methylamine, ethylamine, triethylamine and the like. Examples of suitable inorganic bases include NaOH, KOH, and the like. Additional information on pharmaceutically acceptable salts can be found in Remington's Pharmaceutical Sciences, 19th Edition, Mack Publishing Co., Easton, Pa.

1995. In the case of agents that are solids, it is understood by those skilled in the art that the inventive compounds, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

As stated above the compounds of the invention have the formula (I):

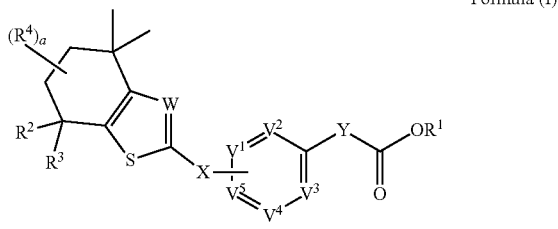

Formula (I)

As with any group of structurally related compounds which possess a particular utility, certain embodiments of variables of the compounds of the Formula (I), are particularly useful in their end use application.

In some embodiments $R^1$ is H. In some embodiments R is $C_1$-$C_6$alkyl. In some embodiments $R^1$ is a carboxylic acid protecting group.

In some embodiments Y is a bond. In some embodiments Y is a linking moiety. The linking moiety can be any suitable moiety that provides a link between the aromatic ring and the carboxyl moiety. Examples of suitable linker moieties include optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$haloalkyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, and optionally substituted $C_2$-$C_{12}$heterocycloalkenyl. Specific examples of suitable linkers include trans-ethenyl and the cyclopropyl group.

In the compounds of the invention a is an integer selected from the group consisting of 0, 1, 2, 3, and 4. In some embodiments a is 0. In some embodiments a is 1. In some embodiments a is 2. In some embodiments a is 3. In some embodiments a is 4.

In some embodiments of the compounds of the invention R is H, Y is a bond and a is 0. This provides compounds of formula (II):

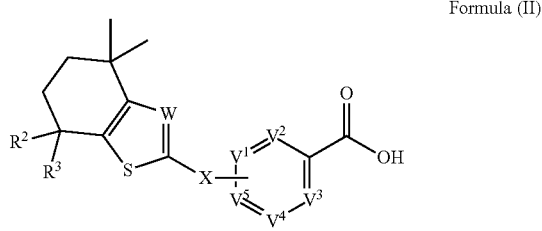

Formula (II)

or a pharmaceutically acceptable salt thereof;

wherein $R^2$, $R^3$, W, X, $V^1$, $V^2$, $V^3$, $V^4$ and $V^5$ are as described above.

In the compounds of the invention $R^2$ and $R^3$ are selected from the group consisting of H and $C_1$-$C_6$alkyl. Examples of suitable values for $R^2$ and $R^3$ are H, methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl. In some embodiments $R^2$ and $R^3$ are H. In some embodiments $R^2$ and $R^3$ are methyl.

In the compounds of the invention W is selected from N or $CR^9$. In some embodiments W is N. in some embodiments W is $CR^9$.

In some embodiments of the compounds of the invention $R^1$ is H, Y is a bond, a is 0 and W is N. This provides compounds of formula (IIa):

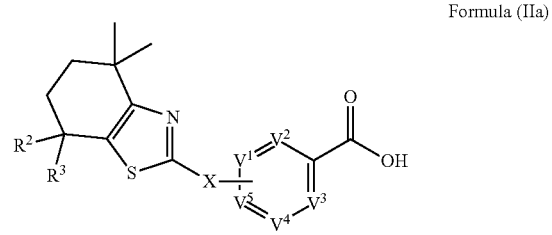

Formula (IIa)

or a pharmaceutically acceptable salt thereof;

wherein $R^2$, $R^3$, X, $V^1$, $V^2$, $V^3$, $V^4$ and $V^5$ are as described above.

In some embodiments of the compounds of the invention $R^1$ is H, Y is a bond, a is 0 and W is $CR^9$. This provides compounds of formula (IIb):

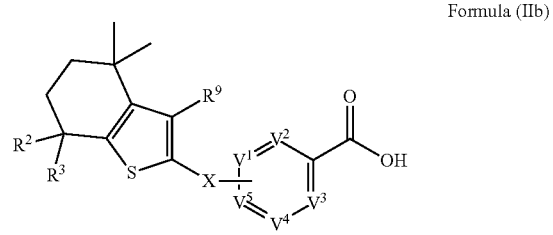

Formula (IIb)

or a pharmaceutically acceptable salt thereof;

wherein $R^2$, $R^3$, $R^9$, X, $V^1$, $V^2$, $V^3$, $V^4$ and $V^5$ are as described above.

In the compounds of the invention X is a bond or a linking moiety. In some embodiments X is a bond. In some embodiments X is a linking moiety. In some embodiments of the compounds of the invention X is a linking moiety selected from the group consisting of a bond, —O—, —S—, —$NR^{10}$—, $NR^{10}C(=O)$—, —$C(=R^{11})$— and —$(CR^{12}R^{13})_b$—;

wherein $R^{10}$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$haloalkyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_3$-$C_{12}$cycloalkyl$C_1$-$C_{12}$alkyl, optionally substituted $C_2$-$C_{12}$heterocycloalkyl$C_1$-$C_{12}$alkyl, optionally substituted $C_6$-$C_{18}$aryl$C_1$-$C_{12}$alkyl, optionally substituted $C_1$-$C_{18}$heteroaryl$C_1$-$C_{12}$alkyl, $SO_3H$, $SO_2NR^5R^5$, $SO_2R^5$, $SONR^5R^5$, $SOR^5$, $COR^5$, COOH, $COOR^5$, $CONR^5R^5$ and acyl;

wherein $R^{11}$ is selected from the group consisting of O, $NR^{14}$, $NOR^{14}$ and $CR^{14}R^{15}$, wherein each $R^{14}$ and $R^{15}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$haloalkyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_3$-$C_{12}$cycloalkyl$C_1$-$C_{12}$alkyl, optionally substituted $C_2$-$C_{12}$heterocycloalkyl$C_1$-$C_{12}$alkyl, optionally substituted $C_6$-$C_{18}$aryl$C_1$-$C_{12}$alkyl, optionally substituted $C_1$-$C_{18}$heteroaryl$C_1$-$C_{12}$alkyl, and acyl;

each $R^{12}$ and $R^{13}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$haloalkyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_3$-$C_{12}$cycloalkyl$C_1$-$C_{12}$alkyl, optionally substituted $C_2$-$C_{12}$heterocycloalkyl$C_1$-$C_{12}$alkyl, optionally substituted $C_6$-$C_{18}$aryl$C_1$-$C_{12}$alkyl, optionally substituted $C_1$-$C_{18}$heteroaryl$C_1$-$C_{12}$alkyl, and acyl, or $R^{12}$ and $R^{13}$ on the same carbon atom when taken together form a cyclic moiety or $R^{12}$ and $R^{13}$ on adjacent carbon atoms when taken together form a double bond;

b is an integer selected from the group consisting of 0, 1, 2, 3 and 4;

In some embodiments X is a bond. In some embodiments X is —O—, In some embodiments X is —S—. In some embodiments X is —$NR^{10}$—. In some embodiments X is $NR^{10}C(=O)$—. In some embodiments X is —$C(=R^{11})$—. In some embodiments X is —$(CR^{12}R^{13})_b$—.

The compounds of formula (I) contain a moiety of formula (B).

Formula (B)

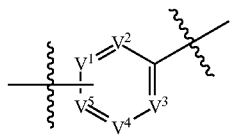

In some embodiments $V^2$ is $CR^6$. In some embodiments $V^2$ is N. In some embodiments $V^3$ is $CR^6$. In some embodiments $V^3$ is N. In some embodiments $V^4$ is $CR^6$. In some embodiments $V^4$ is N.

$V^1$ and $V^5$ are selected from the group consisting of N, $CR^7$ and $CR^8$ such that one of $V^1$ and $V^5$ is $CR^8$ and the other is N or $CR^7$. That is the point of attachment of the group X to the aromatic ring occurs at either $V^1$ or $V^5$. In some embodiments $V^1$ is $CR^7$. In some embodiments $V^1$ is N. In some embodiments $V^1$ is $CR^8$. In some embodiments $V^5$ is $CR^7$. In some embodiments $V^5$ is $CR^8$. In some embodiments $V^5$ is N.

In some embodiments of the compounds of the invention $R^1$ is H, Y is a bond, a is 0, W is N, and $V^1$ is $CR^8$. This provides compounds of formula (IIIa):

Formula (IIIa)

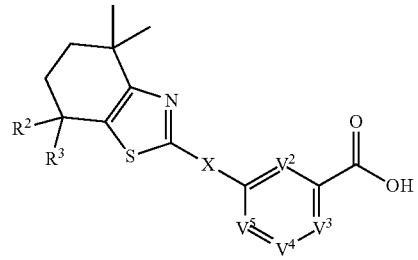

or a pharmaceutically acceptable salt thereof;

wherein $R^2$, $R^3$, X, $V^2$, $V^3$, $V^4$ and $V^5$ are as described above.

In some embodiments of the compounds of the invention R is H, Y is a bond, a is 0, W is N, and $V^5$ is $CR^8$. This provides compounds of formula (IIIb):

Formula (IIIb)

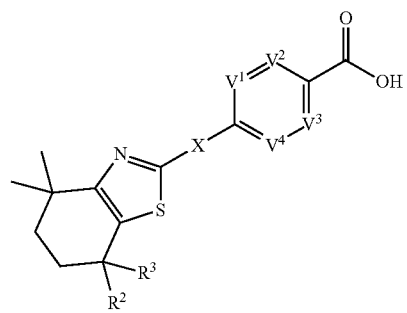

or a pharmaceutically acceptable salt thereof;

wherein $R^2$, $R^3$, X, $V^1$, $V^2$, $V^3$, $V^4$ and $V^5$ are as described above.

In some embodiments of the compounds of the invention R is H, Y is a bond, a is 0, W is $CR^9$, and $V^1$ is $CR^8$. This provides compounds of formula (IIIc):

Formula (IIIc)

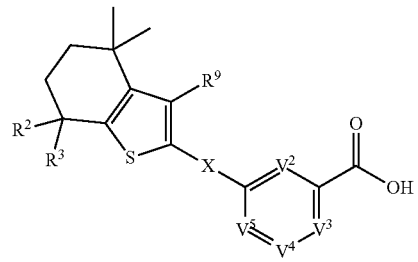

or a pharmaceutically acceptable salt thereof;

wherein $R^2$, $R^3$, $R^9$, X, $V^2$, $V^3$, $V^4$ and $V^5$ are as described above.

In some embodiments of the compounds of the invention R$^1$ is H, Y is a bond, a is 0, W is CR$^9$, and V$^5$ is CR$^8$. This provides compounds of formula (IIId):

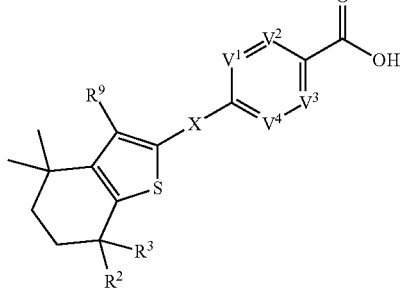

Formula (IIId)

or a pharmaceutically acceptable salt thereof;
wherein R$^2$, R$^3$, R$^9$, X, V$^1$, V$^2$, V$^3$, and V$^4$ are as described above.

As a result of the combinations of V$^1$, V$^2$, V$^3$, V$^4$ and V$^5$ in some embodiments of the invention the moiety of formula (B) is selected from the group consisting of:

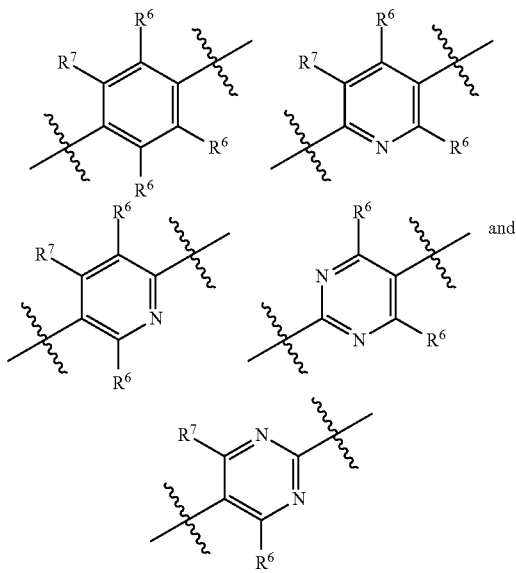

and wherein R$^6$ and R$^7$ is as defined above.
In some embodiments of the invention the moiety of formula (B) is a group of formula

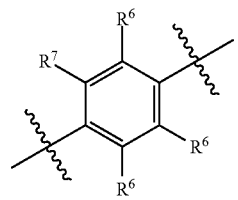

wherein R$^6$ and R$^7$ is as defined above.
In some embodiments of the invention the moiety of formula (B) is a group of formula

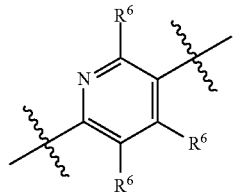

wherein R$^6$ is as defined above.
In some embodiments of the invention the moiety of formula (B) is a group of formula

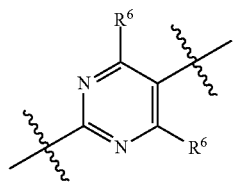

wherein R$^6$ is as defined above.
In some embodiments of the invention containing an R$^4$ moiety, each R$^4$ is independently selected from the group consisting of H, halogen, OH, NO$_2$, CN, SH, NH$_2$, CF$_3$, OCF$_3$, C$_1$-C$_{12}$alkyl and C$_1$-C$_{12}$alkyloxy, or two R$^4$ on the same carbon when taken together form a =O moiety. In some embodiments each R$^4$ is independently selected from the group consisting of H, OH, OCH$_3$, OCH$_2$CH$_3$, and NHBn. In a particularly preferred embodiment each R$^4$ is H.

In some embodiments of the invention containing an R$^5$ moiety, each R$^5$ is independently selected from the group consisting of H, and C$_1$-C$_{12}$alkyl.

In some embodiments of the invention each R$^6$ is independently selected from the group consisting of H, halogen, OH, NO$_2$, CN, SH, NH$_2$, CF$_3$, OCF$_3$, C$_1$-C$_{12}$alkyl and C$_1$-C$_{12}$alkyloxy.

In some embodiments each R$^6$ is independently selected from the group consisting of H, CH$_3$, CH$_2$CH$_3$, CH$_2$CH$_2$CH$_3$, CH(CH$_3$)$_2$, (CH$_2$)$_3$CH$_3$, Cl, Br, F, I, OH, NO$_2$, NH$_2$, NHSO$_2$CH2CH$_2$CH$_3$, CN, OCH$_3$, OCH$_2$CH$_2$CH$_3$, OC$_6$H$_5$, OCH$_2$CCH, OCH$_2$cycloproply, CF$_3$, and OCF$_3$.

In some embodiments each R$^7$ is independently selected from the group consisting of H, CH$_3$, CH$_2$CH$_3$, CH$_2$CH$_2$CH$_3$, CH(CH$_3$)$_2$, (CH$_2$)$_3$CH$_3$, Cl, Br, F, I, OH, NO$_2$, NH$_2$, CN, OCH$_3$, OCH$_2$CH$_2$CH$_3$, CF$_3$, and OCF$_3$.

In some embodiments of the compounds of the invention containing an R$^9$ group, the R$^9$ group is selected from the group consisting of H, methyl, ethyl, isopropyl, propyl, 3,3-dimethyl-propyl, butyl, isobutyl, 3,3-dimethyl-butyl, 2-ethyl-butyl, pentyl, and hexyl. In some embodiments R$^9$ is selected from the group consisting of H, methyl and ethyl. In some embodiments R$^9$ is H. In some embodiments R$^9$ is methyl. In some embodiments R$^9$ is ethyl.

In some embodiments of the compounds of the invention containing an R$^{10}$ group, the R$^{10}$ group is selected from the group consisting of H, methyl, cyclopropylmethyl, ethyl, isopropyl, propyl, cyclopropyl, 3,3-dimethyl-propyl, butyl, isobutyl, cyclobutyl, 3,3-dimethyl-butyl, 2-ethyl-butyl, pentyl, hexyl, phenyl and pyridine-2-yl. In some embodiments R$^{10}$ is selected from the group consisting of H, methyl and ethyl. In some embodiments R$^{10}$ is H. In some embodiments R$^{10}$ is methyl. In some embodiments R$^{10}$ is ethyl.

In some embodiments $R^{11}$ is O. In some embodiments $R^{11}$ is $NR^{14}$. In some embodiments $R^{11}$ is $NOR^{14}$. In some embodiments $R^{11}$ is $CR^{14}R^{15}$.

In some embodiments of the compounds of the invention containing an $R^{12}$ group or $R^{13}$ group, the $R^{12}$ or $R^{13}$ group is independently selected from the group consisting of H, methyl, cyclopropylmethyl, ethyl, isopropyl, propyl, cyclopropyl, 3,3-dimethyl-propyl, butyl, isobutyl, 3,3-dimethyl-butyl, 2-ethyl-butyl, pentyl, and hexyl.

In some embodiments of the compounds of the invention containing an $R^{14}$ group or $R^{15}$ group, the $R^{14}$ or $R^{15}$ group is independently selected from the group consisting of H, methyl, cyclopropylmethyl, ethyl, isopropyl, propyl, cyclopropyl, 3,3-dimethyl-propyl, butyl, isobutyl, 3,3-dimethyl-butyl, 2-ethyl-butyl, pentyl, and hexyl.

Many if not all of the variables discussed above may be optionally substituted. If the variable is optionally substituted then in some embodiments each optional substituent is independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^e$, —C(=O)OR$^e$, C(=O)NR$^e$R$^f$, C(=NOH)R$^e$, C(=NR$^e$)NR$^f$R$^g$, NR$^e$R$^f$, NR$^e$C(=O)R$^f$, NR$^e$C(=O)OR$^f$, NR$^e$C(=O)NR$^f$R$^g$, NR$^e$C(=NR$^f$)NR$^g$R$^h$, NR$^e$SO$_2$R$^f$, —SR$^e$, SO$_2$NR$^e$R$^f$, —OR$^e$, OC(=O)NR$^e$R$^f$, OC(=O)R$^e$ and acyl, wherein R$^e$, R$^f$, R$^g$ and R$^h$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, C$_1$-C$_{10}$heteroalkyl, C$_3$-C$_{12}$cycloalkyl, C$_3$-C$_{12}$cycloalkenyl, C$_1$-C$_{12}$heterocycloalkyl, C$_1$-C$_{12}$heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments each optional substituent is independently selected from the group consisting of: F, Cl, Br, =O, =S, —CN, —NO$_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)OR$^a$, COOH, SH, and acyl.

In some embodiments each optional substituent is independently selected from the group consisting of: F, Br, Cl, =O, =S, —CN methyl, trifluoro-methyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, NH$_2$, —NO$_2$, phenoxy, hydroxy, methoxy, trifluoro-methoxy, ethoxy, and methylenedioxy.

In some embodiments each optional substituent is independently selected from the group consisting of H, CH$_3$, CH$_2$CH$_3$, CH$_2$CH$_2$CH$_3$, CH(CH$_3$)$_2$, (CH$_2$)$_3$CH$_3$, Cl, Br, F, I, OH, NO$_2$, NH$_2$, CN, OCH$_3$, OCH$_2$CH$_2$CH$_3$, CF$_3$, and OCF$_3$.

Alternatively, two optional substituents on the same moiety when taken together may be joined to form a fused cyclic substituent attached to the moiety that is optionally substituted. Accordingly the term optionally substituted includes a fused ring such as a cycloalkyl ring, a heterocycloalkyl ring, an aryl ring or a heteroaryl ring.

In addition to compounds of formula I, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The invention also relates to pharmaceutical compositions including a compound of the invention and a pharmaceutically acceptable carrier, diluent or excipient.

Specific compounds of the invention include the following:

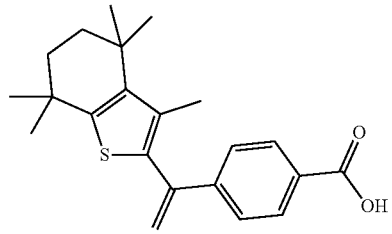

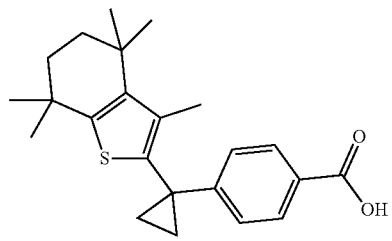

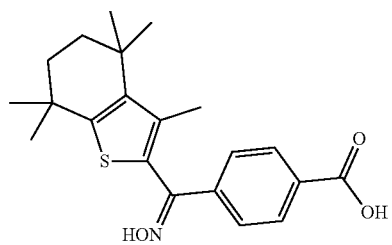

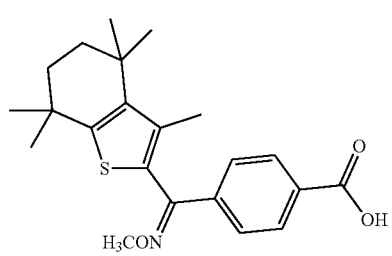

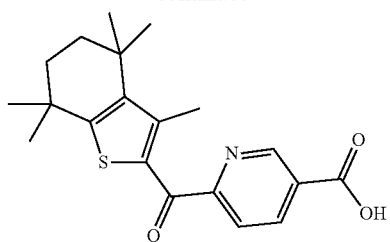
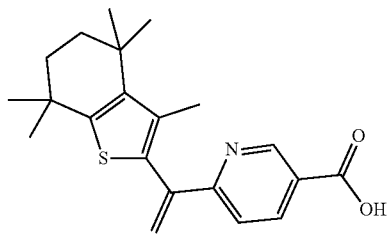
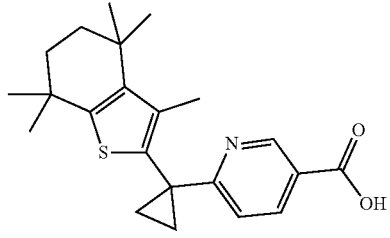
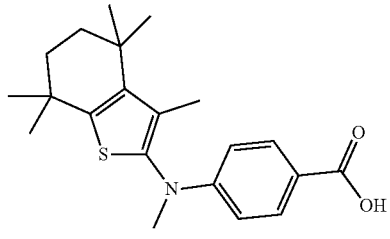
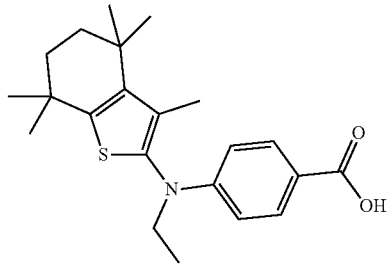
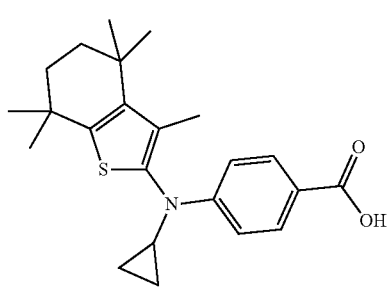
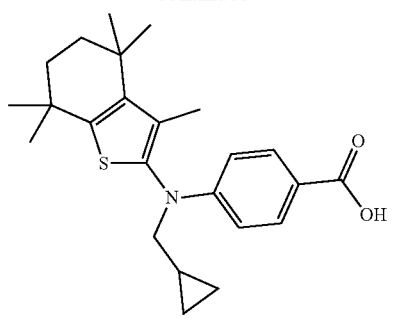
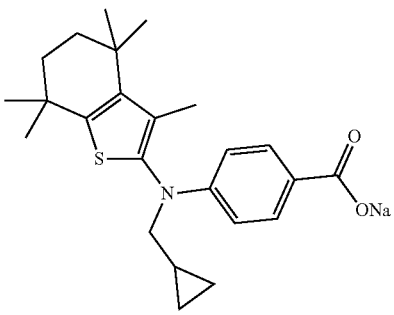
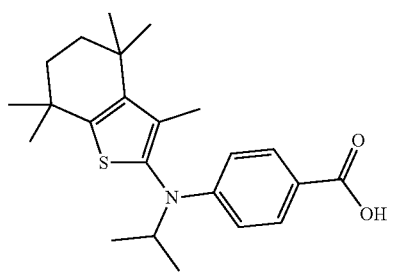
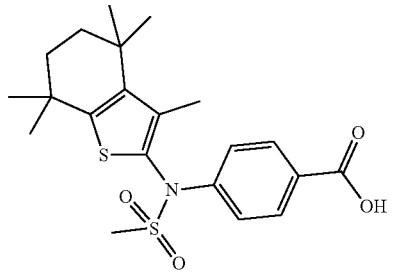
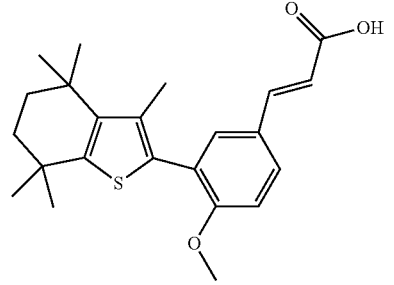
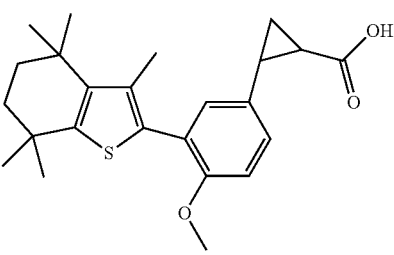

25
-continued
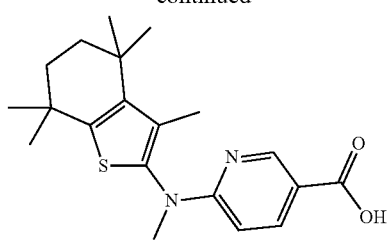
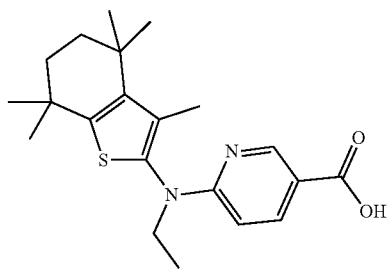
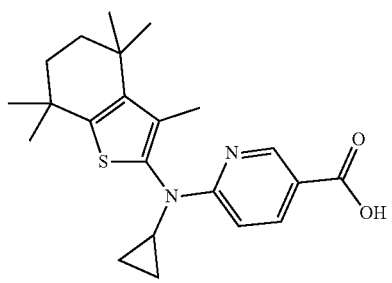
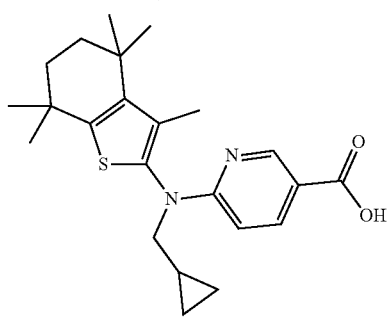
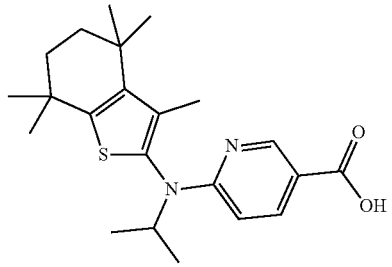
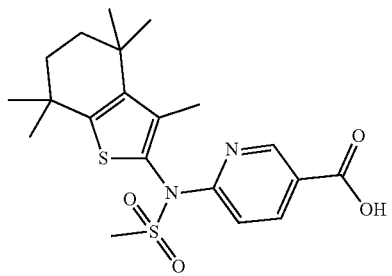
26
-continued
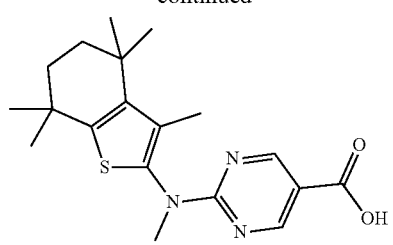
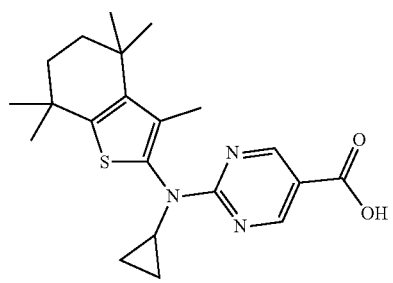
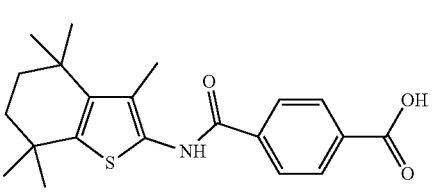
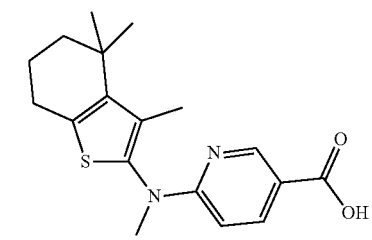
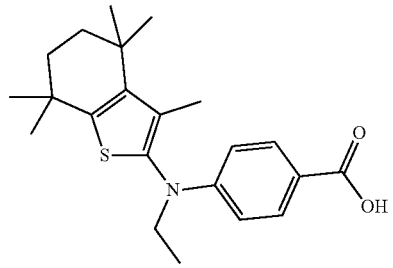
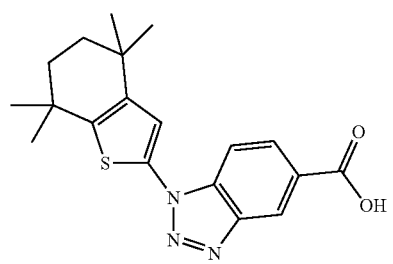
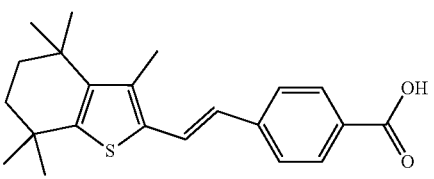

-continued
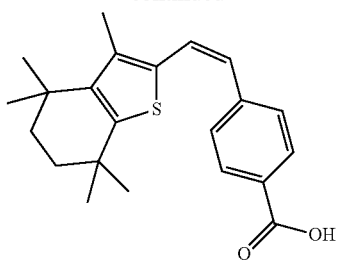
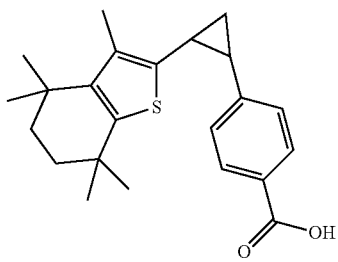
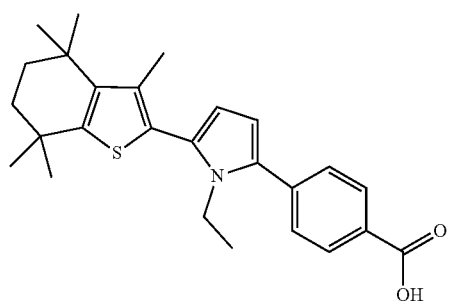
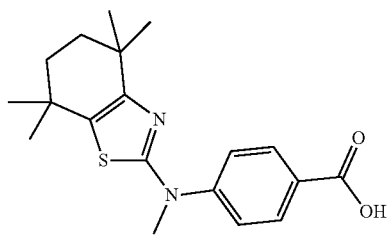
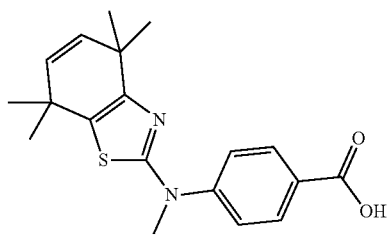
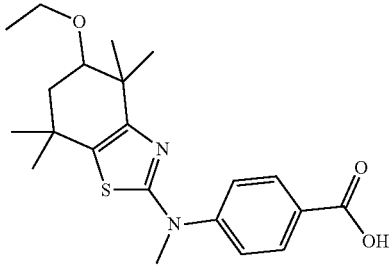
-continued
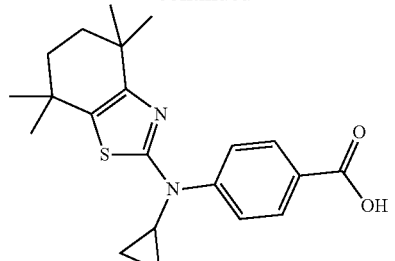
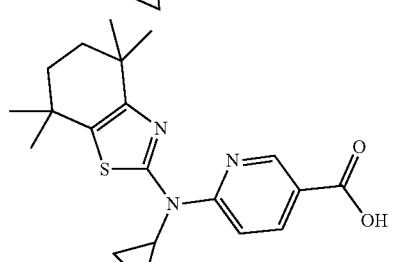
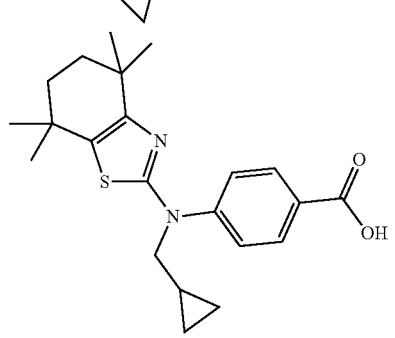
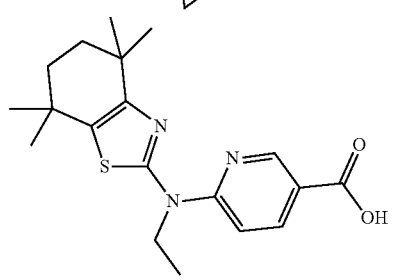
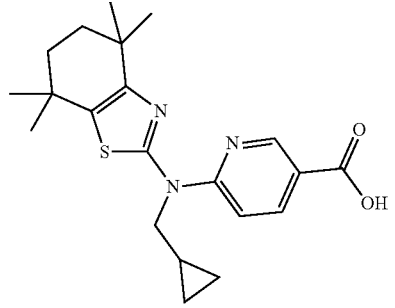
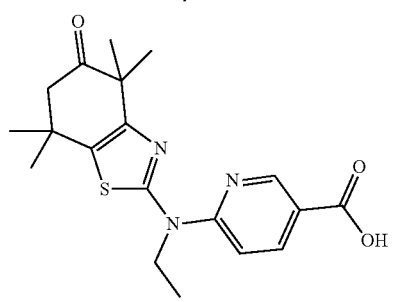

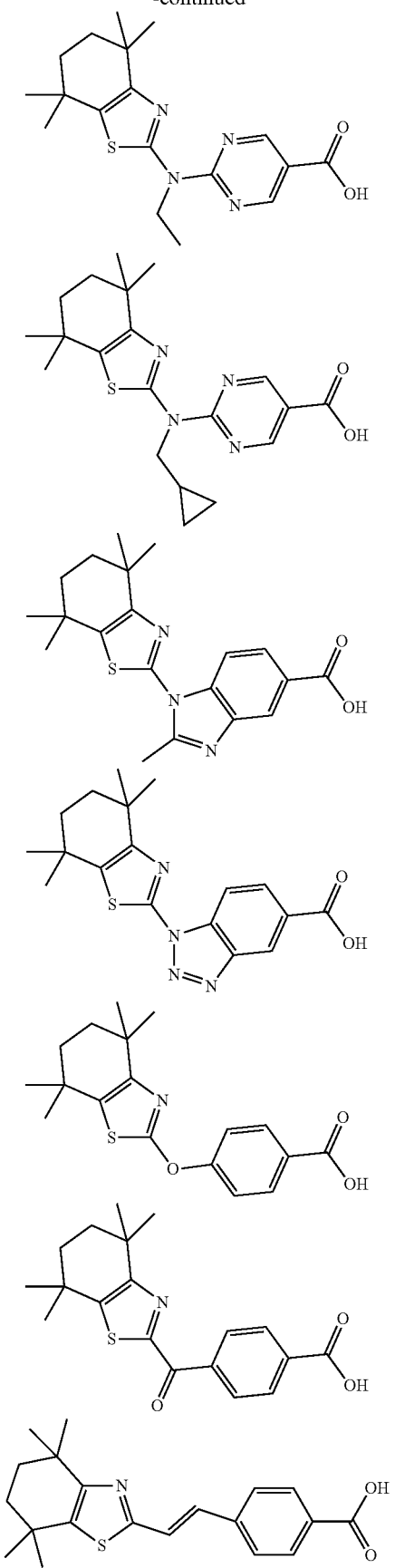
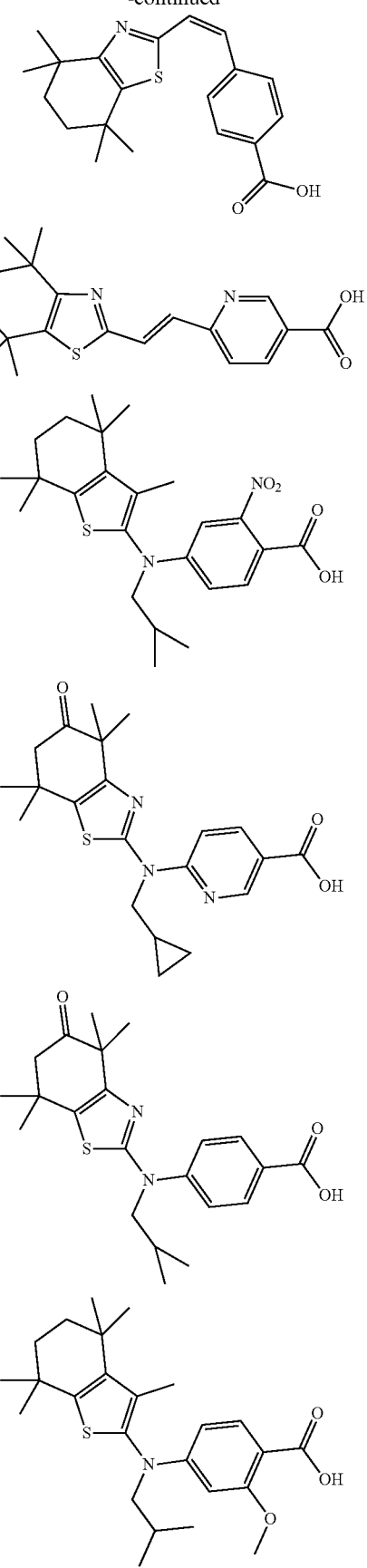

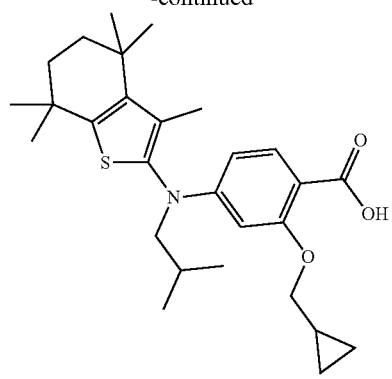
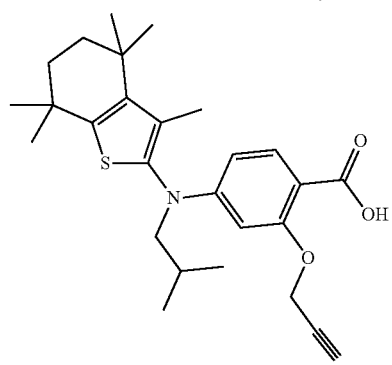
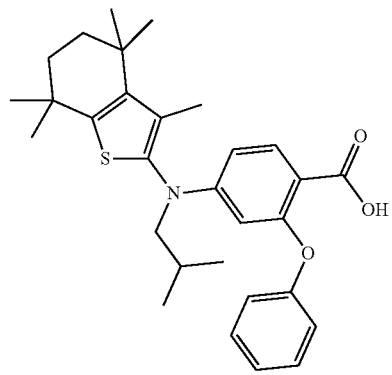
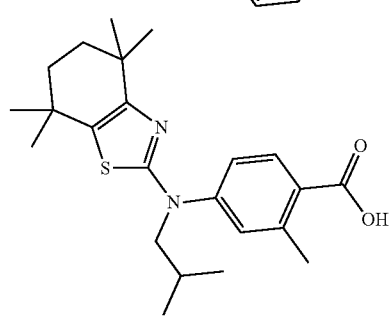
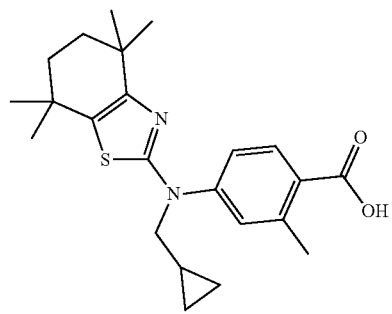
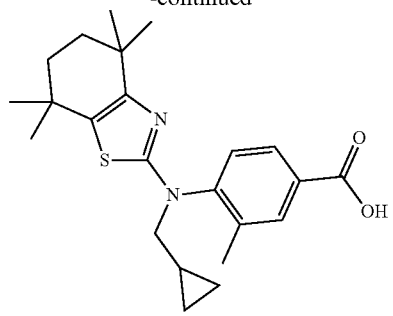
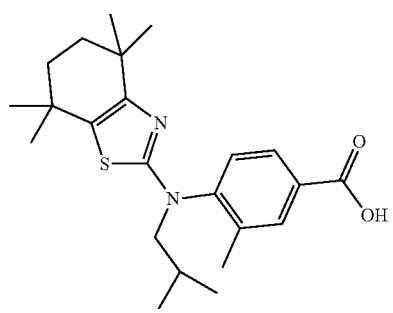
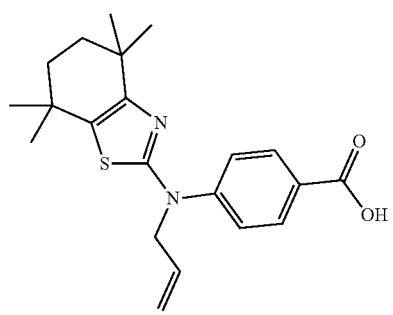
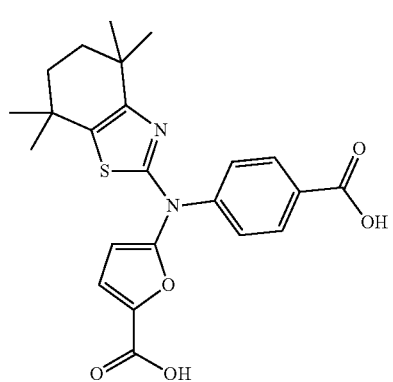
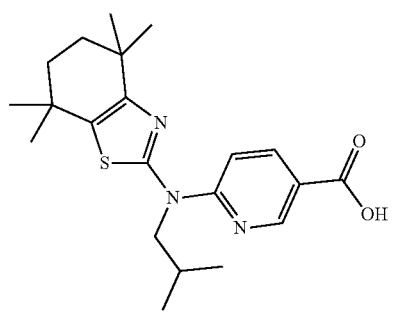

33
-continued
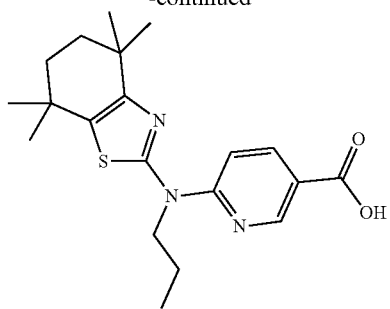
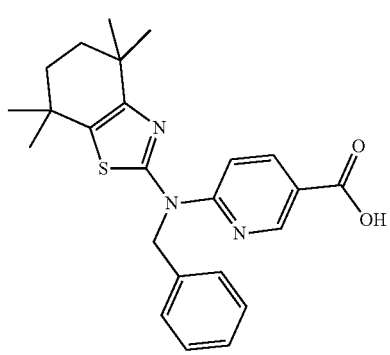
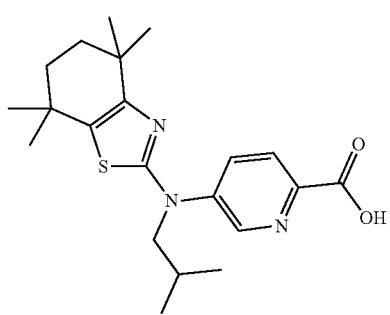
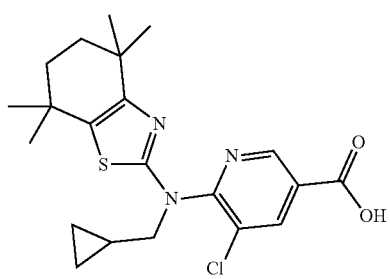
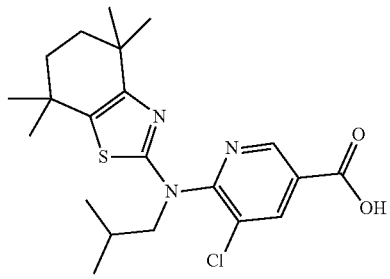
34
-continued
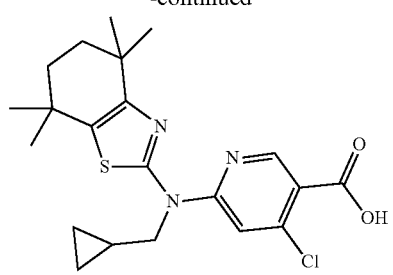
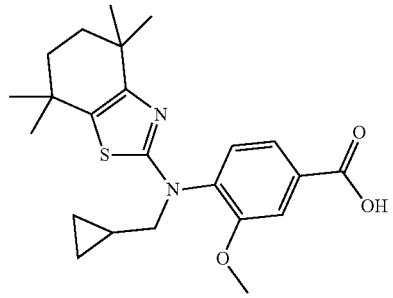
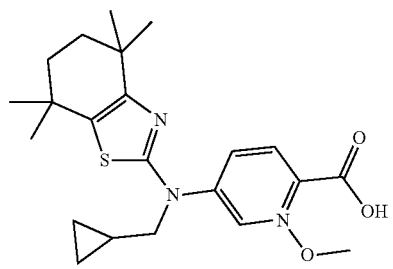
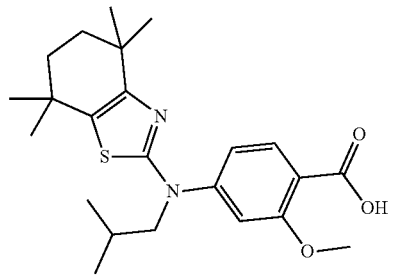
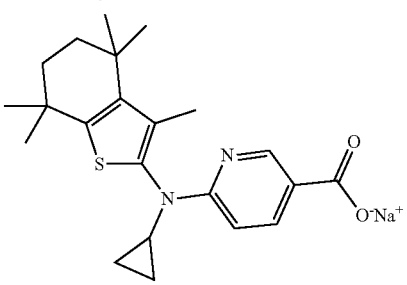
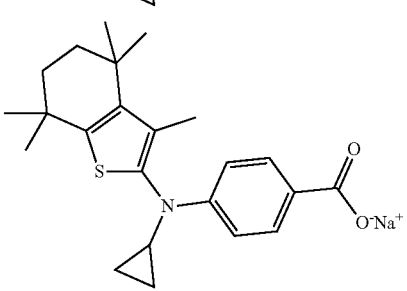

-continued
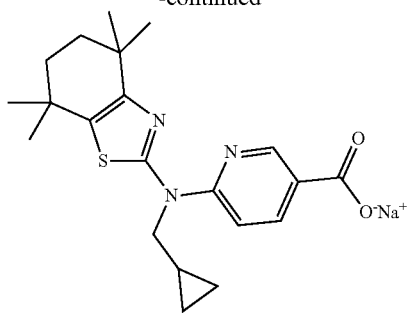
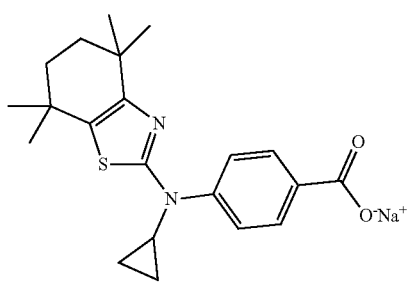
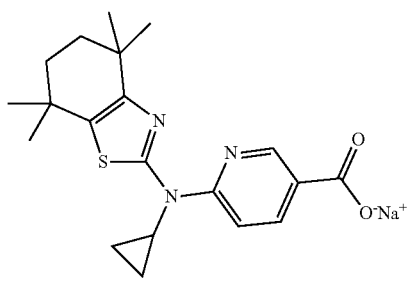
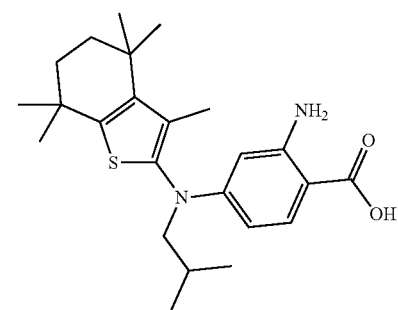
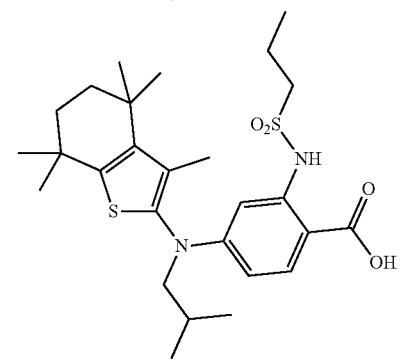
-continued
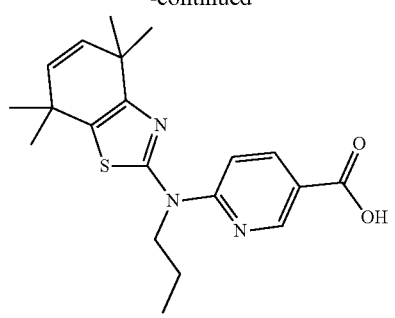
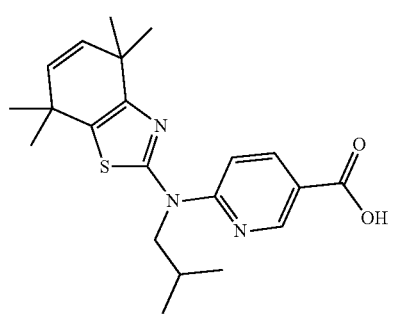
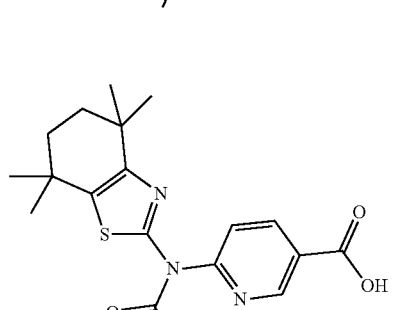
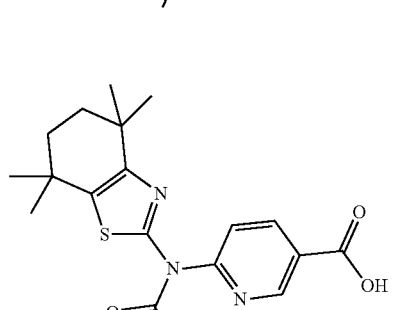
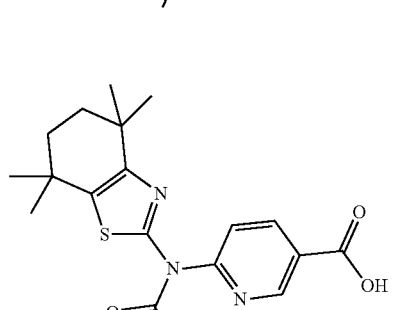

-continued
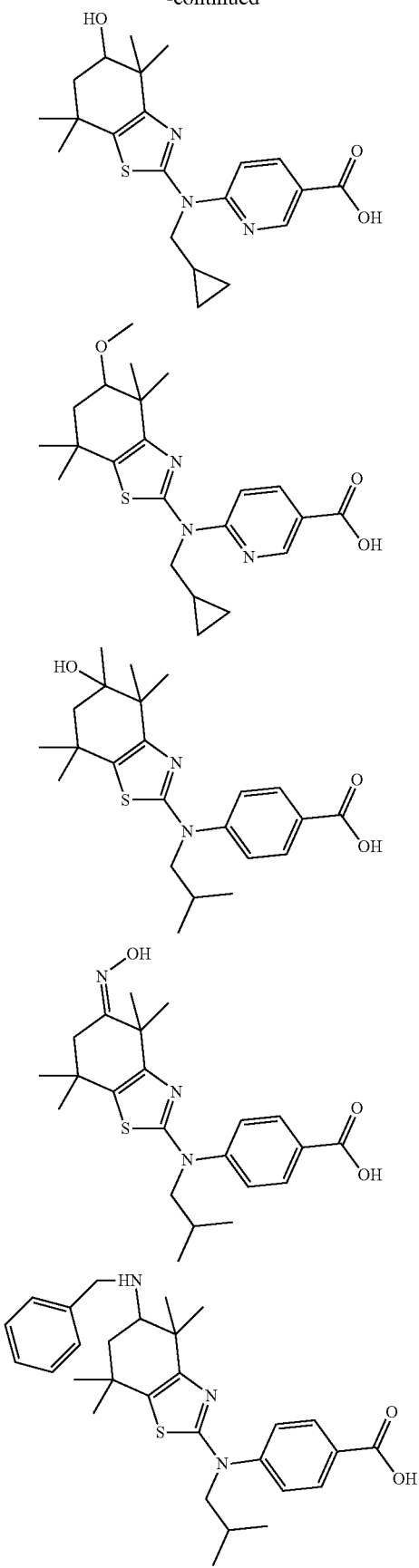
-continued
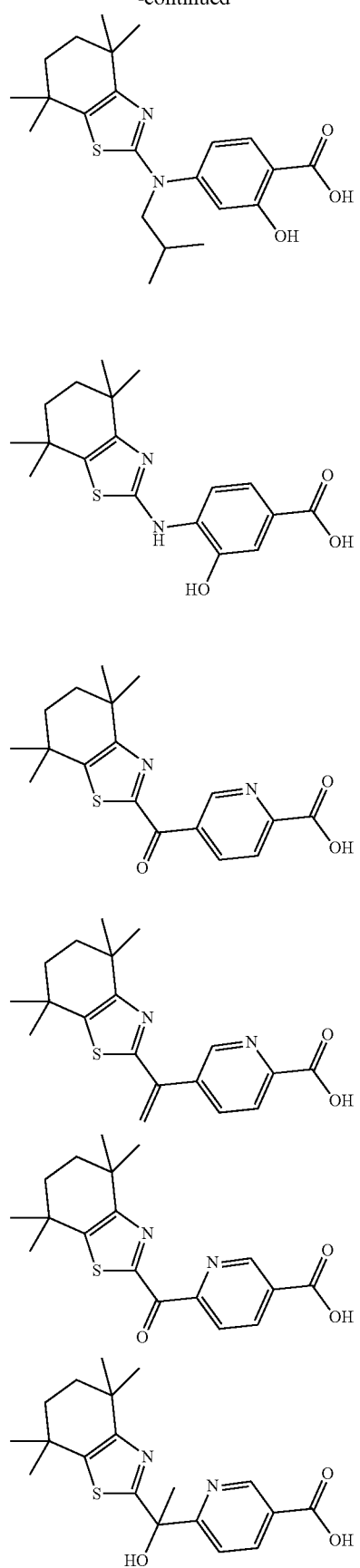

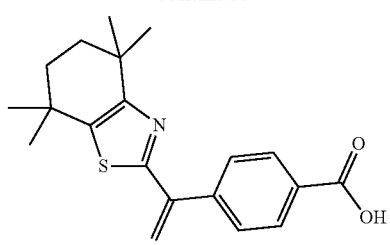
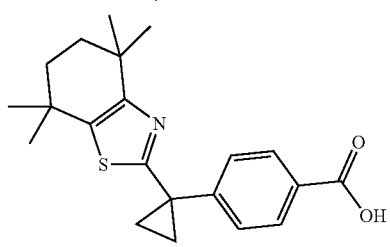
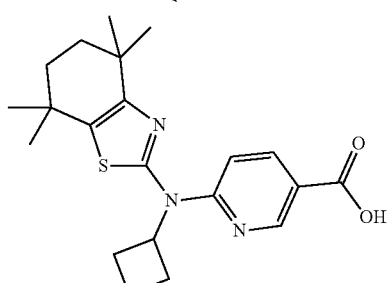
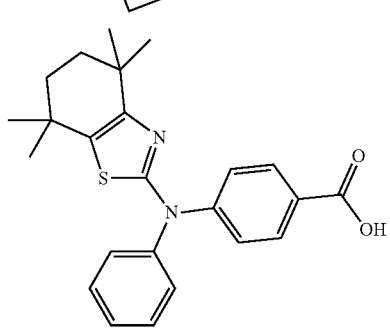
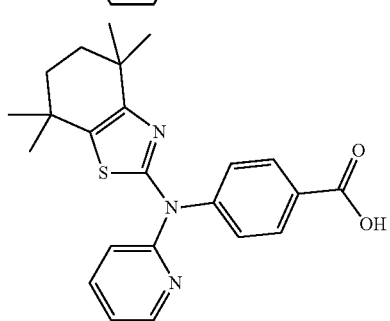
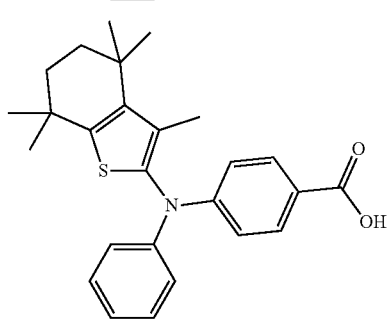
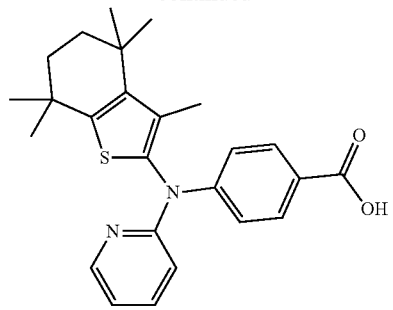
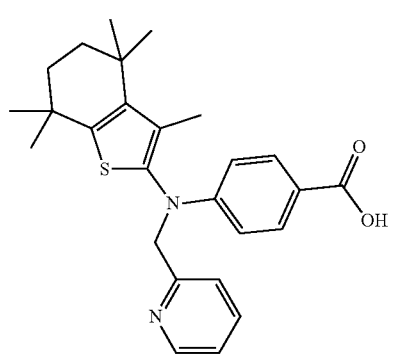
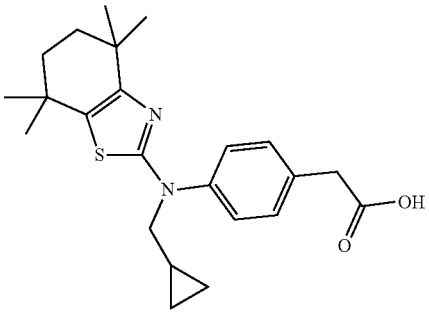
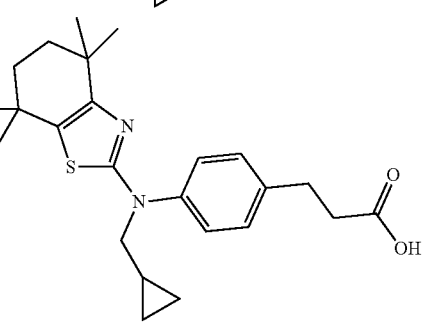
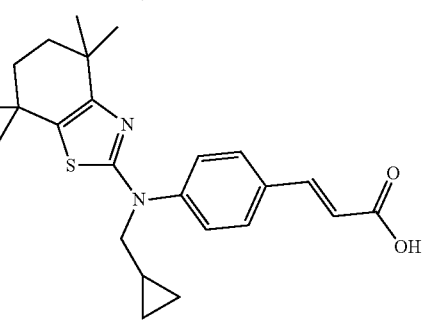

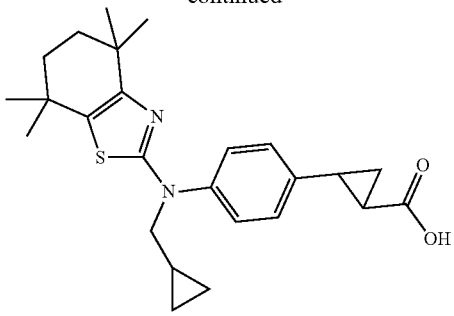

or pharmaceutically acceptable salt, or prodrug thereof.

The compounds of the invention are agonists of RXR's and therefore have the ability to activate these receptors. The ability activate the receptors may be a result of the compounds acting directly and solely on the receptor to modulate/potentiate biological activity. However, it is understood that the compounds may also act at least partially on other factors associated with the activity of the receptor.

The activation of an RXR may be carried out in any of a number of ways known in the art. For example if activation in vitro is desired an appropriate amount of the compound may be added to a solution containing the RXR. In circumstances where it is desired to activate RXR in a mammal, the activation of the RXR typically involves administering the compound to a mammal containing the RXR.

In a further aspect the present invention provides a method of prevention or treatment of a condition in a mammal, the method comprising administering an effective amount of a compound of the invention. In one embodiment the condition is a condition that can be treated by activation of RXR.

In yet an even further aspect the invention provides the use of a compound of the invention in the preparation of a medicament for the treatment of a condition in a mammal. In one embodiment the condition is a condition that can be treated by activation of RXR.

In yet an even further aspect the invention provides the use of a compound of the invention in the treatment of a condition in a mammal. In one embodiment the condition is a condition that can be treated by activation of RXR.

In some embodiments the condition is selected from the group consisting of Cancers such as premalignant and malignant hyperproliferative diseases such as cancers of the breast, pancreas, skin, prostate, cervix, uterus, colon, bladder, esophagus, stomach, lung, larynx, Liver, oral cavity, pancreas, blood and lymphatic system, metaplasias, dysplasias, neoplasias, leukoplakias and papillomas of the mucous membranes and in the treatment of Kaposis sarcoma, Cutaneous T Cell Lymphoma, promyelocytic leukemia, Non-Small-Cell Lung Cancer, Kidney Cancer (Advanced Renal Cell Cancer), Gastrointestinal Cancer, Mesothelioma, Bronchial Metaplasia; Skin disorders such as Dermatitis (Severe Chronic Hand Eczema in Adults) Psoriasis (Severe Plaque Psoriasis), Alopecia (Hair Loss), actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin pigmentation agents and to treat and reverse the effects of age and photo damage to the skin; Metabolic Diseases such as diabetes, Type II Diabetes, Obesity, Hyperglycemia, Hypercholesterimia, Hypertriglyceridimia; hyperinsulinaemia, Cardio vascular Diseases including diseases associated with lipid metabolism such as dyslipidemias, prevention of restenosis and as an agent to increase the level of circulating tissue plasminogen activator (TPA), NASH, Steatosis, Steatohepatitis, Cirrhosis; liver disease, Fibrosis including Pulmonary fibrosis, renal fibrosis and liver fibrosis, Eye disorders such as proliferative vitreoretinopathy (PVR), retinal detachment, dry eye and other corneopathies; and Inflammatory Diseases, inflammation, oxidative stress, pulmonary fibrosis, ileitis, colitis and Krohn's disease; neurodegenerative diseases such as Alzheimer's disease, Parkinson's disease and Amyotrophic Lateral Sclerosis (ALS), Multiple sclerosis, improper pituitary function, including insufficient production of growth hormone, modulation of apoptosis, including both the induction of apoptosis and inhibition of T-Cell activated apoptosis, restoration of hair growth and multiple sclerosis.

In some embodiments the condition is diabetes. In some embodiments the condition is type II diabetes. In some embodiments the condition is obesity. In some embodiments the condition is cardiovascular disease.

The compounds of the invention may also be used to provide a number of beneficial effects to a mammal. Examples of beneficial effects that may be provided include increasing muscle endurance, improving cardiac function and achieving an exercise mimetic effect.

In one embodiment the beneficial effect is increasing muscle endurance in a mammal. In one embodiment the beneficial effect is improving cardiac function in a mammal. Examples of cardiac function that may be improved include stroke work, stroke volume, ejection fraction and ventricular refilling. In one embodiment the beneficial effect is achieving an exercise mimetic effect in a mammal.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the activator compound may be selectively toxic or more toxic to rapidly proliferating cells, e.g. cancerous tumours, than to normal cells.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

The symbols, abbreviations and conventions in the processes, schemes, and examples are consistent with those used in the contemporary scientific literature. Specifically but not meant as limiting, the following abbreviations may be used in the examples and throughout the specification g (grams)
L (liters)
Hz (Hertz)
mol (moles)
RT (room temperature)
min (minutes)
MeOH (methanol)
$CHCl_3$ (chloroform)
DCM (dichloromethane)
DMSO (dimethylsulfoxide)
EtOAc (ethyl acetate)
mg (milligrams)
mL (milliliters)
psi (pounds per square inch)
mM (millimolar)
MHz (megahertz)
h (hours)
TLC (thin layer chromatography)
EtOH (ethanol)
$CDCl_3$ (deuterated chloroform)
HCl (hydrochloric acid)
DMF (N, N-dimethylformamide)
THF (tetrahydrofuran)
$K_2CO_3$ (potassium carbonate)
$Na_2SO_4$ (sodium sulfate)
RM (Reaction Mixture)

Unless otherwise indicated, all temperatures are expressed in ° C. (degree centigrade). All reactions conducted at room temperature unless otherwise mentioned.

All the solvents and reagents used are commercially available and purchased from Sigma Aldrich, Fluka, Acros, Spectrochem, Alfa Aesar, Avra, Qualigens, Merck, Rankem and Leonid Chemicals.

$^1$H NMR spectra were recorded on a Bruker AV 300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on single quadruple 6120 LCMS from Agilent technologies, using either atmospheric chemical ionization (APCI) or Electrospray ionization (ESI) or in the combination of these two sources.

All samples were run on SHIMADZU system with an LC-20 AD pump, SPD-M20A diode array detector, SIL-20A auto sampler.

Synthetic Schemes

Scheme for making certain compounds of the invention is shown in scheme 1 below. Thus using the standard techniques the chlorination of 2,5-dimethyl-2,5-hexanediol in presence of HCl to give the 2,5-dichloro-2,5-dimethyl-hexane (intermediate 1) and followed by Friedel-Crafts alkylation of 3-methylthiophene to obtain 3,4,4,7,7-pentamethyl-4,5,6,7-tetrahydro-1-benzothiophene (intermediate 2). The Friedel-Crafts acylation of 3,4,4,7,7-pentamethyl-4,5,6,7-tetrahydro-1-benzothiophene with methyl 4-(chlorocarbonyl)benzoate (intermediate 3) to give methyl 4-[(3,4,4,7,7-pentamethyl-4,5,6,7-tetrahydro-1-benzothiophen-2-yl)carbonyl]benzoate (intermediate 4). The alkene formation (of intermediate 4) under writing conditions to give the corresponding ester methyl 4-[1-(3,4,4,7,7-pentamethyl-4,5,6,7-tetrahydro-1-benzothiophen-2-yl)ethenyl]benzoate (intermediate 5), and followed by hydrolysis to yield the respective acid.

Scheme 1:

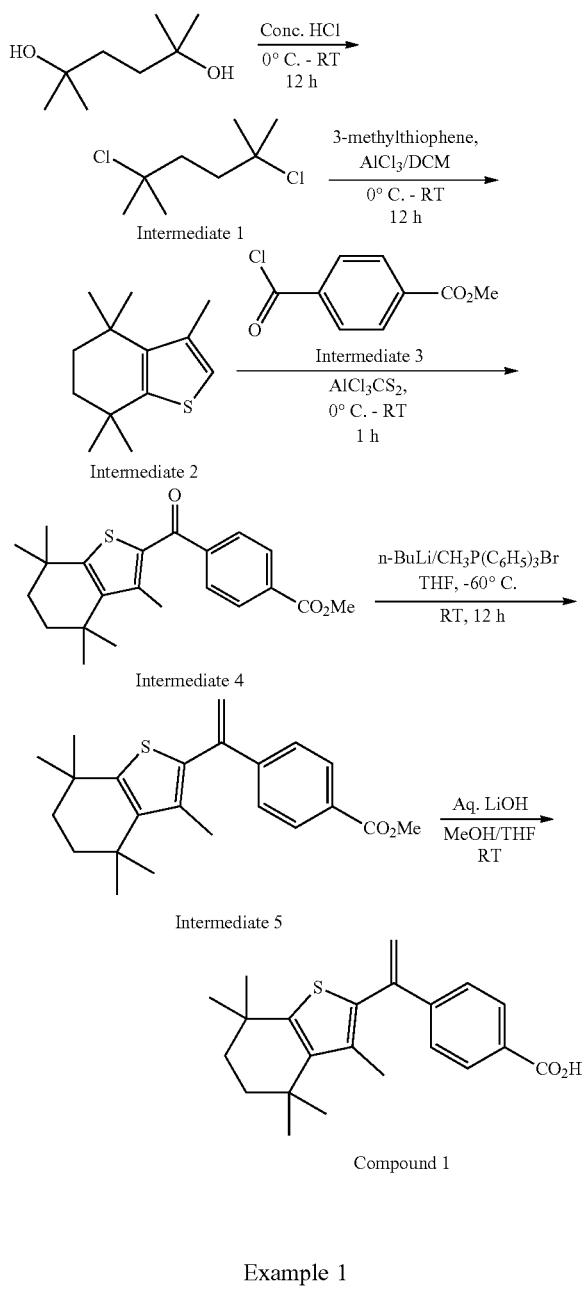

Intermediate 1

Intermediate 2

Intermediate 4

Intermediate 5

Compound 1

Example 1

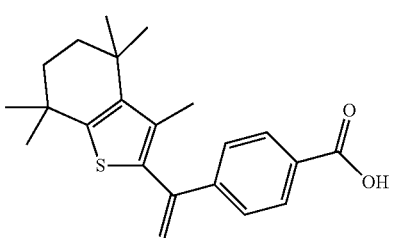

Compound 1 was synthesized from 3,4,4,7,7-pentamethyl-4,5,6,7-tetrahydro-1-benzothiophene and methyl 4-(chlorocarbonyl)benzoate by following the procedure described in scheme 1; purity: 98.87%.

Intermediate 1: 2,5-Dichloro-2,5-dimethylhexane

To a two-neck 250 mL RB flask charged with 2,5-dimethyl-2,5-hexanediol (15 g, 102.6 mmol), conc. HCl (60 mL) was added slowly at 0° C., and stirred at RT overnight. The reaction mixture was quenched with ice, obtained heterogeneous mixture was filtered and washed with water and dried under vacuum to yield a title compound as a white solid (15.0 g, yield: 79.91%): $^1$H NMR (300 MHz, CDCl$_3$): 1.88 (s, 4H), 1.53 (s, 12H).

Intermediate 2: 3,4,4,7,7-Pentamethyl-4,5,6,7-tetrahydro-1-benzothiophene

To a three-neck 250 mL RB flask charged with 2,5-dichloro-2,5-dimethylhexane (6.7 g, 36.6 mmol) and 3-methylthiophene (3.6 g, 36.6 mmol) in dry DCM (50 mL), fitted with a water condenser, AlCl$_3$ (4.9 g, 36.6 mmol) was added in small portions at 0° C. The reaction mixture was stirred at RT overnight and then heated to reflux for 15 min. The reaction mixture was cooled to RT, quenched with ice and extracted with ethyl acetate. The combined extracts were washed with water and brine solution. The organic layer was dried over anhydrous Na$_2$SO$_4$ and concentrated reduced pressure. The crude product obtained was purified by column chromatography to yield the title compound as pale yellow oily product (3.5 g, yield: 46.0%).

Intermediate 3: Methyl 4-(chlorocarbonyl)benzoate

To a single-neck 100 mL RB flask fitted with a water cooled condenser, charged with 4-(methoxycarbonyl)benzoic acid (7.0 g, 38.8 mmol) and dry DCM (70 mL), SOCl$_2$ (9.2 g, 77.7 mmol) was added drop wise at 0° C., followed by DMF (0.5 mL). Then reaction mixture was refluxed for 1 h (or until reaction mixture become clear solution). The reaction mixture was concentrated under N$_2$ atmosphere to obtain the crude product as a yellow oil (6.9 g, yield: 89.5%), which was taken for next step without purification.

Intermediate 4: Methyl 4-[(3,4,4,7,7-pentamethyl-4,5,6,7-tetrahydro-1-benzothiophen-2-yl) carbonyl] benzoate To a two-neck 250 mL RB flask charged with methyl 4-(chloro carbonyl)benzoate (6.9 g, 34.6 mmol) dissolved in CS$_2$ (30.0 mL), AlCl$_3$ (11.5 g, 86.5 mmol) was added at 0° C. The 3,4,4,7,7-pentamethyl-4,5,6,7-tetrahydro-1-benzothiophene (6.0 g, 28.8 mmol) dissolved in CS$_2$ (30 mL) was added slowly drop wise to the reaction mixture. The reaction mixture was stirred at RT overnight and then heated to reflux for 15 min. The reaction mixture was quenched with ice and extracted with ethyl acetate, washed with water and brine solution. The organic layer was dried over anhydrous Na$_2$SO$_4$ and concentrated under vacuum to obtain the crude oil, which was purified by column chromatography to give title compound as yellow oily product (1.5 g, yield: 14.0%).

Intermediate 5: Methyl 4-[1-(3,4,4,7,7-pentamethyl-4,5,6,7-tetrahydro-1-benzothiophen-2-yl) ethenyl] benzoate To a two-neck 100 mL RB flask charged with methyltriphenylphosphonium bromide (0.965 g, 2.7 mmol) and dry THF (10 mL), n-BuLi [0.8 mL (1.6M solution), 2.7 mmol] was added drop wise at −60° C. under N$_2$ atmosphere. The reaction mixture was stirred at room temperature (RT) for 1 h, and the formation of yellow colour solution was observed, which was then slowly added to a 50 mL round-bottom flask containing (0.5 g, 1.35 mmol) of compound methyl 4-[(3,4,4,7,7-pentamethyl-4,5,6,7-tetrahydro-1-benzothiophen-2-yl)carbonyl]benzoate (0.5 g, 1.35 mmol) in dry THF (10 mL). The reaction mixture was stirred at RT overnight. The reaction mixture was quenched with cold water and extracted with ethyl acetate. The organic layer was washed with water and brine. The organic layer was dried over anhydrous $Na_2SO_4$ and concentrated under vacuum; the crude product obtained was purified by column chromatography to give the title compound as a pale yellow solid. (0.11 g, yield: 22.0%): $^1$H NMR (300 MHz, $CDCl_3$): 7.90-7.93 (d, 2H), 7.33-7.36 (d, 2H), 5.65 (s, 1H), 5.38 (s, 1H), 3.85 (s, 3H), 1.88 (s, 3H), 1.50 (s, 4H), 1.25 (s, 6H), 1.21 (s, 6H).

Compound 1: 4-[1-(3,4,4,7,7-Pentamethyl-4,5,6,7-tetrahydro-1-benzothiophen-2-yl) ethenyl]benzoic acid To a 25 mL RB flask charged with methyl 4-[1-(3,4,4,7,7-pentamethyl-4, 5,6,7-tetrahydro-1-benzothiophen-2-yl) ethenyl]benzoate (0.06 g, 0.16 mmol) and THF (3 mL), aqueous solution of NaOH (0.013 g, 0.32 mmol) and methanol (3 mL) was added. The reaction mixture was stirred at room temperature for 3 h. The reaction mixture was concentrated; the obtained residue was dissolved in minimum amount of water, acidified to pH 3 under cooling, extracted with ethyl acetate. The organic layer was washed with water and brine, dried over anhydrous $Na_2SO_4$, filtered and concentrated. The crude product obtained was purified by trituration with hexane to give the title compound as a pale yellow solid (0.02 g, yield: 34.7%): MS (ESI, 120 eV): m/z=353.1 (M−H)$^+$.

Scheme 2:

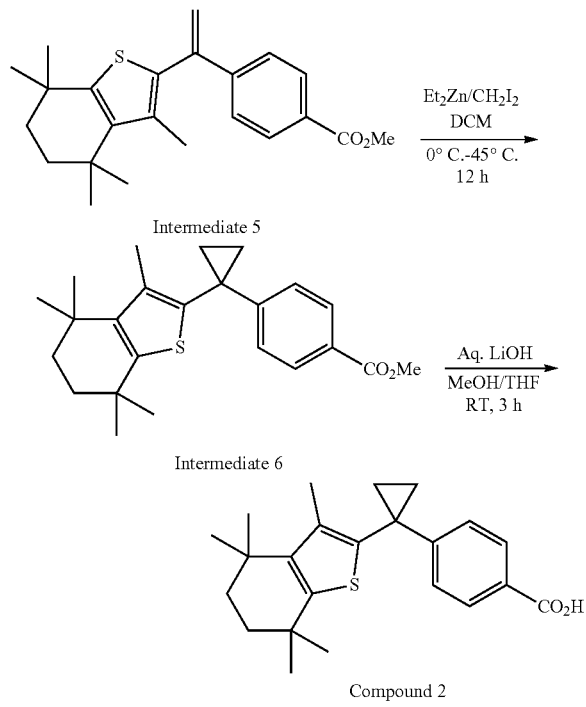

Compound 2

Example 2

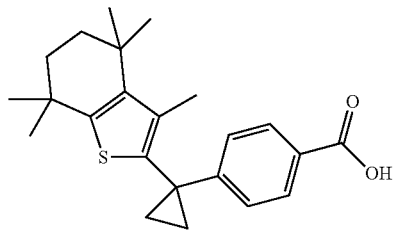

Compound 2 was synthesized from methyl 4-[1-(3,4,4,7,7-pentamethyl-4,5,6,7-tetrahydro-1-benzothiophen-2-yl) ethenyl]benzoate and hydrolysis of methyl 4-[1-(3,4,4,7,7-pentamethyl-4,5,6,7-tetrahydro-1-benzothiophen-2-yl)cyclopropyl]benzoate by following the procedure described in scheme 2. purity: 95.69%.

Intermediate 6: Methyl 4-[1-(3,4,4,7,7-pentamethyl-4,5,6,7-tetrahydro-1-benzothiophen-2-yl)cyclopropyl]benzoate To a two-neck 50 RB flask with methyl 4-[1-(3,4,4,7,7-pentamethyl-4,5, 6,7-tetrahydro-1-benzothiophen-2-yl) ethenyl]benzoate (0.1 g, 0.27 mmol) in DCM (10 mL) was charged. To the stirred solution, diethyl zinc (1.6 ML, 1.6 mmol) was added drop wise at 0° C. and after 10 min, $CH_2I_2$ (0.87 g, 3.2 mmol) was added and then reaction mixture was heated at RT overnight. The reaction mixture was quenched with ice, extracted with DCM and the organic extracts were combined, washed with water and brine, dried over anhydrous $Na_2SO_4$, and concentrated. The crude product obtained was purified by preparative TLC to give the title compound as colourless oily product (0.015 g, yield: 15.0%).

Compound 2: 4-[1-(3,4,4,7,7-pentamethyl-4,5,6,7-tetrahydro-1-benzothiophen-2-yl)cyclopropyl]benzoic acid To a 50 mL RB flask charged with methyl 4-[1-(3,4,4,7,7-pentamethyl-4, 5,6,7-tetrahydro-1-benzothiophen-2-yl) cyclopropyl]benzoate (0.015 g, 0.04 mmol) and THF (2 mL), aqueous solution of LiOH (0.0037 g, 0.16 mmol) and methanol (2 mL) was added. The reaction solution was stirred at RT for about 3 h. The solvent was removed under reduced pressure. The obtained residue was dissolved in minimum amount of water, acidified to pH 3 under cooling, extracted with ethyl acetate. The organic layer was washed with water and brine, dried over $Na_2SO_4$, filtered and concentrated in vacuum. The obtained solid was further purified by trituration with hexane to give compound as a pale yellow solid (0.01 g, yield: 69.2%): MS (ESI, 120 eV): m/z=367.1 (M−H)$^+$.

Scheme 3

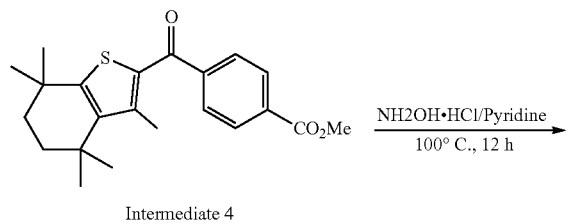

Intermediate 4

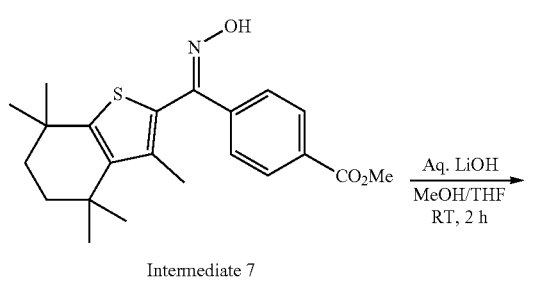

Intermediate 7

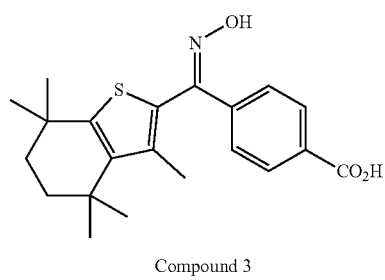

Compound 3

Example 3

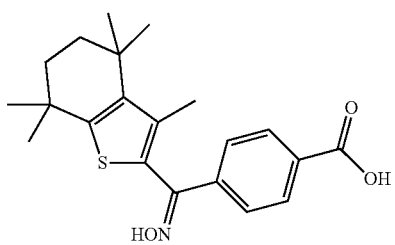

3

Compound 3 was synthesized from methyl 4-[(3,4,4,7,7-pentamethyl-4, 5,6,7-tetrahydro-1-benzothiophen-2-yl)carbonyl]benzoate and hydrolysis of methyl 4-[(E)-(hydroxyimino)(3,4,4,7,7-pentamethyl-4,5,6,7-tetrahydro-1-benzothiophen-2-yl)methyl]benzoate by following the procedure described in scheme 3; purity: 97.84%.

Intermediate 7: Methyl 4-[(E,Z)-(hydroxyimino)(3,4,4,7,7-pentamethyl-4,5,6,7-tetrahydro-1-benzothiophen-2-yl)methyl]benzoate To a stirred solution of methyl 4-[(3,4,4,7,7-pentamethyl-4,5,6,7-tetrahydro-1-benzothiophen-2-yl) carbonyl]benzoate (0.3 g, 0.8 mmol) in pyridine (4.9 g, 62.0 mmol), $NH_4OH \cdot HCl$ (0.11 g, 1.6 mmol) was added under $N_2$ atmosphere. Then the reaction mixture was heated at 100° C. overnight. The pyridine was removed completely under vacuum; the residue was dissolved in ethyl acetate, washed with water and brine, dried over $Na_2SO_4$, filtered and concentrated in vacuum. The crude mass thus obtained was purified by column chromatography on silica gel, using petroleum ether (60-80) and ethyl acetate as eluent. The product (isomer-1) separated and was obtained as yellow liquid (0.2 g, yield: 64.85%): MS (ESI, 120 eV): m/z=386.0 $(M+H)^+$.

Compound 3: 4-[(E)-(Hydroxyimino) (3,4,4,7,7-pentamethyl-4,5,6,7-tetrahydro-1-benzothiophen-2-yl)methyl]benzoic acid A 50 mL RB flask charged with methyl 4-[(E,Z)-(hydroxyimino)(3,4,4,7,7-pentamethyl-4,5,6,7-tetrahydro-1-benzothiophen-2-yl)methyl]benzoate (0.2 g, 0.5 mmol) and THF (1 mL), was stirred and to the stirred solution a 5M aqueous solution of NaOH (0.2 g, 10.0 mmol) and methanol (1 mL) was added. The reaction mixture was further stirred at RT for about 2 h. The reaction mixture was concentrated; the residue was dissolved in minimum amount of water, acidified to pH 3 under cooling, extracted with ethyl acetate. The organic layer was washed with water and brine, dried over anhydrous $Na_2SO_4$, filtered and concentrated in vacuum. One of the isomer was separated by crystallization; dissolved compound in minimum amount of ethyl acetate, added few drops of ether, followed by hexane to give the title compound as a yellow solid (0.17 g, yield: 91.52%): MS (ESI, 120 eV): m/z=372.2 $(M+H)^+$.

Example 4: 4-[(E,Z)-(Methoxyimino) (3,4,4,7,7-pentamethyl-4,5,6,7-tetrahydro-1-benzothiophen-2-yl)methyl]benzoic acid

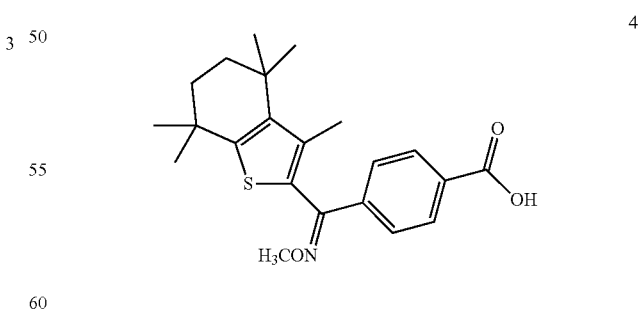

4

Compound 4 was synthesized from methyl 4-[(3,4,4,7,7-pentamethyl-4,5,6,7-tetrahydro-1-benzothiophen-2-yl)carbonyl]benzoate and hydrolysis of methyl 4-[(E,Z)-(methoxyimino)(3,4,4,7,7-pentamethyl-4,5,6,7-tetrahydro-1-benzothiophen-2-yl)methyl]benzoate by following the similar procedure described in scheme 3 (0.025 g, yield: 26.0%); purity: 98.96%.

Example 5: 6-[(3,4,4,7,7-Pentamethyl-4,5,6,7-tetrahydro-1-benzothiophen-2-yl) carbonyl]pyridine-3-carboxylic acid

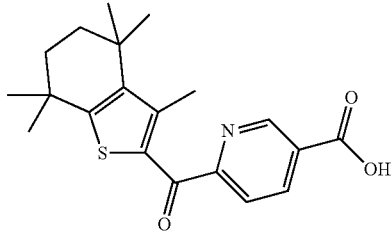

Compound 5 was synthesized from 3,4,4,7,7-pentamethyl-4,5,6,7-tetrahydro-1-benzothiophene and methyl 6-(chlorocarbonyl)pyridine-3-carboxylate by following the similar procedure in scheme 1 (0.008 g, yield: 55.47%); purity: 99.38%.

Example 6: 6-[1-(3,4,4,7,7-Pentamethyl-4,5,6,7-tetrahydro-1-benzothiophen-2-yl) ethenyl]pyridine-3-carboxylic acid

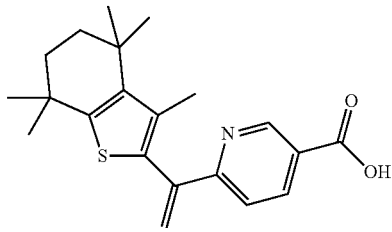

Compound 6 was synthesized from 3,4,4,7,7-pentamethyl-4,5,6,7-tetrahydro-1-benzothiophene and methyl 6-(chlorocarbonyl)pyridine-3-carboxylate by following the similar procedure in scheme 1 (0.012 g, yield: 62.44%); purity: 98.37%.

Example 7: 6-[1-(3,4,4,7,7-Pentamethyl-4,5,6,7-tetrahydro-1-benzothiophen-2-yl)cyclopropyl]pyridine-3-carboxylic acid

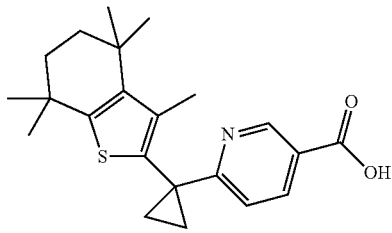

Compound 7 was synthesized from methyl 6-[1-(3,4,4,7,7-pentamethyl-4,5,6,7-tetrahydro-1-benzothiophen-2-yl) ethenyl]pyridine-3-carboxylate and hydrolysis of methyl6-[1-(3,4,4,7,7-pentamethyl-4,5,6,7-tetrahydro-1-benzothiophen-2-yl)cyclopropyl]pyridine-3-carboxylate by following the procedure described in scheme 2 (0.015 g, yield: 40.6%); purity: 99.26%.

Scheme 4

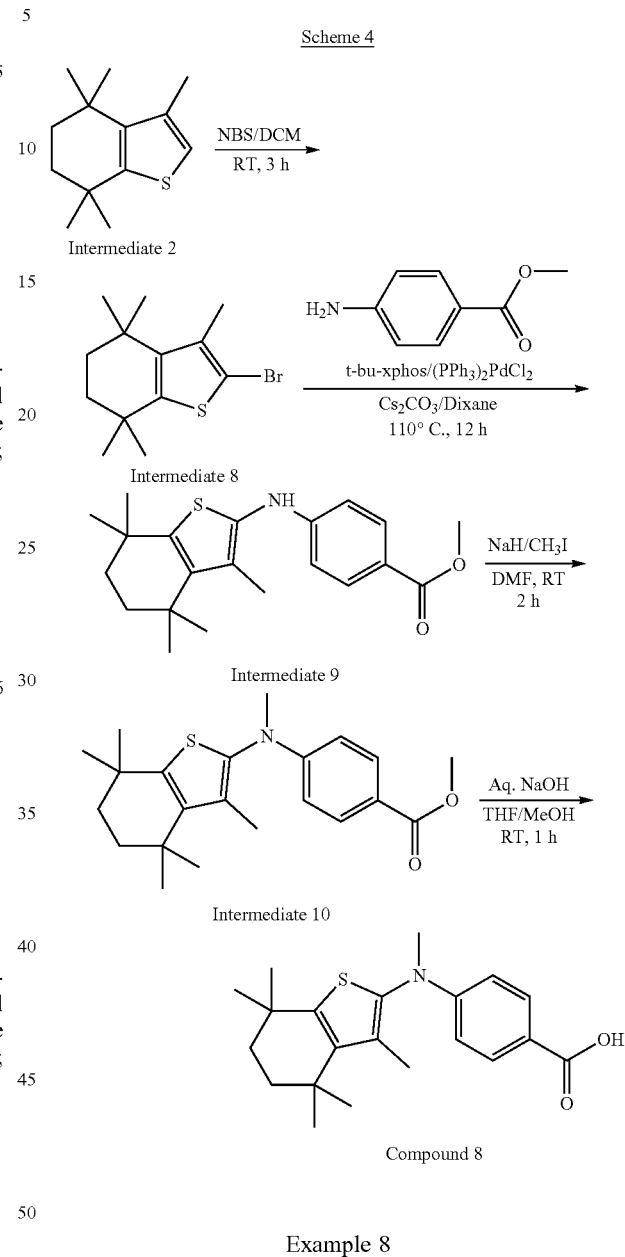

Example 8

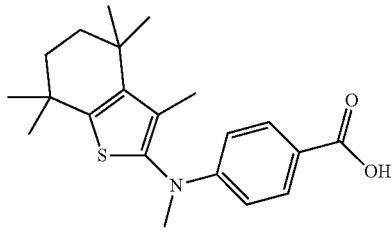

Compound 8 was synthesized from 2-bromo-3,4,4,7,7-pentamethyl-4,5, 6,7-tetrahydro-1-benzothiophene and methyl 4-aminobenzoate by following the procedure described in scheme 4; purity: 97.45%.

Intermediate 8: 2-Bromo-3,4,4,7,7-pentamethyl-4,5,6,7-tetrahydro-1-benzothiophene To a stirred solution of 3,4,4,7,7-pentamethyl-4,5,6,7-tetrahydro-1-benzothiophene (1.2 g, 5.8 mmol) in DCM (5 mL), NBS (1 g, 5.6 mmol) was added and stirred at RT for 3 h. The reaction mixture was quenched with ice, extracted with DCM and the organic extracts were combined, washed with water and brine, dried over anhydrous $Na_2SO_4$, and concentrated in vacuum. The resulting crude product was purified by silica gel column chromatography to give the title compound as colourless liquid (1.0 g, yield: 62.5%): $^1$H NMR (300 MHz, $CDCl_3$): δ 2.16 (s, 3H), 1.58 (s, 4H), 1.19-1.20 (d, 12H).

Intermediate 9: Methyl 4-[(3,4,4,7,7-pentamethyl-4,5,6,7-tetrahydro-1-benzothiophen-2-yl)amino]benzoate To a stirred solution of 2-bromo-3,4,4,7,7-pentamethyl-4,5,6,7-tetrahydro-1-benzothiophene (0.26 g, 0.9 mmol) in dioxane (5 mL), methyl 4-aminobenzoate (0.16 g, 1.1 mmol), $Cs_2CO_3$ (0.88 g, 6.5 mmol) was added under argon atmosphere. After purging the reaction mixture with argon for about 10 minutes, t-butylxphos (0.007 g, 0.02 mmol) and Pd $(PPh_3)_2Cl_2$ (0.031 g, 0.044 mmol) was added and the reaction mixture was heated at 110° C. overnight. The reaction mixture was quenched with water and extracted with ethyl acetate and the organic extracts were washed with water and brine, dried over anhydrous $Na_2SO_4$, and concentrated in vacuum. The resulting crude product was purified by column chromatography on silica gel, using petroleum ether (60-80) and ethyl acetate as eluent to give the title product as a yellow solid (0.09 g, yield: 27.97%).

Intermediate 10: Methyl 4-[methyl(3,4,4,7,7-pentamethyl-4,5,6,7-tetrahydro-1-benzothiophen-2-yl)amino]benzoate To a stirred solution of NaH (0.042 g, 0.31 mmol) in DMF (2 mL), 6-[(3,4,4,7,7-pentamethyl-4,5,6,7-tetrahydro-1-benzothiophen-2-yl)amino]pyridine-3-carboxylate (0.07 g, 0.2 mmol) in DMF (2 mL) was added drop wise at 0° C. After 30 min, $CH_3I$ (0.045 g, 0.31 mmol) was added to the above solution and the resulting solution was allowed to stir at RT for 2 h. The reaction mixture was quenched with saturated $NH_4Cl$ solution and extracted with ethyl acetate. The organic extracts were washed with water and brine, dried over anhydrous $Na_2SO_4$, and concentrated in vacuum. The resulting crude product was purified by column chromatography on silica gel, using petroleum ether (60-80) and ethyl acetate as eluent to give the title product as a white solid (0.025 g, yield: 33.65%): $^1$H NMR (300 MHz, $CDCl_3$): δ 7.80-7.83 (d, 2H), 6.52-6.55 (d, 2H), 3.78 (s, 3H), 3.20 (s, 3H), 1.90 (s, 3H), 1.63 (s, 4H), 1.22-1.23 (d, 12H).

Compound 8: 4-[Methyl(3,4,4,7,7-pentamethyl-4,5,6,7-tetrahydro-1-benzothiophen-2-yl)amino]benzoic acid To a 25 mL RB flask charged with methyl 4-[methyl(3,4,4,7,7-pentamethyl-4,5,6,7-tetrahydro-1-benzothiophen-2-yl)amino]benzoate (0.025 g, 0.0672 mmol) and THF (0.5 mL), a 5 M aqueous solution of NaOH (0.04 g, 1.7 mmol) and methanol (0.5 mL) was added. The reaction solution was stirred at RT for about 1 h. The reaction mixture was concentrated; the residue was dissolved in minimum amount of water, acidified to pH 3 under cooling and extracted with ethyl acetate. The organic layer was washed with water and brine, dried over anhydrous $Na_2SO_4$, and concentrated in vacuum. The obtained solid was further purified by trituration with hexane to give the title compound as a yellow solid (0.011 g, yield: 45.83%): MS (ESI, 120 eV): m/z=358.1 $(M+H)^+$.

Example 9: 4-[Ethyl(3,4,4,7,7-pentamethyl-4,5,6,7-tetrahydro-1-benzothiophen-2-yl)amino]benzoic acid

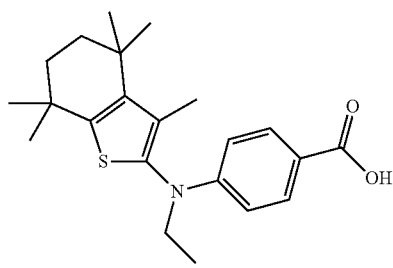

9

Compound 9 was synthesized from 2-bromo-3,4,4,7,7-pentamethyl-4,5, 6,7-tetrahydro-1-benzothiophene and methyl 4-aminobenzoate by following the similar procedure described in scheme 4 (0.03 g, yield: 50.25%); purity: 99.17%.

Scheme 5

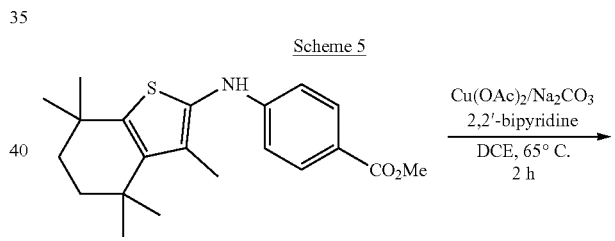

Intermediate 9

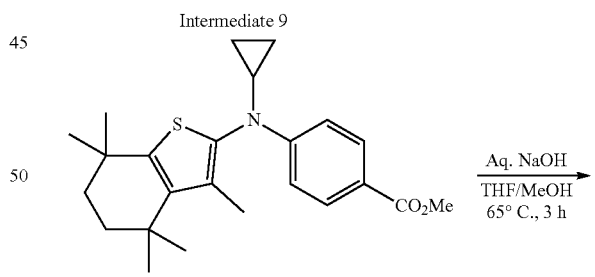

Intermediate 11

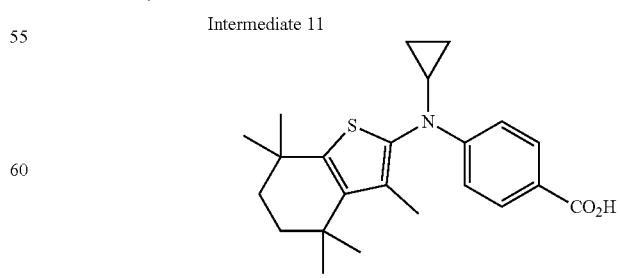

Compound 10

Example 10: 4-[Cyclopropyl(3,4,4,7,7-pentamethyl-4,5,6,7-tetrahydro-1-benzo thiophen-2-yl)amino] benzoic acid

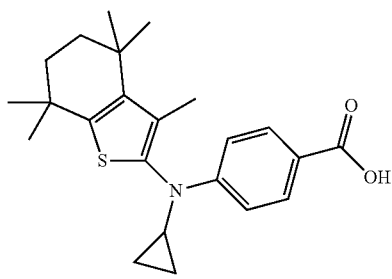

Compound 10 was synthesized from 2-bromo-3,4,4,7,7-pentamethyl-4,5, 6,7-tetrahydro-1-benzothiophene and methyl 4-aminobenzoate and the N-alkylation of ester (intermediate 9) with cyclopropylboronic acid in presence of copper acetate and followed by hydrolysis procedure described in scheme 5; purity: 98.42%.

Intermediate 11: Methyl 4-[cyclopropyl(3,4,4,7,7-pentamethyl-4,5,6,7-tetrahydro-1-benzothiophen-2-yl)amino]benzoate To a two-neck 25 mL RB flask charged with copper (II) acetate (0.11 g, 0.56 mmol), 2,2'-bipyridine (0.087 g, 0.56 mmol) in DCE (5 mL) was added. The reaction mixture was heated at 70° C. for 30 min, following which cyclopropylboronic acid (0.096 g, 1.12 mmol), methyl 4-[(3,4,4,7,7-pentamethyl-4,5,6,7-tetrahydro-1-benzothiophen-2-yl)amino]benzoate (0.2 g, 0.6 mmol), Na$_2$CO$_3$ (0.12 g, 1.12 mmol) and molecular sieves (0.2 g) were added at 70° C. and was continued to be heated overnight. The reaction mixture was quenched with water, extracted with ethyl acetate. The combined extracts were washed with water and brine solution. The organic layer was dried over anhydrous Na$_2$SO$_4$ and concentrated under reduced pressure. The obtained crude product was purified preparative TLC to give title compound as a yellow semi solid (0.04 g, yield: 18.06%): $^1$H NMR (300 MHz, CDCl$_3$): δ 7.80-7.83 (d, 2H), 6.73-6.76 (d, 2H), 3.78 (s, 3H), 2.69-2.74 (m, 1H), 1.83 (s, 3H), 1.63 (s, 4H), 1.21-1.23 (d, 12H), 0.80-0.82 (m, 2H), 0.60-0.61 (m, 2H).

Compound 10: 4-[Cyclopropyl(3,4,4,7,7-pentamethyl-4,5,6,7-tetrahydro-1-benzo thiophen-2-yl) amino]benzoic acid To a 25 mL RB flask charged with methyl 4-[cyclopropyl (3,4,4,7,7-pentamethyl-4,5,6,7-tetrahydro-1-benzothiophen-2-yl)amino]benzoate (0.04 g, 0.1 mmol) and THF (0.5 mL), a 5 M aqueous solution of sodium hydroxide (0.024 g, 0.6 mmol) and methanol (0.5 mL) was added. The reaction solution was heated at 50° C. overnight. The reaction mixture was concentrated; the residue was dissolved in minimum amount of water, acidified to pH 3 under cooling and extracted with ethyl acetate. The organic layer was washed with water and brine, dried over anhydrous Na$_2$SO$_4$, and concentrated in vacuum. The obtained solid was further purified by trituration with hexane to give the title compound as a white solid (0.012 g, yield: 31.3%): MS (ESI, 120 eV): m/z=384.2 (M+H)$^+$.

Example 11: 4-[(Cyclopropylmethyl) (3,4,4,7,7-pentamethyl-4,5,6,7-tetrahydro-1-benzothiophen-2-yl)amino]benzoic acid

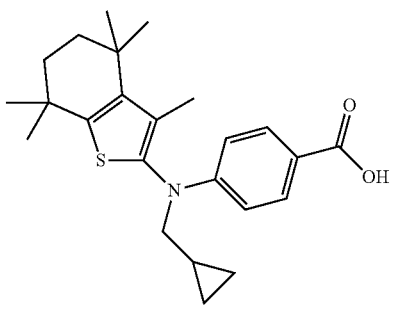

Compound 11 was synthesized from 2-bromo-3,4,4,7,7-pentamethyl-4,5, 6,7-tetrahydro-1-benzothiophene and methyl 4-aminobenzoate by following the similar procedure described in scheme 4 (0.025 g, yield: 52.08%). purity: 98.83%.

Scheme 6

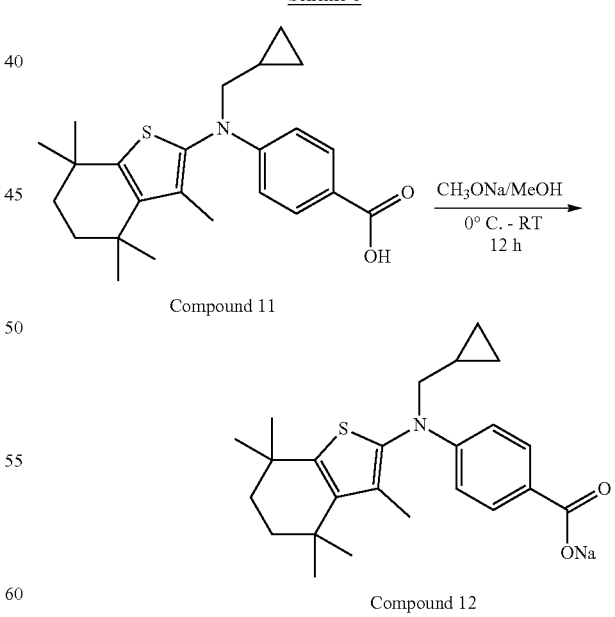

Compound 12 was synthesized from 4-[(cyclopropylmethyl)(3,4,4,7,7-pentamethyl-4,5,6,7-tetrahydro-1-benzothiophen-2-yl)amino]benzoic acid and sodium methoxide in methanol by following the procedure described in scheme 6; purity: 96.75%.

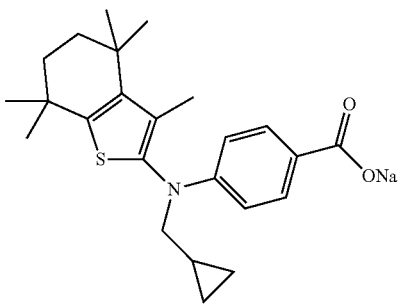

Compound 12: Sodium 4-[(cyclopropylmethyl) (3,4,4,7,7-pentamethyl-4,5,6,7-tetrahydro-1-benzothiophen-2-yl)amino]benzoate To a stirred solution of 4-[(cyclopropylmethyl)(3,4,4,7,7-pentamethyl-4, 5,6,7-tetrahydro-1-benzothiophen-2-yl) amino]benzoic acid (0.1 g, 0.25 mmol) in MeOH, 1M CH$_3$ONa (0.014 g, 0.25 mmol) solution was added slowly at 0° C. The reaction mixture was stirred at RT for 12 h. The solvent was removed under reduced pressure. Methanol was added to the resulting gummy and was removed completely under high vacuum. This process was repeated until there was no water. The obtained gummy material was crystallized with ethyl acetate and n-hexane to yield an off white solid (0.04 g, yield: 32.00%): MS (ESI, 120 eV): m/z=398.1 (M−22)$^+$.

Example 13: 4-[(3,4,4,7,7-Pentamethyl-4,5,6,7-tetrahydro-1-benzothiophen-2-yl) (propan-2-yl)amino] benzoic acid

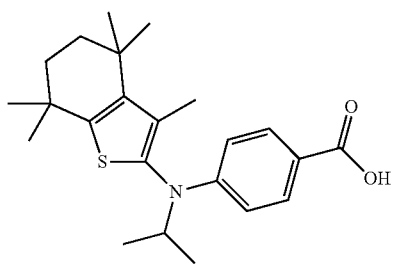

Compound 13 was synthesized from 2-bromo-3,4,4,7,7-pentamethyl-4,5, 6,7-tetrahydro-1-benzothiophene and methyl 4-aminobenzoate by following the similar procedure described in scheme 4 (0.007 g, yield: 72.72%); purity: 85.93%.

Example 14: 4-[(Methylsulfonyl) (3,4,4,7,7-pentamethyl-4,5,6,7-tetrahydro-1-benzothiophen-2-yl) amino]benzoic acid

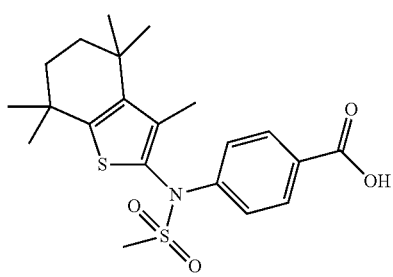

Compound 14 was synthesized from 2-bromo-3,4,4,7,7-pentamethyl-4,5, 6,7-tetrahydro-1-benzothiophene and methyl 4-aminobenzoate by following the similar procedure described in scheme 4 (0.020 g, yield: 58.99%); purity: 91.67%.

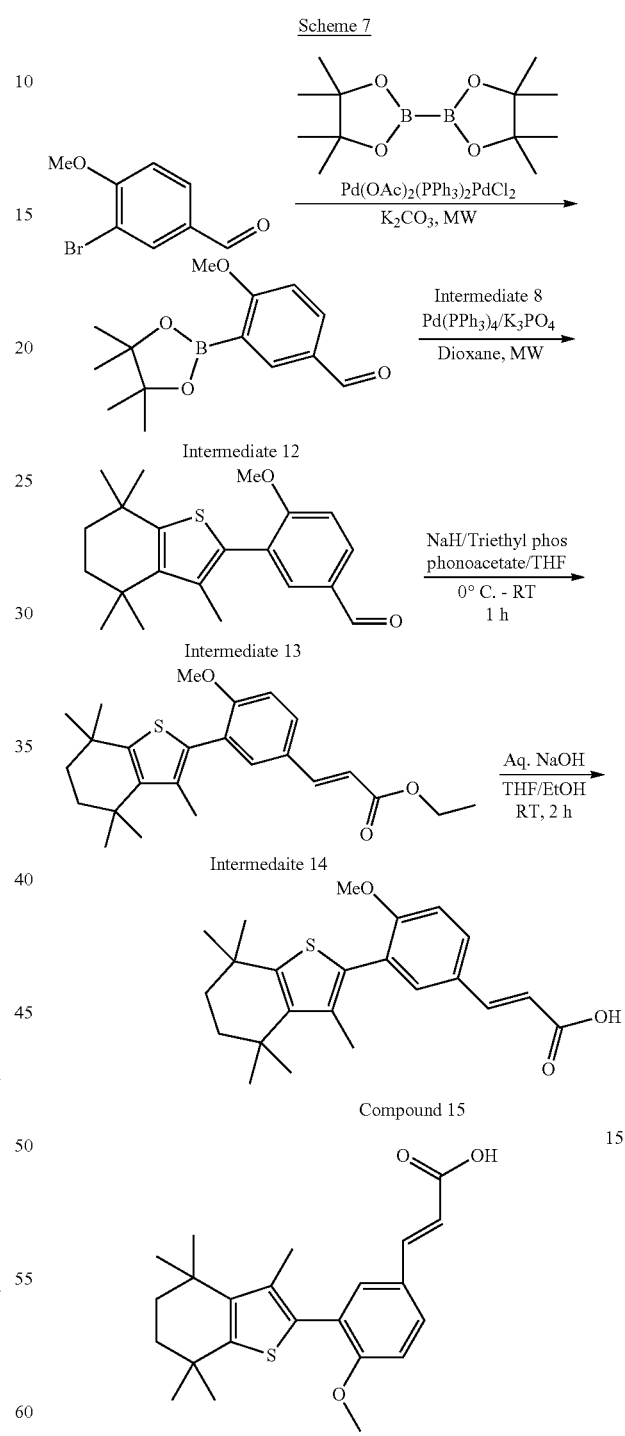

Compound 15 was synthesized from 2-bromo-3,4,4,7,7-pentamethyl-4,5, 6,7-tetrahydro-1-benzothiophene and 4-methoxy-3-(4,4,5,5-tetramethyl-1,3,2-dioxa borolan-2-yl) benzaldehyde by following the procedure described in scheme 7; purity: 94.87%.

Intermediate 12: 4-Methoxy-3-(4,4,5,5-tetramethyl-1,3,2-dioxaborolan-2-yl)benzaldehyde To a stirred solution of 3-bromo-4-methoxybenzaldehyde (2.0 g, 9.3 mmol) in dioxane (5 mL), bis(pinacolato)diboron (2.82 g, 11.1 mmol) in 1,4 dioxane (10.0 mL) and potassium acetate (2.73 g, 27.9 mmol) was added at 0° C. under argon atmosphere. Then (PPh$_3$)$_2$PdCl$_2$ (0.38 g, 0.465 mmol) was added and the reaction was allowed to be completed under Microwave condition. The reaction mixture thus obtained was diluted with ethyl acetate, washed with water and brine solution dried over anhydrous Na$_2$SO$_4$ and concentrated in vacuum. The resulting crude product was purified by combiflash, to give the title compound as a pale pink solid (1.3 g, yield: 53.76%): $^1$H NMR (300 MHz, CDCl$_3$): δ 9.83 (s, 1H), 8.13 (s, 1H), 7.88-7.91 (d, 1H), 6.89-6.92 (d, 1H), 3.86 (s, 3H), 1.3 (s, 12H).

Intermediate 13: 4-Methoxy-3-(3,4,4,7,7-pentamethyl-4,5,6,7-tetrahydro-1-benzothiophen-2-yl)benzaldehyde To a stirred solution of 4-methoxy-3-(4,4,5,5-tetramethyl-1,3,2-dioxaborolan-2-yl)benzaldehyde (1.0 g, 3.8 mmol) in dioxane (10 mL), 2-bromo-3,4,4,7,7-pentamethyl-4,5,6,7-tetrahydro-1-benzothiophene (1.2 g, 4.1 mmol) in 1,4 dioxane (10 mL), water (3 mL) and potassium phosphate tribasic (2.42 g, 11.4 mmol) was added. The reaction mixture was purged with argon for about 10 min, followed by addition of Pd(PPh$_3$)$_4$ (0.2 g, 0.1 mmol). The reaction was done under microwave condition. The reaction mixture was diluted with ethyl acetate, washed with water and brine solution, dried over anhydrous Na$_2$SO$_4$ and concentrated in vacuum. The resulting crude product was purified by combiflash, to give the title compound as a pale yellow semi solid (0.7 g, yield: 52.63%).

Intermediate 14: Ethyl (2E)-3-[4-methoxy-3-(3,4,4,7,7-pentamethyl-4,5,6,7-tetrahydro-1-benzothiophen-2-yl)phenyl]prop-2-enoate To a 50 mL RB flask charged with NaH (0.098 g, 4.0 mmol) and THF (20.0 mL), 4-methoxy-3-(3,4,4,7,7-pentamethyl-4,5,6,7-tetrahydro-1-benzo thiophen-2-yl)benzaldehyde (0.7 g, 2.0 mmol) was added at 0° C. followed by triethyl phosphinoacetate (0.92 g, 4.0 mmol) and the flask was stirred at RT for 1 h. The reaction mixture was quenched with water and extracted with ethyl acetate. The organic layer was washed with water and brine solution, dried over anhydrous Na$_2$SO$_4$ and concentrated in vacuum. The resulting crude product was purified by combiflash to give the title compound as colourless oil (0.74 g, yield: 89.68%).

Compound 15: (2E)-3-[4-Methoxy-3-(3,4,4,7,7-pentamethyl-4,5,6,7-tetrahydro-1-benzothiophen-2-yl)phenyl]prop-2-enoic acid To a 50 mL RB flask charged with ethyl (2E)-3-[4-methoxy-3-(3,4,4,7,7-pentamethyl-4,5,6,7-tetrahydro-1-benzothiophen-2-yl)phenyl]prop-2-enoate 0.065 g, 0.15 mmol) and THF (2 mL), NaOH (0.012 g, 0.31 mmol) and EtOH (2 mL) was added and stirred at RT for 2 h. The reaction mixture was concentrated under reduced pressure and washed with ether. The obtained residue was acidified with 1N HCl and extracted with ethyl acetate. The combined extract was then washed with water, brine solution and dried over anhydrous Na$_2$SO$_4$, filtered and concentrated. The obtained product was triturated with n-hexane to yield the title product as a white solid (0.035 g, yield: 45.5%): MS (ESI, 120 eV): m/z=385.2 (M+H)$^+$.

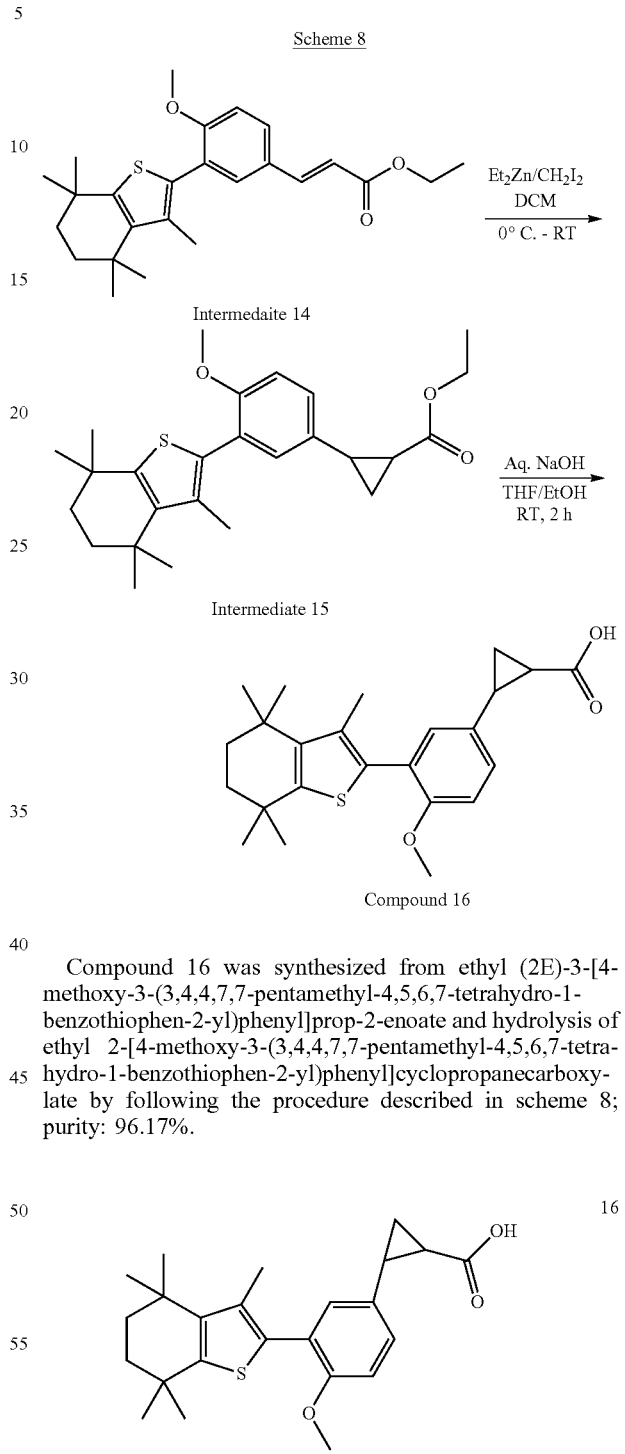

Scheme 8

Intermedaite 14

Intermediate 15

Compound 16

Compound 16 was synthesized from ethyl (2E)-3-[4-methoxy-3-(3,4,4,7,7-pentamethyl-4,5,6,7-tetrahydro-1-benzothiophen-2-yl)phenyl]prop-2-enoate and hydrolysis of ethyl 2-[4-methoxy-3-(3,4,4,7,7-pentamethyl-4,5,6,7-tetrahydro-1-benzothiophen-2-yl)phenyl]cyclopropanecarboxylate by following the procedure described in scheme 8; purity: 96.17%.

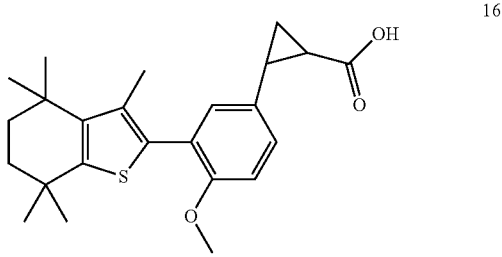 [SMILES: COc1ccc(C2CC2C(=O)O)cc1-c1sc2c(c1C)C(C)(C)CCC2(C)C]

Intermediate 15: Ethyl 2-[4-methoxy-3-(3,4,4,7,7-pentamethyl-4,5,6,7-tetrahydro-1-benzothiophen-2-yl)phenyl]cyclopropanecarboxylate To a stirred solution of ethyl (2E)-3-[3-methoxy-4-(3,4,4,7,7-pentamethyl-4,5,6,7-tetrahydro-1-benzothiophen-2- yl)phenyl]prop-2-enoate (0.1 g, 0.24 mmol) in DCM (2 mL), CH$_2$I$_2$ (0.78 g, 2.9 mmol) was added followed by addition of diethyl zinc [1.45 mL (1M solution in heptane), 1.4 mmol] at 0° C. The reaction mixture was stirred at RT until completion. The reaction mixture was then quenched with ice and extracted with ethyl acetate and washed with water and brine solution, dried over anhydrous Na$_2$SO$_4$ and concentrated under reduced vacuum. The obtained product was purified by preparative TLC to yield the title product as colourless oil (0.017 g, yield: 19.9%).

Compound 16: 2-[4-Methoxy-3-(3,4,4,7,7-pentamethyl-4,5,6,7-tetrahydro-1-benzothiophen-2-yl)phenyl]cyclopropanecarboxylic acid To a 25 mL RB flask charged with ethyl 2-[4-methoxy-3-(3,4,4,7,7-pentamethyl-4,5,6,7-tetrahydro-1-benzothiophen-2-yl)phenyl]cyclopropanecarboxylate (0.017 g, 0.04 mmol) in THF (1 mL), NaOH (0.008 g, 0.2 mmol) in water and ethanol (1 mL) was added. The reaction mixture was stirred at RT for 2 h. The reaction mixture was concentrated under reduced pressure and washed with ether. The obtained residue was acidified with 1N HCl and extracted with ethyl acetate. The combined extract was washed with water, brine solution and dried over anhydrous Na$_2$SO$_4$ and concentrated. The obtained product was purified by preparative TLC to yield the title product as a pale yellow semi solid (0.0011 g, yield: 6.27%): MS (ESI, 120 eV): m/z=399.2 (M+H)$^+$.

Scheme 9

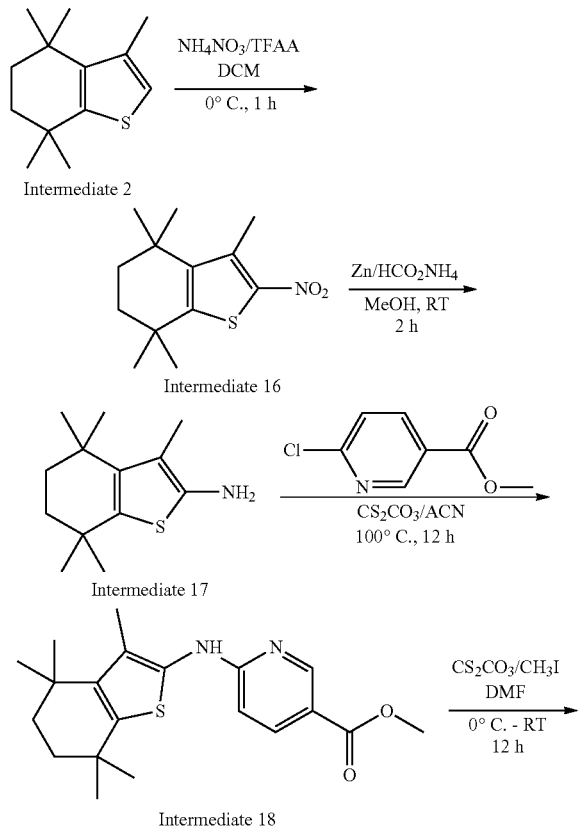

Intermediate 2

Intermediate 16

Intermediate 17

Intermediate 18

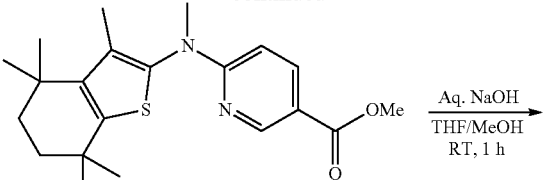

Intermediate 19

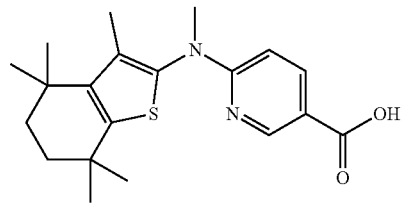

Compound 17

Compound 17 was synthesized from 3,4,4,7,7-pentamethyl-4,5,6,7-tetrahydro-1-benzothiophen-2-amine and methyl 6-chloropyridine-3-carboxylate by following the procedure described in scheme 9; purity: 98.40%.

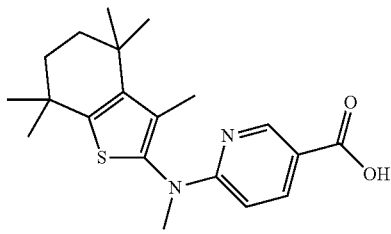

17

Intermediate 16: 3,4,4,7,7-Pentamethyl-2-nitro-4,5,6,7-tetrahydro-1-benzo thiophene To a stirred solution of 3,4,4,7,7-pentamethyl-4,5,6,7-tetrahydro-1-benzothiophene (4.8 g, 23.1 mmol) in DCM (15 mL), NH$_4$NO$_3$ (2.22 g, 27.7 mmol) and TFAA (14.5 g, 69.2 mmol) was added drop wise at 0° C. The reaction mixture was kept at 0° C. for 1 h. The mixture was then quenched with ice and extracted with ethyl acetate, washed with water and brine solution. The organic layer was dried over anhydrous Na$_2$SO$_4$ and concentrated under vacuum to obtain the crude oil, which was purified by silica gel column chromatography to give title compound as yellow liquid (1.2 g, yield: 20.44%).

Intermediate 17: 3,4,4,7,7-Pentamethyl-4,5,6,7-tetrahydro-1-benzothiophen-2-amine To a stirred solution of 3,4,4,7,7-pentamethyl-2-nitro-4,5,6,7-tetrahydro-1-benzothiophene (1.6 g, 6.3 mmol) in methanol (15 mL), ammonium formate (1.99 g, 31.6 mmol) was added followed by addition of zinc dust (2.0 g, 30.6 mmol) at 0° C. The reaction mixture was stirred at RT for 2 h. The reaction mixture was concentrated under reduced pressure. The obtained residue was washed with water, brine solution and dried over anhydrous Na$_2$SO$_4$ and concentrated in vacuum. The crude product obtained was purified by silica gel column chromatography to give title compound as a yellow liquid (0.8 g, yield: 57.14%).

Intermediate 18: Methyl 6-[(3,4,4,7,7-pentamethyl-4,5,6,7-tetrahydro-1-benzothiophen-2-yl)amino]pyridine-3-carboxylate To a stirred solution of 3,4,4,7,7-pentamethyl-4,5,6,7-tetrahydro-1-benzothiophen-2-amine (0.25 g, 1.17 mmol) in acetonitrile (3 mL), methyl 6-chloropyridine-3-carboxylate (0.1 g, 0.58 mmol) and $Cs_2CO_3$ (0.6 g, 1.74 mmol) was added. The reaction mixture was heated reflux at 100° C. overnight. The reaction mixture was quenched with water and extracted with ethyl acetate, washed with water and brine solution. The organic layer was dried over anhydrous $Na_2SO_4$ and concentrated under vacuum to obtain the crude oil, which was purified by silica gel column chromatography to give title compound as a yellow solid (0.15 g, yield: 72.58%).

Intermediate 19: Methyl 6-[methyl(3,4,4,7,7-pentamethyl-4,5,6,7-tetrahydro-1-benzothiophen-2-yl)amino]pyridine-3-carboxylate To a stirred solution of NaH (0.011 g, 0.45 mmol) in DMF (4 mL), methyl 6-[(3,4,4,7,7-pentamethyl-4,5,6,7-tetrahydro-1-benzothiophen-2-yl)amino]pyridine-3-carboxylate (0.1 g, 0.28 mmol) in DMF (4 mL) was added at 0° C. After 30 min, $CH_3I$ (0.063 g, 0.45 mmol) was added at 0° C. The reaction mixture was allowed to stir at RT for 1 h. The reaction mixture was quenched with ice and extracted with ethyl acetate, washed with water and brine solution. The organic layer was dried over anhydrous $Na_2SO_4$ and concentrated under vacuum to obtain the title compound as a yellow liquid, it was taken as such for next step (0.1 g, yield: 89.47%).

Compound 17: 6-[Methyl(3,4,4,7,7-pentamethyl-4,5,6,7-tetrahydro-1-benzothiophen-2-yl)amino]pyridine-3-carboxylic acid To a stirred solution of methyl 6-[methyl(3,4,4,7,7-pentamethyl-4,5,6,7-tetrahydro-1-benzothiophen-2-yl)amino]pyridine-3-carboxylate (0.1 g, 0.3 mmol) in THF (2 mL), methanol (2 mL) and water (2 mL), NaOH (0.043 g, 1.0 mmol) was added at 0° C. Then it was stirred at RT overnight. The reaction mixture was concentrated. The salt thus obtained was washed with ether. The residue was dissolved in minimum amount of water, acidified with 1.5 N HCl and extracted with ethyl acetate, dried and concentrated to obtain the crude product. It was purified by preparative TLC to yield the title compound as yellow solid (0.02 g, yield: 18.6%). MS (ESI, 120 eV): m/z=359.1 (M+H)$^+$.

Example 18: 6-[Ethyl(3,4,4,7,7-pentamethyl-4,5,6,7-tetrahydro-1-benzothiophen-2-yl)amino]pyridine-3-carboxylic acid

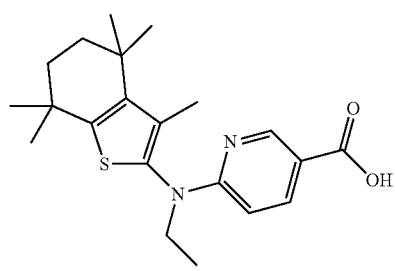

18

Compound 18 was synthesized from 3,4,4,7,7-pentamethyl-4,5,6,7-tetrahydro-1-benzothiophen-2-amine and methyl 6-chloropyridine-3-carboxylate by following the similar procedure described in scheme 9 (0.025 g, yield: 21.57%); purity: 94.38%.

Example 19: 6-[Cyclopropyl(3,4,4,7,7-pentamethyl-4,5,6,7-tetrahydro-1-benzo thiophen-2-yl)amino]pyridine-3-carboxylic acid

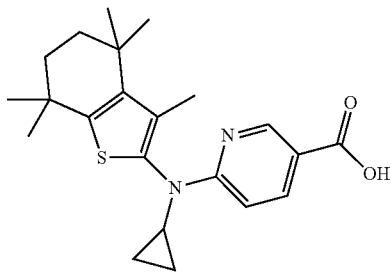

19

Compound 19 was synthesized from 3,4,4,7,7-pentamethyl-4,5,6,7-tetrahydro-1-benzothiophen-2-amine and methyl 6-chloropyridine-3-carboxylate by similar procedure mentioned in scheme 9. Further, the N-alkylation of ester (intermediate 18) with cyclopropylboronic acid was achieved by followed the similar procedure described for making intermediate 11 in scheme 5 (0.109 g, yield: 52.02%); purity: 98.35%.

Example 20: 6-[(Cyclopropylmethyl) (3,4,4,7,7-pentamethyl-4,5,6,7-tetrahydro-1-benzothiophen-2-yl)amino]pyridine-3-carboxylic acid

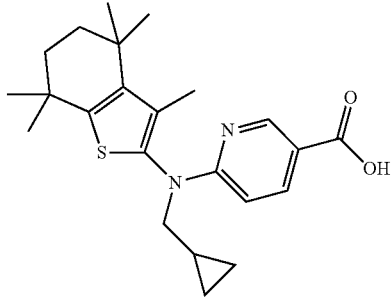

20

Compound 20 was synthesized from 3,4,4,7,7-pentamethyl-4,5,6,7-tetrahydro-1-benzothiophen-2-amine and methyl 6-chloropyridine-3-carboxylate by following the similar procedure in scheme 9 (0.025 g, yield: 17.85%); purity: 98.96%.

Example 21: 6-[(3,4,4,7,7-Pentamethyl-4,5,6,7-tetrahydro-1-benzothiophen-2-yl)(propan-2-yl)amino]pyridine-3-carboxylic acid

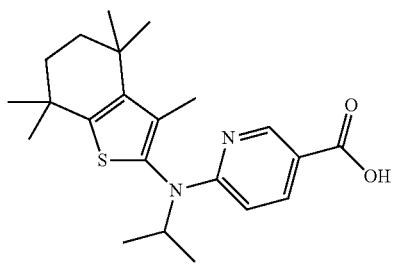

21

Compound 21 was synthesized from 3,4,4,7,7-pentamethyl-4,5,6,7-tetrahydro-1-benzothiophen-2-amine and methyl 6-chloropyridine-3-carboxylate by following the similar procedure in scheme 9 (0.012 g, yield: 25.94%); purity: 95.69%.

Example 22: 6-[(Methylsulfonyl)(3,4,4,7,7-pentamethyl-4,5,6,7-tetrahydro-1-benzothiophen-2-yl)amino]pyridine-3-carboxylic acid

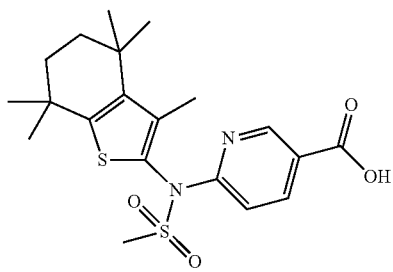

22

Compound 22 was synthesized from 3,4,4,7,7-pentamethyl-4,5,6,7-tetrahydro-1-benzothiophen-2-amine and methyl 6-chloropyridine-3-carboxylate by following the similar procedure in scheme 9 (0.02 g, yield: 64.52%); purity: 98.13%: purity: 98.13%.

Scheme 10

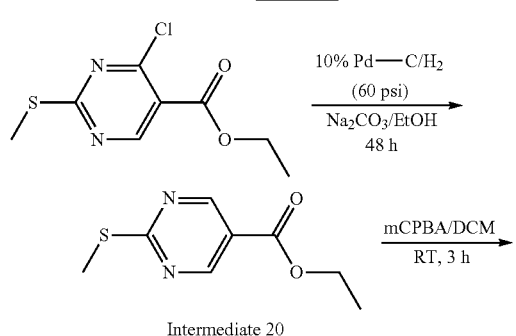

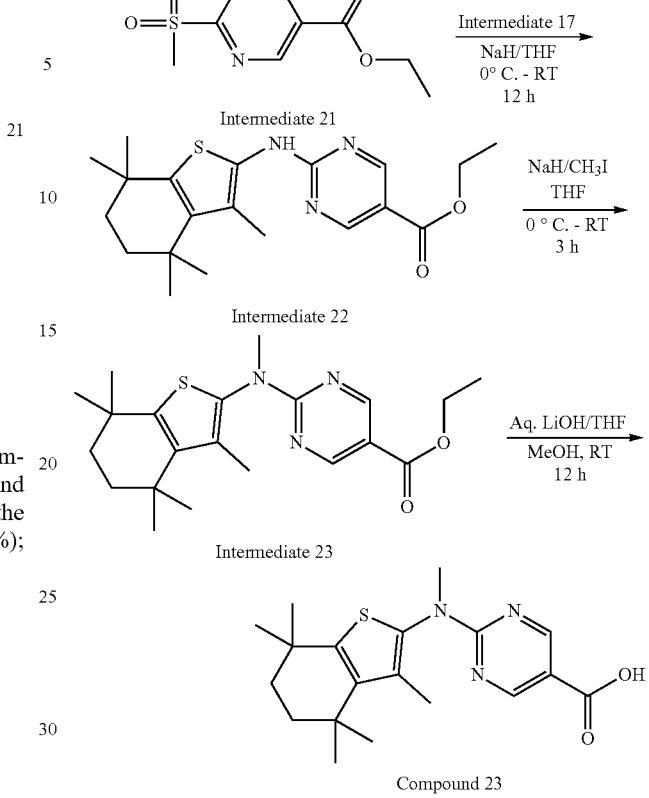

Example 23: 2-[Methyl(3,4,4,7,7-pentamethyl-4,5,6,7-tetrahydro-1-benzothiophen-2-yl)amino]pyrimidine-5-carboxylic acid

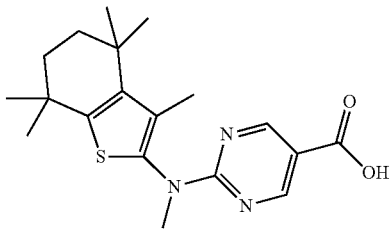

23

Compound 23 was synthesized from 3,4,4,7,7-pentamethyl-4,5,6,7-tetrahydro-1-benzothiophen-2-amine and ethyl 2-(methylsulfonyl)pyrimidine-5-carboxylate by following the procedure described in scheme 10; purity: 90.31%.

Intermediate 20: Ethyl 2-(methylsulfanyl)pyrimidine-5-carboxylate

To the stirred solution of ethyl 4-chloro-2-(methylsulfanyl)pyrimidine-5-carboxylate (4.0 g, 17.2 mmol) in ethanol in hydrogenation vessel, $Na_2CO_3$ (1.4 g, 16.7 mmol) and 10% Pd—C (2.0 g) was added and degassed for about 10 min. The reaction mixture was kept in hydrogenation parr shaker (60 psi) for 48 h. The reaction mixture was filtered through the celite, washed with ethanol, concentrated under reduced pressure to get the title product as a pale yellow liquid (3.3 g. yield: 98.2 g, %). m/z=199.1 (M+H)⁺.

Intermediate 21: Ethyl 2-(methylsulfonyl)pyrimidine-5-carboxylate

To a stirred solution of ethyl 2-(methylsulfanyl)pyrimidine-5-carboxylate (3.3 g, 16.6 mmol) in DCM (30 mL), m-CPBA (11.49 g, 66.5 mmol) in DCM (30 mL) was added drop wise. The reaction mixture was stirred at RT for 3 h. The reaction mixture was quenched with water and extracted with ethyl acetate, washed with saturated NaHCO₃ solution, water and brine. The organic layer was dried over anhydrous Na₂SO₄ and concentrated under vacuum to obtain the product as off white solid. This has been taken as such for the next step (2.0 g, yield: 52.0%); $^1$H NMR (300 MHz, DMSO-d₆): δ 9.48 (s, 2H), 4.39-4.46 (q, 2H), 3.48 (s, 3H), 1.33-1.39 (t, 3H).

Intermediate 22: Ethyl 2-[(3,4,4,7,7-pentamethyl-4,5,6,7-tetrahydro-1-benzothiophen-2-yl)amino]pyrimidine-5-carboxylate To a stirred solution of NaH (0.31 g, 12.5 mmol) in THF (10.0 mL), 3,4,4,7,7-pentamethyl-4,5,6,7-tetrahydro-1-benzothiophen-2-amine (2.0 g, 8.6 mmol) and ethyl 2-(methylsulfonyl)pyrimidine-5-carboxylate (1.93 g, 8.6 mmol) in THF (10 mL) was added at 0° C. The reaction mixture was stirred at RT for 12 h. The reaction mixture was quenched with water and extracted with ethyl acetate, washed with water and brine. The organic layer was dried over anhydrous Na₂SO₄ and concentrated under vacuum to obtain the crude product as an orange colour liquid. This has been taken as such for the next step (1.4 g, yield: 44.5%); m/z=374.2 (M+H)⁺.

Intermediate 23: Ethyl 2-[methyl(3,4,4,7,7-pentamethyl-4,5,6,7-tetrahydro-1-benzothiophen-2-yl)amino]pyrimidine-5-carboxylate To a stirred solution of NaH (0.11 g, 4.6 mmol) in THF (3 mL), ethyl 2-[(3, 4,4,7,7-pentamethyl-4,5,6,7-tetrahydro-1-benzothiophen-2-yl)amino]pyrimidine-5-carboxylate (0.7 g, 1.87 mmol) in THF was slowly added at 0° C., followed by addition of CH₃I (0.43 g, 2.9 mmol). The reaction mixture was stirred at RT for 3 h. The reaction mixture was quenched with ice and extracted with ethyl acetate, washed with water and brine. The organic layer was dried over anhydrous Na₂SO₄ and concentrated under vacuum to obtain the crude product as an orange colour liquid. This has been taken as such for the next step (0.04 g, yield: 5.4%); m/z=388.3 (M+H)⁺.

Compound 23: 2-[Methyl(3,4,4,7,7-pentamethyl-4,5,6,7-tetrahydro-1-benzothiophen-2-yl)amino]pyrimidine-5-carboxylic acid To a stirred solution of ethyl 2-[methyl(3,4,4,7,7-pentamethyl-4,5,6,7-tetrahydro-1-benzothiophen-2-yl)amino]pyrimidine-5-carboxylate (0.007 g, 0.018 mmol) in THF (1 mL), aqueous LiOH (0.0017 g, 0.074 mmol) and methanol (1 mL) was added and the solution was stirred at RT overnight. The reaction mixture was concentrated; obtained salt was washed with ether. The residue was dissolved in minimum amount of water, acidified with 1.5 N HCl and extracted with ethyl acetate, dried and concentrated to obtain the title product as a white solid (0.002 g, yield: 30.93%). MS (ESI, 120 eV): m/z=360.1 (M+H)⁺.

Example 24: 2-[Cyclopropyl(3,4,4,7,7-pentamethyl-4,5,6,7-tetrahydro-1-benzothiophen-2-yl)amino]pyrimidine-5-carboxylic acid

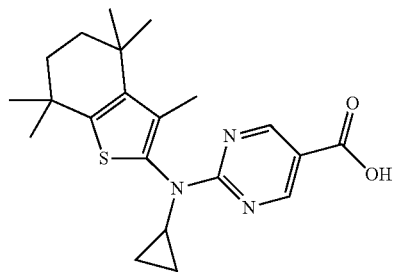

24

Compound 24 was synthesized from 3,4,4,7,7-pentamethyl-4,5,6,7-tetrahydro-1-benzothiophen-2-amine and ethyl 2-(methylsulfonyl)pyrimidine-5-carboxylate by following the similar procedure described in scheme 10. Further, the N-alkylation of ester (intermediate 22) with cyclopropylboronic acid was achieved by followed the similar procedure described for making intermediate 11 in scheme 5 (0.0035 g, yield: 15.05%); purity: 95.10%.

Scheme 11

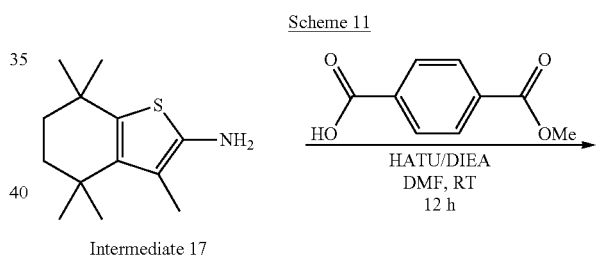

Intermediate 17

Intermediate 24

Intermediate 25

Example 25: 4-[(3,4,4,7,7-Pentamethyl-4,5,6,7-tetrahydro-1-benzothiophen-2-yl) carbamoyl]benzoic acid

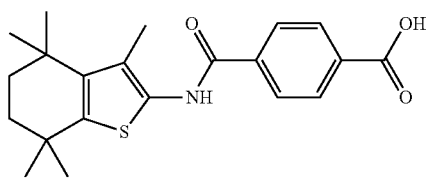

Compound 25 was synthesized from 3,4,4,7,7-pentamethyl-4,5,6,7-tetrahydro-1-benzothiophen-2-amine and 4-(methoxycarbonyl)benzoic acid by following the procedure described in scheme 11; purity: 98.24%.

Intermediate 24: Methyl 4-[(3,4,4,7,7-pentamethyl-4,5,6,7-tetrahydro-1-benzothiophen-2-yl) carbamoyl]benzoate To a stirred solution of 4-(methoxycarbonyl)benzoic acid (0.16 g, 0.9 mmol) in DMF (3 mL), 3,4,4,7,7-pentamethyl-4,5,6,7-tetrahydro-1-benzothiophen-2-amine (0.2 g, 0.9 mmol) and HATU (0.41 g, 1.1 mmol) was added under $N_2$ atmosphere. Finally, DIEA (0.69 g, 5.4 mmol) was added at 0° C. Reaction mixture was allowed to stir at RT overnight. The reaction mixture was quenched with ice and extracted with ethyl acetate, washed with water and brine solution. The organic layer was dried over anhydrous $Na_2SO_4$ and concentrated. The crude product obtained was purified by column chromatography to give title compound as a yellow solid (0.04 g, yield: 11.53%). $^1$H NMR (300 MHz, DMSO-$d_6$): δ 10.21 (s, 1H), 8.02-8.10 (m, 4H), 3.90 (s, 3H), 2.14 (s, 3H), 1.66 (s, 4H), 1.23-1.26 (d, 12H).

Compound 25: 4-[(3,4,4,7,7-Pentamethyl-4,5,6,7-tetrahydro-1-benzothiophen-2-yl) carbamoyl]benzoic acid To a stirred solution of methyl 4-[(3,4,4,7,7-pentamethyl-4,5,6,7-tetrahydro-1-benzothiophen-2-yl)carbamoyl]benzoate (0.04 g, 0.1 mmol) in THF (1 mL), methanol (1 mL) and water (1 mL), LiOH (0.025 g, 1.0 mmol) was added at 0° C. The reaction mixture was stirred at RT overnight. The reaction mixture was quenched with dil. HCl. The aqueous solution was extracted with ethyl acetate and the organic extracts were combined, washed with water and brine, dried over anhydrous $Na_2SO_4$, and concentrated in vacuum. The obtained solid was further purified by preparative TLC to give the title compound as a yellow solid (0.009 g, yield: 2.42%): MS (ESI, 120 eV): m/z=372.2 (M+H)$^+$.

Scheme 12

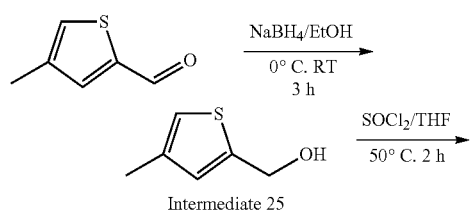

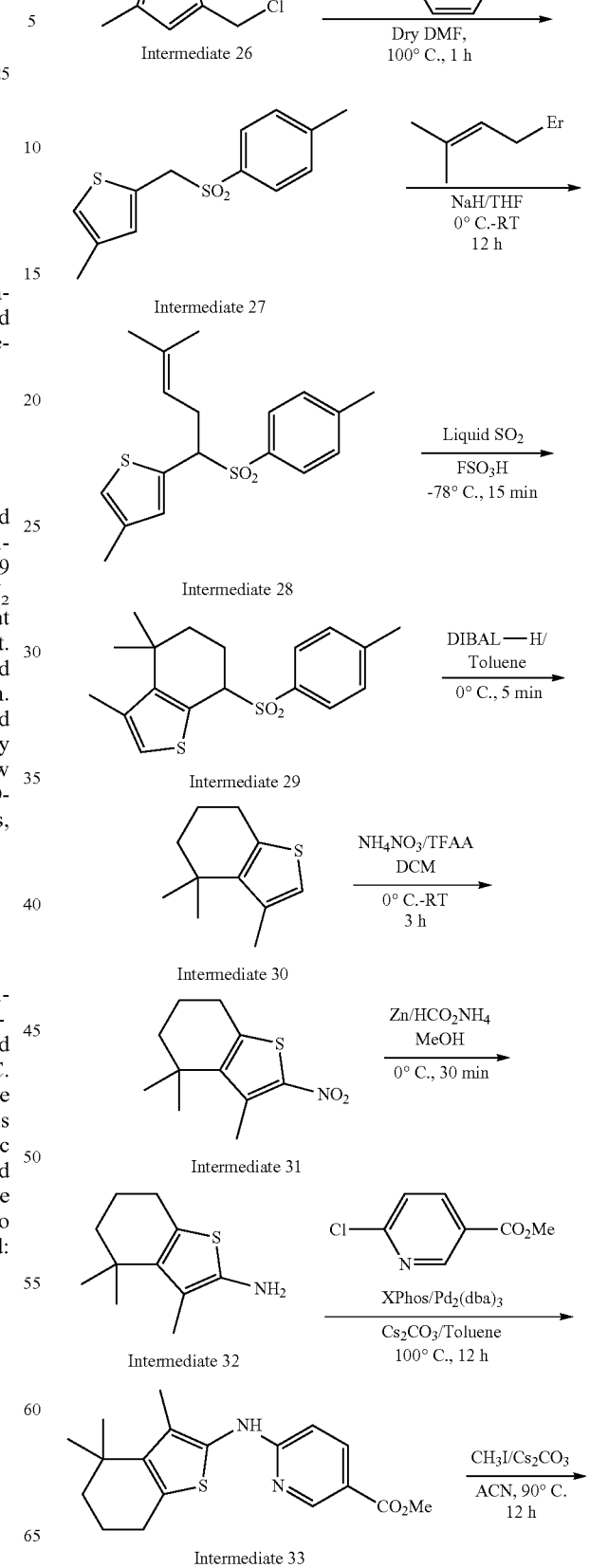

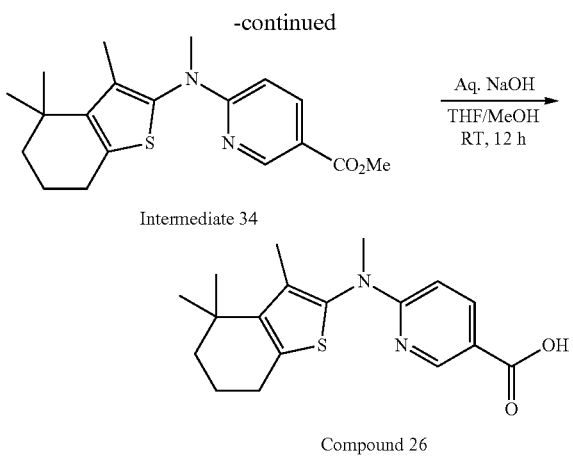

Intermediate 34

Compound 26

Example 26: 6-[Methyl(3,4,4-trimethyl-4,5,6,7-tetrahydro-1-benzothiophen-2-yl)amino]pyridine-3-carboxylic acid

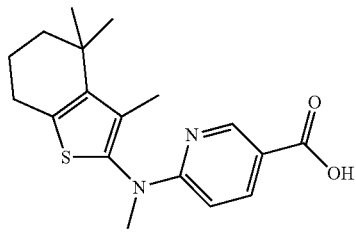

Compound 26 was synthesized from 3,4,4-trimethyl-4,5,6,7-tetrahydro-1-benzothiophen-2-amine and methyl 6-chloropyridine-3-carboxylate by following the procedure in scheme 12; purity: 92.31%.

Intermediate 25: (4-Methylthiophen-2-yl) methanol

To a stirred solution of 4-methylthiophene-2-carbaldehyde (6.0 g, 47.6 mmol) in ethanol (15 mL), NaBH$_4$ (2.1 g, 57.0 mmol) was added at 0° C. under N$_2$ atmosphere and was continued to be stirred at RT 12 h. The reaction mixture was quenched with ice and extracted with ethyl acetate, washed with water and brine. The organic layer was dried over anhydrous Na$_2$SO$_4$ and concentrated under vacuum to obtain the title product as orange colour liquid (5.2 g, yield: 85.2%). $^1$H NMR (300 MHz, DMSO-d$_6$): δ 6.96 (s, 1H), 6.76 (s, 1H), 5.34-5.38 (t, 1H), 4.55-4.56 (d, 2H), 2.16 (t, 3H).

Intermediate 26: 2-(Chloromethyl)-4-methylthiophene

To a stirred solution of (4-methylthiophen-2-yl) methanol (5.2 g, 40.5 mmol) in THF (50 mL), SOCl$_2$ (5.78 g, 48.6 mmol) was added and heated at 50° C. for 3 h. The reaction mixture was quenched with ice and extracted with ethyl acetate, washed with water and brine. The organic layer was dried over anhydrous Na$_2$SO$_4$ and concentrated under vacuum to obtain the title product as light brown colour liquid (5.0 g, yield: 83.9%). $^1$H NMR (300 MHz, DMSO-d$_6$): δ 7.14 (s, 1H), 7.00 (s, 1H), 4.97 (s 2H), 2.16 (t, 3H).

Intermediate 27: 4-Methyl-2-{[(4-methylphenyl)sulfonyl]methyl}thiophene

To a stirred solution of 2-(chloromethyl)-4-methylthiophene (5.0 g, 33.3 mmol) in DMF (50 mL), sodium p-toluene sulfinate (5.9 g, 33.3 mmol) was added. The reaction mixture was heated at 100° C. for 2 h. The reaction mixture was then quenched with water and extracted with diethyl ether and washed with water and brine. The organic layer was dried over anhydrous Na$_2$SO$_4$ and concentrated under vacuum to obtain the crude product. The crude product obtained was purified by silica gel column chromatography, using petroleum ether (60-80) and ethyl acetate as eluent to give the title product as off white solid (5.2 g, yield: 58.9%): $^1$H NMR (300 MHz, CDCl$_3$): δ 7.52-7.55 (d, 2H), 7.19-7.22 (d, 2H), 6.76 (s, 1H), 6.65 (s, 1H), 4.36 (s, 2H), 2.36 (s, 3H), 2.11 (s, 3H).

Intermediate 28: 4-Methyl-1-(4-methylthiophen-2-yl) pent-3-en-1-yl 4-methylphenylsulfone To a suspension of NaH (0.16 g, 6.8 mmol) in THF (3 mL), 4-methyl-2-{[(4-methylphenyl)sulfonyl]methyl}thiophene (0.9 g, 3.4 mmol) in THF (3 mL) was added and the resulting mass was stirred at 0° C. for 30 min. To the above solution 1-bromo-3-methylbut-2-ene (0.51 g, 3.4 mmol) in THF (3 mL) was added slowly at 0° C. and the resulting mixture was stirred RT for overnight. The reaction mixture was quenched with water and extracted with ethyl acetate, washed with water and brine. The organic layer was dried over anhydrous Na$_2$SO$_4$ and concentrated. The crude product obtained was purified by combiflash to give the title compound as white solid (1.0 g, yield: 88.0%).

Intermediate 29: 3,4,4-Trimethyl-7-[(4-methylphenyl)sulfonyl]-4,5,6,7-tetrahydro-1-benzothiophene To a solution of 4-methyl-1-(4-methylthiophen-2-yl)pent-3-en-1-yl 4-methylphenyl sulfone (2.5 g, 7.23 mol) in liquid SO$_2$ (40 mL), FSO$_3$H (0.4 mL) was added at −78° C., and stirred at the same temperature for 15 min. The reaction mixture was quenched with CH$_3$ONa and then neutralized with NaOH solution and extracted with diethyl ether. The organic layer was washed with water and brine solution, dried over Na$_2$SO$_4$, filtered and concentrated. The crude product obtained was purified by combiflash to give the title compound as colourless gummy material (1.5 g, yield: 60.0%).

Intermediate 30: 3,4,4-Trimethyl-4,5,6,7-tetrahydro-1-benzothiophene

To a solution of 3,4,4-trimethyl-7-[(4-methylphenyl)sulfonyl]-4,5,6,7-tetrahydro-1-benzothiophene (1.5 g, 4.4 mmol) in toluene (10 mL), DIBAL-H (6.5 mL, 1M soln. 1.5 eq) was added at RT in one lot. Then it was stirred at 0° C. for 5 min and carefully quenched with ethanol (0.5 mL), water (1.0 mL) and conc. HCl (0.5 mL). The reaction mixture was extracted with diethyl ether, washed with aqueous NaOH solution, water and brine. The organic layer was dried over anhydrous Na$_2$SO$_4$ and concentrated. The crude product obtained was purified by combiflash to give the title product as colourless oily product (0.5 g, yield:

61.2%): $^1$H NMR (300 MHz, CDCl$_3$): δ 6.64 (s, 1H), 2.70-2.74 (m, 2H), 2.31 (s, 3H), 1.78-1.86 (m, 2H), 1.59-1.63 (m, 2H), 1.28 (s, 6H).

Intermediate 31: 3,4,4-Trimethyl-2-nitro-4,5,6,7-tetrahydro-1-benzothiophene To a solution of 3,4,4-trimethyl-4,5,6,7-tetrahydro-1-benzothiophene (0.25 g, 1.4 mmol) in DCM (2 mL), NH$_4$NO$_3$ (0.13 g, 1.62 mmol) was added at 0° C. followed by slow addition of TFAA (0.58 g, 2.8 mmol). The resulting solution was stirred at 0° C. for 30 min followed by continued stirring at RT for 3 h. The reaction mixture was then quenched with ice water and extracted with DCM. The organic layer thus obtained was washed with water and brine, dried over Na$_2$SO$_4$, filtered and concentrated to obtain a black mass. The resultant mass was purified by preparative TLC to obtain the title compound as colourless oily product (0.07 g, yield: 22.4%): $^1$H NMR (300 MHz, CDCl$_3$): δ 2.71-2.75 (m, 2H), 2.69 (s, 3H), 1.79-1.87 (m, 2H), 1.63-1.67 (m, 2H), 1.33 (s, 6H).

Intermediate 32: 3,4,4-Trimethyl-4,5,6,7-tetrahydro-1-benzothiophen-2-amine

To a solution of 3,4,4-trimethyl-2-nitro-4,5,6,7-tetrahydro-1-benzothiophene (0.14 g, 0.62 mmol) in methanol (3 mL), ammonium formate (0.19 g, 3 mmol) and zinc dust (0.2 g, 3.0 mmol) was added and stirred at 0° C. for 30 min. The reaction mixture was quenched with water and then filtered through celite. Methanol was removed under vacuum and the crude was diluted with ethyl acetate, organic layer was washed with water and brine solution, dried over Na$_2$SO$_4$, filtered and concentrated to give the title compound as a brown oily product (0.1 g, yield: 82.3%); MS (ESI, 120 eV): m/z=196.1 (M+H)$^+$.

Intermediate 33: Methyl 6-[(3,4,4-trimethyl-4,5,6,7-tetrahydro-1-benzothiophen-2-yl)amino]pyridine-3-carboxylate A 20 ml pressure tube with screw cap was charged with 3,4,4-trimethyl-4,5,6,7-tetrahydro-1-benzothiophen-2-amine (0.1 g, 0.5 mmol), methyl 6-chloro pyridine-3-carboxylate (0.043 g, 0.25 mmol), CS$_2$CO$_3$ (0.325 g, 1.0 mmol), toluene and xantphos (0.014 g, 0.025 mmol). Argon was purged through the reaction mass for 15 min followed by addition of Pd$_2$(dba)$_3$ (0.022 g, 0.025 mmol) and the reaction mixture was then heated at 100° C. overnight. The reaction mass was diluted with water and extracted with ethyl acetate, organic layer and was washed with water and brine solution, dried over Na$_2$SO$_4$, filtered and concentrated. The crude product obtained was purified by combiflash to give the title compound as brown oily product (0.04 g, yield: 24.2%); MS (ESI, 120 eV): m/z=331.1 (M+H)$^+$.

Intermediate 34: Methyl 6-[methyl(3,4,4-trimethyl-4,5,6,7-tetrahydro-1-benzothiophen-2-yl)amino]pyridine-3-carboxylate To a 20 ml pressure tube with screw cap, methyl 6-[(3,4,4-trimethyl-4,5,6,7-tetrahydro-1-benzothiophen-2-yl)amino]pyridine-3-carboxylate (0.04 g, 0.12 mmol), CS$_2$CO$_3$ (0.078 g, 0.24 mmol), CH$_3$I (0.03 g, 0.24 mmol) and DMF (2 mL) was charged and the resultant mixture was heated at 80° C. overnight. The reaction mass was diluted with water and extracted with diethyl ether. The organic layer thus obtained was washed with water and brine solutions, dried over Na$_2$SO$_4$ and concentrated. The crude mass was taken as such for the next step (0.05 g); MS (ESI, 120 eV): m/z=345.0 (M+H)$^+$.

Compound 26: 6-[Methyl(3,4,4-trimethyl-4,5,6,7-tetrahydro-1-benzothiophen-2-yl)amino]pyridine-3-carboxylic acid A 25 mL RB flask fitted with magnetic stirrer was charged with methanol (1 mL) and THF (2 mL). To the stirred solvent methyl 6-[methyl(3,4,4-trimethyl-4,5,6,7-tetrahydro-1-benzothiophen-2-yl)amino]pyridine-3-carboxylate (0.05 g, 0.14 mmol) and aq. NaOH (0.011 g, 0.28 mmol) was added and the flask was stirred at RT for 12 h. The reaction mixture was concentrated completely and the crude was washed with ether, and diluted with water, neutralized with citric acid and extracted with ethyl acetate. The organic layer thus obtained was washed with water and brine, dried over Na$_2$SO$_4$, filtered and concentrated. It was purified by preparative TLC to yield the product as colourless solid (0.01 g, yield: 30.3%): MS (ESI, 120 eV): m/z=331.1 (M+H)$^+$.

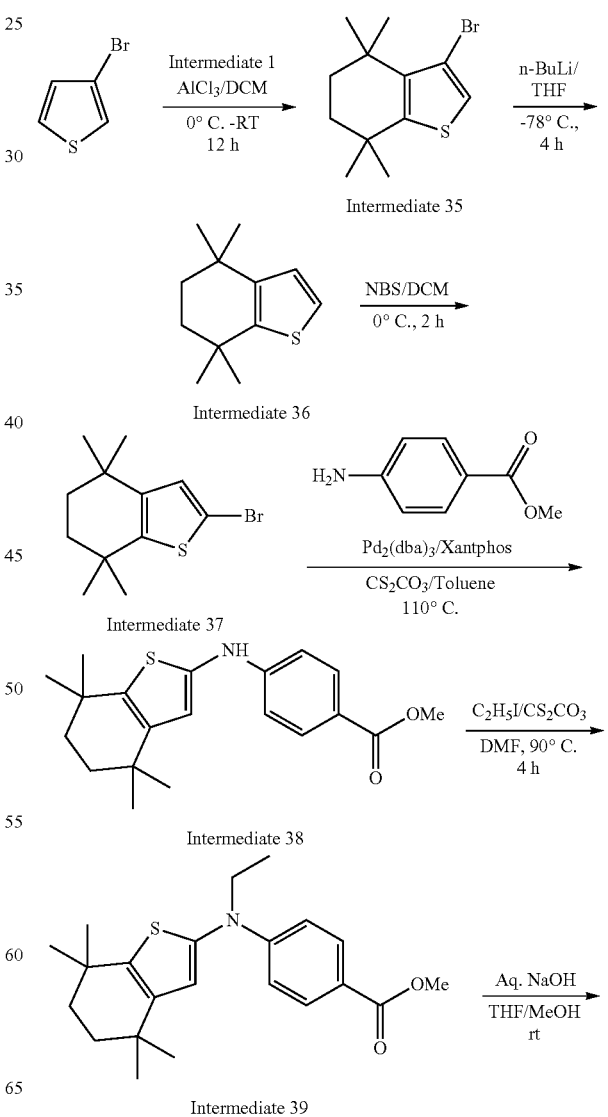

Scheme 13

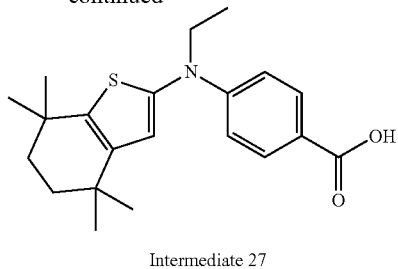

Intermediate 27

Example 27: 4-[Ethyl(4,4,7,7-tetramethyl-4,5,6,7-tetrahydro-1-benzothiophen-2-yl)amino]benzoic acid

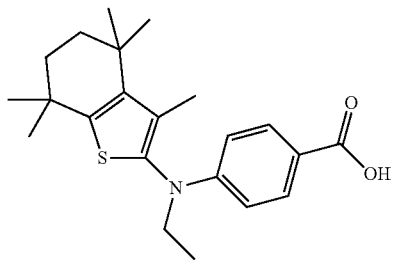

27

Compound 27 was synthesized from 2-bromo-4,4,7,7-tetramethyl-4,5,6,7-tetrahydro-1-benzothiophene and methyl 4-aminobenzoate by following the procedure described in scheme 13; purity: 96.71%.

Intermediate 35: 3-Bromo-4,4,7,7-tetramethyl-4,5,6,7-tetrahydro-1-benzo thiophene To a suspension of $AlCl_3$ (12.2 g, 92.0 mmol) in DCM (100 mL) at 0° C., a solution of 2,5-dichloro-2,5-dimethylhexane (16.8 g, 92.0 mmol) and 3-bromothiophene (15.0 g, 92.0 mmol) in DCM (50 mL) was slowly added and stirred at RT overnight. The reaction mixture was poured in to a beaker containing ice and extracted with DCM. The combined organic layer was washed with water and brine, dried over $Na_2SO_4$ and concentrated to obtain a black mass. It was purified by silica gel (230-400 mesh) column chromatography to give the compound pale yellow oily product (8.0 g, yield: 31.84%). $^1$H NMR (300 MHz, $CDCl_3$): δ 6.99 (s, 1H), 1.62 (s, 4H), 1.34 (s, 6H), 1.23 (s, 6H).

Intermediate 36: 4,4,7,7-Tetramethyl-4,5,6,7-tetrahydro-1-benzothiophene

To a stirred solution of 3-bromo-4,4,7,7-tetramethyl-4,5,6,7-tetrahydro-1-benzothiophene (4.0 g, 14.0 mol. 0.029 mmol), n-BuLi (18.0 mL, 1.6M in hexane) was added at −78° C. under $N_2$ atmosphere and stirred at the same temperature for 4 h. The reaction mixture was quenched with saturated $NH_4Cl$ solution and extracted with diethyl ether. The combined organic layer was washed with water and brine, dried over $Na_2SO_4$, filtered and concentrated. It was purified by silica gel (230-400 mesh) column chromatography to give the title compound as pale yellow oily product (2.5 g, yield: 88.0%). $^1$H NMR (300 MHz, $CDCl_3$): δ 6.98-6.99 (d, 1H), 6.76-6.78 (d, 1H), 1.59-1.67 (m, 4H), 1.24 (s, 6H), 1.15 (s, 6H).

Intermediate 37: 2-Bromo-4,4,7,7-tetramethyl-4,5,6,7-tetrahydro-1-benzo thiophene To a solution of 4,4,7,7-tetramethyl-4,5,6,7-tetrahydro-1-benzothiophene (0.5 g, 2.5 mmol) in DCM (5 mL), NBS (0.5 g, 2.8 mmol) was added in portions at 0° C. and stirred at the same temperature for 2 h. The reaction mixture was quenched with water and extracted with DCM. The organic layer was washed with water and brine, dried over $Na_2SO_4$, filtered and concentrated. The crude material obtained was purified by combiflash to give colourless oily product (0.55 g, yield: 76.9%). $^1$H NMR (300 MHz, $CDCl_3$): δ 6.69 (s, 1H), 1.55-1.64 (m, 4H), 1.20 (s, 6H), 1.11 (s, 6H).

Intermediate 38: Methyl 4-[(4,4,7,7-tetramethyl-4,5,6,7-tetrahydro-1-benzothiophen-2-yl)amino]benzoate A 25 ml pressure tube with screw cap was charged with 2-bromo-4,4,7,7-tetramethyl-4,5,6,7-tetrahydro-1-benzothiophene (0.55 g, 2.0 mmol), methyl 4-aminobenzoate (0.61 g, 4.0 mmol), $CS_2CO_3$ (1.3 g, 4.0 mmol), toluene (10 mL) and xphos (0.06 g, 0.1 mmol). Argon was purged through the reaction mass for 15 min followed by addition of $Pd_2(dba)_3$ (0.036 g, 0.04 mmol) and the mass thus obtained was heated at 100° C. overnight. The reaction mass was diluted with water and extracted with ethyl acetate. The organic layer was washed with water and brine solution, dried over $Na_2SO_4$, filtered and concentrated, which was purified by combiflash to give pale yellow solid (0.17 g, yield: 24.5%); MS (ESI, 120 eV): m/z=344.1 (M+H).

Intermediate 39: Methyl 4-[ethyl(4,4,7,7-tetramethyl-4,5,6,7-tetrahydro-1-benzothiophen-2-yl)amino]benzoate A 20 ml pressure tube was charged with methyl 4-[(4,4,7,7-tetramethyl-4, 5,6,7-tetrahydro-1-benzothiophen-2-yl)amino]benzoate (0.17 g, 0.5 mmol), $CS_2CO_3$ (0.48 g, 1.5 mmol) and DMF (3 mL). The reaction mixture was stirred at RT for 30 min, followed by addition of $C_2H_5I$ (0.11 g, 0.74 mmol) and was heated at 90° C. for 4 h. The reaction mixture was diluted with water and extracted with diethyl ether. The organic layer was washed with water and brine, dried over $Na_2SO_4$, filtered and concentrated to brown oil, which was purified by combiflash to give the title compound as a white solid (0.11 g, yield: 59.8%). $^1$H NMR (300 MHz, $CDCl_3$): δ 7.77-7.80 (d, 2H), 6.65-6.68 (d, 2H), 6.44 (s, 1H), 3.78 (s, 3H), 3.61-3.68 (q, 2H), 1.60-1.68 (m, 4H), 1.24 (s, 6H), 1.18-1.20 (t, 3H), 1.13 (s, 6H).

Compound 27: 4-[Ethyl(4,4,7,7-tetramethyl-4,5,6,7-tetrahydro-1-benzothiophen-2-yl)amino]benzoic acid A 25 mL RB flask fitted with magnetic stirrer was charged with methanol (1 mL) and THF (2 mL). To the stirred solvent methyl 4-[ethyl(4,4,7,7-tetramethyl-4,5,6,7-tetrahydro-1-benzothiophen-2-yl)amino]benzoate (0.11 g, 0.3 mmol) and aqueous NaOH (0.023 g, 0.6 mmol) was added and stirred at RT for 12 h. The reaction mixture was concentrated; the crude obtained was washed with ether, and diluted with water and then neutralized with 1N HCl. It was extracted with ethyl acetate, washed with water and brine, dried over Na$_2$SO$_4$, filtered and concentrated. The obtained solid was further purified by preparative TLC to give the title compound as a pale brown solid (0.05 g, yield: 50.0%); MS (ESI, 120 eV): m/z=358.2 (M+H)$^+$.

Scheme 14

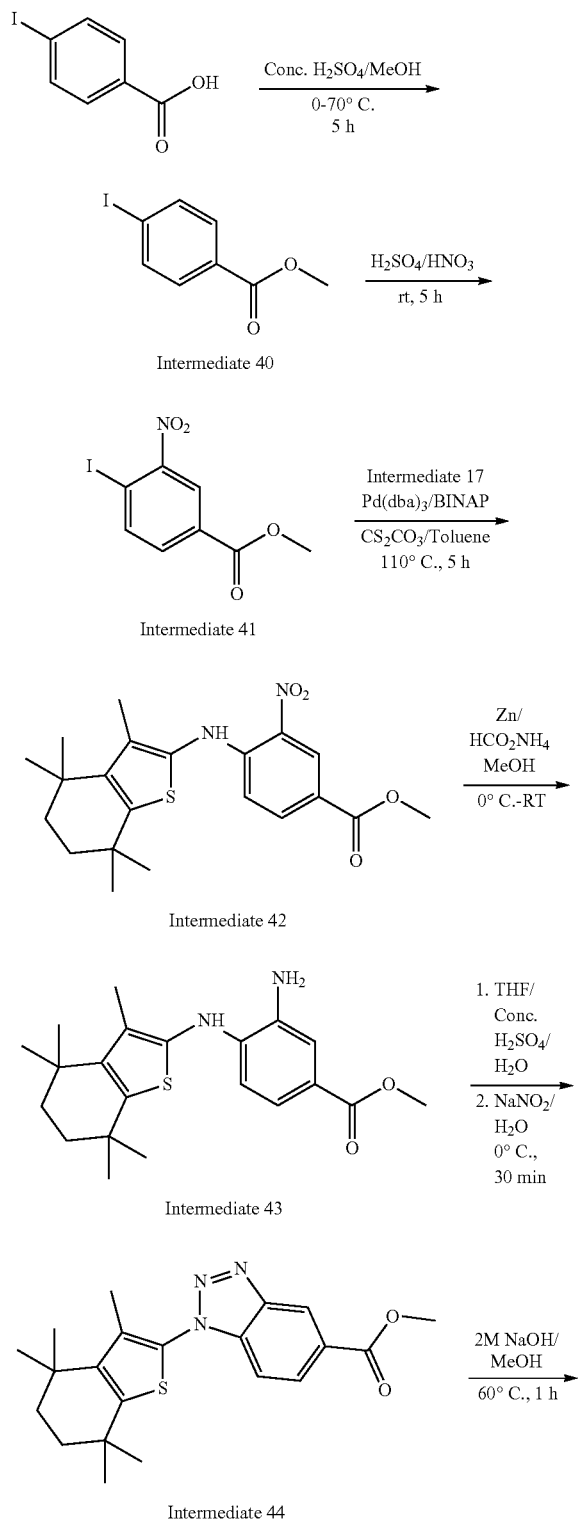

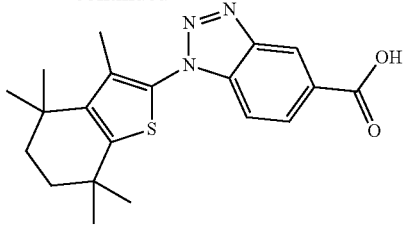

Compound 28

Example 28: 1-(3,4,4,7,7-Pentamethyl-4,5,6,7-tetrahydro-1-benzothiophen-2-yl)-1H-benzotriazole-5-carboxylic acid

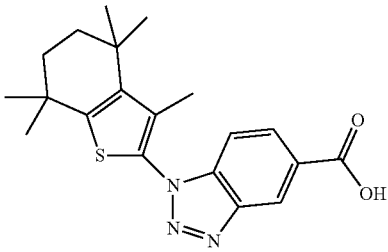

28

Compound 28 was synthesized from 3,4,4,7,7-pentamethyl-4,5,6,7-tetrahydro-1-benzothiophen-2-amine and methyl 4-iodo-3-nitrobenzoate by following the procedure described in scheme 14; purity: 86.18%.

Intermediate 40: Methyl 4-iodobenzoate

To solution of 4-iodobenzoic acid (8.0 g, 32.2 mmol) in MeOH (80 mL), H$_2$SO$_4$ (2.0 mL) was added at 0° C. The reaction mixture was refluxed at 70° C. for 5 h. The solvent was removed under vacuum, the residue obtained was dissolved in ethyl acetate, washed with saturated NaHCO$_3$ solution and brine, dried over anhydrous Na$_2$SO$_4$ and concentrated. It was further purified by crystallization with DCM/n-hexane mixture to yield the title compound as a white solid (8.0 g, yield: 94.0%): $^1$H NMR (300 MHz, CDCl$_3$): δ 7.73-7.82 (m, 2H), 3.91 (s, 3H).

Intermediate 41: Methyl 4-iodo-3-nitrobenzoate

To an ice-cooled solution of methyl 4-iodobenzoate (8.0 g, 30.5 mmol) in conc. H$_2$SO$_4$ (57 mL), a solution of conc. HNO$_3$ (45 mL) and conc. H$_2$SO$_4$ (38.0 mL) was added drop wise. The reaction mixture was stirred at RT for 5 h, then quenched with ice, and extracted with ethyl acetate. The organic layer was washed with saturated NaHCO$_3$ and brine (50 mL), dried over anhydrous Na$_2$SO$_4$ and evaporated under reduced pressure. The residue was recrystallized from DCM/n-hexane to yield the title compound as yellow solid (7.0 g, yield: 74.71%).

Intermediate 42: Methyl 3-nitro-4-[(3,4,4,7,7-pentamethyl-4,5,6,7-tetrahydro-1-benzothiophen-2-yl) amino]benzoate To a solution of methyl 4-iodo-3-nitrobenzoate (1.0 g, 3.26 mmol) and intermediate 17 (1.5 g, 6.5 mmol) in dry toluene (20 mL), Pd$_2$(dba)$_3$ (0.15 g, 0.16 mmol), xantphos (0.16 g, 0.33 mmol) and Cs$_2$CO$_3$ (3.2 g, 9.8 mmol) were added under inert atmosphere. The mixture was refluxed at 110° C. under Argon atmosphere for 5 h, and then filtered through celite. The filtrate was washed with water and brine, dried over anhydrous Na$_2$SO$_4$ and evaporated under reduced pressure. The residue obtained was purified by column chromatography and crystallized from n-hexane to yield title compound as red colour liquid product (0.9 g, yield: 68.7%).

Intermediate 43: Methyl 3-amino-4-[(3,4,4,7,7-pentamethyl-4,5,6,7-tetrahydro-1-benzothiophen-2-yl)amino]benzoate To a solution of methyl 3-nitro-4-[(3,4,4,7,7-pentamethyl-4,5,6,7-tetrahydro-1-benzothiophen-2-yl)amino]benzoate (0.9 g, 2.2 mmol) in methanol (10 mL), zinc dust (0.71 g, 11.2 mmol) was added at 0° C. The mixture was stirred at RT until completion, and then filtered through celite. The filtrate was evaporated under reduced pressure. The residue was extracted with ethyl acetate. The combined extracts were washed with water and brine solution. The organic layer was dried over anhydrous Na$_2$SO$_4$ and concentrated reduced pressure to give title compound as a yellow fluffy solid (0.8 g, yield: 96.39%).

Intermediate 44: Methyl 1-(3,4,4,7,7-pentamethyl-4,5,6,7-tetrahydro-1-benzothiophen-2-yl)-1H-benzotriazole-5-carboxylate To an ice-cooled solution of methyl 3-amino-4-[(3,4,4,7,7-pentamethyl-4,5,6,7-tetrahydro-1-benzothiophen-2-yl)amino]benzoate (0.4 g, 1.08 mmol) in THF (5.0 mL), a mixture of conc. H$_2$SO$_4$ (2.0 mL) in H$_2$O (20 mL), was added followed by addition of solution of NaNO$_2$ (0.12 g, 1.73 mmol) in water (2.0 mL) drop wise. The mixture was stirred at 0° C. for 30 min, then poured into water and extracted with ethyl acetate. The organic layer was washed with water and brine (30 mL), dried over anhydrous Na$_2$SO$_4$ and evaporated under reduced pressure. The residue was purified by flash column chromatography to yield title compound as an pale yellow solid (0.1 g, yield: 24.33%): MS (ESI, 120 eV): m/z=(M+H)$^+$; $^1$H NMR (300 MHz, CDCl$_3$): 8.85 (s, 1H), 8.21-8.24 (d, 1H), 7.50-7.53 (d, 1H), 4.00 (s, 3H), 2.04 (s, 3H), 1.77 (s, 4H), 1.36-1.37 (d, 12H).

Compound 28: 1-(3,4,4,7,7-Pentamethyl-4,5,6,7-tetrahydro-1-benzothiophen-2-yl)-1H-benzotriazole-5-carboxylic acid To a solution of methyl 1-(3,4,4,7,7-pentamethyl-4,5,6,7-tetrahydro-1-benzothiophen-2-yl)-1H-benzotriazole-5-carboxylate (0.1 mg, 0.26 mmol) in MeOH (2 mL) and THF (2 mL), Aq. NaOH (0.052 g, 1.3 mmol) was added. The reaction mixture was stirred at RT for 1 h. The solvents were removed under reduced pressure completely; the residue obtained was dissolved in minimum amount of water, acidified to pH 3 under cooling, extracted with ethyl acetate. The organic layer was washed with water and brine, dried over anhydrous Na$_2$SO$_4$, and concentrated in vacuum. The obtained solid was further purified by trituration with hexane to give the title compound as a white solid (0.025 g, yield: 26.04%): MS (ESI, 120 eV): m/z=370.1 (M+H)$^+$.

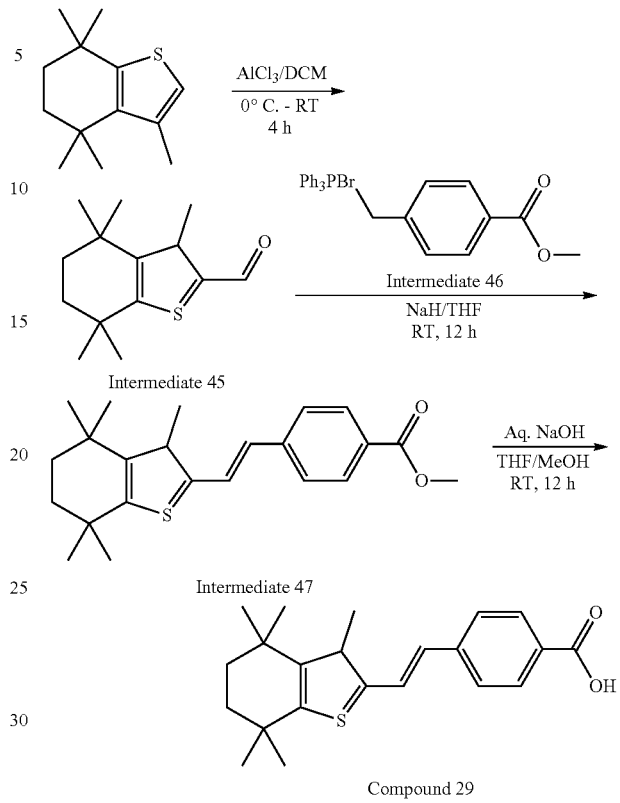

Scheme 15

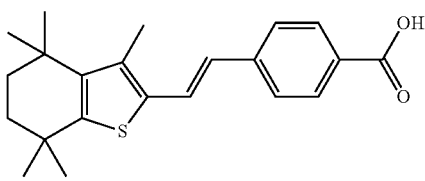

Example 29: 4-[(E)-2-(3,4,4,7,7-Pentamethyl-4,5,6,7-tetrahydro-1-benzothiophen-2-yl) ethenyl]benzoic acid Compound 29 was synthesized from 3,4,4,7,7-pentamethyl-4,5,6,7-tetrahydro-1-benzothiophene-2-carbaldehyde and methyl 4-{[bromo (triphenyl)-15-phosphanyl]methyl}benzoate by following the procedure described in scheme 15; purity: 97.20%.

Intermediate 45: 3,4,4,7,7-Pentamethyl-4,5,6,7-tetrahydro-1-benzothiophene-2-carbaldehyde To a stirred two-neck 250 mL RB flask charged with AlCl$_3$ (1.18 g, 5.6 mmol) and DCM (60 mL), 3,4,4,7,7-pentamethyl-4,5,6,7-tetrahydro-1-benzothiophene (0.96 g, 5.6 mmol) and dichloromethylmethyl ether (0.5 mL) was added at 0° C. and the flask was continued to be stirred at RT for 4 h. The reaction mixture was brought to RT, quenched with ice and extracted with ethyl acetate. The combined extracts were washed with water and brine. The organic layer was dried over anhydrous Na₂SO₄ and concentrated at reduced pressure. The obtained crude product was purified by silica gel column chromatography to yield the title compound as a white solid (0.6 g, yield: 47.0%): MS (ESI, 120 eV): m/z=237.1 (M+H)⁺. ¹H NMR (300 MHz, CDCl₃): δ 9.94 (s, 1H), 2.55 (s, 3H), 1.62 (s, 4H), 1.26-1.27 (s, 12H).

Intermediate 46: Methyl 4-{[bromo (triphenyl)-λ⁵-phosphanyl]methyl}benzoate

To a stirred solution of methyl 4-(bromomethyl)benzoate (1.0 g, 4.3 mmol) in acetonitrile (10 mL), PPh₃ (1.71 g, 6.5 mmol) was added and heated at 60° C. for 2 h. The reaction mixture was concentrated. The obtained residue was washed with water, brine solution and dried over anhydrous Na₂SO₄ and concentrated. It was purified by crystallization with toluene give the title compound as white solid (1.5 g, yield: 70.4%).

Intermediate 47: Methyl 4-[(E)-2-(3,4,4,7,7-pentamethyl-4,5,6,7-tetrahydro-1-benzothiophen-2-yl) ethenyl]benzoate To a stirred solution of NaH (0.067 g, 2.6 mmol) in THF (3 mL), methyl 4-{[bromo(triphenyl)-=⁵-phosphanyl]methyl}benzoate (0.81 g, 1.65 mmol) was added slowly at 0° C. under N₂ atmosphere and continued the stirring at same temperature for 45 min. To the above solution 3,4,4,7,7-pentamethyl-4,5,6,7-tetrahydro-1-benzothiophene-2-carbaldehyde (0.3 g, 1.2 mmol) in THF (3 mL) was added, and the solution as continued to be stirred at RT for 12 h. The reaction mixture was then quenched with water and extracted with ethyl acetate. The organic layer was washed with water and brine solution, dried over anhydrous Na₂SO₄ and concentrated in vacuum. The resulting crude product was purified by silica gel column chromatography to give the title compound as yellow solid (0.18 g, yield: 32.0%): MS (ESI, 120 eV): m/z=369.1 (M+H)⁺.

Compound 29: 4-[(E)-2-(3,4,4,7,7-Pentamethyl-4,5,6,7-tetrahydro-1-benzothiophen-2-yl) ethenyl]benzoic acid To a stirred solution of methyl 4-[(E)-2-(3,4,4,7,7-pentamethyl-4,5,6,7-tetrahydro-1-benzothiophen-2-yl) ethenyl] benzoate (0.05 g, 0.13 mmol) in THF (2 ml), aqueous NaOH (0.0065 g, 0.27 mmol) was added. The mixture was stirred at RT for 12 h. The reaction mixture was concentrated, and the residue was dissolved in minimum amount of water, acidified to pH 3 under cooling, extracted with ethyl acetate. The organic layer was washed with water and brine, dried over anhydrous Na₂SO₄ and concentrated in vacuum. The obtained solid was further purified by preparative TLC to give the title compound as a yellow solid (0.004 g, yield: 8.31%): MS (ESI, 120 eV): m/z=353.0 (M−H)⁺.

Example 30: 4-[(Z)-2-(3,4,4,7,7-Pentamethyl-4,5,6,7-tetrahydro-1-benzothiophen-2-yl) ethenyl]benzoic acid

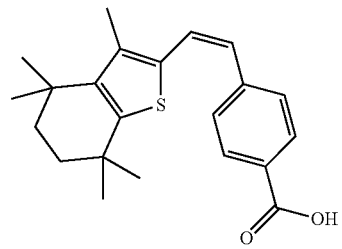

30

Compound 30 was synthesized from 3,4,4,7,7-pentamethyl-4,5,6,7-tetrahydro-1-benzothiophene-2-carbaldehyde and methyl 4-{[bromo (triphenyl)-15-phosphanyl] methyl}benzoate by following the procedure described in scheme 15 (0.0028 g, yield: 5.82%); purity: 98.45%.

Example 31: 4-[2-(3,4,4,7,7-Pentamethyl-4,5,6,7-tetrahydro-1-benzothiophen-2-yl)cyclopropyl]benzoic acid

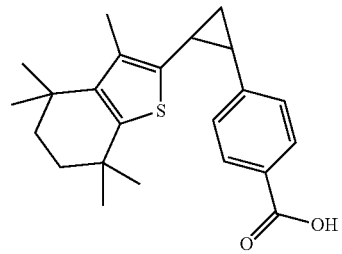

31

Compound 31 was synthesized from 3,4,4,7,7-pentamethyl-4,5,6,7-tetrahydro-1-benzothiophene-2-carbaldehyde and methyl 4-{[bromo (triphenyl)-15-phosphanyl] methyl}benzoate by following the procedure described in scheme 15. Then the cyclopropanation done by the procedure is as same as described for intermediate 6 in scheme 2, followed by hydrolysis to yield the title product (0.004 g, yield: 4.17%); purity: 96.84%.

Scheme 16

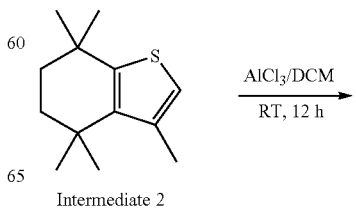

Intermediate 2

-continued

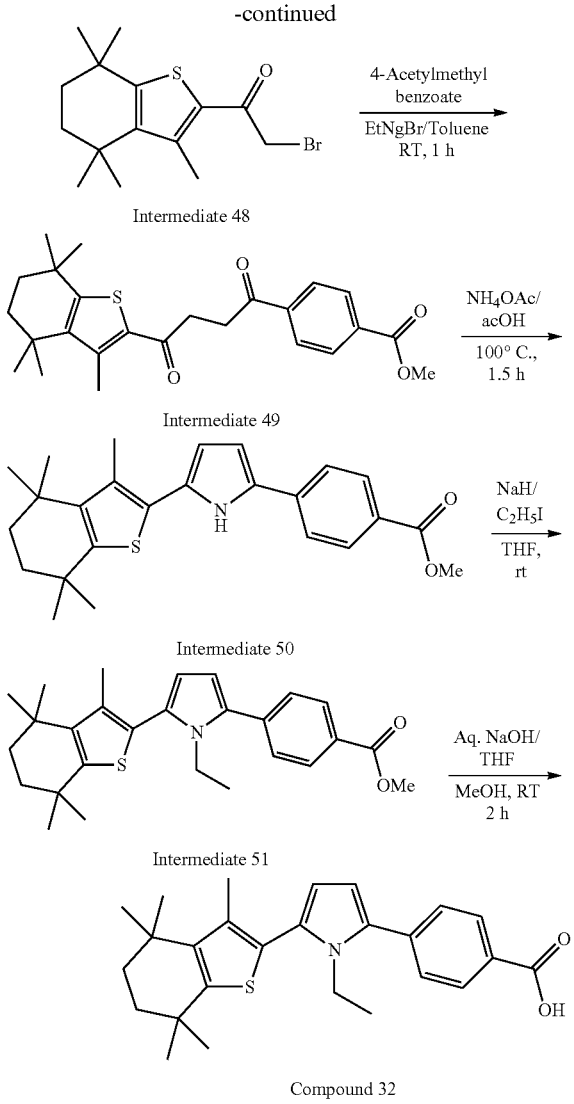

Example 32: 4-[1-Ethyl-5-(3,4,4,7,7-pentamethyl-4,5,6,7-tetrahydro-1-benzothiophen-2-yl)-1H-pyrrol-2-yl]benzoic acid

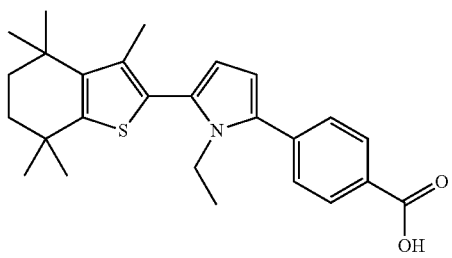

Compound 32 was synthesized from 2-bromo-1-(3,4,4,7,7-pentamethyl-4,5,6,7-tetrahydro-1-benzothiophen-2-yl)ethanone and 4-acetylmethylbenzoate by following the procedure described in scheme 16; purity: 96.40%.

Intermediate 48: 2-Bromo-1-(3,4,4,7,7-pentamethyl-4,5,6,7-tetrahydro-1-benzothiophen-2-yl)ethanone To a stirred solution of $AlCl_3$ (1.54 g, 11.5 mmol) in DCM (10 mL), bromoacetylchloride (0.76 g, 1.1 mmol) was added at 0° C. After 25 minutes, 3,4,4,7,7-pentamethyl-4,5,6,7-tetrahydro-1-benzothiophene (2.4 g, 1.15 mmol) in DCM was added drop wise to the above solution. The reaction mixture was stirred at RT overnight and then refluxed for 1 h. The reaction mixture was cooled to RT, quenched with ice and extracted with ethyl acetate. The combined extracts were washed with water and brine. The organic layer was dried over anhydrous $Na_2SO_4$ and concentrated under reduced pressure. The obtained crude product was purified by silica gel column chromatography to yield the title compound as a brown colour liquid (1.8 g, yield: 48.65%).

Intermediate 49: Methyl 4-[4-oxo-4-(3,4,4,7,7-pentamethyl-4,5,6,7-tetrahydro-1-benzothiophen-2-yl)butanoyl]benzoate To a stirred solution of ethyl magnesium bromide [(1.0 mL, 3M solution), 3.2 mmol)] in toluene (10 mL), diethyl amine (0.24 g, 3.24 mmol) was added and the reaction mixture was stirred at RT 15 minutes. Then the 2-bromo-1-(3,4,4,7,7-pentamethyl-4,5,6,7-tetrahydro-1-benzothiophen-2-yl)ethanone (0.9 g, 2.7 mmol) and methyl-4-acetylbenzoate (0.39 g, 2.2 mmol) in toluene (10 mL) were added to the above solution at 0° C. The reaction mixture was cooled to RT, quenched with water and extracted with ethyl acetate. The combined extracts were washed with water and brine. The organic layer was dried over anhydrous $Na_2SO_4$ and concentrated reduced pressure. The obtained crude product was purified by silica gel column chromatography to yield the title compound as a yellow solid (0.35 g, yield: 37.29%): $^1H$ NMR (300 MHz, DMSO-$d_6$): δ 8.11 (s, 4H), 3.90 (s, 3H), 3.37-3.41 (t, 2H), 3.18-3.22 (t, 2H), 2.54 (s, 3H), 1.68 (s, 4H), 1.29-1.33 (d, 12H).

Intermediate 50: Methyl 4-[5-(3,4,4,7,7-Pentamethyl-4,5,6,7-tetrahydro-1-benzothiophen-2-yl)-1H-pyrrol-2-yl]benzoate To a stirred solution of methyl 4-[4-oxo-4-(3,4,4,7,7-pentamethyl-4,5,6,7-tetrahydro-1-benzothiophen-2-yl)butanoyl]benzoate (0.29 g, 0.68 mmol) in acetic acid (5 mL), ammonium acetate (2.63 g, 34.0 mmol) was added. The reaction mixture was refluxed for 1.5 h. The reaction mixture was then quenched with water and extracted with ethyl acetate. The combined extracts were washed with water and brine. The organic layer was dried over anhydrous $Na_2SO_4$ and concentrated under reduced pressure. The obtained crude product was purified by silica gel column chromatography to yield the title compound as a yellow fluffy solid (0.1 g, yield: 35.06%): $^1H$ NMR (300 MHz, $CDCl_3$): δ 8.39 (s, 1H), 7.93-7.95 (d, 2H), 7.43-7.46 (d, 2H), 6.61-6.62 (d, 1H), 6.27-6.28 (d, 1H), 3.83 (s, 3H), 2.32 (s, 3H), 1.63 (s, 4H), 1.25-1.26 (d, 12H).

Intermediate 51: Methyl 4-[1-ethyl-5-(3,4,4,7,7-pentamethyl-4,5,6,7-tetrahydro-1-benzothiophen-2-yl)-1H-pyrrol-2-yl]benzoate To a stirred solution of NaH (0.007 g, 0.31 mmol) in DMF (2 mL), methyl 4-[5-(3,4,4,7,7-pentamethyl-4,5,6,7-tetrahydro-1-benzothiophen-2-yl)-1H-pyrrol-2-yl]benzoate in DMF (1 mL) (0.09 g, 0.22 mmol) was added drop wise at 0°

C. After 20 min, ethyl iodide (0.048 g, 0.31 mmol) was added. The reaction mixture was allowed to stir at RT for 1 h. The reaction mixture quenched with water, extracted and ethyl acetate. The combined extracts were washed with water and brine. The organic layer was dried over anhydrous Na$_2$SO$_4$ and concentrated under reduced pressure. The obtained crude product was purified by silica gel column chromatography to yield the title compound as a yellow fluffy solid (0.06 g, yield: 68.85%): $^1$H NMR (300 MHz, CDCl$_3$): δ 7.99-8.02 (d, 2H), 7.43-7.46 (d, 2H), 6.27-6.28 (d, 1H), 6.16-6.17 (d, 1H), 3.89-3.93 (q, 2H), 3.87 (s, 3H), 2.12 (s, 3H), 1.65 (s, 4H), 1.26-1.27 (d, 12H), 0.79-0.86 (t, 3H).

Compound 32: 4-[1-Ethyl-5-(3,4,4,7,7-pentamethyl-4,5,6,7-tetrahydro-1-benzothiophen-2-yl)-1H-pyrrol-2-yl]benzoic acid To a stirred solution of 4-[5-(3,4,4,7,7-pentamethyl-4,5,6,7-tetrahydro-1-benzothiophen-2-yl)-1H-pyrrol-2-yl]benzoate (0.06 g, 0.14 mmol) in THF (1 mL) and methanol (1 mL), aqueous NaOH (0.033 g, 0.83 mmol) was added at 0° C. The mixture was stirred at RT for 2 h. The reaction mixture was concentrated, and the residue was dissolved in minimum amount of water, acidified to pH 3 under cooling, extracted with ethyl acetate. The organic layer was washed with water and brine, dried over anhydrous Na$_2$SO$_4$ and concentrated. It was purified by trituration with n-hexane to yield the title compound as a yellow solid (0.034 g, yield: 78.0%): MS (ESI, 120 eV): m/z=420.2 (M-H)$^+$.

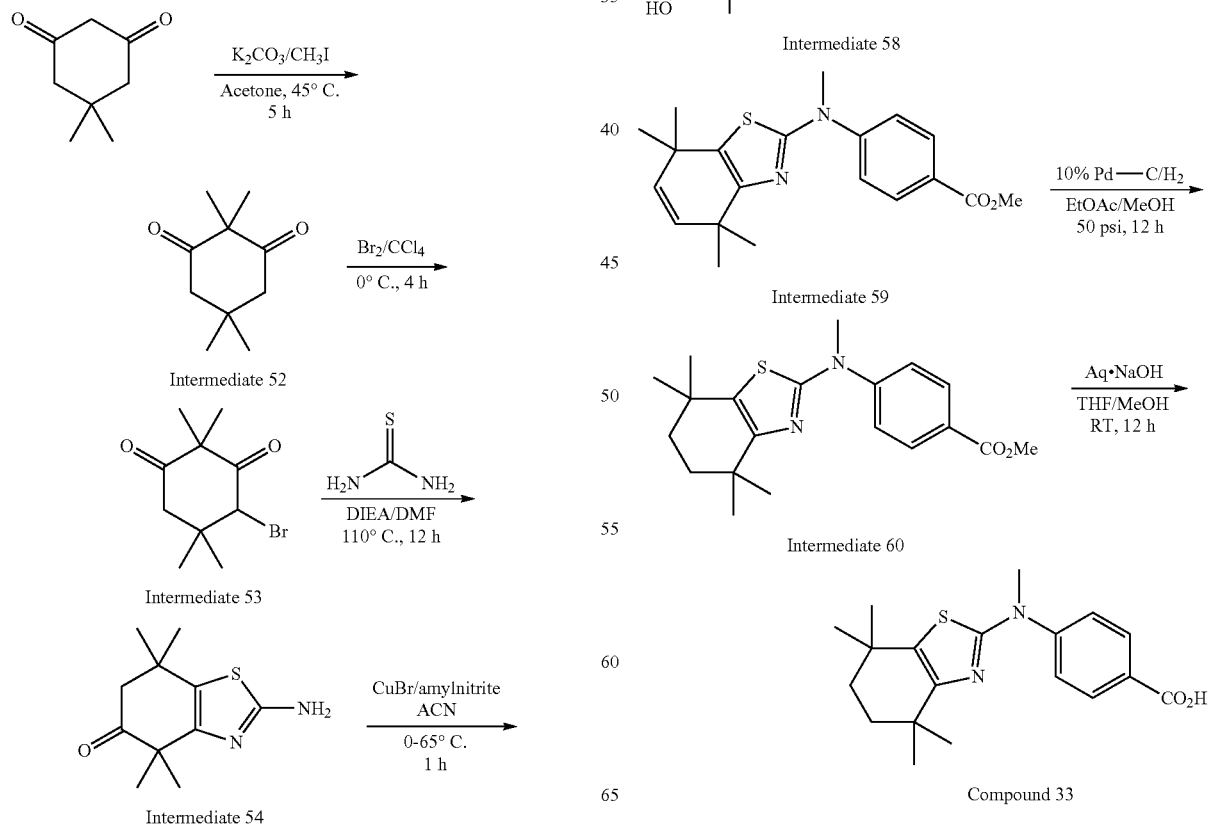

Example 33: 4-[Methyl(4,4,7,7-tetramethyl-4,5,6,7-tetrahydro-1,3-benzothiazol-2-yl)amino]benzoic acid

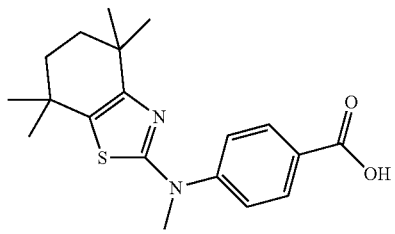

Compound 33 was synthesized from 2-bromo-4,4,7,7-tetramethyl-6,7-dihydro-1,3-benzothiazol-5(4H)-one and methyl 4-aminobenzoate by following the procedure described in scheme 17; purity: 92.66%.

Intermediate 52: 2,2,5,5-Tetramethylcyclohexane-1,3-dione

To a solution of 5,5-dimethylcyclohexane-1,3-dione (100.0 g, 713.4 mmol) in acetone (1 L), potassium carbonate (294.3 g, 2140.2 mmol) was added and stirred at RT for 30 min. The reaction mass was cooled to 0° C. and methyl iodide (404.9 g, 2852.6 mmol) was added and the reaction mixture was heated at 45° C. for 5 h. The reaction mixture was concentrated, diluted with water and extracted with ethyl acetate. The combined organic layer was washed with water and brine, dried over Na2SO4 and concentrated. It was purified by crystallization using 2% ethyl acetate in n-hexane to yield the title compound as colourless needles (55.0 g, yield: 45.83%): $^1$H NMR (300 MHz, CDCl$_3$): δ 2.54 (s, 4H), 1.23 (s, 6H), 0.92 (s, 6H).

Intermediate 53: 4-Bromo-2,2,5,5-tetramethylcyclohexane-1,3-dione

To a solution of 2,2,5,5-tetramethylcyclohexane-1,3-dione (20.0 g, 118.9 mmol) in CCl$_4$, bromine (17.1 g, 107.0 mmol) in CCl$_4$ (50 mL) was added at 0° C. and stirred at same temperature for 4 h. The reaction mixture was quenched with water, extracted and DCM. The combined extracts were washed with water and brine. The organic layer was dried over anhydrous Na$_2$SO$_4$ and concentrated under reduced pressure. The obtained crude product was purified by silica gel (230-400 mesh) column chromatography to yield the title compound as a white solid (15.0 g, yield: 51.04%):

Intermediate 54: 2-Amino-4,4,7,7-tetramethyl-6,7-dihydro-1,3-benzothiazol-5(4H)-one A 200 ml pressure tube was charged with a solution of 4-bromo-2,2,5,5-tetramethylcyclohexane-1,3-dione (15.0 g, 60.0 mmol) in DMF (150 mL) to which thiourea (4.6 g, 60.0 mmol) and N, N-Diisopropylethylamine (23.2 g 180.0 mmol) was added and heated at 100° C. overnight. The reaction mixture was then quenched with water, extracted and DCM. The combined extracts were washed with water and brine. The organic layer was dried over anhydrous Na$_2$SO$_4$ and concentrated under reduced pressure. The obtained crude product was purified by combiflash to yield the title compound as a black solid (2.0 g, yield: 14.6%).

Intermediate 55: 2-Bromo-4,4,7,7-tetramethyl-6,7-dihydro-1,3-benzothiazol-5(4H)-one To a solution of copper(II)bromide (1.29 g, 5.8 mmol) in Acetonitrile, isoamyl nitrite (1.01 g, 8.7 mmol) was added at 0° C. and then stirred for 15 min. To the stirring mass acetonitrile solution of 2-amino-4,4,7,7-tetramethyl-6,7-dihydro-1,3-benzothiazol-5(4H)-one (1.3 g, 5.8 mmol) was added slowly at 0° C. and the reaction mixture was further stirred for 15 min and then heated at 65° C. for 1 h. The reaction mixture was filtered through celite and the filtrate was washed with water and brine solution dried over Na$_2$SO$_4$ and concentrated to give the title product as brown solid (1.3 g, yield: 77.7%): $^1$H NMR (300 MHz, CDCl$_3$): δ 2.59 (s, 2H), 1.37 (s, 6H), 1.26 (s, 6H).

Intermediate 56: Methyl 4-[(4,4,7,7-tetramethyl-5-oxo-4,5,6,7-tetrahydro-1,3-benzothiazol-2-yl)amino]benzoate A 20 ml pressure tube with screw cap was charged with 2-bromo-4,4,7,7-tetramethyl-6,7-dihydro-1,3-benzothiazol-5(4H)-one (1.2 g, 4.2 mmol), methyl 4-aminobenzoate (1.25 g, 8.3 mmol), CS$_2$CO$_3$ (2.69 g, 8.3 mmol), xphos (0.12 g, 0.25 mmol) and 1,4-dioxane (10 mL). Then it was purged with argon for 15 min. To the reaction mixture Pd$_2$(dba)$_3$ (0.078 g, 0.084 mmol) was added and the mixture was heated at 100° C. overnight. The reaction mixture was diluted with water and extracted with ethyl acetate; organic layer was washed with water and brine solution, dried over Na2SO4 and concentrated. The crude product was recrystallized from methanol to give the title product as colourless solid (0.5 g, yield: 33.3%): $^1$H NMR (300 MHz, DMSO-d$_6$): δ 10.61 (s, 1H), 7.89-7.92 (d, 2H), 7.69-7.72 (d, 2H), 3.81 (s, 3H), 2.70 (s, 2H), 1.35 (s, 6H), 1.26 (s, 6H).

Intermediate 57: Methyl 4-[(5-hydroxy-4,4,7,7-tetramethyl-4,5,6,7-tetrahydro-1,3-benzothiazol-2-yl)amino]benzoate To a solution of methyl 4-[(4,4,7,7-tetramethyl-5-oxo-4,5,6,7-tetrahydro-1,3-benzothiazol-2-yl)amino]benzoate (0.05 g, 0.13 mmol) in methanol (2 mL) and THF (1 mL), NaBH$_4$ (0.005 g, 0.13 mmol) was added at 0° C. and stirred at same temperature for 3 h. Reaction mass was quenched with saturated NH$_4$Cl solution and concentrated. The resulting mass was diluted with ethyl acetate and the organic layer was washed with water and brine solution, dried over Na$_2$SO$_4$ and concentrated to give the title product as colourless solid (0.05 g, yield: 99.4%): $^1$H NMR (300 MHz, DMSO-d$_6$): δ 10.44 (s, 1H), 7.87-7.90 (d, 2H), 7.67-7.70 (d, 2H), 4.73-4.74 (d, 1H), 3.80 (s, 3H), 3.69-3.73 (m, 1H), 1.69-1.75 (m, 2H), 1.32 (s, 3H), 1.25-1.27 (d, 6H), 1.05 (s, 3H).

Intermediate 58: Methyl 4-[(5-hydroxy-4,4,7,7-tetramethyl-4,5,6,7-tetrahydro-1,3-benzothiazol-2-yl)(methyl)amino]benzoate To a 20 ml pressure tube with screw a cap was charged with methyl 4-[(5-hydroxy-4,4,7,7-tetramethyl-4,5,6,7-tetrahydro-1,3-benzothiazol-2-yl)amino]benzoate (0.05 g, 0.14 mmol), CS$_2$CO$_3$ (0.13 g, 0.4 mmol), CH$_3$I (0.039 g, 0.28 mmol) and DMF (2 mL). The reaction mixture was heated at 90° C. overnight. The reaction mixture was diluted with water and extracted with diethyl ether, organic layer was washed with water and brine solutions dried over Na₂SO₄ and concentrated to give the title product as pale brown solid (0.04 g, yield: 77.01%).

Intermediate 59: Methyl 4-[methyl(4,4,7,7-tetramethyl-4,7-dihydro-1,3-benzo thiazol-2-yl)amino]benzoate To a solution of methyl 4-[(5-hydroxy-4,4,7,7-tetramethyl-4,5,6,7-tetrahydro-1,3-benzothiazol-2-yl)(methyl)amino]benzoate (0.1 g, 0.26 mmol) in pyridine (5 mL), POCl₃ (0.08 g, 0.53 mmol) was added at 0° C. and heated at 100° C. in a dean stark apparatus for 1 h. The reaction mixture was quenched with water, extracted and DCM. The combined extracts were washed with water and brine. The organic layer was dried over anhydrous Na₂SO₄ and concentrated reduced pressure to give the title compound as a colourless solid (0.08 g, yield: 74.8%): ¹H NMR (300 MHz, CDCl₃): δ 7.94-7.97 (d, 2H), 7.41-7.44 (d, 2H), 5.38-5.48 (dd, 2H), 3.84 (s, 3H), 3.50 (s, 3H), 1.24-1.25 (d, 6H).

Intermediate 60: Methyl 4-[methyl(4,4,7,7-tetramethyl-4,5,6,7-tetrahydro-1,3-benzothiazol-2-yl)amino]benzoate A Parr shaker vessel was charged with methyl 4-[methyl(4,4,7,7-tetramethyl-4,7-dihydro-1,3-benzothiazol-2-yl)amino]benzoate (0.06 g, 0.16 mmol), ethyl acetate (5 mL) and methanol (2 mL), and purged with N₂ for about 2 min. Then 10% Pd—C (0.02 g) was added to the vessel and it was kept for hydrogenation (50 psi) overnight. The product formation was monitored by LCMS. Then additional 10% Pd—C (50.0 mg) was added and the reaction mixture was once again kept for hydrogenation at 50 psi for 2 days. The solvent was removed under reduced pressure. It was purified by preparative HPLC to give the title compound as a white solid (0.012 g, yield: 19.9%).

Compound 33: 4-[Methyl(4,4,7,7-tetramethyl-4,5,6,7-tetrahydro-1,3-benzothiazol-2-yl)amino]benzoic acid A 10 mL RB flask fitted with magnetic stirrer was charged with methanol (1 mL) and THF (2 mL). To the stirred solvent methyl 4-[methyl(4,4,7,7-tetramethyl-4,5,6,7-tetrahydro-1,3-benzothiazol-2-yl)amino]benzoate (0.015 g, 0.041 mmol) and aq. NaOH (0.016 g, 0.41 mmol) was added and stirred at RT for 12 h. The reaction mixture was evaporated completely and the crude was washed with ether, and diluted with water and then neutralized with 1NHCl and then extracted with ethyl acetate. The organic layer was washed with water and brine, dried over Na₂SO₄ and concentrated. It was purified by trituration with n-hexane to yield the title compound as a white solid (0.01 g, yield: 69.4%): MS (ESI, 120 eV): m/z=345.2 (M+H)⁺.

Example 34: 4-[Methyl(4,4,7,7-tetramethyl-4,7-dihydro-1,3-benzothiazol-2-yl)amino]benzoic acid

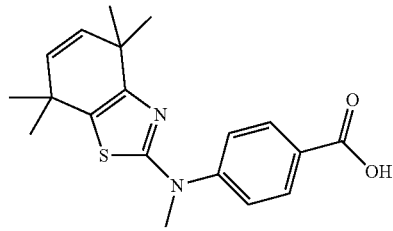

34

Compound 34 was synthesized from 2-bromo-4,4,7,7-tetramethyl-6,7-dihydro-1,3-benzothiazol-5(4H)-one and methyl 4-aminobenzoate by following the procedure described in Scheme 15 (0.01 g, yield: 52.05%); purity: 93.68%.

Example 35: 4-[(5-Ethoxy-4,4,7,7-tetramethyl-4,5,6,7-tetrahydro-1,3-benzothiazol-2-yl)(methyl)amino]benzoic acid

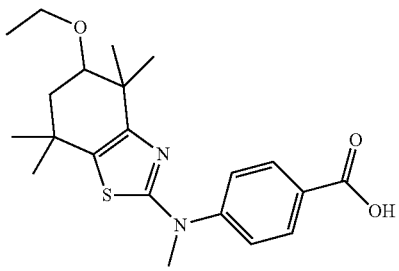

35

Compound 35 was synthesized from 2-bromo-4,4,7,7-tetramethyl-6,7-dihydro-1,3-benzothiazol-5(4H)-one and methyl 4-aminobenzoate by following the procedure described in scheme 16 (0.005 g, yield: 43.28%); purity: 84.49%.

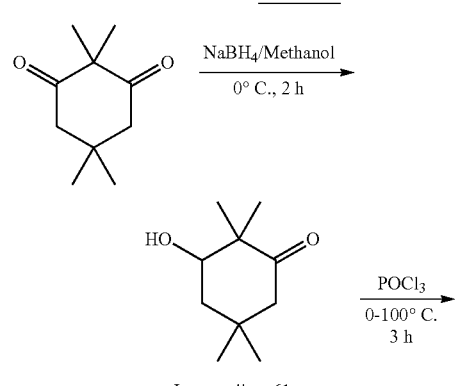

Scheme 18

Intermediate 61

-continued

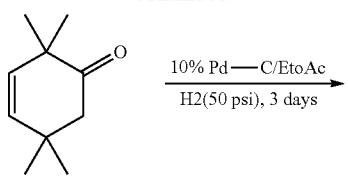

Intermediate 62

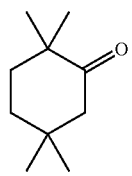

Intermediate 63

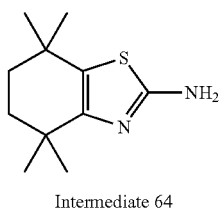

Intermediate 64

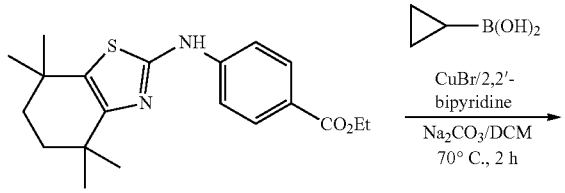

Intermediate 65

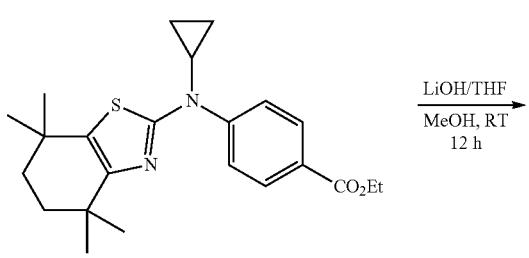

Intermediate 66

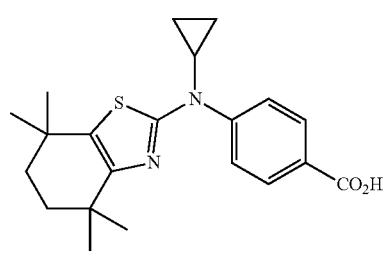

Compound 36

Example 36: 4-[Cyclopropyl(4,4,7,7-tetramethyl-4,5,6,7-tetrahydro-1,3-benzothiazol-2-yl)amino]benzoic acid

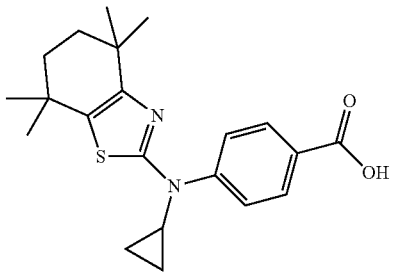

36

Compound 36 was synthesized from 4,4,7,7-tetramethyl-4,5,6,7-tetrahydro-1,3-benzothiazol-2-amine and ethyl 4-iodobenzoate by following the procedure described in scheme 18; purity: 98.84%.

Intermediate 61: 3-Hydroxy-2,2,5,5-tetramethylcyclohexanone

To a stirred solution of 2,2,5,5-tetramethylcyclohexane-1,3-dione (10 g, 59.5 mmol) in methanol (100 mL), $NaBH_4$ (0.67 g, 17.86 mmol) was added at 0° C. portion wise. The reaction mixture was allowed to stir at 0° C. for 2 h. The reaction mixture was quenched with ice. The methanol was removed and extracted with ethyl acetate. The combined extracts were washed with water and brine. The organic layer was dried over anhydrous $Na_2SO_4$ and concentrated. The crude product obtained was purified by column chromatography to give the title compound as a white gummy solid (7.0 g, yield: 100.0%).

Intermediate 62: 2,2,5,5-Tetramethylcyclohex-3-en-1-one

To a stirred solution of 3-hydroxy-2,2,5,5-tetramethylcyclohexanone (8 g, 47.1 mmol) in pyridine (30 mL), was added phosphorous oxy chloride (14.43 g, 94.1 mmol) at 0° C. After addition, reaction mixture was heated to 100° C. with Dean stock apparatus for 2 h. The reaction mixture was quenched with 1.5 N HCl and extracted with ethyl acetate. The combined extracts were washed with water and brine. The organic layer was dried over anhydrous $Na_2SO_4$ and concentrated to give the title compound as yellow liquid (8.0 g, yield: 100.0%).

Intermediate 63: 2,2,5,5-Tetramethylcyclohexanone

A stirred solution of 2,2,5,5-tetramethylcyclohex-3-en-1-one (8 g, 52.6 mmol) in ethyl acetate (80 mL) was purged with nitrogen for 10 min. To the resulting solution 10% Pd—C (3.0 g) was added. The reaction mixture was kept at hydrogenation parr shaker (50 psi) for 3 days. The reaction mixture was filtered through celite pad, washed with ethyl acetate and concentrated to give the title compound as green liquid (3.8 g, yield: 46.76%): $^{13}$C-DEPT NMR (300 MHz, DMSO-$d_6$): δ 50.6, 36.2, 33.8, 28.1, 24.8.

Intermediate 64: 4,4,7,7-Tetramethyl-4,5,6,7-tetrahydro-1,3-benzothiazol-2-amine To a 250 ml pressure tube with screw cap charged with 4,4,7,7-tetramethyl-4,5,6,7-tetrahydro-1,3-benzothiazol-2- amine (6.0 g, 38.9 mmol) in ethanol (30 mL), thiourea (8.9 g, 116.9 mmol) was added and heated at 60° C. for 15 min. To the above solution Iodine (9.8 g, 38.6 mmol) was added and heated at 95° C. overnight. The reaction mixture was quenched with water and extracted with ethyl acetate. The combined extracts were washed with water and brine. The organic layer was dried over anhydrous Na₂SO₄ and concentrated under reduced pressure to give the title compound as yellow solid (0.3 g, yield: 7.51%): MS (ESI, 120 eV): m/z=211.1 (M+H)⁺.

Intermediate 65: Ethyl 4-[(4,4,7,7-tetramethyl-4,5,6,7-tetrahydro-1,3-benzothiazol-2-yl)amino]benzoate To a 100 ml pressure tube with screw cap charged with 3,4,4,7,7-pentamethyl-4,5,6,7-tetrahydro-1-benzothiophen-2-amine (0.3 g, 1.4 mmol) in toluene (5 mL), ethyl 4-iodobenzoate (0.2 g, 0.72 mmol), CS₂CO₃ (0.7 g, 2.16 mmol) and xhos (6.0 g, 38.9 mmol) was added. The reaction mixture was purged with argon for 20 min, after which Pd₂(dba)₃ (0.009 g, 0.04 mmol) was added. The reaction mixture was heated at 100° C. overnight. The reaction mixture was quenched with water and extracted with ethyl acetate. The combined extracts were washed with water and brine. The organic layer was dried over anhydrous Na₂SO₄ and concentrated and reduced. The crude product obtained was purified using combiflash to give the title compound as yellow solid (0.2 g, yield: 39.85%).

Intermediate 66: Ethyl 4-[(cyclopropylmethyl) (4,4,7,7-tetramethyl-4,5,6,7-tetrahydro-1,3-benzothiazol-2-yl)amino]benzoate To a two-neck 25 mL RB flask charged with copper (II) acetate (0.122 g, 0.61 mmol), 2,2'-bipyridine (0.095 g, 0.61 mmol) in DCE (5 mL) was added. The reaction mixture was heated at 70° C. for 30 min, then was added cyclopropylboronic acid (0.1 g, 1.22 mmol), ethyl 4-[(4,4,7,7-tetramethyl-4,5,6,7-tetrahydro-1,3-benzothiazol-2-yl)amino]benzoate (0.22 g, 0.61 mmol), Na₂CO₃ (0.128 g, 1.22 mmol) and molecular sieves (0.25 g) were added at 70° C. and continued the heating overnight. The reaction mixture was quenched with water, extracted with ethyl acetate. The combined extracts were washed with water and brine solution. The organic layer was dried over anhydrous Na₂SO₄ and concentrated under reduced pressure to give the title compound as a yellow semi solid (0.17 g, yield: 71.0%).

Compound 36: 4-[(Cyclopropylmethyl) (4,4,7,7-tetramethyl-4,5,6,7-tetrahydro-1,3-benzothiazol-2-yl)amino]benzoic acid To a stirred solution of ethyl 4-[cyclopropyl(4,4,7,7-tetramethyl-4,5,6,7-tetrahydro-1,3-benzothiazol-2-yl)amino]benzoate (0.17 g, 0.43 mmol) THF (2 mL), was aqueous LiOH (0.1 g, 4.3 mmol) and ethanol 92 mL). The reaction mixture was allowed to stir at RT for overnight. The reaction mixture was concentrated, acidified with 1.5 N HCl and extracted with ethyl acetate. The organic layer was washed with water and brine solution. The organic layer was dried over anhydrous Na₂SO₄ and concentrated under reduced pressure to give the title compound as a white solid (0.12 g, yield: 81.0%): MS (ESI, 120 eV): m/z=371.2 (M+H)⁺.

Example 37: 6-[Cyclopropyl(4,4,7,7-tetramethyl-4,5,6,7-tetrahydro-1,3-benzothiazol-2-yl)amino]pyridine-3-carboxylic acid

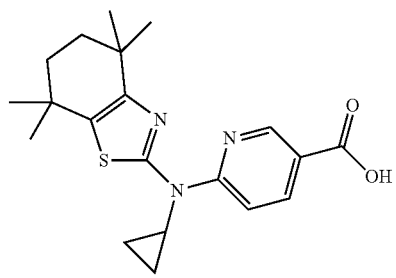

37

Compound 37 was synthesized from 4,4,7,7-tetramethyl-4,5,6,7-tetrahydro-1,3-benzothiazol-2-amine and methyl 6-chloropyridine-3-carboxylate by following the similar procedure described in scheme 18 (0.030 g, yield: 40.4%); purity: 98.66%.

Example 38: 4-[(Cyclopropylmethyl) (4,4,7,7-tetramethyl-4,5,6,7-tetrahydro-1,3-benzothiazol-2-yl)amino]benzoic acid

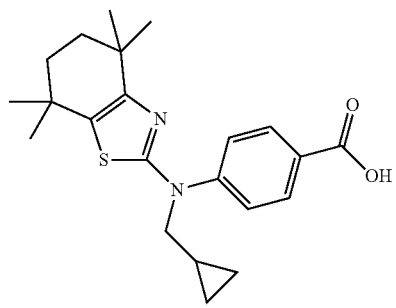

38

Compound 38 was synthesized from 4,4,7,7-tetramethyl-4,5,6,7-tetrahydro-1,3-benzothiazol-2-amine and ethyl 4-iodobenzoate by following the similar procedure described in scheme 18 (0.006 g, yield: 36.4%); purity: 94.93%.

Example 39: 6-[Ethyl(4,4,7,7-tetramethyl-4,5,6,7-tetrahydro-1,3-benzothiazol-2-yl)amino]pyridine-3-carboxylic acid

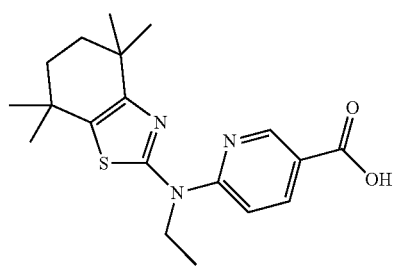

39

Compound 39 was synthesized from 4,4,7,7-tetramethyl-4,5,6,7-tetrahydro-1,3-benzothiazol-2-amine and methyl 6-chloropyridine-3-carboxylate by following the similar procedure described in scheme 18 (0.015 g, yield: 55.63%); purity: 94.07%.

Example 40: 6-[(Cyclopropylmethyl) (4,4,7,7-tetramethyl-4,5,6,7-tetrahydro-1,3-benzothiazol-2-yl)amino]pyridine-3-carboxylic acid

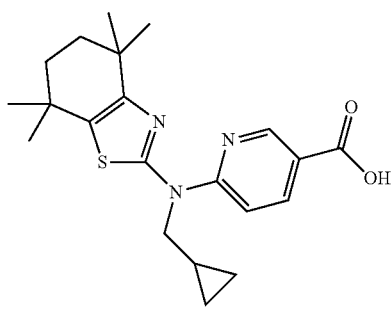

40

Compound 40 was synthesized from 4,4,7,7-tetramethyl-4,5,6,7-tetrahydro-1,3-benzothiazol-2-amine and methyl 6-chloropyridine-3-carboxylate by following the similar procedure described in Scheme 18 (0.04 g, yield: 51.9%); purity: 97.94%.

Scheme 19

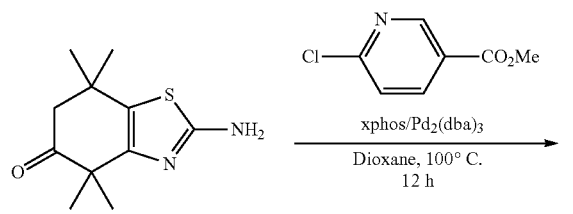

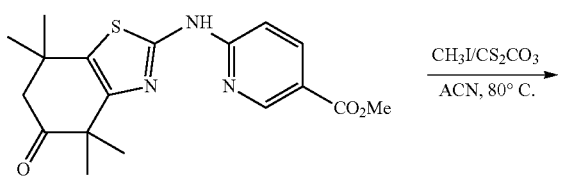

Intermediate 67

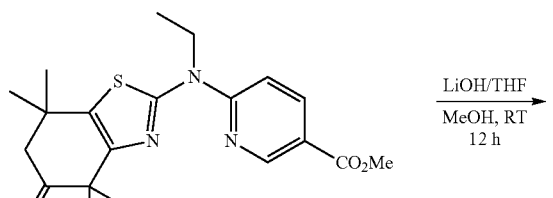

Intermediate 68

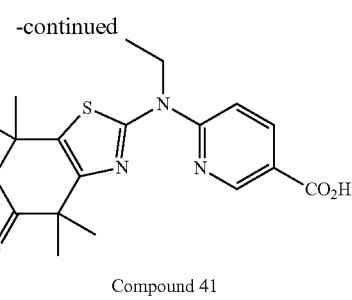

Compound 41

Example 41: 6-[Ethyl(4,4,7,7-tetramethyl-5-oxo-4,5,6,7-tetrahydro-1,3-benzothiazol-2-yl)amino]pyridine-3-carboxylic acid

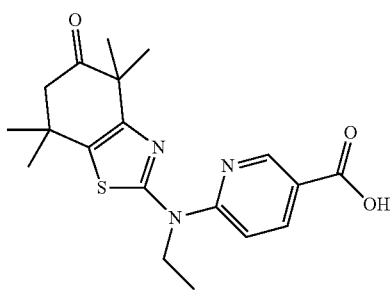

41

Compound 41 was synthesized from 2-amino-4,4,7,7-tetramethyl-6,7-dihydro-1,3-benzothiazol-5(4H)-one and methyl 6-chloropyridine-3-carboxylate by following the procedure described in scheme 19; purity: 91.07%.

Intermediate 67: Methyl 6-[(4,4,7,7-tetramethyl-5-oxo-4,5,6,7-tetrahydro-1,3-benzothiazol-2-yl)amino]pyridine-3-carboxylate To a 100 mL seal tube charged with 2-amino-4,4,7,7-tetramethyl-6,7-dihydro-1,3-benzothiazol-5(4H)-one (0.38 g, 1.75 mmol) and toluene (5 mL), methyl 6-chloropyridine-3-carboxylate (0.15 g, 0.87 mmol, $Cs_2CO_3$ (0.6 g, 1.75 mmol, and xphos (0.05 g, 0.08 mmol) was added at argon atmosphere. The reaction mixture was purged with argon for 20 minutes. Then finally $Pd_2(dba)_3$ (0.032 g, 0.035 mmol) was added to the above solution. The reaction mixture was heated to 100° C. overnight. The reaction mixture was quenched with water and extracted with ethyl acetate. The organic layer was washed with water, brine and dried over anhydrous $Na_2SO_4$, filtered and concentrated. The crude product obtained was purified by silica gel column chromatography to get the title product as a yellow solid (0.025 g, yield: 2.5%).

Intermediate 68: Methyl 6-[ethyl(4,4,7,7-tetramethyl-5-oxo-4,5,6,7-tetrahydro-1,3-benzothiazol-2-yl)amino]pyridine-3-carboxylate To a stirred solution of methyl 6-[(4,4,7,7-tetramethyl-5-oxo-4,5,6,7-tetrahydro-1,3-benzothiazol-2-yl)amino]pyridine-3-carboxylate (0.15 g, 0.42 mmol) in acetonitrile (3 mL), $Cs_2CO_3$ (0.41 g, 1.25 mmol) and $C_2H_5I$ (0.1 g, 0.84 mmol) was added. The reaction mixture was heated to reflux at 90° C. overnight. The reaction mixture was quenched with water and extracted with ethyl acetate, washed with water and brine solution. The organic layer was dried over anhydrous Na₂SO₄ and concentrated under vacuum to obtain the crude oil, which was purified by silica gel column chromatography to give title compound as a pale yellow solid (0.04 g, yield: 25.00%). $^1$H NMR (300 MHz, CDCl₃): δ 8.98-8.99 (d, 1H), 8.16-8.20 (dd, 1H), 6.98-7.01 (d, 1H), 4.35-4.42 (q, 2H), 3.86 (s, 3H), 2.59 (s, 2H), 1.37 (s, 6H), 1.32-1.37 (t, 3H), 1.31 (s, 6H).

Compound 41: 6-[Ethyl(4,4,7,7-tetramethyl-5-oxo-4,5,6,7-tetrahydro-1,3-benzothiazol-2-yl)amino]pyridine-3-carboxylic acid To a stirred solution of methyl 6-[ethyl(4,4,7,7-tetramethyl-5-oxo-4,5,6,7-tetrahydro-1,3-benzothiazol-2-yl)amino]pyridine-3-carboxylate (0.04 g, 0.1 mmol) in THF (1 mL) and methanol (1 mL), LiOH (0.024 g, 1.03 mmol) in water (1 mL) was added. The reaction mixture was allowed to stir at RT overnight. The reaction mixture was concentrated completely and the crude was washed with ether, and diluted with water and then neutralized with citric acid and extracted with ethyl acetate. The organic layer was washed with water and brine, dried over Na₂SO₄, filtered and concentrated. It was purified by trituration with n-hexane to yield the product as white solid (0.02 g, yield: 53.6%): MS (ESI, 120 eV): m/z=374.2 (M+H)⁺.

Scheme 20

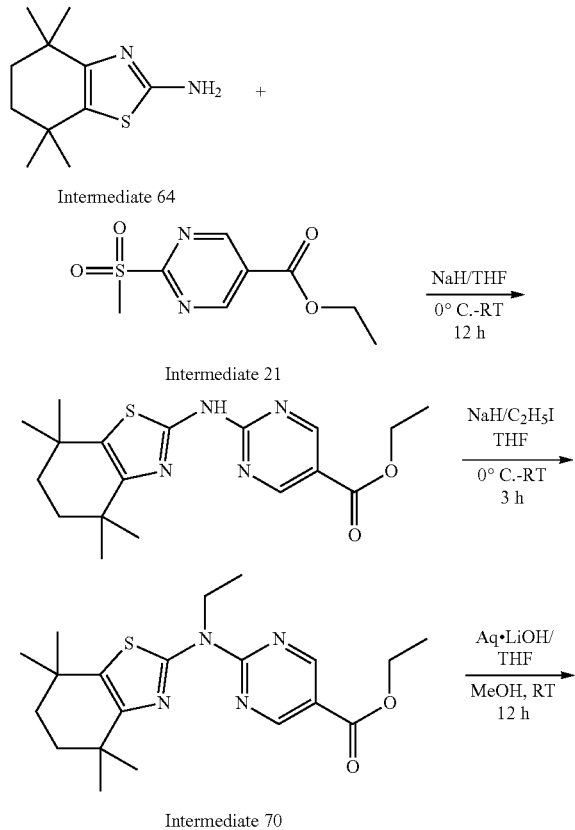

Example 42: 2-[Ethyl(4,4,7,7-tetramethyl-4,5,6,7-tetrahydro-1,3-benzothiazol-2-yl)amino]pyrimidine-5-carboxylic acid

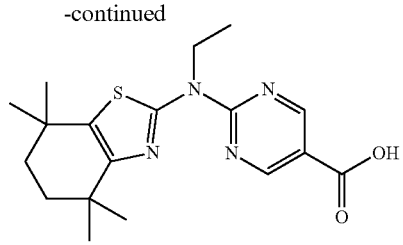

42

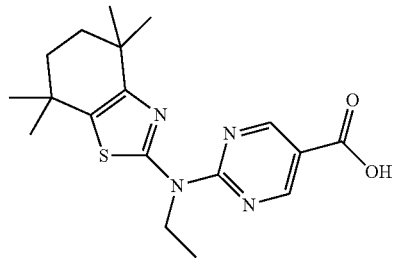

Compound 42 was synthesized from 4,4,7,7-tetramethyl-4,5,6,7-tetrahydro-1,3-benzothiazol-2-amine and ethyl 2-(methylsulfonyl)pyrimidine-5-carboxylate by following the procedure described in scheme 20; purity: 93.88%.

Intermediate 69: Ethyl 2-[(4,4,7,7-tetramethyl-4,5,6,7-tetrahydro-1,3-benzothiazol-2-yl)amino]pyrimidine-5-carboxylate To a stirred solution of NaH (0.2 g, 8.57 mmol) in THF (20 mL), 4,4,7,7-tetramethyl-4,5,6,7-tetrahydro-1,3-benzothiazol-2-amine (1.2 g, 5.71 mmol) and ethyl 2-(methylsulfonyl)pyrimidine-5-carboxylate (2.62 g, 11.43 mmol) in THF (10 mL) was added at 0° C. The reaction mixture was stirred at RT for 12 h. The reaction mixture was quenched with water and extracted with ethyl acetate, washed with water and brine. The organic layer was dried over anhydrous Na₂SO₄ and concentrated under vacuum to obtain the crude product as a yellow gummy solid (2.0 g, yield: 97.00%).

Intermediate 70: Ethyl 2-[ethyl(4,4,7,7-tetramethyl-4,5,6,7-tetrahydro-1,3-benzothiazol-2-yl)amino]pyrimidine-5-carboxylate To a stirred solution of ethyl 2-[(3,4,4,7,7-pentamethyl-4,5,6,7-tetrahydro-1-benzothiophen-2-yl)amino]pyrimidine-5-carboxylate (0.13 g, 0.36 mmol) and CS₂CO₃ (0.29 g, 0.9 mmol) in THF (3 mL), C2H₅I (0.084 g, 0.54 mmol) was added drop wise at 0° C. The reaction mixture was heated at 80° C. for 12 h. The reaction mixture was quenched with ice and extracted with ethyl acetate, washed with water and brine. The organic layer was dried over anhydrous Na₂SO₄ and concentrated under vacuum. The crude product obtained was purified by combiflash to give the title compound as a pale yellow liquid (0.06 g, yield: 38.6%). m/z=389.1 (M+H)⁺. $^1$H NMR (300 MHz, CDCl₃):

δ 9.04 (s, 2H), 4.58-4.65 (q, 2H), 4.28-4.36 (q, 2H), 1.64 (s, 4H), 1.30-1.35 (t, 3H), 1.20 (s, 6H), 1.19 (s, 6H).

Compound 42: 2-[Ethyl(4,4,7,7-tetramethyl-4,5,6,7-tetrahydro-1,3-benzothiazol-2-yl)amino]pyrimidine-5-carboxylic acid To a stirred solution of ethyl 2-[ethyl(4,4,7,7-tetramethyl-4,5,6,7-tetrahydro-1,3-benzothiazol-2-yl)amino]pyrimidine-5-carboxylate (0.06 g, 0.155 mmol) in THF (1 mL), aqueous NaOH (0.062 g, 1.55 mmol) and methanol (1 mL) was added. Then it was stirred at RT overnight. The reaction mixture was concentrated; obtained salt was washed with ether. The residue was dissolved in minimum amount of water, acidified with 1.5 N HCl and extracted with ethyl acetate, dried and concentrated to obtain the title product as an off white solid (0.025 g, yield: 34.67%). MS (ESI, 120 eV): m/z=361.1 (M+H)⁺.

Example 43: 2-[(Cyclopropylmethyl) (4,4,7,7-tetramethyl-4,5,6,7-tetrahydro-1,3-benzothiazol-2-yl)amino]pyrimidine-5-carboxylic acid

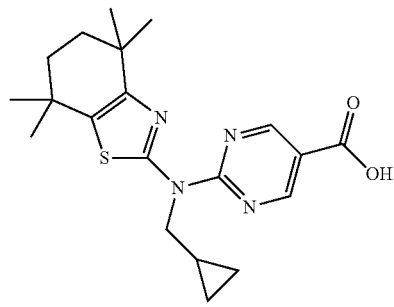

43

Compound 43 was synthesized from 4,4,7,7-tetramethyl-4,5,6,7-tetrahydro-1,3-benzothiazol-2-amine and ethyl 2-(methylsulfonyl)pyrimidine-5-carboxylate by following the procedure described in scheme 20; purity: 97.57%.

Scheme 21

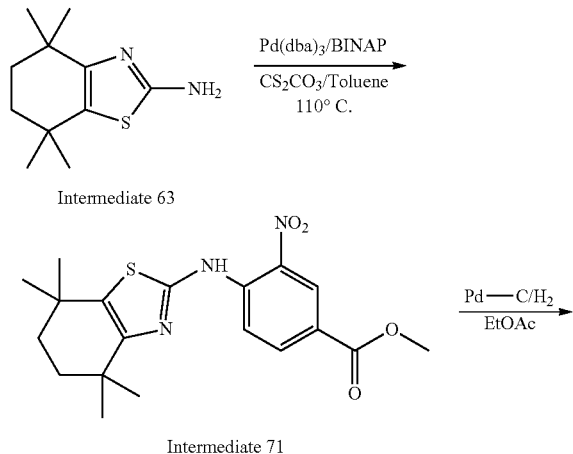

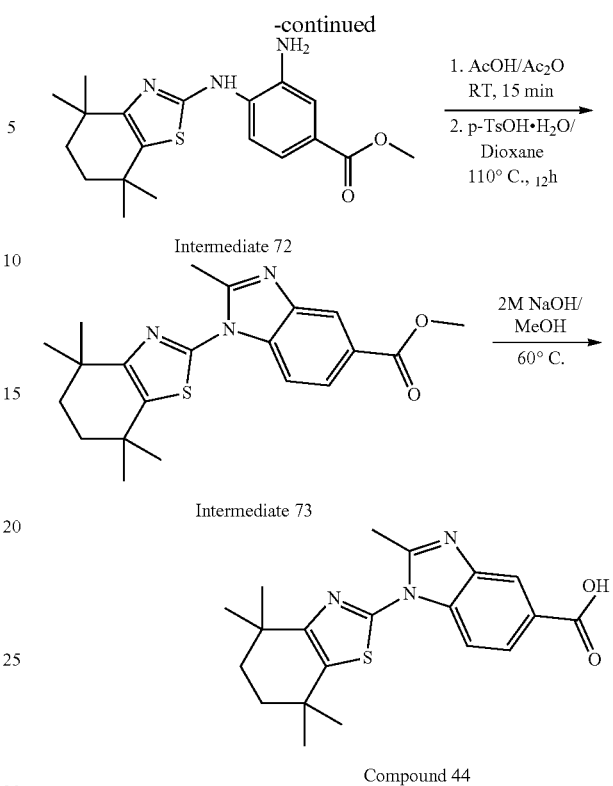

Example 44: 2-Methyl-1-(4,4,7,7-tetramethyl-4,5,6,7-tetrahydro-1,3-benzothiazol-2-yl)-1H-benzimidazole-5-carboxylic acid

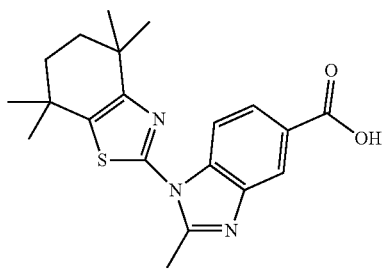

44

Compound 44 was synthesized from 4,4,7,7-tetramethyl-4,5,6,7-tetrahydro-1,3-benzothiazol-2-amine and methyl 4-iodo-3-nitrobenzoate by following the procedure described in scheme 21; purity: 94.22%.

Intermediate 71: Methyl 3-nitro-4-[(4,4,7,7-tetramethyl-4,5,6,7-tetrahydro-1,3-benzothiazol-2-yl)amino]benzoate To a 100 ml pressure tube with screw cap charged with 4-iodo-3-nitrobenzoate (1.0 g, 3.26 mmol) in toluene (10 mL); 4,4,7,7-tetramethyl-4,5,6,7-tetrahydro-1,3-benzothiazol-2-amine (1.3 g, 6.5 mmol), CS₂CO₃ (3.2 g, 9.8 mmol) and xantphos (0.2 g, 0.3 mmol) was added and argon was purged through the reaction mass for 15 min. This was followed by addition of Pd₂(dba)₃ (0.04 g, 0.16 mmol) and heated at 110° C. overnight. The reaction mass was diluted with water and extracted with ethyl acetate. The organic layer was washed with water and brine solution, dried over Na$_2$SO$_4$, filtered and concentrated. The crude product obtained was purified by column chromatography to give the title compound as red colour solid (0.2 g, yield: 15.87%). $^1$H NMR (300 MHz, CDCl$_3$): δ 10.73 (s, 1H), 8.92-8.93 (d, 1H), 8.74-8.77 (d, 1H), 8.20-8.24 (dd, 1H), 3.94 (s, 3H), 1.74 (s, 4H), 1.30-1.31 (d, 12H).

Intermediate 72: Methyl 3-amino-4-[(4,4,7,7-tetramethyl-4,5,6,7-tetrahydro-1,3-benzothiazol-2-yl)amino]benzoate To a stirred solution of methyl 3-nitro-4-[(4,4,7,7-tetramethyl-4,5,6,7-tetrahydro-1,3-benzothiazol-2-yl)amino]benzoate (0.5 g, 1.3 mmol) in methanol (5 mL), ammonium formate (0.41 g, 6.5 mmol) was added followed by addition of zinc dust (0.41 g, 6.4 mmol) at 0° C. The reaction mixture was stirred at RT for 1 h. The reaction mixture was concentrated under reduced pressure. The obtained residue was washed with water, brine solution and dried over anhydrous Na$_2$SO$_4$ and concentrated under vacuum to give title compound as a yellow gummy solid (0.47 g, yield: 100.0%). MS (ESI, 120 eV): m/z=360.1 (M+H)$^+$;

Intermediate 73: Methyl 2-methyl-1-(4,4,7,7-tetramethyl-4,5,6,7-tetrahydro-1,3-benzothiazol-2-yl)-1H-benzimidazole-5-carboxylate To a solution of methyl 3-amino-4-[(4,4,7,7-tetramethyl-4,5,6,7-tetrahydro-1,3-benzothiazol-2-yl)amino]benzoate (0.16 g, 0.45 mmol) in AcOH (4 mL), Ac$_2$O (0.5 mL) was added at RT and stirred at same temperature for 15 min, poured into water (10 mL) and extracted with EtoAc. The organic layer was washed with water and brine, dried over Na$_2$SO$_4$, filtered and evaporated under reduced pressure. The obtained residue was dissolved in dioxane (3 mL), were added p-TsOH.H2O (0.25 g, 1.35 mmol) and dry pyridine (0.1 mL, 1.35 mmol). The mixture was refluxed at 110° C. overnight using dean stark apparatus. The reaction mixture was quenched with water and extracted with EtOAc. The organic layer was washed with water and brine, dried over Na$_2$SO$_4$, filtered and evaporated under reduced pressure. The crude product obtained was purified by column chromatography to give the title compound as yellow liquid (0.05 g, yield: 29.00%). MS (ESI, 120 eV): m/z=384.1 (M+H)$^+$; $^1$H NMR (300 MHz, CDCl$_3$): δ 8.34 (s, 1H), 7.94-7.97 (dd, 1H), 7.63-7.66 (d, 1H), 3.88 (s, 3H), 2.71 (s, 3H), 1.73 (s, 4H), 1.27-1.32 (d, 12H).

Compound 44: 2-Methyl-1-(4,4,7,7-tetramethyl-4,5,6,7-tetrahydro-1,3-benzothiazol-2-yl)-1H-benzimidazole-5-carboxylic acid To a stirred solution of methyl 2-methyl-1-(4,4,7,7-tetramethyl-4,5,6,7-tetrahydro-1,3-benzothiazol-2-yl)-1H-benzimidazole-5-carboxylate (0.05 g, 0.13 mmol) in THF (2 mL), aqueous NaOH (0.03 g, 0.65 mmol) and methanol (2 mL) was added. Then it was stirred at RT overnight. The reaction mixture was concentrated; obtained salt was washed with ether. The residue was dissolved in minimum amount of water, acidified with 1.5 N HCl and extracted with ethyl acetate, dried and concentrated to obtain the title product as a yellow solid (0.02 g, yield: 41.66%). MS (ESI, 120 eV): m/z=370.1 (M+H)$^+$.

Scheme 22:

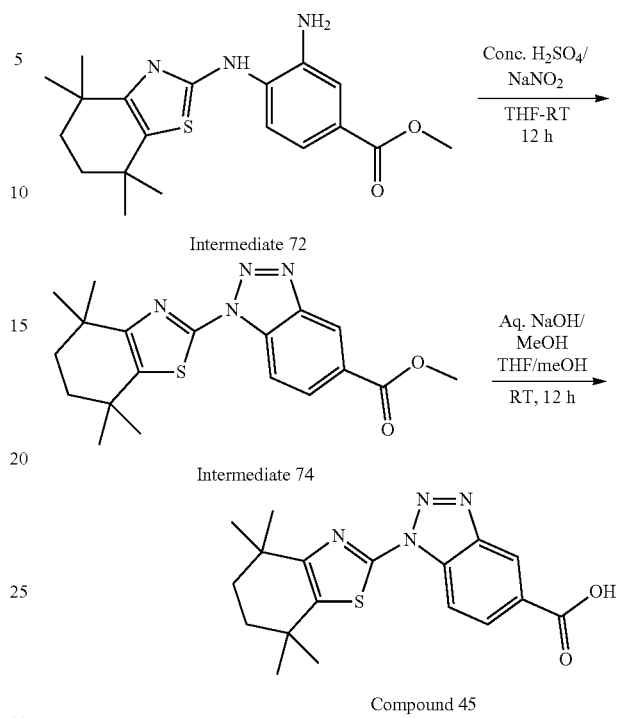

Example 45: 1-(4,4,7,7-Tetramethyl-4,5,6,7-tetrahydro-1,3-benzothiazol-2-yl)-1H-benzotriazole-5-carboxylic acid

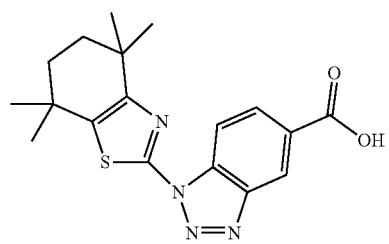

Compound 45 was synthesized from methyl 3-amino-4-[(4,4,7,7-tetramethyl-4,5,6,7-tetrahydro-1,3-benzothiazol-2-yl)amino]benzoate and hydrolysis of ester (intermediate 74) by following the procedure described in scheme 22; purity: 99.81%.

Intermediate 74: Methyl 1-(4,4,7,7-tetramethyl-4,5,6,7-tetrahydro-1,3-benzothiazol-2-yl)-1H-benzotriazole-5-carboxylate To a stirred solution of methyl 3-amino-4-[(4,4,7,7-tetramethyl-4,5,6,7-tetrahydro-1,3-benzothiazol-2-yl)amino]benzoate (0.24 g, 0.67 mmol) in THF (5 mL), Conc.H$_2$SO$_4$ (1.0 mL in 10 mL of water) and NaNO$_2$ (0.075 g, 1.07 mmol) in water was added at 0° C. Then the reaction mixture was stirred at same temperature for 30 min and at RT overnight. The reaction mixture was quenched with NaOH solution (2M solution) and extracted with ethyl acetate. The combined extracts were washed with water and brine solution. The organic layer was dried over anhydrous Na$_2$SO$_4$ and concentrated under reduced pressure. The crude product obtained was purified by silca gel column chromatography to yield the title compound as yellow solid (0.09 g, yield: 36.0%). $^1$H NMR (300 MHz, CDCl$_3$): δ 8.73 (s, 1H), 8.39-8.72 (d, 1H), 8.21-8.25 (dd, 1H), 3.92 (s, 3H), 1.71 (s, 4H), 1.29 (s, 12H).

Compound 45: 1-(4,4,7,7-Tetramethyl-4,5,6,7-tetra-hydro-1,3-benzothiazol-2-yl)-1H-benzotriazole-5-carboxylic acid To a stirred solution of methyl 1-(4,4,7,7-tetramethyl-4,5,6,7-tetrahydro-1,3-benzothiazol-2-yl)-1H-benzotriazole-5-carboxylate (0.09 g, 0.24 mmol) in THF (2 mL), aqueous NaOH (0.048 g, 1.2 mmol) and Methanol (2 mL) was added. Then it was stirred at RT overnight. The reaction mixture was concentrated; obtained salt was washed with ether. The residue was dissolved in minimum amount of water, acidified with 1.5 N HCl and extracted with ethyl acetate, dried and concentrated to obtain the title product as a white solid (0.05 g, yield: 58.13%). MS (ESI, 120 eV): m/z=357.0 (M+H)$^+$.

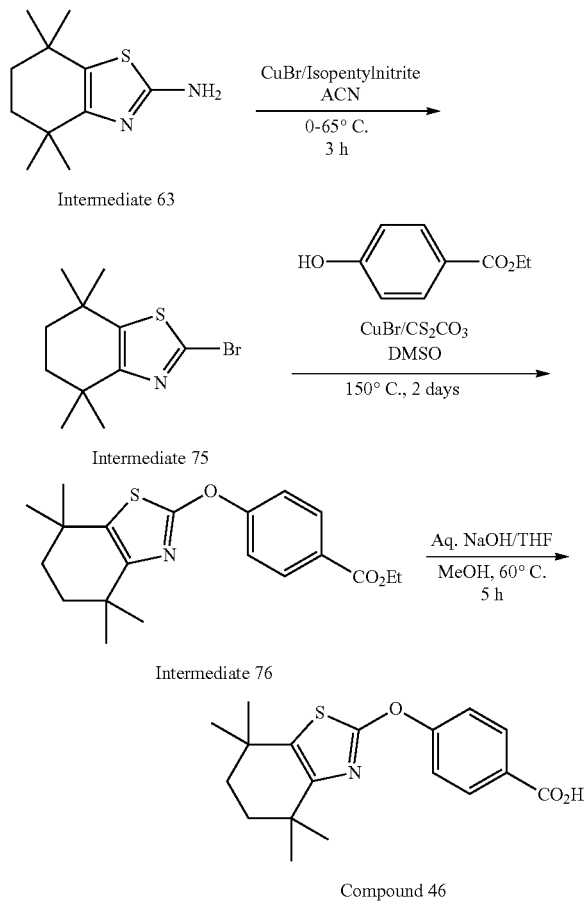

Scheme 23

Example 46: 4-[(4,4,7,7-Tetramethyl-4,5,6,7-tetra-hydro-1,3-benzothiazol-2-yl)oxy]benzoic acid

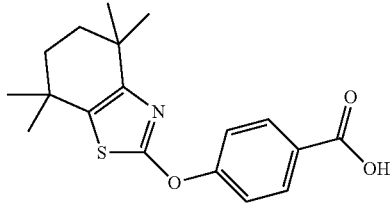

46

Compound 46 was synthesized from 2-bromo-4,4,7,7-tetramethyl-4,5,6,7-tetrahydro-1,3-benzothiazole and methyl 4-hydroxybenzoate by following the procedure described in scheme 23; purity: 95.55%.

Intermediate 75: 2-Bromo-4,4,7,7-tetramethyl-4,5,6,7-tetrahydro-1,3-benzothiazole To a two-neck 250 mL RB flask charged with copper(II) bromide (1.6 g, 7.14 mmol) and acetonitrile (10 mL), Isopentyl nitrite (1.25 g, 10.7 mmol) was added at 0° C. After 15 minutes, 4,4,7,7-tetramethyl-4,5,6,7-tetrahydro-1, and 3-benzothiazol-2-amine (1.5 g, 7.14 mmol) in acetonitrile was added drop wise. It was stirred at 0° C. 15 min and heated at 65° C. for 3 h. The reaction mixture was diluted with water and extracted with ethyl acetate; the organic layer was washed with water and brine solution. The combined extracts were washed with water and brine solution. The organic layer was dried over anhydrous Na$_2$SO$_4$ and concentrated to yield the title compound as yellow liquid (1.5 g, yield: 77.46%). MS (ESI, 120 eV): m/z=276.0 (M+H)$^+$;

Intermediate 76: Methyl 4-[(4,4,7,7-tetramethyl-4,5,6,7-tetrahydro-1,3-benzothiazol-2-yl)oxy]benzoate To a stirred solution of ethyl 4-hydroxybenzoate (0.44 g, 2.6 mmol) in DMSO (10 mL), CS$_2$CO$_3$ (2.1 g, 6.6 mmol) was added. After 10 minutes, 2-bromo-4,4,7,7-tetramethyl-4,5,6,7-tetrahydro-1,3-benzothiazole (0.6 g, 2.2 mmol) was added. Then copper (I) bromide (0.063 g, 4.4 mmol) was added to the above solution. The reaction mixture was heated at 150° C. for 2 days. The reaction mixture was quenched with water and extracted with ethyl acetate. The combined extracts were washed with water and brine. The organic layer was dried over anhydrous Na$_2$SO$_4$ and concentrated and reduced. The crude product obtained was purified silica gel column chromatography to give the title compound as yellow liquid (0.04 g, yield: 25.34%).

Compound 46: 4-[(4,4,7,7-Tetramethyl-4,5,6,7-tetra-hydro-1,3-benzothiazol-2-yl)oxy]benzoic acid To a stirred solution of ethyl 4-[(4,4,7,7-tetramethyl-4,5,6,7-tetrahydro-1,3-benzothiazol-2-yl)oxy]benzoate (0.04 g, 1.0 mmol) in THF (1 mL) and ethanol (1 mL), NaOH (0.018 g, 0.45 mmol) in water (1 mL) was added. The reaction mixture was kept at RT overnight then was heated to 60° C. for 5 h. The reaction mixture was concentrated; obtained salt was washed with ether. The residue was dissolved in minimum amount of water, acidified with 1.5 N HCl and extracted with ethyl acetate, dried and concentrated. Which was further purified by preparative TLC to yield the title compounds as a pale yellow solid (0.01 g, yield: 30.3%). MS (ESI, 120 eV): m/z=332.1 (M+H)+.

Scheme 24

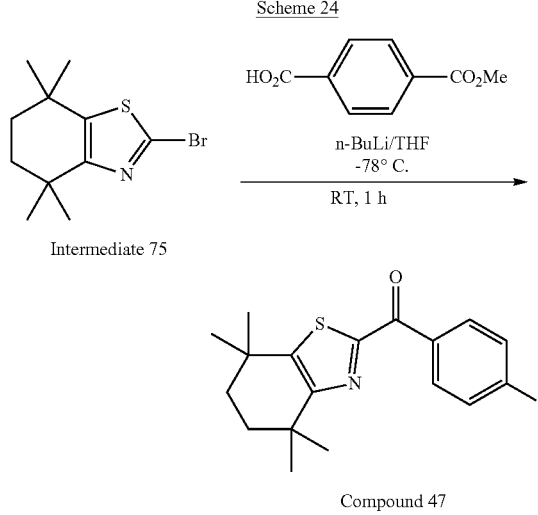

Example 47: 4-[(4,4,7,7-Tetramethyl-4,5,6,7-tetrahydro-1,3-benzothiazol-2-yl) carbonyl]benzoic acid

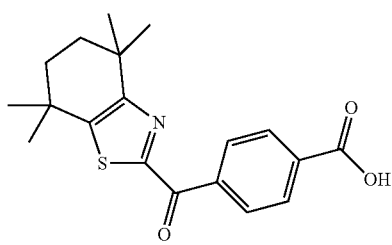

47

Compound 47 was synthesized from 2-bromo-4,4,7,7-tetramethyl-4,5,6,7-tetrahydro-1,3-benzothiazole and 4-(methoxycarbonyl)benzoic acid by following the procedure described in scheme 24; purity: 99.25%.

Compound 47: 4-[(4,4,7,7-Tetramethyl-4,5,6,7-tetrahydro-1,3-benzothiazol-2-yl) carbonyl]benzoic acid To a stirred solution of 4-(methoxycarbonyl)benzoic acid (0.55 g, 2.0 mmol) in THF (10 mL), n-BuLi [1.25 mL (1.6 M solution)] was added at −78° C. under $N_2$ atmosphere. Then 2-bromo-4,4,7,7-tetramethyl-4,5,6,7-tetrahydro-1,3-benzothiazole (0.3 g, 0.0011 mol) in THF (10 mL) was added to the above solution and stir at same temperature about one and half hour and at RT for 1 h. The reaction mixture was quenched with saturated $NH_4Cl$ solution and extracted with ethyl acetate. The combined extracts were washed with water and brine solution. The organic layer was dried over anhydrous $Na_2SO_4$ and concentrated under reduced pressure. The crude product obtained was purified by preparative TLC to yield the title compound as white solid (0.005 g, yield: 0.88%).

Scheme 25

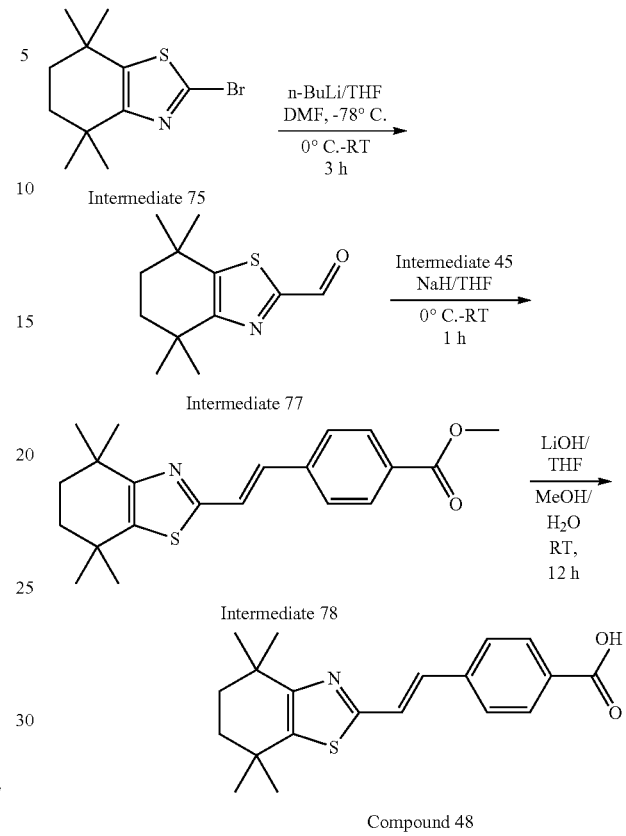

Example 48: 4-[(E)-2-(4,4,7,7-Tetramethyl-4,5,6,7-tetrahydro-1,3-benzothiazol-2-yl) ethenyl]benzoic acid

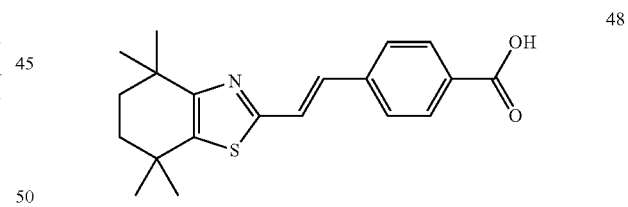

48

Compound 48 was synthesized from 4,4,7,7-tetramethyl-4,5,6,7-tetrahydro-1,3-benzothiazole-2-carbaldehyde and methyl 4-{[bromo (triphenyl)-15-phosphanyl] methyl}benzoate by following the procedure described in scheme 23; purity: 98.05%.

Intermediate 77: 4,4,7,7-Tetramethyl-4,5,6,7-tetrahydro-1,3-benzothiazole-2-carbaldehyde To a two-neck 250 mL RB flask charged with 2-bromo-4,4,7,7-tetramethyl-4,5,6,7-tetrahydro-1,3-benzothiazole (1.0 g, 3.6 mmol) taken in Dry THF (10 mL), n-BuLi [(2.5 mL (1.6M), 4.0 mmol)] was added slowly at −78° C., then it was stirred at −50° C. for 1 h. Then DMF (0.5 mL) was added at the same temperature to the above solution and stirred at RT for 3 h. The reaction mixture was quenched with saturated NH₄Cl solution and was extracted with ethyl acetate. The combined extracts were washed with water and brine solution. The organic layer was dried over anhydrous Na₂SO₄ and concentrated under reduced pressure. The crude product obtained was purified by combiflash to yield the title compound as colourless oily product (0.65 g, yield: 80.55%). ¹H NMR (300 MHz, CDCl₃): δ 9.83 (s, 1H), 1.70 (s, 4H), 1.27-1.29 (d, 2H).

Intermediate 78: Methyl 4-[(E)-2-(4,4,7,7-tetramethyl-4,5,6,7-tetrahydro-1,3-benzothiazol-2-yl) ethenyl]benzoate To a stirred solution of NaH (0.42 g, 1.7 mmol) in dry THF (2 mL), methyl 4-{[bromo (triphenyl)-15-phosphanyl]methyl}benzoate (0.57 g, 1.1 mmol) in THF (2 mL) was added at 0° C. The reaction mixture was stirred at RT for 45 min, then 4,4,7,7-tetramethyl-4,5,6,7-tetrahydro-1,3-benzothiazole-2-carbaldehyde (0.2 g, 0.8 mmol) in THF (1 mL) was added at 0° C. and stirred at RT for 1 h. The reaction mixture was quenched with ice water and extracted with ethyl acetate. The combined extracts were washed with water and brine. The organic layer was dried over anhydrous Na₂SO₄ and concentrated reduced pressure. The crude product obtained was purified by combiflash to yield the title compound as a pale yellow solid (0.266 g, yield: 83.14%).

Compound 48: 4-[(E)-2-(4,4,7,7-Tetramethyl-4,5,6,7-tetrahydro-1,3-benzothiazol-2-yl) ethenyl]benzoic acid A 10 mL RB flask fitted with magnetic stirrer was charged with methanol (3 mL) and THF (3 mL). To the stirred solvent methyl 4-[(E)-2-(4,4,7,7-tetramethyl-4,5,6,7-tetrahydro-1,3-benzothiazol-2-yl) ethenyl]benzoate (0.26 g, 0.7 mmol) and aq. LiOH (0.067 g, 2.8 mmol) was added and stirred at RT for 12 h. The reaction mixture was evaporated completely and the crude was washed with ether, and diluted with water and then neutralized with 1NHCl, then extracted with ethyl acetate, organic layer was washed with water and brine, dried over Na₂SO₄ and concentrated. It was purified by preparative HPLC to yield the title compound as a white solid (0.0022 g, yield: 0.92%): MS (ESI, 120 eV): m/z=342.1 (M+H)⁺.

Example 49: 4-[(Z)-2-(4,4,7,7-Tetramethyl-4,5,6,7-tetrahydro-1,3-benzothiazol-2-yl) ethenyl]benzoic acid

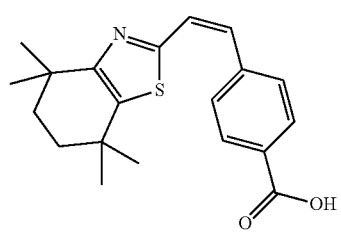

49

Compound 49 was synthesized from 4,4,7,7-tetramethyl-4,5,6,7-tetrahydro-1,3-benzothiazole-2-carbaldehyde and methyl 4-{[bromo (triphenyl)-15-phosphanyl]methyl}benzoate by following the similar procedure described in scheme 25 (0.012 g, yield: 5.02%); purity: 94.64%.

Scheme 26

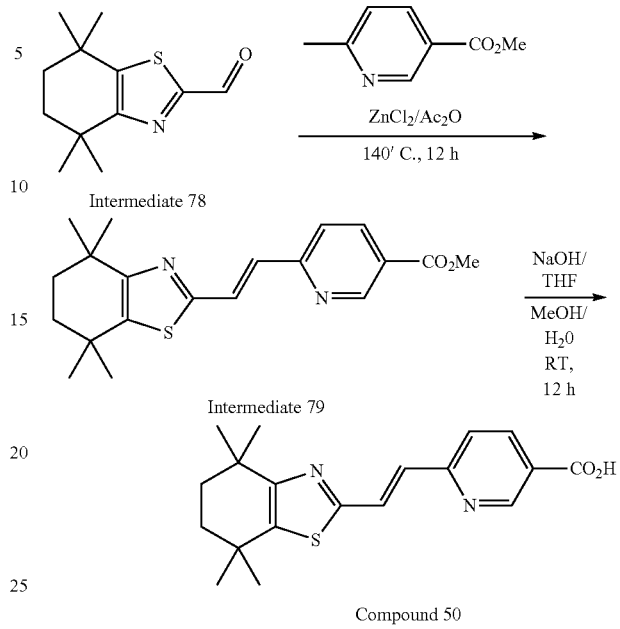

Example 50: 6-[(E)-2-(4,4,7,7-Tetramethyl-4,5,6,7-tetrahydro-1,3-benzothiazol-2-yl) ethenyl]pyridine-3-carboxylic acid

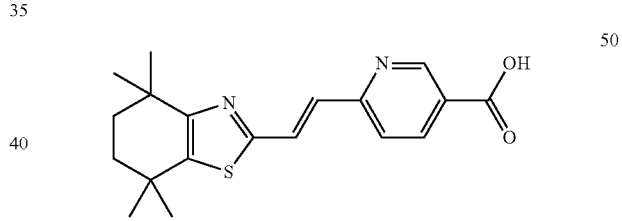

50

Compound 50 was synthesized from 4,4,7,7-tetramethyl-4,5,6,7-tetrahydro-1,3-benzothiazole-2-carbaldehyde and methyl 6-methylpyridine-3-carboxylate by following the procedure described in scheme 26; purity: 91.66%.

Intermediate 79: Methyl 6-[(E)-2-(4,4,7,7-tetramethyl-4,5,6,7-tetrahydro-1,3-benzothiazol-2-yl) ethenyl]pyridine-3-carboxylate To a stirred solution of 4,4,7,7-tetramethyl-4,5,6,7-tetrahydro-1,3-benzothiazole-2-carbaldehyde (0.155 g, 0.6 mmol) in acetic anhydride (0.142 g, 1.3 mmol), methyl 6-methylpyridine-3-carboxylate (0.105 g, 0.6 mmol) and catalytic amount of ZnCl₂ (0.004 g, 0.03 mmol) was added. Then reaction mixture was heated at 140° C. overnight. The reaction mixture was quenched with ice water and extracted with ethyl acetate. The combined extracts were washed with water and brine. The organic layer was dried over anhydrous Na₂SO₄ and concentrated under reduced pressure. The crude product obtained was purified by combiflash to yield the title compound as a pale yellow oily product (0.1 g, yield: 40.07%). ¹H NMR (300 MHz, CDCl₃): δ 9.11 (s, 1H), 8.17-8.20 (d, 1H), 7.73-7.78 (d, 1H), 7.40-7.43 (d, 1H) 7.28-7.33 (d, 1H), 3.89 (s, 3H), 1.67 (s, 4H), 1.26 (s, 12H).

Compound 50: 6-[(E)-2-(4,4,7,7-Tetramethyl-4,5,6, 7-tetrahydro-1,3-benzothiazol-2-yl) ethenyl]pyridine-3-carboxylic acid To a stirred solution of 4-[(E)-2-(4,4,7,7-tetramethyl-4,5, 6,7-tetrahydro-1,3-benzothiazol-2-yl) ethenyl]benzoate (0.1 g, 0.28 mmol) in THF (3 mL), Aq. NaOH (0.022 g, 0.56 mmol) and methanol (3 mL) was added. The reaction mixture stirred at RT for 12 h. The reaction mixture was concentrated completely and the crude was washed with ether, and diluted with water and then neutralized with 1NHCl, then extracted with ethyl acetate, organic layer was washed with water and brine, dried over $Na_2SO_4$ and concentrated. It was purified by preparative TLC to yield the title compound as a yellow solid (0.01 g, yield: 9.73%): MS (ESI, 120 eV): m/z=343.1 $(M+H)^+$.

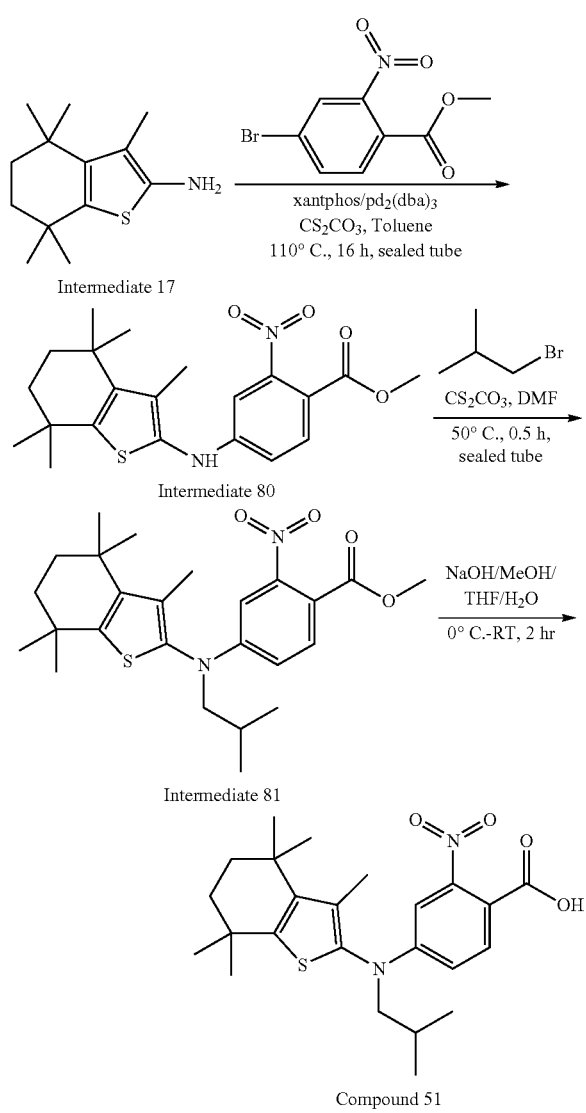

Example 51: 4-[(2-methylpropyl) (3,4,4,7,7-pentamethyl-4,5,6,7-tetrahydro-1-benzothiophen-2-yl) amino]-2-nitrobenzoic acid

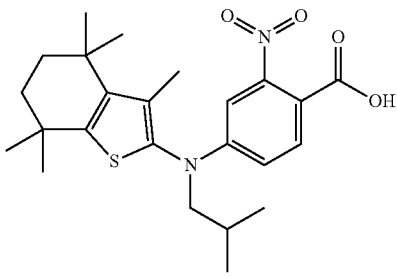 [SMILES: Cc1c(N(CC(C)C)c2ccc(C(=O)O)c([N+](=O)[O-])c2)sc2c1C(C)(C)CCC2(C)C]

Compound 51 was synthesized from methyl 3,4,4,7,7-pentamethyl-4,5, 6,7-tetrahydro-1-benzothiophen-2-amine and methyl 4-bromo-2-nitrobenzoate by following the procedure described in scheme 27; purity: 94.91%.

Intermediate 80: Methyl 2-nitro-4-[(3,4,4,7,7-pentamethyl-4,5,6,7-tetrahydro-1-benzothiophen-2-yl) amino]benzoate To a stirred solution of 3,4,4,7,7-pentamethyl-4,5,6,7-tetrahydro-1-benzothiophen-2-amine (0.31 g, 1.4 mmol) in toluene (3 mL), methyl 4-bromo-2-nitrobenzoate (0.18 g, 0.69 mmol) and $Cs_2CO_3$ (0.67 g, 2.1 mmol) was added. The above solution was purged with argon for 15 min. To the stirred solution Xantphos (0.019 g, 0.03 mmol) was added followed by addition of $Pd_2$ $(dba)_3$ (0.012 g, 0.014 mmol). The reaction mixture was heated to reflux at 110° C. for 16 hours. Then the reaction mixture was cooled to RT, poured into water and extracted with ethyl acetate. The combined extracts were washed with water and brine solution. The organic layer was dried over anhydrous $Na_2SO_4$ and concentrated in vacuum. The crude product obtained was purified by column chromatography to yield the title compound as a yellow gummy product (0.07 g, yield: 25.93%).

Intermediate 81: methyl 4-[(2-methylpropyl) (3,4,4, 7,7-pentamethyl-4,5,6,7-tetrahydro-1-benzothiophen-2-yl)amino]-2-nitrobenzoate To a stirred solution of methyl 2-nitro-4-[(3,4,4,7,7-pentamethyl-4,5,6,7-tetrahydro-1-benzothiophen-2-yl)amino] benzoate (0.07 g, 0.17 mmol) in DMF (3 mL), cesium carbonate (0.17 g, 0.51 mmol) and isobutyl bromide (0.05 g, 0.34 mmol) was added at 0° C. in a sealed tube. Reaction mixture was heated to 50° C. for 30 minutes. Then the reaction mixture was cooled to RT, poured into water and extracted with ethyl acetate. The combined extracts were washed with water and brine solution. The organic layer was dried over anhydrous $Na_2SO_4$ and concentrated in vacuum. The crude product obtained was purified by column chromatography to yield the title compound as a yellow gummy product (0.015 g, yield: 19.48%).

Compound 51: 4-[(2-methylpropyl) (3,4,4,7,7-pentamethyl-4,5,6,7-tetrahydro-1-benzothiophen-2-yl) amino]-2-nitrobenzoic acid A 25 mL RB flask fitted with magnetic stirrer was charged with methanol (0.5 mL) and THF (0.5 mL). To the stirred solvent, methyl 4-[(2-methylpropyl)(3,4,4,7,7-pentamethyl-4,5,6,7-tetrahydro-1-benzothiophen-2-yl)amino]-2-nitrobenzoate (0.015 g, 0.03 mmol) and aq. NaOH (0.006 g, 0.16 mmol) was added at 0° C. Reaction mixture was stirred at RT for 2 h. The reaction mixture was concentrated completely and the crude was washed with ether, and diluted with water and then neutralized with 1.5N hydrochloric acid, then extracted with ethyl acetate. The organic layer was washed with water and brine, dried over $Na_2SO_4$, filtered and concentrated. The obtained solid was triturated with hexane to give the title compound as a yellow solid (0.01 g, yield: 68.49%): MS (ESI, 120 eV): m/z=445.2 $(M+H)^+$.

Example 52: 6-[(cyclopropyl methyl) (4,4,7,7-tetramethyl-5-oxo-4,5,6,7-tetrahydro-1,3-benzothiazol-2-yl)amino]pyridine-3-carboxylic acid

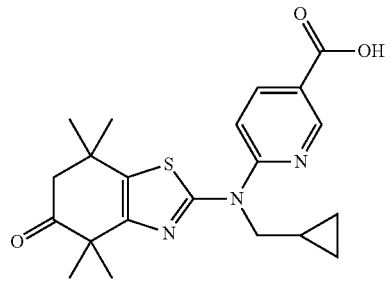 [SMILES: CC1(C)CC(=O)C(C)(C)c2nc(N(CC3CC3)c3ccc(C(=O)O)cn3)sc21]

Compound 52 was synthesized from methyl 6-[(4,4,7,7-tetramethyl-5-oxo-4,5,6,7-tetrahydro-1,3-benzothiazol-2-yl)amino]pyridine-3-carboxylate (Intermediate-67) and (bromomethyl)cyclopropane by following the procedure described in scheme 27; purity: 96.73%.

Example 53: 4-[(2-methylpropyl) (4,4,7,7-tetramethyl-5-oxo-4,5,6,7-tetrahydro-1,3-benzothiazol-2-yl)amino]benzoic acid

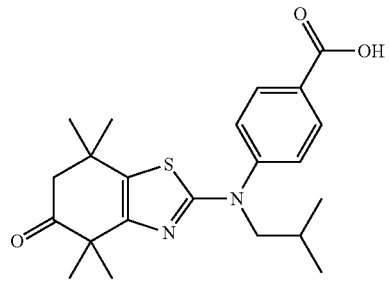 [SMILES: CC(C)CN(c1ccc(C(=O)O)cc1)c1nc2c(s1)C(C)(C)CC(=O)C2(C)C]

Compound 53 was synthesized from methyl 4-[(4,4,7,7-tetramethyl-5-oxo-4,5,6,7-tetrahydro-1,3-benzothiazol-2-yl)amino]benzoate (Intermediate-56) and 1-bromo-2-methylpropane by following the procedure described in scheme 27; purity: 98.52%

Example 54: 2-methoxy-4-[(2-methylpropyl)(3,4,4,7,7-pentamethyl-4,5,6,7-tetrahydro-1-benzothiophen-2-yl)amino]benzoic acid

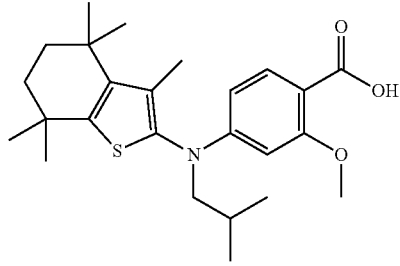 [SMILES: COc1cc(N(CC(C)C)c2sc3c(c2C)C(C)(C)CCC3(C)C)ccc1C(=O)O]

Compound 54 was synthesized from coupling of 3,4,4,7,7-pentamethyl-4,5,6,7-tetrahydro-1-benzothiophen-2-amine (Intermediate-17) and methyl 4-iodo-2-methoxybenzoate, followed by reaction with 1-bromo-2-methylpropane as the procedure described in scheme 27; purity: 78.65%.

Example 55: 2-(cyclopropyl methoxy)-4-[(2-methylpropyl) (3,4,4,7,7-pentamethyl-4,5, 6,7-tetrahydro-1-benzothiophen-2-yl)amino]benzoic acid

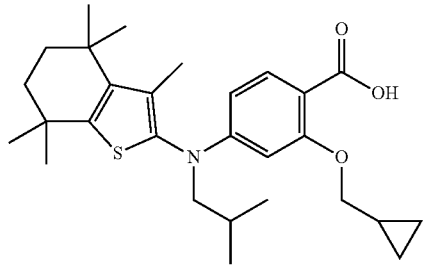 [SMILES: Cc1c(N(CC(C)C)c2ccc(C(=O)O)c(OCC3CC3)c2)sc2c1C(C)(C)CCC2(C)C]

Compound 55 was synthesized from coupling of 3,4,4,7,7-pentamethyl-4,5,6,7-tetrahydro-1-benzothiophen-2-amine (Intermediate-17) and methyl 2-(cyclopropyl methoxy)-4-iodobenzoate, followed by reaction with 1-bromo-2-methylpropane as the procedure described in scheme 27; purity: 93.67%.

Example 56: 4-[(2-methylpropyl) (3,4,4,7,7-pentamethyl-4,5,6,7-tetrahydro-1-benzothiophen-2-yl)amino]-2-(prop-2-yn-1-yloxy)benzoic acid

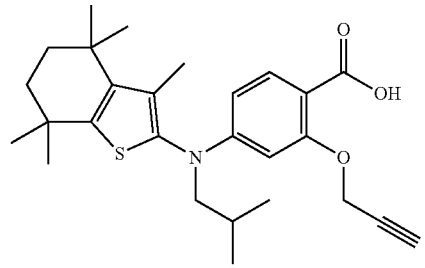 [SMILES: C#CCOc1cc(N(CC(C)C)c2sc3c(c2C)C(C)(C)CCC3(C)C)ccc1C(=O)O]

Compound 56 was synthesized from coupling of 3,4,4,7,7-pentamethyl-4,5,6,7-tetrahydro-1-benzothiophen-2-amine (Intermediate-17) and methyl 4-iodo-2-(prop-2-yn-1-yloxy)benzoate, followed by reaction with 1-bromo-2-methylpropane as the procedure described in scheme 27; purity: 77.64%.

Example 57: 4-[(2-methylpropyl) (3,4,4,7,7-pentamethyl-4,5,6,7-tetrahydro-1-benzothiophen-2-yl)amino]-2-phenoxybenzoic acid

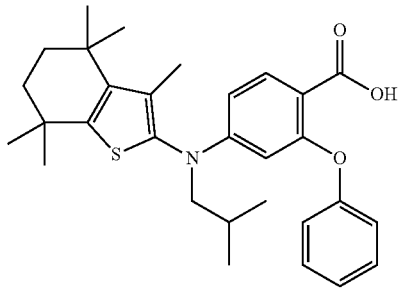 [SMILES: Cc1c(N(CC(C)C)c2ccc(C(=O)O)c(Oc3ccccc3)c2)sc2c1C(C)(C)CCC2(C)C]

Compound 57 was synthesized from coupling of 3,4,4,7,7-pentamethyl-4,5,6,7-tetrahydro-1-benzothiophen-2-amine (Intermediate-17) and methyl 4-iodo-2-phenoxybenzoate, followed by reaction with 1-bromo-2-methylpropane as the procedure described in scheme 27; purity: 93.79%

Example 58: 2-methyl-4-[(2-methylpropyl) (4,4,7,7-tetramethyl-4,5,6,7-tetrahydro-1, 3-benzothiazol-2-yl)amino]benzoic acid

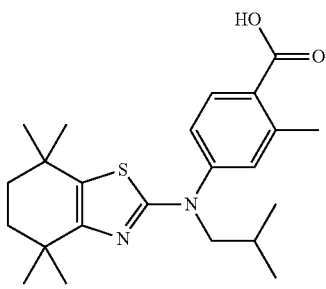 [SMILES: Cc1cc(N(CC(C)C)c2nc3c(s2)C(C)(C)CCC3(C)C)ccc1C(=O)O]

Compound 58 was synthesized from coupling of 4,4,7,7-tetramethyl-4,5, 6,7-tetrahydro-1,3-benzothiazol-2-amine (Intermediate-64) and methyl 4-bromo-2-methylbenzoate, followed by reaction with 1-bromo-2-methylpropane as the procedure described in scheme 27; purity: 97.99%

Example 59: 4-[(cyclopropyl methyl) (4,4,7,7-tetramethyl-4,5,6,7-tetrahydro-1,3-benzothiazol-2-yl)amino]-2-methylbenzoic acid

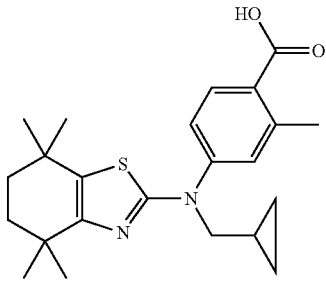 [SMILES: Cc1cc(N(CC2CC2)c2nc3c(s2)C(C)(C)CCC3(C)C)ccc1C(=O)O]

Compound 59 was synthesized from coupling of 4,4,7,7-tetramethyl-4,5, 6,7-tetrahydro-1,3-benzothiazol-2-amine (Intermediate 64) and methyl 4-bromo-2-methylbenzoate, followed by reaction with 1-bromo-2-methylpropane as the procedure described in scheme 27; purity: 98.80%

Example 60: 4-[(cyclopropyl methyl) (4,4,7,7-tetramethyl-4,5,6,7-tetrahydro-1,3-benzothiazol-2-yl)amino]-3-methylbenzoic acid

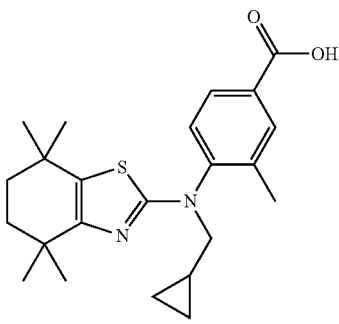 [SMILES: Cc1cc(C(=O)O)ccc1N(CC1CC1)c1nc2c(s1)C(C)(C)CCC2(C)C]

Compound 60 was synthesized from coupling of 4,4,7,7-tetramethyl-4,5, 6,7-tetrahydro-1,3-benzothiazol-2-amine (Intermediate 64) and methyl 4-bromo-3-methylbenzoate, followed by reaction with (bromomethyl)cyclopropane as the procedure described in scheme 27; purity: 93.08%

Example 61: 3-methyl-4-[(2-methylpropyl) (4,4,7,7-tetramethyl-4,5,6,7-tetrahydro-1, 3-benzothiazol-2-yl)amino]benzoic acid

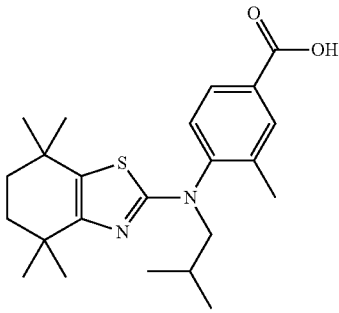 [SMILES: Cc1cc(C(=O)O)ccc1N(CC(C)C)c1nc2c(s1)C(C)(C)CCC2(C)C]

Compound 61 was synthesized from coupling of 4,4,7,7-tetramethyl-4,5, 6,7-tetrahydro-1,3-benzothiazol-2-amine (Intermediate 64) and methyl 4-bromo-3-methylbenzoate, followed by reaction with 1-bromo-2-methylpropane as the procedure described in scheme 27; purity: 98.15%.

Example 62: 4-[prop-2-en-1-yl(4,4,7,7-tetramethyl-4,5,6,7-tetrahydro-1,3-benzothiazol-2-yl)amino]benzoic acid

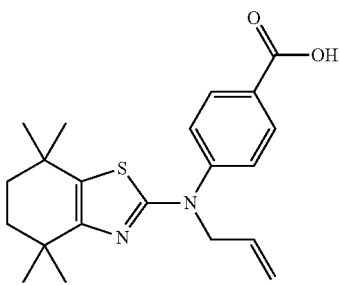 [SMILES: C=CCN(c1ccc(C(=O)O)cc1)c1nc2c(s1)C(C)(C)CCC2(C)C]

Compound 62 was synthesized from ethyl 4-[(4,4,7,7-tetramethyl-4,5,6,7-tetrahydro-1,3-benzothiazol-2-yl)amino]benzoate (Intermediate-65) and 3-bromoprop-1-ene by following the procedure described in scheme 27; purity: 99.06%.

Example 63: 5-[(4-carboxyphenyl) (4,4,7,7-tetramethyl-4,5,6,7-tetrahydro-1,3-benzothiazol-2-yl)amino]furan-2-carboxylic acid

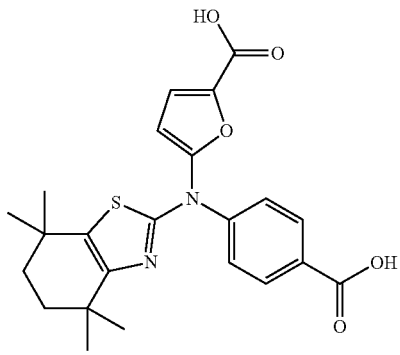 [SMILES: CC1(C)CCC(C)(C)c2sc(N(c3ccc(C(=O)O)cc3)c3ccc(C(=O)O)o3)nc21]

Compound 63 was synthesized from ethyl 4-[(4,4,7,7-tetramethyl-4,5,6,7-tetrahydro-1,3-benzothiazol-2-yl)amino]benzoate (Intermediate-65) and methyl 5-bromofuran-2-carboxylate by following the procedure described in scheme 27; purity: 89.73%

Example 64: 6-[(2-methylpropyl) (4,4,7,7-tetramethyl-4,5,6,7-tetrahydro-1,3-benzothiazol-2-yl)amino]pyridine-3-carboxylic acid

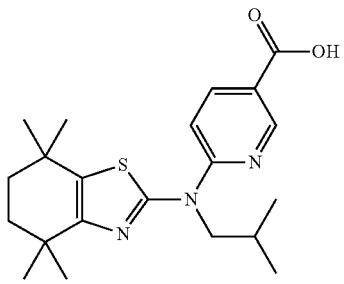 [SMILES: CC(C)CN(c1ccc(C(=O)O)cn1)c1nc2c(s1)C(C)(C)CCC2(C)C]

Compound 64 was synthesized from coupling of 4,4,7,7-tetramethyl-4,5,6,7-tetrahydro-1,3-benzothiazol-2-amine (Intermediate 64) and ethyl 6-chloropyridine-3-carboxylate, followed by reaction with 1-bromo-2-methylpropane as the procedure described in scheme 27; purity: 95.24%.

Example 65: 6-[propyl(4,4,7,7-tetramethyl-4,5,6,7-tetrahydro-1,3-benzothiazol-2-yl)amino]pyridine-3-carboxylic acid

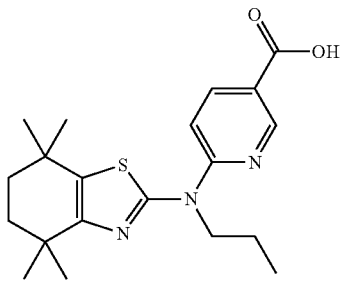 [SMILES: CCCN(c1ccc(C(=O)O)cn1)c1nc2c(s1)C(C)(C)CCC2(C)C]

Compound 65 was synthesized from coupling of 4,4,7,7-tetramethyl-4,5,6,7-tetrahydro-1,3-benzothiazol-2-amine (Intermediate 64) and ethyl 6-chloropyridine-3-carboxylate, followed by reaction with 1-bromopropane as the procedure described in scheme 27; purity: 92.04%

Example 66: 6-[benzyl(4,4,7,7-tetramethyl-4,5,6,7-tetrahydro-1,3-benzothiazol-2-yl)amino]pyridine-3-carboxylic acid

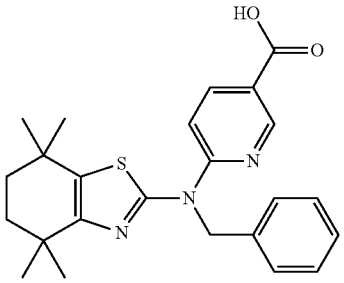 [SMILES: CC1(C)CCC(C)(C)c2sc(N(Cc3ccccc3)c3ccc(C(=O)O)cn3)nc21]

Compound 66 was synthesized from coupling of 4,4,7,7-tetramethyl-4,5,6,7-tetrahydro-1,3-benzothiazol-2-amine (Intermediate 64) and ethyl 6-chloropyridine-3-carboxylate, followed by reaction with (bromomethyl)benzene by following the procedure described in scheme 27; Purity: 94.27%.

Example 67: 5-[(2-methylpropyl) (4,4,7,7-tetramethyl-4,5,6,7-tetrahydro-1,3-benzothiazol-2-yl)amino]pyridine-2-carboxylic acid

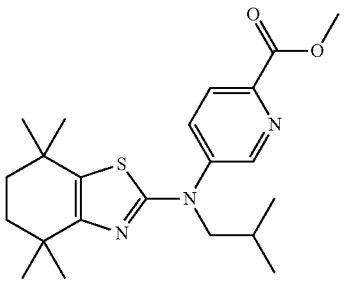 [SMILES: COC(=O)c1ccc(N(CC(C)C)c2nc3c(s2)C(C)(C)CCC3(C)C)cn1]

Compound 67 was synthesized from coupling of 4,4,7,7-tetramethyl-4,5,6,7-tetrahydro-1,3-benzothiazol-2-amine (Intermediate 64) and methyl 5-chloropyridine-2-carboxylate, followed by reaction with 1-bromo-2-methylpropane as the procedure described in scheme 27; purity: 82.46%.

Example 68: 6-[benzyl(4,4,7,7-tetramethyl-4,5,6,7-tetrahydro-1,3-benzothiazol-2-yl)amino]-5-chloropyridine-3-carboxylic acid

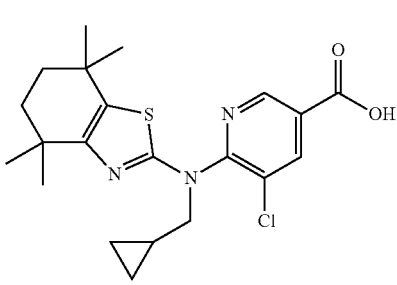 [SMILES: CC1(C)CCC(C)(C)c2sc(N(CC3CC3)c3ncc(C(=O)O)cc3Cl)nc21]

Compound 68 was synthesized from coupling of 4,4,7,7-tetramethyl-4,5, 6,7-tetrahydro-1,3-benzothiazol-2-amine (Intermediate-64) and methyl 5,6-dichloropyridine-3-carboxylate, followed by reaction with (bromomethyl)cyclopropane as the procedure described in scheme 27; purity: 92.59%

Example 69: 5-chloro-6-[(2-methylpropyl) (4,4,7,7-tetramethyl-4,5,6,7-tetrahydro-1, 3-benzothiazol-2-yl)amino]pyridine-3-carboxylic acid

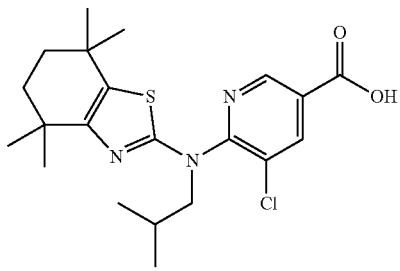 [SMILES: CC(C)CN(c1nc2c(s1)C(C)(C)CCC2(C)C)c1ncc(C(=O)O)cc1Cl]

Compound 69 was synthesized from coupling of 4,4,7,7-tetramethyl-4,5, 6,7-tetrahydro-1,3-benzothiazol-2-amine (Intermediate-64) and methyl 5,6-dichloropyridine-3-carboxylate, followed by reaction with 1-bromo-2-methylpropane as the procedure described in scheme 27; purity: 91.69%.

Example 70: 4-chloro-6-[(cyclopropylmethyl) (4,4,7,7-tetramethyl-4,5,6,7-tetrahydro-1,3-benzothiazol-2-yl)amino]pyridine-3-carboxylic acid

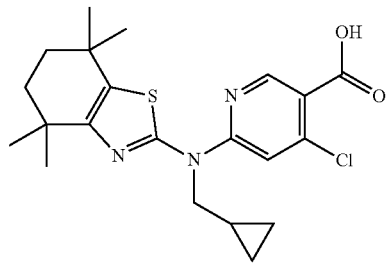 [SMILES: CC1(C)CCC(C)(C)c2sc(N(CC3CC3)c3cc(Cl)c(C(=O)O)cn3)nc21]

Compound 70 was synthesized from coupling of 4,4,7,7-tetramethyl-4,5, 6,7-tetrahydro-1,3-benzothiazol-2-amine (Intermediate-64) and methyl 4,6-dichloropyridine-3-carboxylate, followed by reaction with (bromomethyl)cyclopropane as the procedure described in scheme 27; purity: 93.32%.

Example 71: 4-[(cyclopropyl methyl) (4,4,7,7-tetramethyl-4,5,6,7-tetrahydro-1,3-benzothiazol-2-yl)amino]-3-methoxybenzoic acid

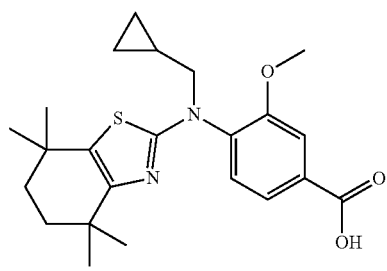 [SMILES: COc1cc(C(=O)O)ccc1N(CC1CC1)c1nc2c(s1)C(C)(C)CCC2(C)C]

Compound 71 was synthesized from coupling of 4,4,7,7-tetramethyl-4,5, 6,7-tetrahydro-1,3-benzothiazol-2-amine (Intermediate-64) and methyl 4-iodo-3-methoxybenzoate, followed by reaction with (bromomethyl)cyclopropane as the procedure described in scheme 27; purity: 92.71%

Example 72: methyl 4-[(cyclopropyl methyl) (4,4,7,7-tetramethyl-4,5,6,7-tetrahydro-1,3-benzothiazol-2-yl)amino]-2-methoxybenzoate

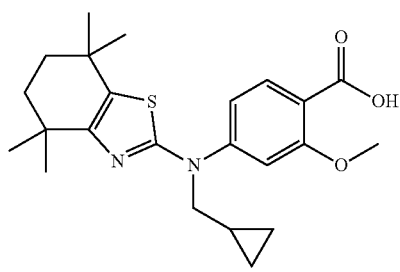

Compound 72 was synthesized from coupling of 4,4,7,7-tetramethyl-4,5, 6,7-tetrahydro-1,3-benzothiazol-2-amine (Intermediate-64) and methyl 4-iodo-2-methoxybenzoate, followed by reaction with (bromomethyl)cyclopropane as the procedure described in scheme 27; purity: 97.96%

Example 73: 2-methoxy-4-[(2-methylpropyl) (4,4,7,7-tetramethyl-4,5,6,7-tetrahydro-1,3-benzothiazol-2-yl)amino]benzoic acid

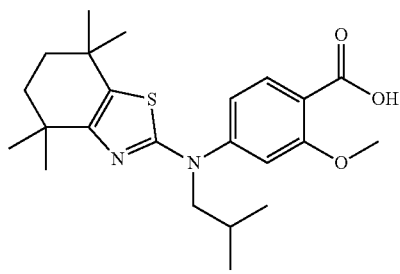

Compound 73 was synthesized from coupling of 4,4,7,7-tetramethyl-4,5, 6,7-tetrahydro-1,3-benzothiazol-2-amine (Intermediate-64) and methyl 4-iodo-2-methoxybenzoate, followed by reaction with 1-bromo-2-methylpropane as the procedure described in scheme 27; purity: 99.39%.

Scheme 28

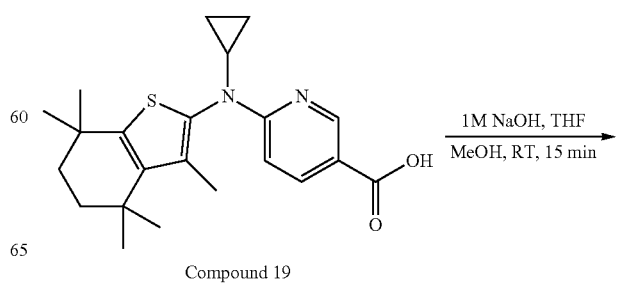

Compound 19

-continued

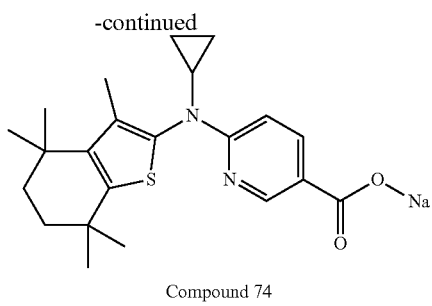

Compound 74

Example 74: sodium 6-[cyclopropyl(3,4,4,7,7-pentamethyl-4,5,6,7-tetrahydro-1-benzothiophen-2-yl)amino]pyridine-3-carboxylate

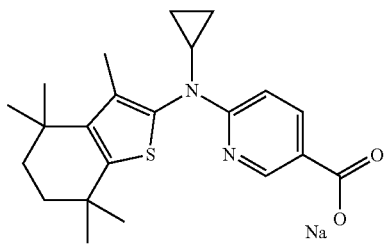

Compound 74 was synthesized from 6-[cyclopropyl(3,4,4,7,7-pentamethyl-4,5,6,7-tetrahydro-1-benzothiophen-2-yl)amino]pyridine-3-carboxylic acid and NaOH by following the procedure described in scheme 28; purity: 98.63%.

Compound 74: sodium 6-[cyclopropyl(3,4,4,7,7-pentamethyl-4,5,6,7-tetrahydro-1-benzothiophen-2-yl)amino]pyridine-3-carboxylate To a stirred solution of 6-[cyclopropyl(3,4,4,7,7-pentamethyl-4,5,6,7-tetrahydro-1-benzothiophen-2-yl)amino]pyridine-3-carboxylic acid (0.02 g, 0.05 mmol) in MeOH (0.5 mL) and THF (0.5 mL), 1M NaOH solution (0.05 mL, 0.05 mmol) was added slowly at 0° C. The reaction mixture was stirred at RT for 15 min. The solvent was removed under reduced pressure. The resulting gummy was added methanol and again removed completely under high vacuum. This has been repeated until there was no water. The obtained gummy material was crystallized with ethyl acetate and n-hexane to yield a white solid (0.01 g, yield: 50%): MS (ESI, 120 eV): m/z=348.18 (M−22)$^+$.

Example 75: sodium 4-[cyclopropyl(3,4,4,7,7-pentamethyl-4,5,6,7-tetrahydro-1-benzothiophen-2-yl)amino]benzoate

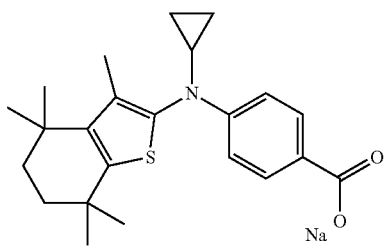

Compound 75 was synthesized from 4-[cyclopropyl(3,4,4,7,7-pentamethyl-4,5,6,7-tetrahydro-1-benzothiophen-2-yl)amino]benzoic acid (Compound-10) and NaOH by following the procedure described in scheme 28; purity: 91.34%.

Example 76: sodium 6-[(cyclopropyl methyl) (4,4,7,7-tetramethyl-4,5,6,7-tetrahydro-1,3-benzothiazol-2-yl)amino]pyridine-3-carboxylate

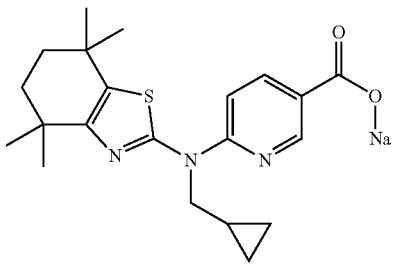

Compound 76 was synthesized from 6-[(cyclopropyl methyl) (4,4,7,7-tetramethyl-4,5,6,7-tetrahydro-1,3-benzothiazol-2-yl)amino]pyridine-3-carboxylic acid (compound-40) and NaOH by following the procedure described in scheme 28; purity: 99.83%.

Example 77: sodium 4-[cyclopropyl(4,4,7,7-tetramethyl-4,5,6,7-tetrahydro-1,3-benzothiazol-2-yl)amino]benzoate

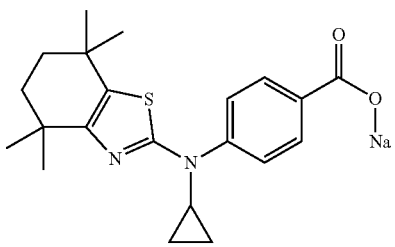

Compound 77 was synthesized from 4-[cyclopropyl(4,4,7,7-tetramethyl-4,5,6,7-tetrahydro-1,3-benzothiazol-2-yl)amino]benzoic acid and NaOH by following the similar procedure described in scheme 28; purity: 98.63%

Example 78: sodium 6-[cyclopropyl(4,4,7,7-tetramethyl-4,5,6,7-tetrahydro-1,3-benzothiazol-2-yl)amino]pyridine-3-carboxylate

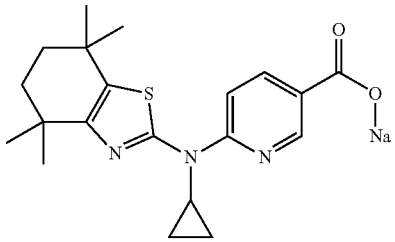

Compound 78 was synthesized from 6-[cyclopropyl(4,4,7,7-tetramethyl-4,5,6,7-tetrahydro-1,3-benzothiazol-2-yl)amino]pyridine-3-carboxylic acid and NaOH by following the similar procedure described in scheme 28; purity: 95.47%.

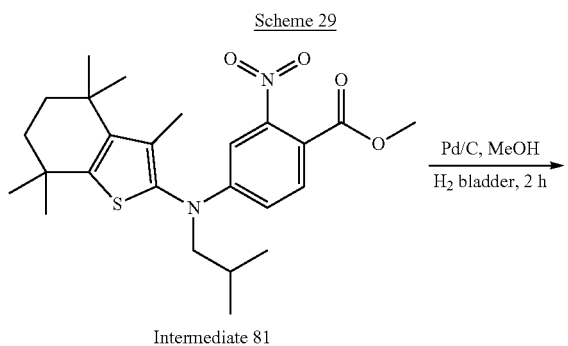

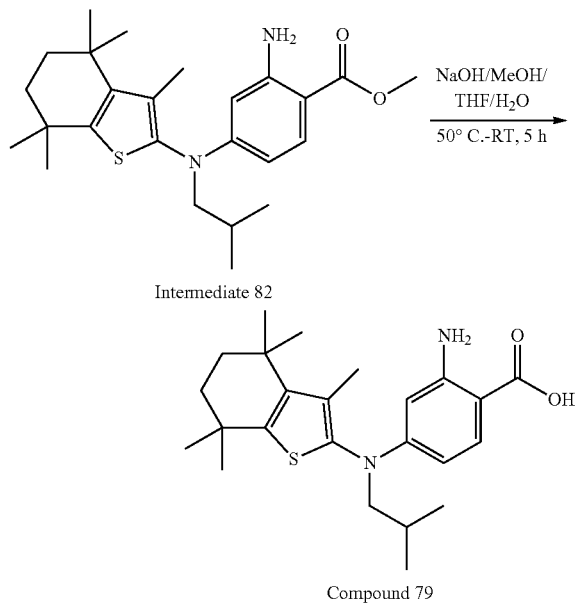

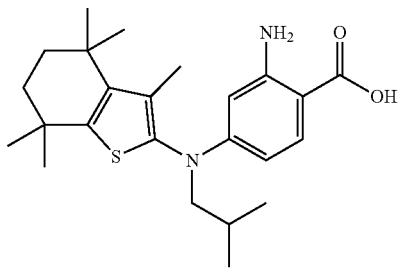 [SMILES: Cc1c(N(CC(C)C)c2ccc(C(=O)O)c(N)c2)sc2c1C(C)(C)CCC2(C)C]

Example 79: 2-amino-4-[(2-methylpropyl) (3,4,4,7,7-pentamethyl-4,5,6,7-tetrahydro-1-benzothiophen-2-yl)amino]benzoic acid Compound 79 was synthesized from methyl 4-[(2-methylpropyl)(3,4,4,7,7-pentamethyl-4,5,6,7-tetrahydro-1-benzothiophen-2-yl)amino]-2-nitrobenzoate (Intermediate 81) by following the procedure described in scheme 29; purity: 95.94%.

Intermediate 82: methyl 2-amino-4-[(2-methylpropyl)(3,4,4,7,7-pentamethyl-4,5,6,7-tetrahydro-1-benzothiophen-2-yl)amino]benzoate A three-neck 25 mL RB flask fitted with rubber bladder filled with hydrogen gas was charged with methanol (5 mL). To the stirred solution methyl 4-[(2-methylpropyl)(3,4,4,7,7-pentamethyl-4,5,6,7-tetrahydro-1-benzothiophen-2-yl)amino]-2-nitrobenzoate (0.05 g, 0.11 mmol) and palladium on carbon (0.005 g, 10%) was added. Reaction mixture was stirred for 2 h. Then the reaction mixture was filtered through celite pad dried over anhydrous $Na_2SO_4$ and concentrated in vacuum. The crude product obtained was purified by column chromatography to yield the title compound as a yellow gummy product (0.03 g, yield: 63.83%).

Compound 79: 2-amino-4-[(2-methylpropyl)(3,4,4,7,7-pentamethyl-4,5,6,7-tetrahydro-1-benzothiophen-2-yl)amino]benzoic acid A 25 mL RB flask fitted with magnetic stirrer was charged with methanol (2 mL) and THF (2 mL). To the stirred solvent methyl 2-amino-4-[(2-methylpropyl)(3,4,4,7,7-pentamethyl-4,5,6,7-tetrahydro-1-benzothiophen-2-yl)amino]benzoate (0.03 g, 0.07 mmol) and aq. NaOH (0.02 g, 0.35 mmol) was added at 0° C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated. The obtained solid was triturated with hexane to give the title compound as a yellow gummy product (0.015 g, yield: 51.72%): MS (ESI, 120 eV): m/z=415.2 $(M+H)^+$.

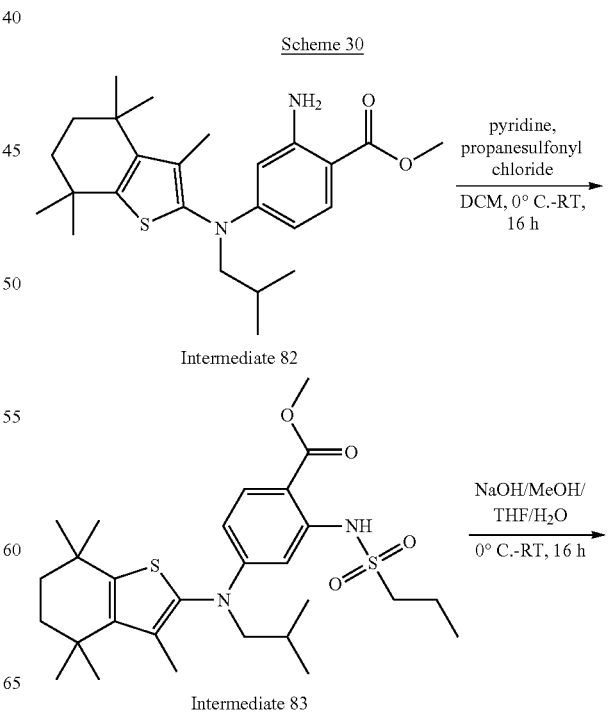

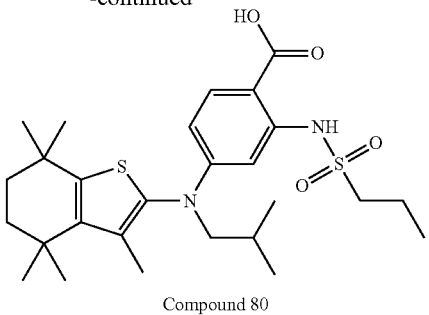

Compound 80

Example 80: 4-[(2-methylpropyl) (3,4,4,7,7-pentamethyl-4,5,6,7-tetrahydro-1-benzothiophen-2-yl)amino]-2-[(propyl sulfonyl)amino]benzoic acid

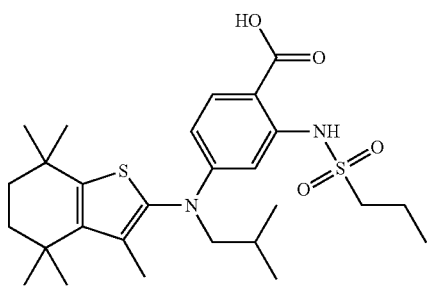 [SMILES: CCCS(=O)(=O)Nc1cc(N(CC(C)C)c2sc3c(c2C)C(C)(C)CCC3(C)C)ccc1C(=O)O]

Compound 80 was synthesized from methyl 2-amino-4-[(2-methylpropyl)(3,4,4,7,7-pentamethyl-4,5,6,7-tetrahydro-1-benzothiophen-2-yl)amino]benzoate (Intermediate-82) by following the procedure described in scheme 30; purity: 88.10%

Intermediate 83: methyl 4-[(2-methylpropyl) (3,4,4,7,7-pentamethyl-4,5,6,7-tetrahydro-1-benzothiophen-2-yl)amino]-2-[(propylsulfonyl)amino]benzoate To a two-neck 25 mL RB flask charged with methyl 2-amino-4-[(2-methylpropyl) (3,4,4,7,7-pentamethyl-4,5,6,7-tetrahydro-1-benzothiophen-2-yl)amino]benzoate (0.05 g, 0.11 mmol) in dry DCM (3 mL), pyridine (0.03 g, 0.33 mmol) was added drop wise at 0° C. Then propane sulfonyl chloride (0.017 g, 0.12 mmol) was added to the above solution at 0° C. Reaction mixture was stirred at RT for 16 h. Reaction mixture was poured into water and extracted with ethyl acetate. The combined extracts were washed with water and brine solution. The organic layer was dried over anhydrous $Na_2SO_4$ and concentrated in vacuum. The crude product obtained was purified by column chromatography to yield the title compound as a yellow liquid (0.019 g, yield: 33.33%).

Compound 80: 4-[(2-methylpropyl) (3,4,4,7,7-pentamethyl-4,5,6,7-tetrahydro-1-benzothiophen-2-yl)amino]-2-[(propylsulfonyl)amino]benzoic acid A 25 mL RB flask fitted with magnetic stirrer was charged with methanol (2 mL) and THF (2 mL). To this stirred solvent methyl 2-amino-4-[(2-methylpropyl)(3,4,4,7,7-pentamethyl-4,5,6,7-tetrahydro-1-benzothiophen-2-yl)amino] benzoate (0.03 g, 0.07 mmol) and aq. NaOH (0.02 g, 0.35 mmol) was added at 0° C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated. The obtained solid was triturated with hexane to give the title compound as a yellow gummy product (0.015 g, yield: 51.72%): MS (ESI, 120 eV): m/z=415.2 $(M+H)^+$.

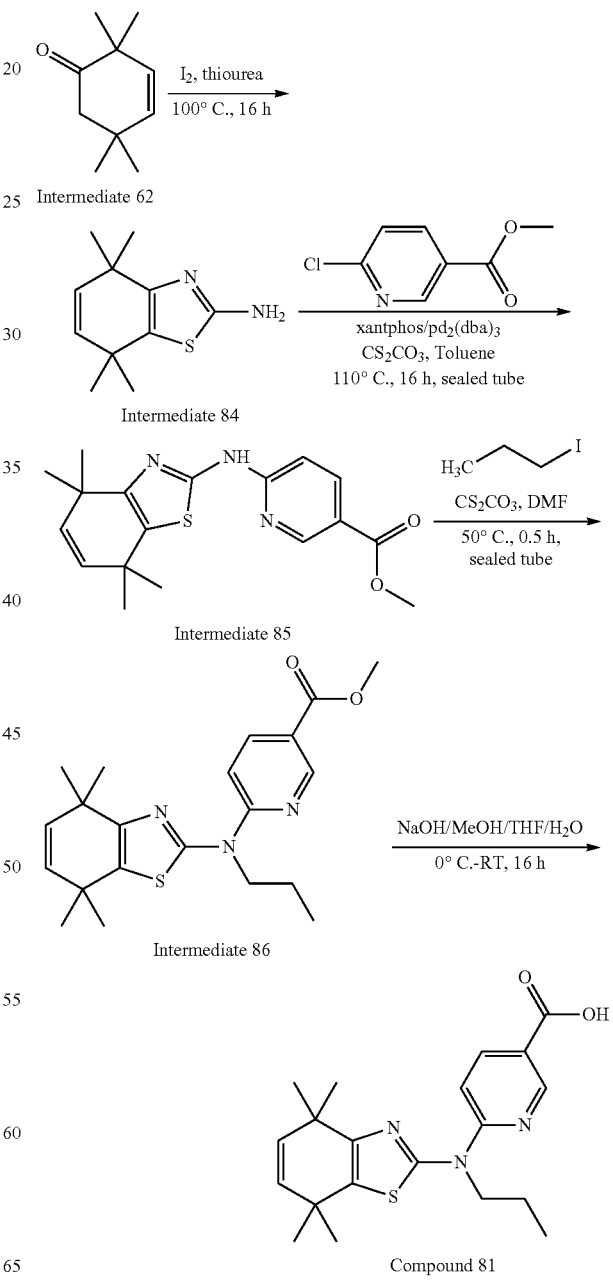

Scheme 31

Example 81: 6-[propyl(4,4,7,7-tetramethyl-4,7-dihydro-1,3-benzothiazol-2-yl)amino]pyridine-3-carboxylic acid

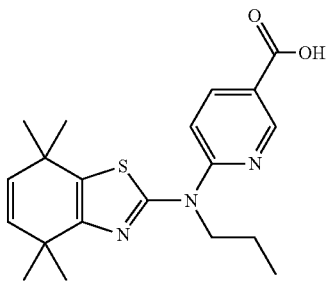 [SMILES: CCCN(c1ccc(C(=O)O)cn1)c1nc2c(s1)C(C)(C)C=CC2(C)C]

Compound 81 was synthesized from 4,4,7,7-tetramethyl-4,7-dihydro-1,3-benzothiazol-2-amine and methyl 6-chloropyridine-3-carboxylate by following the procedure described in scheme 31; purity: 99.83%

Intermediate 84: 4,4,7,7-tetramethyl-4,7-dihydro-1,3-benzothiazol-2-amine

To a single neck 100 mL RB flask fitted with magnetic stirrer and condenser charged with 2,2,5,5-Tetramethylcyclohex-3-en-1-one (8.0 g, 53 mmol), Iodine (13.36 g, 53 mmol) and thiourea (10.0 g, 131 mmol) was added. Reaction mixture was heated to 100° C. for 20 h. Reaction mixture was cooled to RT, poured into aqueous NaOH solution and extracted with ethyl acetate. The combined extracts were washed with water and brine. The organic layer was dried over anhydrous $Na_2SO_4$ and concentrated in vacuum to get the crude product. The crude product obtained was purified by column chromatography to give the title compound as a yellow solid (2 g, yield: 18.28%)

Intermediate 85: methyl 6-[(4,4,7,7-tetramethyl-4,7-dihydro-1,3-benzothiazol-2-yl)amino]pyridine-3-carboxylate To a 100 ml pressure tube with screwed cap charged with 4,4,7,7-tetramethyl-4,7-dihydro-1,3-benzothiazol-2-amine (1.7 g, 8.2 mmol) in toluene (6 mL), methyl 6-chloronicotinate (0.7 g, 4.1 mmol) was added. To this stirred solvent $CS_2CO_3$ (3.9 g, 12.32 mmol) and Xantphos (0.11 g, 0.21 mmol was added. Above solution was degassed with nitrogen for 10 minutes. Then $Pd_2(dba)_3$ (0.075 g, 0.08 mmol) was added to the reaction mixture. The reaction mixture was heated to 100° C. for 16 h. Reaction mixture was cooled to RT, and poured into water and extracted with ethyl acetate. The combined extracts were washed with water and brine. The organic layer was dried over anhydrous $Na_2SO_4$ and concentrated in vacuum. The crude product obtained was purified by column to give the title compound as a pale yellow solid (0.6 g, yield: 42.85%).

Intermediate 86: methyl 6-[propyl(4,4,7,7-tetramethyl-4,7-dihydro-1,3-benzothiazol-2-yl)amino]pyridine-3-carboxylate To a stirred solution of methyl 6-[(4,4,7,7-tetramethyl-4,7-dihydro-1,3-benzothiazol-2-yl)amino]pyridine-3-carboxylate (0.14 g, 0.41 mmol) in DMF (3 mL), cesium carbonate (0.4 g, 1.2 mmol) and 1-iodopropane (0.11 g, 0.8 mmol) was added at 0° C. in a sealed tube. Reaction mixture was heated to 50° C. for 30 minutes. Then the reaction mixture was cooled to RT, poured into water and extracted with ethyl acetate. The combined extracts were washed with water and brine solution. The organic layer was dried over anhydrous $Na_2SO_4$ and concentrated in vacuum. The crude product obtained was purified by column chromatography to yield the title compound as a yellow gummy product (0.1 g, yield: 62.5%).

Compound 81: 6-[propyl(4,4,7,7-tetramethyl-4,7-dihydro-1,3-benzothiazol-2-yl)amino]pyridine-3-carboxylic acid A 25 mL RB flask fitted with magnetic stirrer was charged with methanol (1 mL) and THF (1 mL). To the stirred solvent methyl 6-[propyl(4,4,7,7-tetramethyl-4,7-dihydro-1,3-benzothiazol-2-yl)amino]pyridine-3-carboxylate (0.1 g, 0.25 mmol) and aq. NaOH (0.05 g, 1.2 mmol) was added at 0° C. Reaction mixture was stirred at RT for 2 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated. The obtained solid was triturated with hexane to give the title compound as a yellow gummy product (0.05 g, yield: 52.63%): MS (ESI, 120 eV): m/z=372.1 (M+H)$^+$.

Example 82: 6-[(2-methylpropyl) (4,4,7,7-tetramethyl-4,7-dihydro-1,3-benzothiazol-2-yl)amino]pyridine-3-carboxylic acid

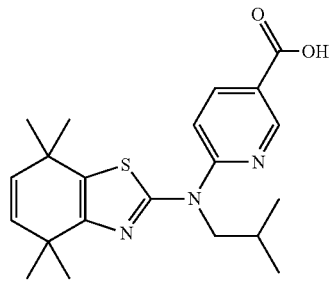 [SMILES: CC(C)CN(c1ccc(C(=O)O)cn1)c1nc2c(s1)C(C)(C)C=CC2(C)C]

Compound 82 was synthesized from methyl 6-[(4,4,7,7-tetramethyl-4,7-dihydro-1,3-benzothiazol-2-yl)amino]pyridine-3-carboxylate (Intermediate 85) and 1-bromo-2-methylpropane by following the procedure described in scheme 31 (0.06 g, yield: 62.5%); purity: 99.65%.

Example 83: 4-[(2-methylpropyl) (4,4,7,7-tetramethyl-4,7-dihydro-1,3-benzothiazol-2-yl)amino]benzoic acid

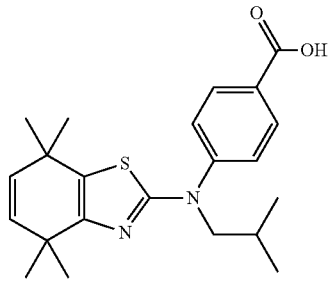 [SMILES: CC(C)CN(c1ccc(C(=O)O)cc1)c1nc2c(s1)C(C)(C)C=CC2(C)C]

Compound 83 was synthesized from coupling of 4,4,7,7-tetramethyl-4,7-dihydro-1,3-benzothiazol-2-amine (Intermediate 84) and methyl 4-iodobenzoate, followed by reaction with 1-bromo-2-methylpropane as the procedure described in scheme 31 (0.14 g, 29.78%); purity: 98.91%

Scheme 32

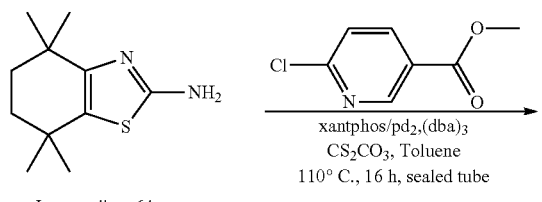

xantphos/pd$_2$(dba)$_3$
CS$_2$CO$_3$, Toluene
110° C., 16 h, sealed tube

Intermediate 64

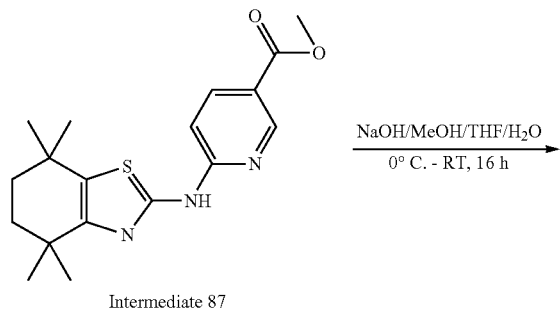

NaOH/MeOH/THF/H$_2$O
0° C. - RT, 16 h

Intermediate 87

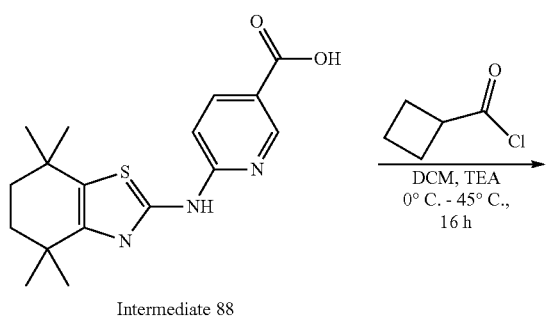

DCM, TEA
0° C. - 45° C., 16 h

Intermediate 88

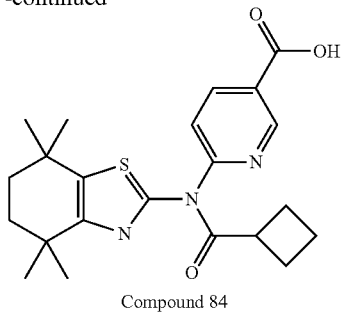

Compound 84

Example 84: 6-[(cyclobutylcarbonyl) (4,4,7,7-tetramethyl-4,5,6,7-tetrahydro-1,3-benzothiazol-2-yl)amino]pyridine-3-carboxylic acid

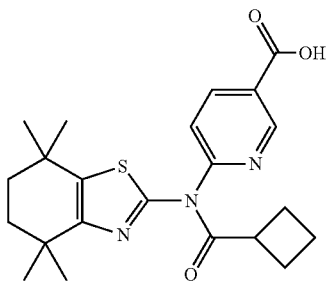 [SMILES: CC1(C)CCC(C)(C)c2sc(N(C(=O)C3CCC3)c3ccc(C(=O)O)cn3)nc21]

Compound 84 was synthesized from 4,4,7,7-tetramethyl-4,5,6,7-tetrahydro-1,3-benzothiazol-2-amine and methyl 6-chloropyridine-3-carboxylate by following the procedure described in scheme 32; purity: 98.33%.

Intermediate 87: methyl 6-[(4,4,7,7-tetramethyl-4,5,6,7-tetrahydro-1,3-benzothiazol-2-yl)amino]pyridine-3-carboxylate To a 100 ml pressure tube with screwed cap charged with 4,4,7,7-tetramethyl-4,5,6,7-tetrahydro-1,3-benzothiazol-2-amine (1.8 g, 8.2 mmol) in toluene (6 mL), methyl 6-chloronicotinate (0.7 g, 4.1 mmol) was added. To the stirred solvent CS$_2$CO$_3$ (3.9 g, 12.32 mmol) and Xantphos (0.11 g, 0.21 mmol) was added. The above solution was degassed with nitrogen for 10 minutes. Then Pd$_2$ (dba)$_3$ (0.075 g, 0.08 mmol) was added to the reaction mixture. The reaction mixture was heated to 100° C. for 16 h. Reaction mixture was cooled to RT, and poured into water and extracted with ethyl acetate. The combined extracts were washed with water and brine. The organic layer was dried over anhydrous Na$_2$SO$_4$ and concentrated in vacuum. The crude product obtained was purified by column to give the title compound as a yellow solid (0.6 g, yield: 42.86%).

Intermediate 88: 6-[(4,4,7,7-tetramethyl-4,5,6,7-tetrahydro-1,3-benzothiazol-2-yl)amino]pyridine-3-carboxylic acid A 25 mL RB flask fitted with magnetic stirrer was with charged methanol (15 mL) and THF (5 mL). To the stirred solvent methyl 6-[(4,4,7,7-tetramethyl-4,5,6,7-tetrahydro-1,3-benzothiazol-2-yl)amino]pyridine-3-carboxylate (0.35 g, 1.0 mmol) and aq. NaOH (0.2 g, 5.0 mmol) was added at 0°

C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over Na$_2$SO$_4$, filtered and concentrated. The obtained solid was triturated with hexane to give the title compound as a pale yellow solid (0.25 g, yield: 75.75%).

Compound 84: 6-[(cyclobutylcarbonyl) (4,4,7,7-tetramethyl-4,5,6,7-tetrahydro-1,3-benzothiazol-2-yl)amino]pyridine-3-carboxylic acid To a two-neck 50 mL RB flask charged with 6-[(4,4,7,7-tetramethyl-4,5, 6,7-tetrahydro-1 and 3-benzothiazol-2-yl) amino]pyridine-3-carboxylic acid (0.12 g, 0.36 mmol) in dry DCM (4 mL), triethyl amine (0.25 g, 2.5 mmol) was added drop wise at 0° C. Then cyclobutylcarbonylchlroide (0.17 g, 1.44 mmol) was added to the above solution at 0° C. Reaction mixture was heated to 45° C. for 16 h. Reaction mixture was poured into water and extracted with ethyl acetate. The combined extracts were washed with water and brine solution. The organic layer was dried over anhydrous Na$_2$SO$_4$ and concentrated in vacuum. The crude product obtained was purified by preparative HPLC to yield the title compound as a yellow solid (0.002 g, yield: 1.43%). MS (ESI, 120 eV): m/z=414.2 (M+H)$^+$.

Example 85: 6-[acetyl(4,4,7,7-tetramethyl-4,5,6,7-tetrahydro-1,3-benzothiazol-2-yl)amino]pyridine-3-carboxylic acid

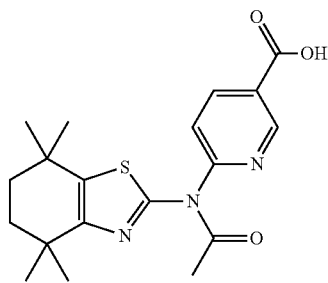 [SMILES: CC(=O)N(c1ccc(C(=O)O)cn1)c1nc2c(s1)C(C)(C)CCC2(C)C]

Compound 85 was synthesized from coupling of 4,4,7,7-tetramethyl-4,5, 6,7-tetrahydro-1,3-benzothiazol-2-amine and methyl 6-chloropyridine-3-carboxylate, followed by reaction with acetyl chloride as the procedure described in scheme 32; purity: 99.17%.

Scheme 33

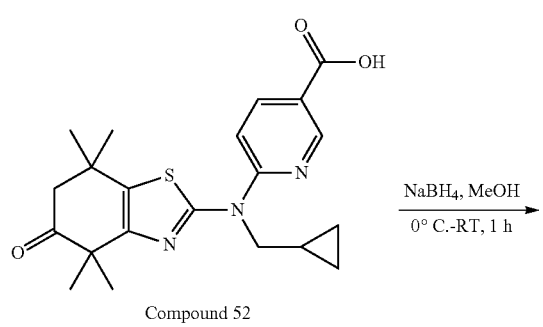

Compound 52

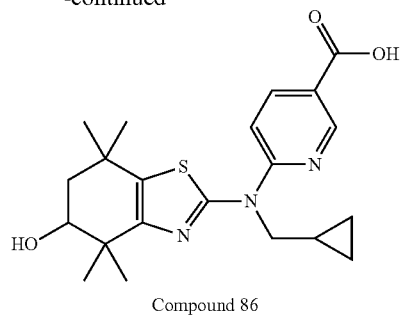

Compound 86

Example 86: 6-[(cyclopropylmethyl) (5-hydroxy-4,4,7,7-tetramethyl-4,5,6,7-tetrahydro-1,3-benzothiazol-2-yl)amino]pyridine-3-carboxylic acid

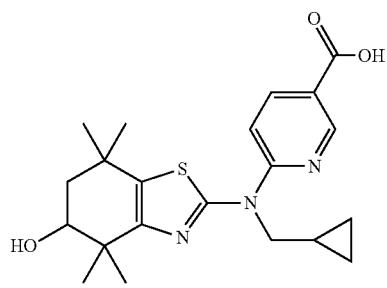 [SMILES: CC1(C)CC(O)C(C)(C)c2nc(N(CC3CC3)c3ccc(C(=O)O)cn3)sc21]

Compound 86 was synthesized from 6-[(cyclopropylmethyl)(4,4,7,7-tetramethyl-5-oxo-4,5,6,7-tetrahydro-1,3-benzothiazol-2-yl)amino]pyridine-3-carboxylic acid by following the procedure described in scheme 33; purity: 97.76%

Compound 86: 6-[(cyclopropylmethyl) (5-hydroxy-4,4,7,7-tetramethyl-4,5,6,7-tetrahydro-1,3-benzothiazol-2-yl)amino]pyridine-3-carboxylic acid To a stirred solution of 6-[(cyclopropylmethyl) (5-hydroxy-4,4,7,7-tetramethyl-4,5,6,7-tetrahydro-1,3-benzothiazol-2-yl)amino]pyridine-3-carboxylic acid (0.075 g, 0.18 mmol) in methanol (3 mL), NaBH$_4$ (0.0068 g, 0.18 mmol) was added at 0° C. Reaction mixture was stirred at RT for 1 h. Reaction mixture was quenched with ice and extracted with ethyl acetate. The combined extracts were washed with water and brine solution. The organic layer was dried over anhydrous Na$_2$SO$_4$ and concentrated in vacuum to get the pure product as a yellow solid (0.058 g, yield: 85.71%). MS (ESI, 120 eV): m/z=402.1 (M+H)$^+$.

Scheme 34

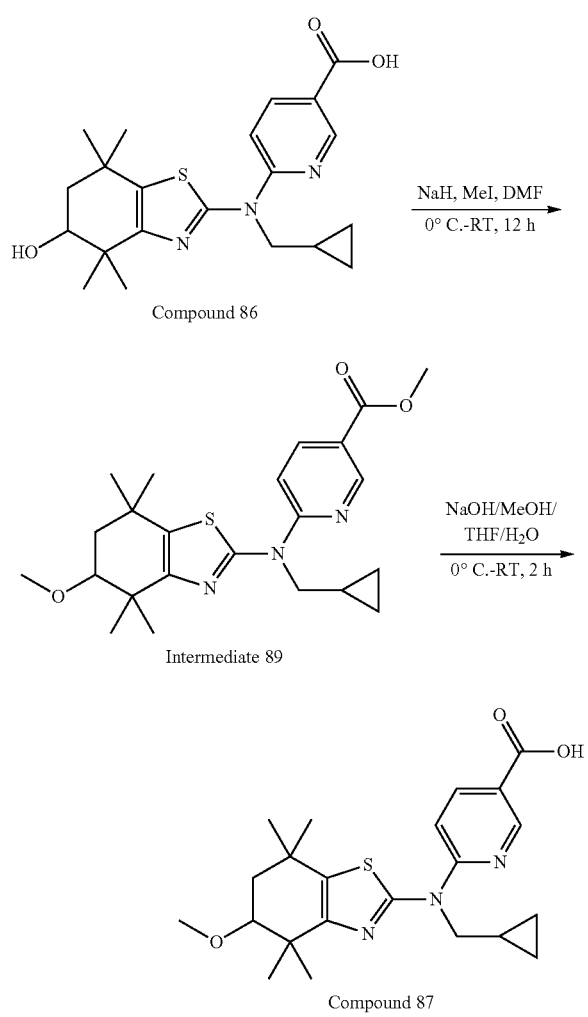

Example 87: 6-[(cyclopropylmethyl) (5-methoxy-4,4,7,7-tetramethyl-4,5,6,7-tetrahydro-1,3-benzothiazol-2-yl)amino]pyridine-3-carboxylic acid

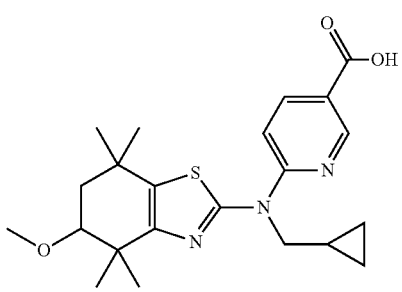 [SMILES: COC1CC(C)(C)c2sc(N(CC3CC3)c3ccc(C(=O)O)cn3)nc2C1(C)C]

Compound 87 was synthesized from 6-[(cyclopropylmethyl)(5-hydroxy-4,4,7,7-tetramethyl-4,5,6,7-tetrahydro-1,3-benzothiazol-2-yl)amino]pyridine-3-carboxylic acid by following the procedure described in scheme 34; purity: 98.09%

Intermediate 89: methyl 6-[(cyclopropylmethyl)(5-methoxy-4,4,7,7-tetramethyl-4,5,6,7-tetrahydro-1,3-benzothiazol-2-yl)amino]pyridine-3-carboxylate To a stirred solution of NaH (0.012 g, 0.49 mmol) in dry DMF (3 mL), 6-[(cyclopropylmethyl)(5-hydroxy-4,4,7,7-tetramethyl-4,5,6,7-tetrahydro-1,3-benzothiazol-2-yl)amino]pyridine-3-carboxylic acid (0.05 g, 0.12 mmol) in DMF (2 mL) was added at 0° C. The reaction mixture was stirred at RT for 30 minutes. To the stirred solution, methyl iodide (0.09 g, 0.6 mmol) in DMF (1 mL) was added at 0° C. and stirred at RT for 16 h. The reaction mixture was quenched with 1.5 N HCl and extracted with ethyl acetate. The combined extracts were washed with water and brine. The organic layer was dried over anhydrous $Na_2SO_4$ and concentrated reduced pressure. The crude product obtained was purified by combiflash to yield the title compound as a colorless liquid (0.02 g, yield: 40%).

Compound 87: 6-[(cyclopropylmethyl) (5-methoxy-4,4,7,7-tetramethyl-4,5,6,7-tetrahydro-1,3-benzothiazol-2-yl)amino]pyridine-3-carboxylic acid A 25 mL RB flask fitted with magnetic stirrer was charged with methanol (1 mL) and THF (1 mL). To the stirred solvent methyl 6-[(cyclopropylmethyl) (5-methoxy-4,4,7,7-tetramethyl-4,5,6,7-tetrahydro-1,3-benzothiazol-2-yl)amino]pyridine-3-carboxylate (0.02 g, 0.46 mmol) and aq. NaOH (0.01 g, 2.3 mmol) was added at 0° C. Reaction mixture was stirred at RT for 2 h. The reaction mixture was concentrated completely and the crude was washed with ether, and diluted with water and then neutralized with 1.5 N HCl and extracted with ethyl acetate. The organic layer was washed with water and brine, dried over $Na_2SO_4$, filtered and concentrated. The obtained solid was triturated with hexane to give the title compound as a yellow solid (0.017 g, yield: 89.47%): MS (ESI, 120 eV): m/z=416.2 $(M+H)^+$.

Scheme 35

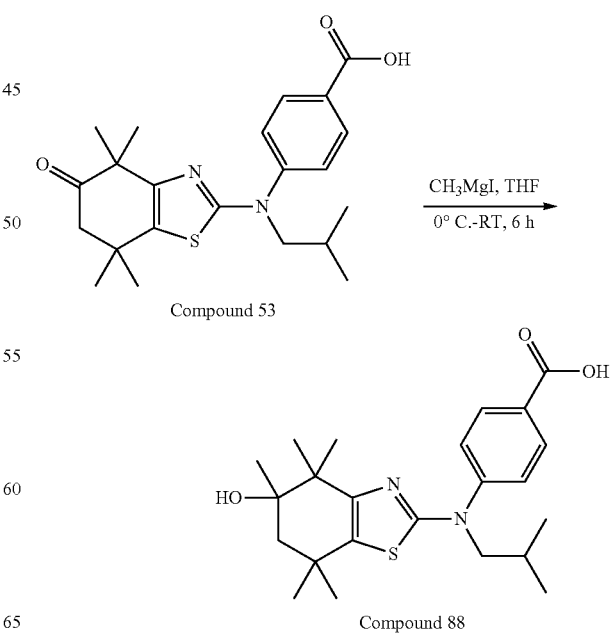

Example 88: 4-[(5-hydroxy-4,4,5,7,7-pentamethyl-4,5,6,7-tetrahydro-1,3-benzothiazol-2-yl) (2-methylpropyl)amino]benzoic acid

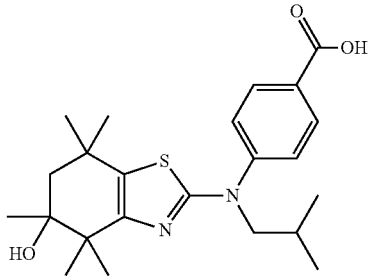 [SMILES: CC(C)CN(c1ccc(C(=O)O)cc1)c1nc2c(s1)C(C)(C)CC(C)(O)C2(C)C]

Compound 88 was synthesized by treating 4-[(2-methylpropyl)(4,4,7,7-tetramethyl-5-oxo-4,5,6,7-tetrahydro-1,3-benzothiazol-2-yl)amino]benzoic acid with Grignard reagent as the procedure described in scheme 35; purity: 94.80%.

Compound 88: 4-[(5-hydroxy-4,4,5,7,7-pentamethyl-4,5,6,7-tetrahydro-1,3-benzothiazol-2-yl) (2-methylpropyl)amino]benzoic acid To a two-neck 25 mL RB flask charged with 4-[(2-methylpropyl)(4,4,7,7-tetramethyl-5-oxo-4,5,6,7 tetrahydro-1,3-benzothiazol-2-yl)amino]benzoic acid (0.14 g, 0.35 mmol), THF (4 mL) was added. Methyl magnesium iodide (0.5 mL, 1.39 mmol) was added drop wise at 0° C. to the stirred above solution. Reaction mixture was stirred at RT for 6 h. Then reaction mixture was quenched with 1.5N HCl and extracted with ethyl acetate. The organic layer was washed with water and brine, dried over $Na_2SO_4$, filtered and concentrated. The crude product obtained was purified by column chromatography to give the title compound as a yellow solid (0.007 g, yield: 4.66%): MS (ESI, 120 eV): m/z=417.2 (M+H)$^+$.

Scheme 36

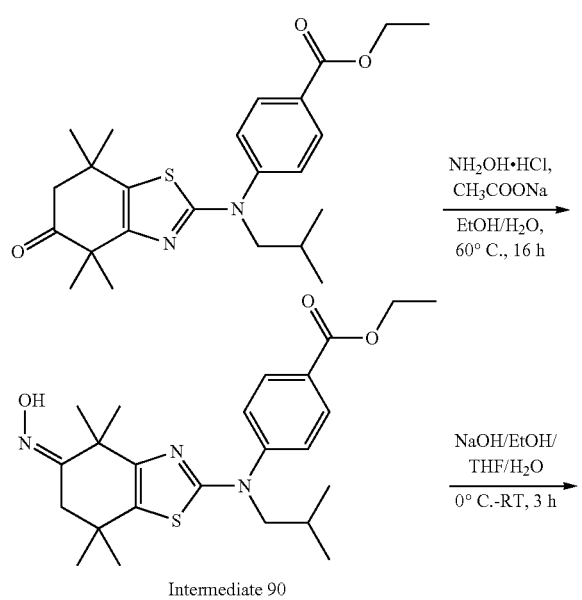

Example 89: 4-{[(5Z)-5-(hydroxyimino)-4,4,7,7-tetramethyl-4,5,6,7-tetrahydro-1,3-benzothiazol-2-yl](2-methylpropyl)amino}benzoic acid

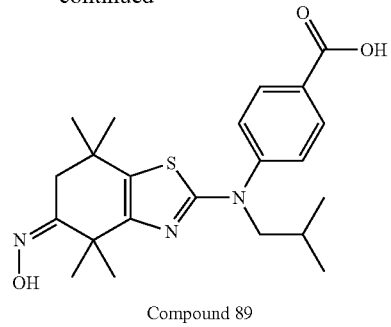

Compound 89

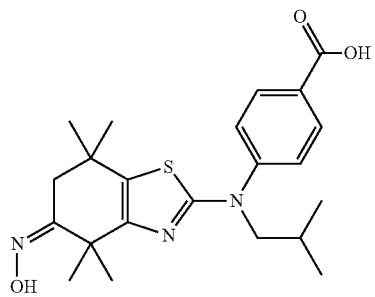 [SMILES: CC(C)CN(c1ccc(C(=O)O)cc1)c1nc2c(s1)C(C)(C)C/C(=N/O)C2(C)C]

Compound 89 was synthesized from ethyl 4-[(2-methylpropyl)(4,4,7,7-tetramethyl-5-oxo-4,5,6,7-tetrahydro-1,3-benzothiazol-2-yl)amino]benzoate by following the procedure described in scheme 36; purity: 93.04%

Intermediate 90: ethyl 4-{[(5Z)-5-(hydroxyimino)-4,4,7,7-tetramethyl-4,5,6,7-tetrahydro-1,3-benzothiazol-2-yl](2-methylpropyl)amino}benzoate To the stirred solution of ethyl 4-[(2-methylpropyl)(4,4,7,7-tetramethyl-5-oxo-4,5,6,7-tetrahydro-1,3-benzothiazol-2-yl)amino]benzoate (0.1 g, 0.23 mmol) in ethanol (1 mL) and water (1 mL), sodium acetate (0.037 g, 0.46 mmol) was added followed by addition of hydroxylamine hydrochloride (0.03 g, 0.46 mmol). Reaction mixture was heated to 60° C. for 16 h. After completion of the reaction, water was added to the reaction mixture and extracted with ethyl acetate. The organic layer was washed with water and brine, dried over $Na_2SO_4$, filtered and concentrated. The crude product obtained was purified by column chromatography to give the title compound as a white solid (0.05 g, yield: 50%): MS (ESI, 120 eV): m/z=417.2 (M+H)$^+$.

Compound 89: 4-{[(5Z)-5-(hydroxyimino)-4,4,7,7-tetramethyl-4,5,6,7-tetrahydro-1, 3-benzothiazol-2-yl](2-methylpropyl)amino}benzoic acid A 25 mL RB flask fitted with magnetic stirrer was charged with ethanol (1 mL) and THF (1 mL). To the stirred solvent ethyl 4-{[(5Z)-5-(hydroxyimino)-4,4,7,7-tetramethyl-4,5,6,7-tetrahydro-1,3-benzothiazol-2-yl](2-methylpropyl)amino}benzoate (0.05 g, 0.12 mmol) and aq. NaOH (0.02 g, 0.56 mmol) was added at 0° C. Reaction mixture was stirred at RT for 3 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated. The obtained solid was triturated with hexane to give the title compound as a white solid (0.03 g, yield: 60%): MS (ESI, 120 eV): m/z=416.2 $(M+H)^+$.

Scheme 37

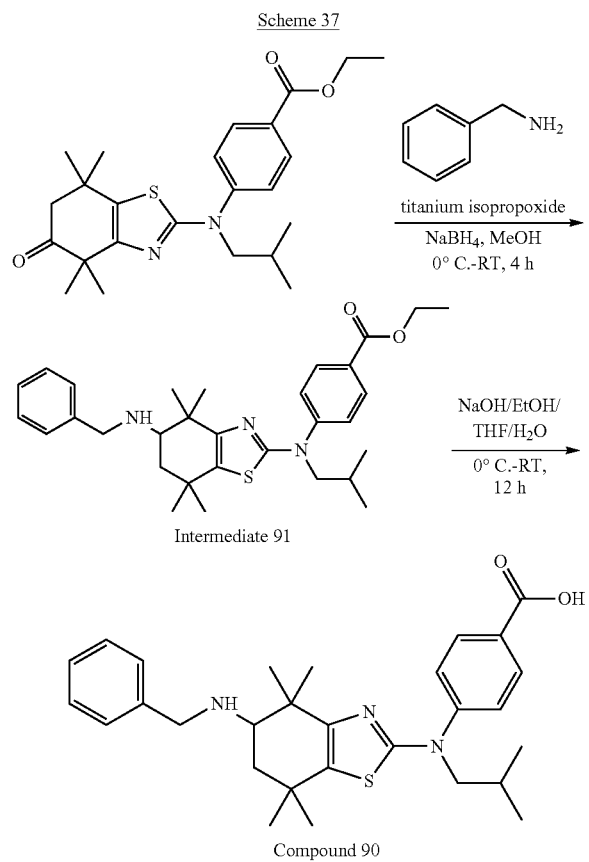

Intermediate 91

Compound 90

Example 90: 4-{[5-(benzylamino)-4,4,7,7-tetramethyl-4,5,6,7-tetrahydro-1,3-benzothiazol-2-yl](2-methylpropyl)amino}benzoic acid

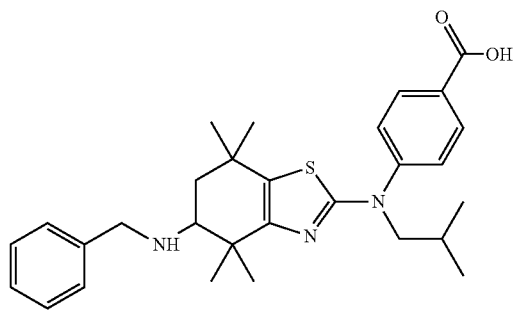 [SMILES: CC(C)CN(c1ccc(C(=O)O)cc1)c1nc2c(s1)C(C)(C)CC(NCc1ccccc1)C2(C)C]

Compound 90 was synthesized from ethyl 4-[(2-methylpropyl)(4,4,7,7-tetramethyl-5-oxo-4,5,6,7-tetrahydro-1,3-benzothiazol-2-yl)amino]benzoate by following the procedure described in scheme 37; purity: 98.76%

Intermediate 91: ethyl 4-{[5-(benzylamino)-4,4,7,7-tetramethyl-4,5,6,7-tetrahydro-1, 3-benzothiazol-2-yl](2-methylpropyl)amino}benzoate A 25 mL RB flask fitted with magnetic stirrer was charged with ethyl 4-[(2-methylpropyl)(4,4,7,7-tetramethyl-5-oxo-4, 5,6,7-tetrahydro-1,3-benzothiazol-2-yl)amino]benzoate (0.1 g, 0.23 mmol), benzyl amine (0.032 g, 0.34 mmol) was added. Reaction mixture was stirred at RT for 12 h. To the stirred solution, methanol (10 mL) was added followed by $NaBH_4$ (0.017 g, 0.46 mmol) at 0° C. Then reaction mixture was allowed to stir at RT for 4 h. Reaction mixture was poured into ice and extracted with ethyl acetate. The organic layer was washed with water and brine, dried over $Na_2SO_4$, filtered and concentrated. The crude product obtained was purified by column chromatography to give the title compound as an off white solid (0.05 g, yield: 41.66%).

Compound 90: 4-{[5-(benzylamino)-4,4,7,7-tetramethyl-4,5,6,7-tetrahydro-1,3-benzothiazol-2-yl](2-methylpropyl)amino}benzoic acid A 25 mL RB flask fitted with magnetic stirrer was charged with ethanol (6 mL) and THF (12 mL). To the stirred solvent ethyl 4-{[5-(benzylamino)-4,4,7,7-tetramethyl-4,5,6,7-tetrahydro-1,3-benzothiazol-2-yl](2-methylpropyl) amino}benzoate (0.025 g, 0.05 mmol) and aq. NaOH (0.01 g, 0.22 mmol) was added at 0° C. Reaction mixture was stirred at RT for 3 h. The reaction mixture was concentrated completely and the crude was washed with ether and diluted with water and then neutralized with 1.5 N HCl, extracted with ethyl acetate. The organic layer was washed with water and brine, dried over $Na_2SO_4$, filtered and concentrated to get the crude product. The crude product obtained was purified by preparative HPLC to yield the title compound as a white solid (0.03 g, yield: 60%): MS (ESI, 120 eV): m/z=492.2 $(M+H)^+$.

Scheme 38

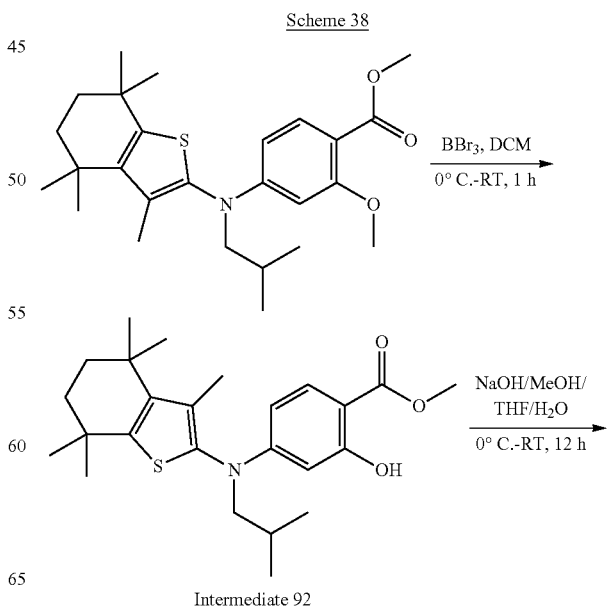

Intermediate 92

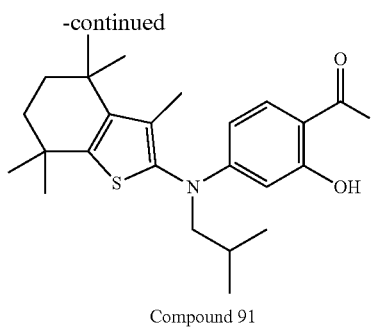

Compound 91

Example 91: 2-hydroxy-4-[(2-methylpropyl) (3,4,4,7,7-pentamethyl-4,5,6,7-tetrahydro-1-benzothiophen-2-yl)amino]benzoic acid

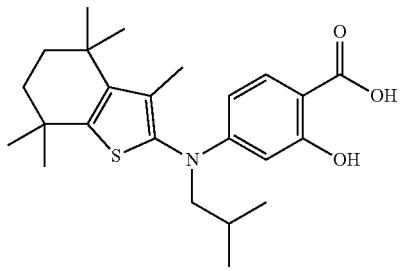 [SMILES: Cc1c(N(CC(C)C)c2ccc(C(=O)O)c(O)c2)sc2c1C(C)(C)CCC2(C)C]

Compound 91 was synthesized from methyl 2-methoxy-4-[(2-methylpropyl)(3,4,4,7,7-pentamethyl-4,5,6,7-tetrahydro-1-benzothiophen-2-yl)amino]benzoate by following the procedure described in scheme 38; purity: 90.27%

Intermediate 92: methyl 2-methoxy-4-[(2-methylpropyl) (3,4,4,7,7-pentamethyl-4,5,6,7-tetrahydro-1-benzothiophen-2-yl)amino]benzoate To a stirred solution of methyl 2-methoxy-4-[(2-methylpropyl)(3,4,4,7,7-pentamethyl-4,5,6,7-tetrahydro-1-benzothiophen-2-yl)amino]benzoate (0.02 g, 0.45 mmol) in DCM (2 mL), boron tribromide (0.02 g, 0.9 mmol) was added at 0° C. drop wise. Reaction mixture was stirred at RT for 1 h. Reaction mixture was quenched with bicarbonate solution and extracted with ethyl acetate. The organic layer was washed with water and brine, dried over $Na_2SO_4$, filtered and concentrated to get the title compound as a brown liquid (0.012 g, yield: 63%).

Compound 91: 2-hydroxy-4-[(2-methylpropyl) (3,4,4,7,7-pentamethyl-4,5,6,7-tetrahydro-1-benzothiophen-2-yl)amino]benzoic acid A 25 mL RB flask fitted with magnetic stirrer was charged with methanol (1 mL) and THF (1 mL). To the stirred solvent, methyl 2-methoxy-4-[(2-methylpropyl)(3,4,4,7,7-pentamethyl-4,5,6,7-tetrahydro-1-benzothiophen-2-yl)amino]benzoate (0.012 g, 0.03 mmol) and aq. NaOH (0.006 g, 0.14 mmol) was added at 0° C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated. The obtained product was triturated with hexane to yield the title compound as a pale yellow solid (0.006 g, yield: 54.44%): MS (ESI, 120 eV): m/z=414.2 (M–H)+.

Scheme 39

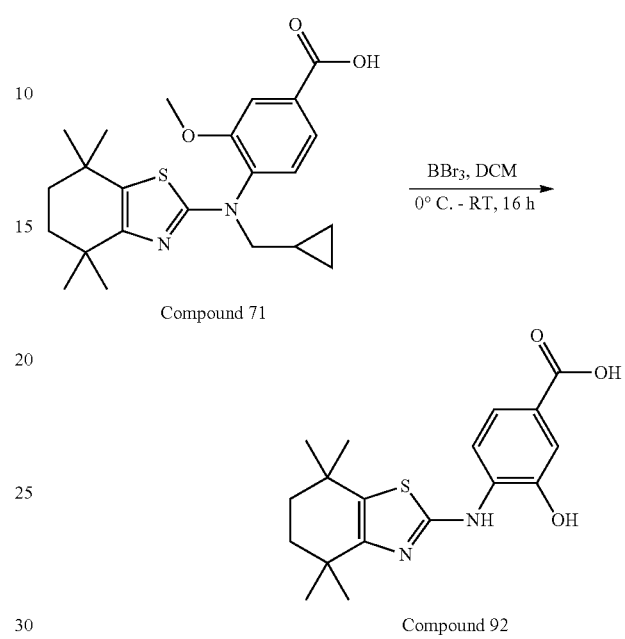

Compound 71

Compound 92

Example 92: 3-hydroxy-4-[(4,4,7,7-tetramethyl-4,5,6,7-tetrahydro-1,3-benzothiazol-2-yl)amino]benzoic acid

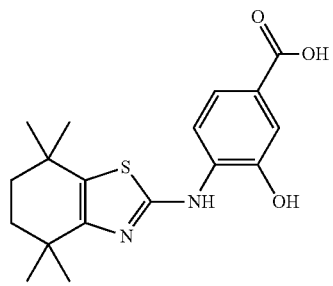 [SMILES: CC1(C)CCC(C)(C)c2sc(Nc3ccc(C(=O)O)cc3O)nc21]

Compound 92 was synthesized from 4-[(cyclopropylmethyl)(4,4,7,7-tetramethyl-4,5,6,7-tetrahydro-1,3-benzothiazol-2-yl)amino]-3-methoxybenzoic acid by following the procedure described in scheme 39; purity: 94.26%.

Compound 92: 3-hydroxy-4-[(4,4,7,7-tetramethyl-4,5,6,7-tetrahydro-1,3-benzothiazol-2-yl)amino]benzoic acid To a suspension of 4-[(cyclopropylmethyl)(4,4,7,7-tetramethyl-4,5,6,7-tetrahydro-1,3-benzothiazol-2-yl)amino]-3-methoxybenzoic acid (0.14 g, 0.34 mmol) in DCM (5 mL), $BBr_3$ (0.17 g, 0.68 mmol) was added drop wise at 0° C. Reaction mixture was stirred at RT for 16 h. Then reaction mixture was quenched with ice and extracted with ethyl acetate. The combined extracts were washed with water and brine, dried over Na$_2$SO$_4$, filtered and concentrated to yield the title compound as a brown solid (0.55 g, 40.39%). MS (ESI, 120 eV): m/z=[M+H]$^-$: 347.1 obtained was purified by column chromatography to yield the title compound as a white solid (2.5 g, yield: 96.15%). MS (ESI, 120 eV): m/z=345.12 (M+H)$^+$.

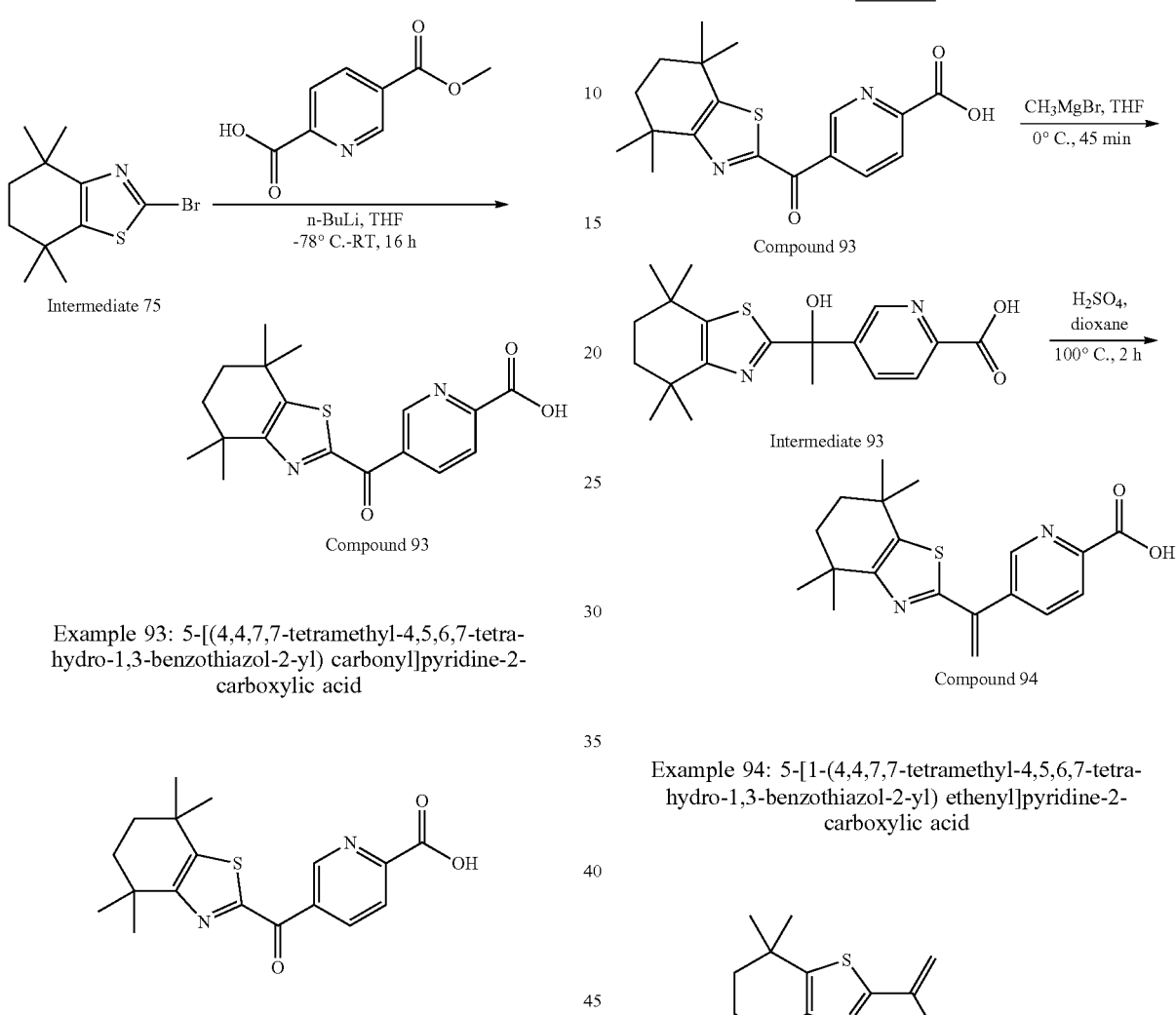

Scheme 40

Intermediate 75

Compound 93

Example 93: 5-[(4,4,7,7-tetramethyl-4,5,6,7-tetrahydro-1,3-benzothiazol-2-yl) carbonyl]pyridine-2-carboxylic acid Compound 93 was synthesized from 2-bromo-4,4,7,7-tetramethyl-4,5,6,7-tetrahydro-1,3-benzothiazole and 5-(methoxycarbonyl)pyridine-2-carboxylic acid by following the procedure described in scheme 40; purity: 90.19%.

Compound 93: 5-[(4,4,7,7-tetramethyl-4,5,6,7-tetrahydro-1,3-benzothiazol-2-yl) carbonyl]pyridine-2-carboxylic acid To a two-neck 100 mL RB flask fitted with magnetic stirrer charged with 2-bromo-4,4,7,7-tetramethyl-4,5,6,7-tetrahydro-1,3-benzothiazole (2.5 g, 9.12 mmol) in THF (30 mL), n-butyl lithium (7.3 mL, 18.24 mmol, 2.5M solution) was added drop wise at −78° C. The above solution was stirred at −78° C. for 1 h. Then 5-(methoxycarbonyl)pyridine-2-carboxylic acid (1.4 g, 7.7 mmol) in THF (20 mL) was added to the above solution drop wise. Reaction mixture was allowed to stir at RT for 16 h. Reaction mixture was quenched with saturated ammonium chloride solution and extracted with ethyl acetate. The organic layer was washed with water and brine, dried over Na$_2$SO$_4$, filtered and concentrated to yield the crude product. The product Scheme 41

Compound 93

Intermediate 93

Compound 94

Example 94: 5-[1-(4,4,7,7-tetramethyl-4,5,6,7-tetrahydro-1,3-benzothiazol-2-yl) ethenyl]pyridine-2-carboxylic acid Compound 94 was synthesized from 5-[(4,4,7,7-tetramethyl-4,5,6,7-tetrahydro-1,3-benzothiazol-2-yl)carbonyl] pyridine-2-carboxylic acid by following the procedure described in scheme 41; purity: 87.82%

Intermediate 93: 5-[1-hydroxy-1-(4,4,7,7-tetramethyl-4,5,6,7-tetrahydro-1,3-benzothiazol-2-yl)ethyl] pyridine-2-carboxylic acid To a single-neck 100 mL RB flask fitted with magnetic stirrer charged with 5-[(4,4,7,7-tetramethyl-4,5,6,7-tetrahydro-1,3-benzothiazol-2-yl)carbonyl]pyridine-2-carboxylic acid (0.8 g, 2.3 mmol) in THF (20 mL), methyl magnesium iodide (1.74 mL, 6.9 mmol, 4M solution) was added drop wise at 0° C. Reaction mixture was stirred at 0° C. only for 40 minutes. After completion of the reaction, reaction mixture was quenched with HCL and extracted with ethyl acetate. The organic layer was washed with water and brine, dried over Na₂SO₄, filtered and concentrated to yield the crude product. The product obtained was purified by column chromatography to yield the title compound as a yellow gummy (0.65 g, yield: 78.31%).

Compound 94: 5-[1-(4,4,7,7-tetramethyl-4,5,6,7-tetrahydro-1,3-benzothiazol-2-yl) ethenyl]pyridine-2-carboxylic acid To a stirred solution of 5-[1-hydroxy-1-(4,4,7,7-tetramethyl-4,5,6,7-tetrahydro-1,3-benzothiazol-2-yl)ethyl]pyridine-2-carboxylic acid (0.5 g, 1.39 mmol) in dioxane (20 mL), con.H₂SO₄ was added. Reaction mixture was heated to 100° C. for 4 h. Reaction progress was monitored by LCMS. Water was added to the reaction mixture and extracted with ethyl acetate. The organic layer was washed with water and brine, dried over Na₂SO₄, filtered and concentrated to yield the crude product. The product obtained was purified by preparative HPLC to yield the title compound as a yellow solid (0.045 g, yield: 9.37%). MS (ESI, 120 eV): m/z=343.15 (M+H)⁺.

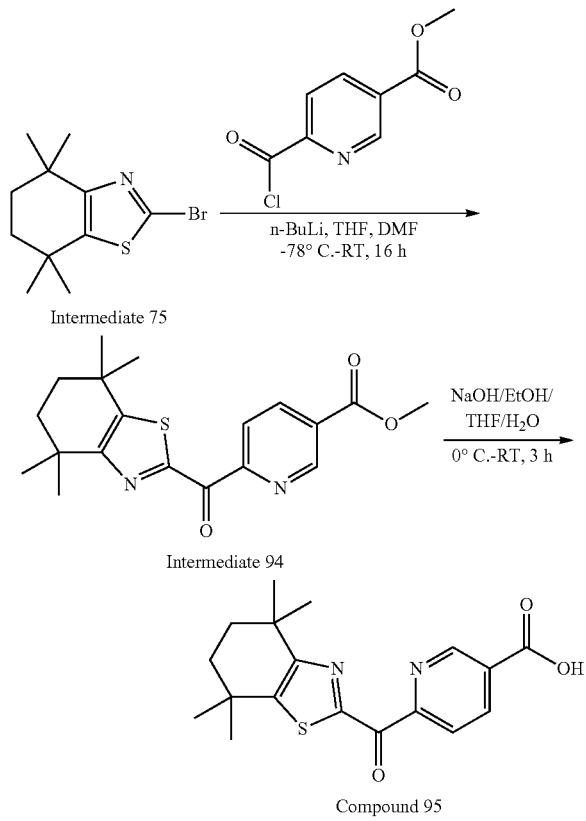

Compound 95

Example 95: 6-[(4,4,7,7-tetramethyl-4,5,6,7-tetrahydro-1,3-benzothiazol-2-yl) carbonyl]pyridine-3-carboxylic acid

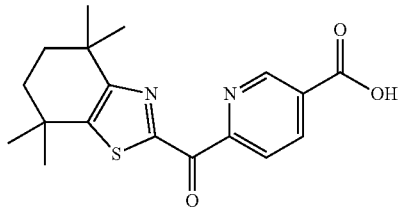 [SMILES: CC1(C)CCC(C)(C)c2sc(C(=O)c3ccc(C(=O)O)cn3)nc21]

Compound 95 was synthesized from 2-bromo-4,4,7,7-tetramethyl-4,5,6,7-tetrahydro-1,3-benzothiazole and methyl 6-(chlorocarbonyl)pyridine-3-carboxylate by following the procedure described in scheme 42; purity: 90.94%

Intermediate 94: methyl 6-[(4,4,7,7-tetramethyl-4,5,6,7-tetrahydro-1,3-benzothiazol-2-yl) carbonyl]pyridine-3-carboxylate To a stirred solution of 2-bromo-4,4,7,7-tetramethyl-4,5,6,7-tetrahydro-1,3-benzothiazole (1 g, 3.64 mmol) in THF (10 mL), n-butyl lithium was added at −78° C. drop wise. The above solution was stirred for 45 min at −78° C. To the stirred solution, methyl 6-(chlorocarbonyl)pyridine-3-carboxylate (1.32 g, 7.3 mmol) [which was prepared by reacting thionyl chloride (15 mL) with 5-(methoxycarbonyl)pyridine-2-carboxylic acid] was added. Reaction mixture was heated to 75° C. for 3 h then RT for 16 h. Reaction mixture was quenched with saturated ammonium chloride solution and extracted with ethyl acetate. The organic layer was washed with water and brine, dried over Na₂SO₄, filtered and concentrated to yield the crude product. The product obtained was purified by column chromatography to yield the title compound as a brown gummy (0.06 g, yield: 4.6%). MS (ESI, 120 eV): m/z=345.1 (M+H)⁺.

Compound 95: 6-[(4,4,7,7-tetramethyl-4,5,6,7-tetrahydro-1,3-benzothiazol-2-yl) carbonyl]pyridine-3-carboxylic acid A 25 mL RB flask fitted with magnetic stirrer was charged methanol (10 mL) and THF (5 mL). To the stirred solvent was added methyl 6-[(4,4,7,7-tetramethyl-4,5, 6,7-tetrahydro-1,3-benzothiazol-2-yl) carbonyl]pyridine-3-carboxylate (0.06 g, 0.16 mmol) and aq. NaOH (0.067 g, 1.6 mmol) at 0° C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over Na₂SO₄, filtered and concentrated to yield the product. The product obtained was triturated with hexane to yield the title compound as a brown gummy (0.015 g, yield: 26.3%): MS (ESI, 120 eV): m/z=345.1 (M+H)⁺.

145

Scheme 43

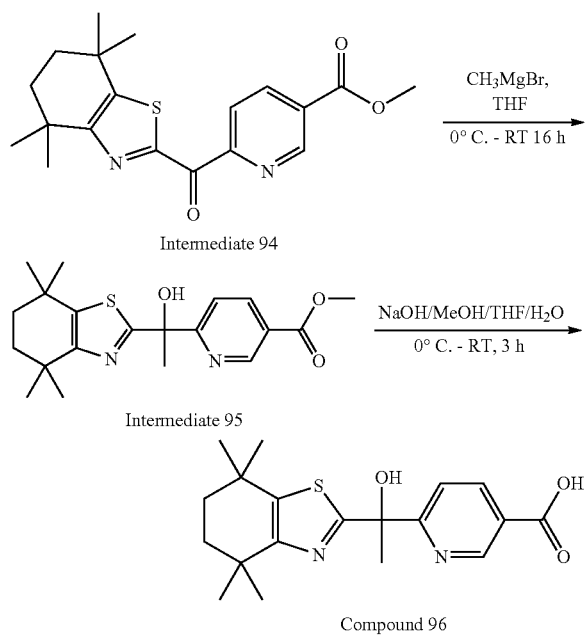

Compound 96

Example 96: 6-[1-hydroxy-1-(4,4,7,7-tetramethyl-4,5,6,7-tetrahydro-1,3-benzothiazol-2-yl)ethyl]pyridine-3-carboxylic acid

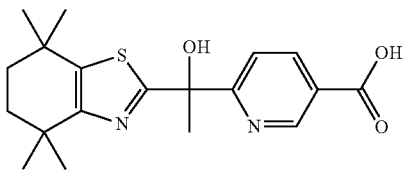 [SMILES: CC1(C)CCC(C)(C)c2sc(C(C)(O)c3ccc(C(=O)O)cn3)nc21]

Compound 96 was synthesized from methyl 6-[(4,4,7,7-tetramethyl-4,5,6,7-tetrahydro-1,3-benzothiazol-2-yl)carbonyl]pyridine-3-carboxylate by following the procedure described in scheme 43; purity: 89.16%

Intermediate 95: methyl 6-[1-hydroxy-1-(4,4,7,7-tetramethyl-4,5,6,7-tetrahydro-1,3-benzothiazol-2-yl)ethyl]pyridine-3-carboxylate To a single-neck 100 mL RB flask fitted with magnetic stirrer charged with methyl 6-[(4,4,7,7-tetramethyl-4,5,6,7-tetrahydro-1,3-benzothiazol-2-yl)carbonyl]pyridine-3-carboxylate (0.06 g, 0.17 mmol) in THF (5 mL), methyl magnesium bromide (0.17 mL, 0.5 mmol, 3M solution) was added drop wise at 0° C. Reaction mixture was stirred at 0° C. for 12 h. After completion of the reaction, reaction mixture was quenched with ice and extracted with ethyl acetate. The organic layer was washed with water and brine, dried over $Na_2SO_4$, filtered and concentrated to yield the crude product. The product obtained was purified by preparative TLC to yield the title compound as a white solid (0.025 g, yield: 43.8%).

146

Compound 96: 6-[1-hydroxy-1-(4,4,7,7-tetramethyl-4,5,6,7-tetrahydro-1,3-benzothiazol-2-yl)ethyl]pyridine-3-carboxylic acid A 25 mL RB flask fitted with magnetic stirrer was with charged methanol (10 mL) and THF (5 mL). To the stirred solvent methyl 6-[1-hydroxy-1-(4,4,7,7-tetramethyl-4,5,6,7-tetrahydro-1,3-benzothiazol-2-yl)ethyl]pyridine-3-carboxylate (0.012 g, 0.03 mmol) and aq. NaOH (0.13 g, 0.32 mmol) was added at 0° C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated to yield the product. The product obtained was triturated with hexane to yield the title compound as a brown solid (0.01 g, yield: 90.90%): MS (ESI, 120 eV): m/z=361.1 $(M+H)^+$.

Scheme 44

147

Example 97: 4-[1-(4,4,7,7-tetramethyl-4,5,6,7-tetrahydro-1,3-benzothiazol-2-yl) ethenyl]benzoic acid

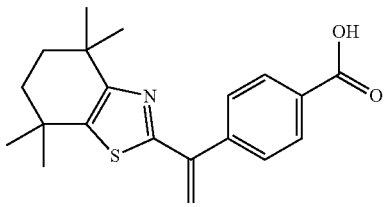 [SMILES: C=C(c1ccc(C(=O)O)cc1)c1nc2c(s1)C(C)(C)CCC2(C)C]

Compound 97 was synthesized from 2-bromo-4,4,7,7-tetramethyl-4,5,6,7-tetrahydro-1,3-benzothiazole and 4-(ethoxycarbonyl)benzoic acid by following the procedure indicated in scheme 44; purity: 99.77%

Intermediate 96: 4-[(4,4,7,7-tetramethyl-4,5,6,7-tetrahydro-1,3-benzothiazol-2-yl) carbonyl]benzoic acid To a two-neck 100 mL RB flask fitted with magnetic stirrer charged with 2-bromo-4,4,7,7-tetramethyl-4,5,6,7-tetrahydro-1,3-benzothiazole (0.91 g, 3.3 mmol) in THF (5 mL), n-butyl lithium (2.2 mL, 5.5 mmol, 2.5M solution) was added drop wise at −78° C. The above solution was stirred at −78° C. for 1 h. Then 4-(ethoxycarbonyl)benzoic acid (0.5 g, 2.7 mmol) in THF (5 mL) was added to the above solution drop wise. Reaction mixture was allowed to stir at RT for 16 h. Reaction mixture was quenched with saturated ammonium chloride solution and extracted with ethyl acetate. The organic layer was washed with water and brine, dried over $Na_2SO_4$, filtered and concentrated to yield the crude product. The product obtained was purified by column chromatography to yield the title compound as a white solid (0.1 g, yield: 10.5%). MS (ESI, 120 eV): m/z=344.1 (M+H)$^+$.

Intermediate 97: 4-[1-hydroxy-1-(4,4,7,7-tetramethyl-4,5,6,7-tetrahydro-1,3-benzothiazol-2-yl)ethyl] benzoic acid To a single-neck 100 mL RB flask fitted with magnetic stirrer charged with 4-[(4,4,7,7-tetramethyl-4,5,6,7-tetrahydro-1,3-benzothiazol-2-yl)carbonyl]benzoic acid (0.1 g, 0.29 mmol) in THF (5 mL), methyl magnesium iodide (0.15 mL, 0.6 mmol, 4M solution) was added drop wise at 0° C. Reaction mixture was stirred at RT for 1 h. After completion of the reaction, reaction mixture was quenched with 1N HCl and extracted with ethyl acetate. The organic layer was washed with water and brine, dried over $Na_2SO_4$, filtered and concentrated to yield the crude product. The product obtained was purified by preparative TLC to yield the title compound as a brown solid (0.05 g, yield: 50%).

Compound 97: 4-[1-(4,4,7,7-tetramethyl-4,5,6,7-tetrahydro-1,3-benzothiazol-2-yl) ethenyl]benzoic acid To a stirred solution of 4-[1-hydroxy-1-(4,4,7,7-tetramethyl-4,5,6,7-tetrahydro-1,3-benzothiazol-2-yl)ethyl]benzoic acid (0.04 g, 0.1 mmol) in TFA (0.2 mL), con.$H_2SO_4$ (6.8 mL) was added drop wise. Reaction mixture was kept at RT for 1 h. Then reaction mixture was quenched with saturated $NaHCO_3$ solution and extracted with ethyl acetate. The organic layer was washed with water and brine, dried over $Na_2SO_4$, filtered and concentrated to yield the crude product. The product obtained was purified by preparative HPLC to yield the title compound as a white solid (0.015 g, yield: 39.5%). MS (ESI, 120 eV): m/z=342.15 (M+H)$^+$.

Scheme 45

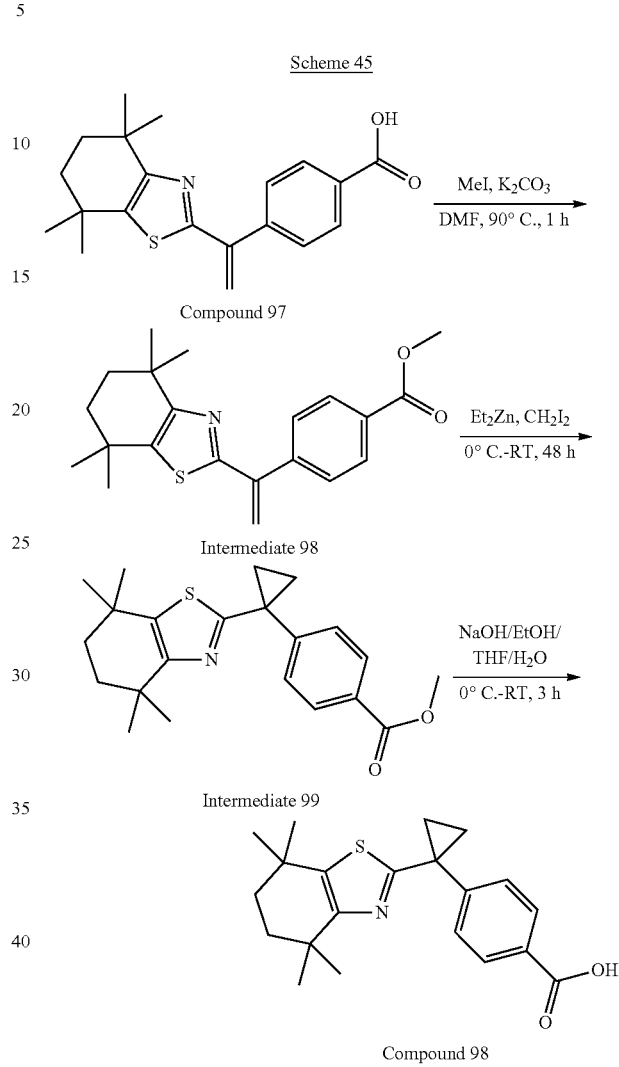

Example 98: 4-[1-(4,4,7,7-tetramethyl-4,5,6,7-tetrahydro-1,3-benzothiazol-2-yl)cyclopropyl]benzoic acid

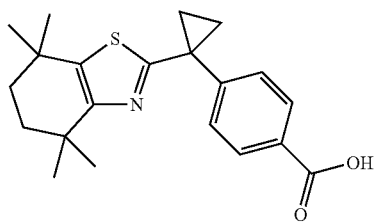 [SMILES: CC1(C)CCC(C)(C)c2sc(C3(c4ccc(C(=O)O)cc4)CC3)nc21]

Compound 98 was synthesized from 4-[1-(4,4,7,7-tetramethyl-4,5,6,7-tetrahydro-1,3-benzothiazol-2-yl)ethenyl]benzoic acid by following the procedure indicated in scheme 45; purity: 98.93%

Intermediate 98: methyl 4-[1-(4,4,7,7-tetramethyl-4,5,6,7-tetrahydro-1,3-benzothiazol-2-yl) ethenyl] benzoate To a stirred solution of 4-[1-(4,4,7,7-tetramethyl-4,5,6,7-tetrahydro-1, 3-benzothiazol-2-yl) ethenyl]benzoic acid (0.5 g, 1.46 mmol) in DMF (3 mL), $K_2CO_3$ (0.8 g, 5.85 mmol) was added. Then methyl iodide (0.3 mL, 4.4 mmol) was added to the above stirred solution. Reaction mixture was heated to 90° C. for 1 h. Reaction mixture was poured into water and extracted with ethyl acetate. The organic layer was washed with water and brine, dried over $Na_2SO_4$, filtered and concentrated to yield the crude product. The product obtained was purified by column chromatography to yield the title compound as a pale yellow oil (0.13 g, yield: 25%).

Intermediate 99: methyl 4-[1-(4,4,7,7-tetramethyl-4,5,6,7-tetrahydro-1,3-benzothiazol-2-yl)cyclopropyl] benzoate To a two-neck 25 mL RB flask fitted with magnetic stirrer charged with 4-[1-(4,4,7,7-tetramethyl-4,5,6,7-tetrahydro-1, 3-benzothiazol-2-yl)ethenyl]benzoic acid (0.13 g, 0.4 mmol) in DCM (5 mL), diiodomethane (0.35 mL, 4.3 mmol) was added at 0° C. To the stirred solution, diethyl zinc (2.2 mL, 2.1 mmol) was added drop wise at the same temperature. Reaction mixture was allowed to stir at RT for 48 h. Reaction mixture was quenched with 1 N HCl and extracted with ethyl acetate. The organic layer was washed with water and brine, dried over $Na_2SO_4$, filtered and concentrated to yield the crude product. The crude product (pale yellow oil) obtained was as such taken for next step without further purification (0.15 g, yield: 25%).

Compound 98: 4-[1-(4,4,7,7-tetramethyl-4,5,6,7-tetrahydro-1,3-benzothiazol-2-yl)cyclopropyl]benzoic acid A 25 mL RB flask fitted with magnetic stirrer was charged with methanol (10 mL) and THF (2 mL). To the stirred solvent methyl 4-[1-(4,4,7,7-tetramethyl-4,5,6,7-tetrahydro-1,3-benzothiazol-2-yl)cyclopropyl]benzoate (0.15 g, 0.41 mmol) and aq. NaOH (0.08 g, 2.02 mmol) was added at 0° C. Reaction mixture was stirred at RT for 16 h. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated to yield the product. The product obtained was again purified by preparative HPLC to yield the title compound as a white solid (0.002 g, yield: 1.5%): MS (ESI, 120 eV): m/z=356.1 (M+H)$^+$.

Example 99: 6-[cyclobutyl(4,4,7,7-tetramethyl-4,5,6,7-tetrahydro-1,3-benzothiazol-2-yl)amino]pyridine-3-carboxylic acid

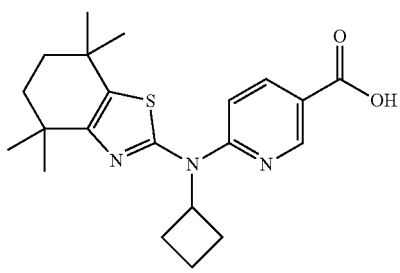 [SMILES: CC1(C)CCC(C)(C)c2sc(N(c3ccc(C(=O)O)cn3)C3CCC3)nc21]

Compound 99 was synthesized from 4,4,7,7-tetramethyl-4,5,6,7-tetrahydro-1,3-benzothiazol-2-amine and methyl 6-chloropyridine-3-carboxylate by following the similar procedure described in scheme 18; purity: 97.43%.

Example 100: 4-[phenyl(4,4,7,7-tetramethyl-4,5,6,7-tetrahydro-1,3-benzothiazol-2-yl)amino]benzoic acid

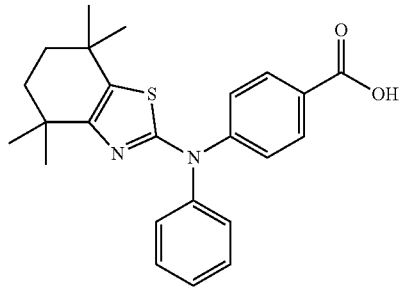 [SMILES: CC1(C)CCC(C)(C)c2sc(N(c3ccccc3)c3ccc(C(=O)O)cc3)nc21]

Compound 100 was synthesized from ethyl 4-[(4,4,7,7-tetramethyl-4,5, 6,7-tetrahydro-1,3-benzothiazol-2-yl)amino]benzoate (intermediate 65) and iodobenzene by following the similar procedure described in scheme 27; purity: 96.86%.

Example 101: 4-[pyridin-2-yl(4,4,7,7-tetramethyl-4,5,6,7-tetrahydro-1,3-benzothiazol-2-yl)amino]benzoic acid

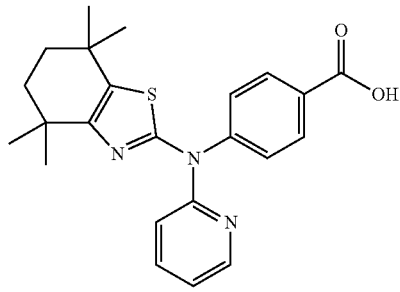 [SMILES: CC1(C)CCC(C)(C)c2sc(N(c3ccc(C(=O)O)cc3)c3ccccn3)nc21]

Compound 101 was synthesized from ethyl 4-[(4,4,7,7-tetramethyl-4,5, 6,7-tetrahydro-1,3-benzothiazol-2-yl)amino]benzoate (intermediate 65) and 2-bromopyridine by following the similar procedure described in scheme 27; purity: 97.95%.

Example 102: 4-[(3,4,4,7,7-pentamethyl-4,5,6,7-tetrahydro-1-benzothiophen-2-yl) (phenyl)amino] benzoic acid

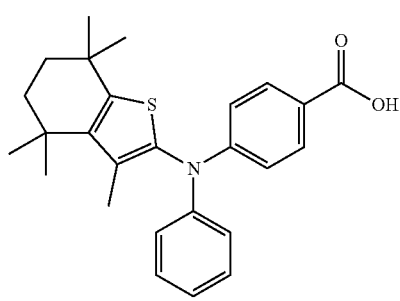 [SMILES: Cc1c(N(c2ccccc2)c2ccc(C(=O)O)cc2)sc2c1C(C)(C)CCC2(C)C]

Compound 102 was synthesized from methyl 4-[(3,4,4,7,7-pentamethyl-4,5,6,7-tetrahydro-1-benzothiophen-2-yl)amino]benzoate (Intermediate-9) and iodobenzene by following the similar procedure described in scheme 27; purity: 99.04%.

Example 103: 4-[(3,4,4,7,7-pentamethyl-4,5,6,7-tetrahydro-1-benzothiophen-2-yl) (pyridin-2-yl)amino]benzoic acid

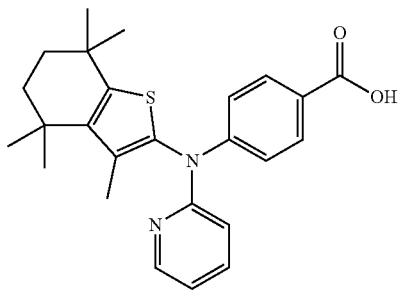 [SMILES: Cc1c(N(c2ccc(C(=O)O)cc2)c2ccccn2)sc2c1C(C)(C)CCC2(C)C]

Compound 103 was synthesized from methyl 4-[(3,4,4,7,7-pentamethyl-4,5,6,7-tetrahydro-1-benzothiophen-2-yl)amino]benzoate (Intermediate-9) and 2-bromopyridine by following the similar procedure described in scheme 27; purity: 91.19%.

Example 104: 4-[(3,4,4,7,7-pentamethyl-4,5,6,7-tetrahydro-1-benzothiophen-2-yl) (pyridin-2-ylmethyl)amino]benzoic acid

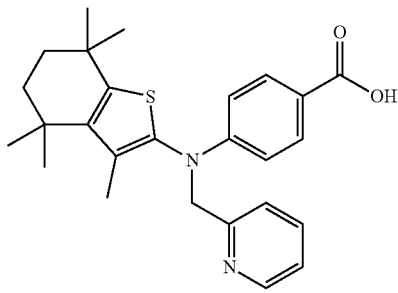 [SMILES: Cc1c(N(Cc2ccccn2)c2ccc(C(=O)O)cc2)sc2c1C(C)(C)CCC2(C)C]

Compound 104 was synthesized from methyl 4-[(3,4,4,7,7-pentamethyl-4,5,6,7-tetrahydro-1-benzothiophen-2-yl)amino]benzoate (Intermediate-9) and 2-(bromomethyl)pyridine by following the similar procedure described in scheme 27; purity: 99.23%.

Scheme 46

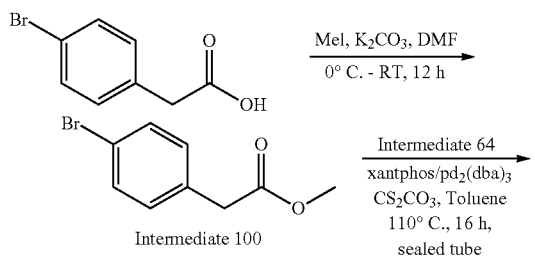

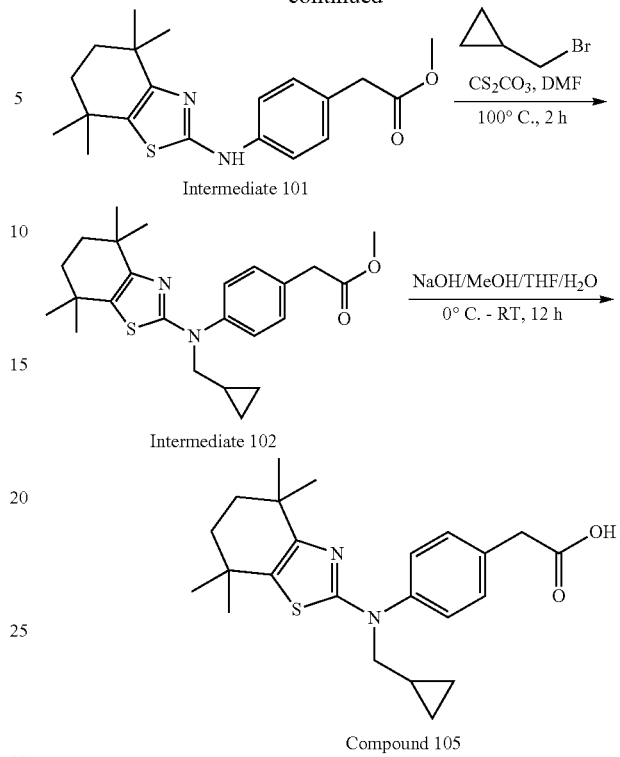

Example 105: {4-[(cyclopropylmethyl) (4,4,7,7-tetramethyl-4,5,6,7-tetrahydro-1,3-benzothiazol-2-yl)amino]phenyl}acetic acid

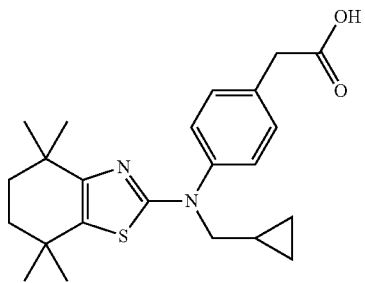 [SMILES: CC1(C)CCC(C)(C)c2sc(N(CC3CC3)c3ccc(CC(=O)O)cc3)nc21]

Compound 105 was synthesized from 4,4,7,7-tetramethyl-4,5,6,7-tetrahydro-1,3-benzothiazol-2-amine and methyl(4-bromophenyl)acetate by following the procedure described in scheme 46; purity: 98.65%

Intermediate 100: methyl(4-bromophenyl)acetate

To a stirred solution of (4-bromophenyl) acetic acid (1.5 g, 6.9 mmol) in DMF (10 mL), potassium carbonate (1.92 g, 14 mmol) and methyl iodide (1.46 g, 10 mmol) was added at 0° C. in a RB flask. Reaction mixture was kept at RT for 2 h. Then the reaction mixture was cooled to RT, poured into water and extracted with ethyl acetate. The combined extracts were washed with water and brine solution. The organic layer was dried over anhydrous Na₂SO₄ and concentrated in vacuum. The crude product obtained was purified by column chromatography to get the title compound as a yellow liquid (1 g, yield: 63.69%).

Intermediate 101: methyl {4-[(4,4,7,7-tetramethyl-4,5,6,7-tetrahydro-1,3-benzothiazol-2-yl)amino]phenyl}acetate To a 100 ml pressure tube with screwed cap charged with 4,4,7,7-tetramethyl-4,5,6,7-tetrahydro-1,3-benzothiazol-2-amine (0.23 g, 1 mmol) in toluene (5 mL), methyl(4-bromophenyl)acetate (0.42 g, 2 mmol) was added. To a stirred solvent $CS_2CO_3$ (0.97 g, 3 mmol) and Xantphos (0.03 g, 0.05 mmol) was added. Above solution was degassed with nitrogen for 10 minutes. Then $Pd_2$ (dba)$_3$ (0.02 g, 0.02 mmol) was added to the reaction mixture. The reaction mixture was heated to 100° C. for 16 h. Reaction mixture was cooled to RT, and poured into water and extracted with ethyl acetate. The combined extracts were washed with water and brine. The organic layer was dried over anhydrous $Na_2SO_4$ and concentrated in vacuum. The crude product obtained was purified by column to give the title compound as a yellow solid (0.2 g, yield: 55.86%).

Intermediate 102: methyl {4-[(cyclopropylmethyl)(4,4,7,7-tetramethyl-4,5,6,7-tetrahydro-1,3-benzothiazol-2-yl)amino]phenyl}acetate To a stirred solution of methyl {4-[(4,4,7,7-tetramethyl-4,5,6,7-tetrahydro-1,3-benzothiazol-2-yl)amino]phenyl}acetate (0.2 g, 0.55 mmol) in DMF (5 mL), cesium carbonate (0.53 g, 1.65 mmol) and cyclo propyl methyl bromide (0.11 g, 0.82 mmol) was added at 0° C. in a RB flask. Reaction mixture was heated to 100° C. for 2 h. Then the reaction mixture was cooled to RT, poured into water and extracted with ethyl acetate. The combined extracts were washed with water and brine solution. The organic layer was dried over anhydrous $Na_2SO_4$ and concentrated in vacuum. The crude product obtained was purified by column chromatography to get the title compound as a yellow liquid (0.018 g, yield: 78.26%).

Compound 105: {4-[(cyclopropylmethyl)(4,4,7,7-tetramethyl-4,5,6,7-tetrahydro-1,3-benzothiazol-2-yl)amino]phenyl}acetic acid A 25 mL RB flask fitted with magnetic stirrer was charged with methanol (0.5 mL) and THF (0.5 mL). To the stirred solvent methyl {4-[(cyclopropylmethyl) (4,4,7,7-tetramethyl-4,5,6,7-tetrahydro-1,3-benzothiazol-2-yl)amino]phenyl}acetate (0.018 g, 0.04 mmol) and aq. NaOH (0.005 g, 0.13 mmol) was added at 0° C. Reaction mixture was stirred at RT for 20 minutes. The reaction mixture was concentrated completely and the crude was washed with ether, and diluted with water and then neutralized with 1.5 N HCl, extracted with ethyl acetate. The organic layer was washed with water and brine, dried over $Na_2SO_4$, filtered and concentrated. The obtained solid was triturated with hexane to give the title compound as a white solid (0.01 g, yield: 58.82%): MS (ESI, 120 eV): m/z=398.2 (M+H)$^+$.

Example 106: 3-{4-[(cyclopropylmethyl) (4,4,7,7-tetramethyl-4,5,6,7-tetrahydro-1,3-benzothiazol-2-yl)amino]phenyl}propanoic acid

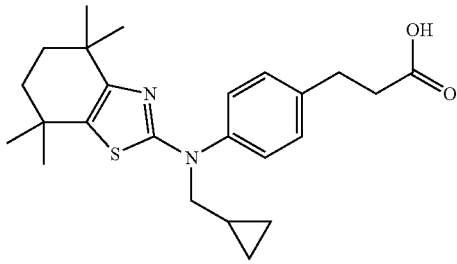 [SMILES: CC1(C)CCC(C)(C)c2sc(N(CC3CC3)c3ccc(CCC(=O)O)cc3)nc21]

Compound 106 was synthesized from 4,4,7,7-tetramethyl-4,5,6,7-tetrahydro-1,3-benzothiazol-2-amine and methyl 3-(4-bromophenyl) propanoate by following the procedure described in scheme 46; purity: 90.67%.

Example 107: ((2E)-3-{4-[(cyclopropylmethyl) (4,4,7,7-tetramethyl-4,5,6,7-tetrahydro-1,3-benzothiazol-2-yl)amino]phenyl}prop-2-enoic acid

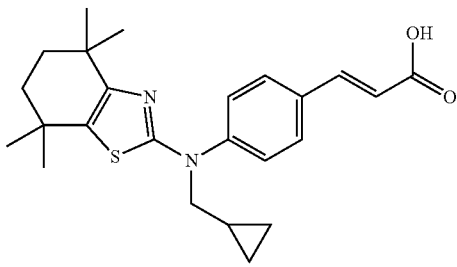 [SMILES: CC1(C)CCC(C)(C)c2sc(N(CC3CC3)c3ccc(/C=C/C(=O)O)cc3)nc21]

Compound 3 was synthesized from 4,4,7,7-tetramethyl-4,5,6,7-tetrahydro-1,3-benzothiazol-2-amine and methyl (2E)-3-(4-iodophenyl) prop-2-enoate by following the procedure described in scheme 46; purity: 95.98%.

Example 108: 2-{4-[(cyclopropylmethyl) (4,4,7,7-tetramethyl-4,5,6,7-tetrahydro-1,3-benzothiazol-2-yl)amino]phenyl}cyclopropanecarboxylic acid

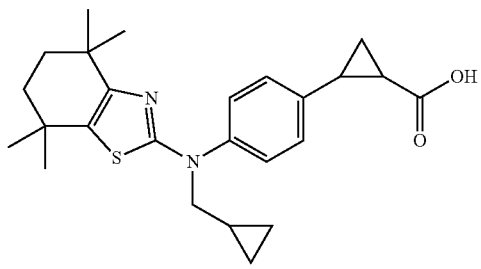 [SMILES: CC1(C)CCC(C)(C)c2sc(N(CC3CC3)c3ccc(C4CC4C(=O)O)cc3)nc21]

Compound 108 was synthesized from 4,4,7,7-tetramethyl-4,5,6,7-tetrahydro-1,3-benzothiazol-2-amine and methyl 2-(4-iodophenyl)cyclopropanecarboxylate by following the procedure described in scheme 46; purity: 97.59%

The compounds outlined in Table 1 were synthesized following the procedures outlined above or variations thereof.

TABLE 1

| NO | Structure | ¹HNMR | m/z |
|---|---|---|---|
| 1 | 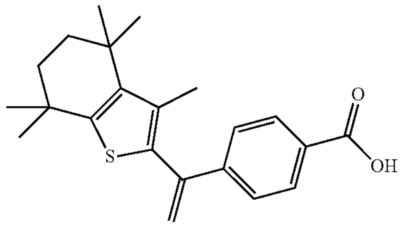 [SMILES: C=C(c1ccc(C(=O)O)cc1)c1sc2c(c1C)C(C)(C)CCC2(C)C] | δ 12.96 (s, 1H), 7.91-7.94 (d, 2H), 7.39-7.42 (d, 2H), 5.84 (s, 1H), 5.42 (s, 1H), 1.94 (s, 3H), 1.66 (s, 4H), 1.25-1.27 (d, 12H) | 353.1 (M − H)⁺ |
| 2 | 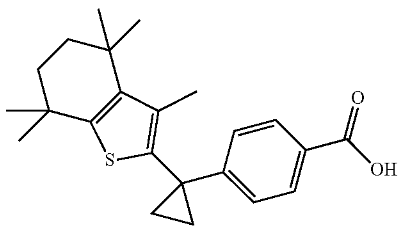 [SMILES: Cc1c(C2(c3ccc(C(=O)O)cc3)CC2)sc2c1C(C)(C)CCC2(C)C] | δ 7.87-7.89 (d, 2H), 6.99-7.02 (d, 2H), 2.06 (s, 3H), 1.61 (s, 4H), 1.41-1.42 (d, 2H), 1.35-1.37 (d, 2H), 1.24 (s, 6H), 1.2 (s, 6H) | 367.1 (M − H)⁺ |
| 3 | 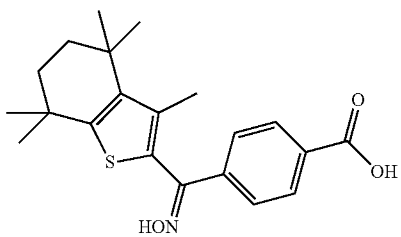 | δ 13.06 (s, 1H), 11.46 (s, 1H), 7.97-8.00 (d, 2H), 7.45-7.47 (d, 2H), 2.03 (s, 3H), 1.63 (s, 4H), 1.23 (s, 12H) | 372.2 (M + H)⁺ |
| 4 | 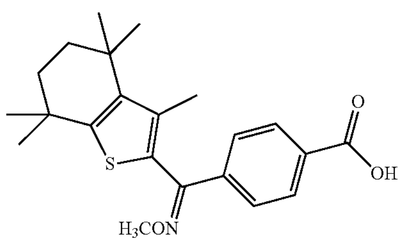 | δ 13.10 (s, 2H), 7.95-8.01 (d, 2H), 7.43-7.51 (d, 2H), 3.97 (s, 3H), 2.07 (s, 3H), 1.68 (s, 2H), 1.63 (s, 2H), 1.27 (s, 6H), 1.24 (s, 6H) | 386.2 (M + H)⁺ |
| 5 | 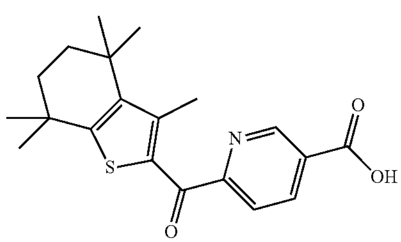 [SMILES: Cc1c(C(=O)c2ccc(C(=O)O)cn2)sc2c1C(C)(C)CCC2(C)C] | δ 13.72 (s, 1H), 9.14-9.15 (d, 1H), 8.44-8.48 (dd, 1H), 8.01-8.03 (d, 1H), 2.59 (s, 3H), 1.68 (s, 4H), 1.32 (s, 12H) | 358.1 (M + H)⁺ |
| 6 | 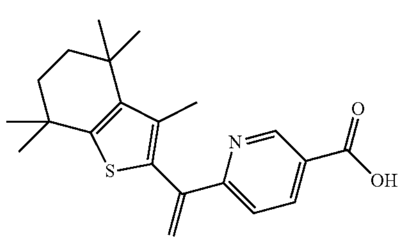 [SMILES: C=C(c1ccc(C(=O)O)cn1)c1sc2c(c1C)C(C)(C)CCC2(C)C] | δ 13.40 (s, 1H), 9.06-9.07 (d, 1H), 8.25-8.28 (dd, 1H), 7.29-7.32 (d, 1H), 6.38 (s, 1H), 5.60 (s, 1H), 1.93 (s, 3H), 1.67 (s, 4H), 1.26-1.28 (d, 12H) | 356.2 (M + H)⁺ |

TABLE 1-continued

| NO | Structure | ¹HNMR | m/z |
|---|---|---|---|
| 7 | 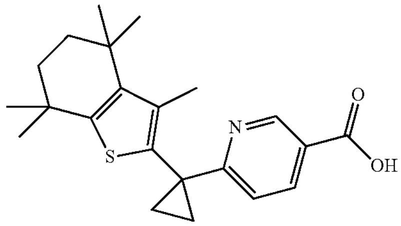 [SMILES: Cc1c(C2(c3ccc(C(=O)O)cn3)CC2)sc2c1C(C)(C)CCC2(C)C] | δ 13.18 (s, 1H), 8.95 (s, 1H), 8.10-8.13 (t, 1H), 6.88-6.91 (d, 1H), 2.08-2.09 (d, 3H), 1.76 (br, 2H), 1.66 (s, 4H), 1.36 (br, 2H), 1.26 (s, 12H) | 370.2 (M + H)⁺ |
| 8 | 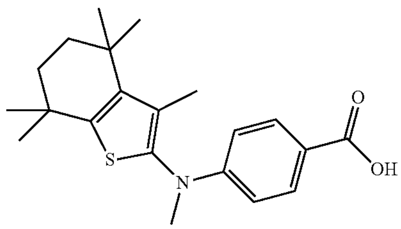 [SMILES: Cc1c(N(C)c2ccc(C(=O)O)cc2)sc2c1C(C)(C)CCC2(C)C] | δ 7.86-7.89 (d, 2H), 6.54-6.57 (d, 2H), 3.22 (s, 3H), 1.91 (s, 3H), 1.64 (s, 4H), 1.22-1.24 (d, 12H) | 358.1 (M + H)⁺ |
| 9 | 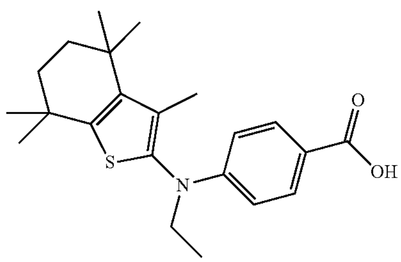 [SMILES: CCN(c1ccc(C(=O)O)cc1)c1sc2c(c1C)C(C)(C)CCC2(C)C] | δ 12.24 (s, 1H), 7.74-7.77 (d, 2H), 6.57-6.60 (d, 2H), 3.64-3.66 (q, 2H), 1.94 (s, 3H), 1.68 (s, 4H), 1.26 (s, 12H), 1.14-1.19 (t, 3H) | 372.2 (M + H)⁺ |
| 10 | 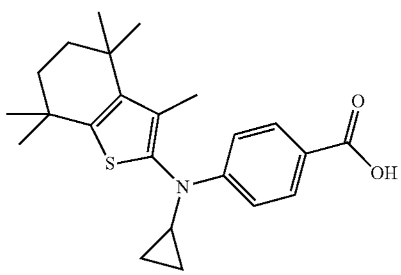 [SMILES: Cc1c(N(c2ccc(C(=O)O)cc2)C2CC2)sc2c1C(C)(C)CCC2(C)C] | δ 7.86-7.89 (d, 2H), 6.76-6.79 (d, 2H), 2.70-2.77 (m, 1H), 1.84 (s, 3H), 1.64 (s, 4H), 1.22-1.23 (d, 12H), 0.82-0.84 (m, 2H), 0.62 (br, 2H) | 384.2 (M + H)⁺ |
| 11 | 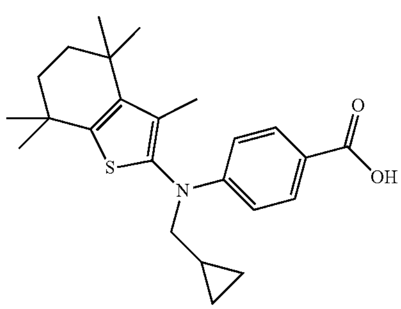 [SMILES: Cc1c(N(CC2CC2)c2ccc(C(=O)O)cc2)sc2c1C(C)(C)CCC2(C)C] | δ 7.84-7.87 (d, 2H), 6.56-6.59 (d, 2H), 3.42-3.44 (d, 2H), 1.92 (s, 3H), 1.64 (s, 4H), 1.24 (s, 6H), 1.21 (s, 6H), 0.76-0.81 (m, 1H), 0.44-0.47 (m, 2H), 0.15-0.19 (m, 2H) | 398.1 (M + H)⁺ |
| 12 | 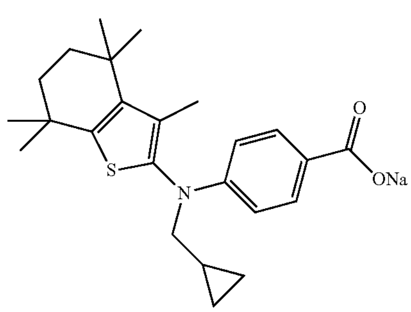 | δ 7.71-7.74 (d, 2H), 6.56-6.59 (d, 2H), 3.44-3.46 (d, 2H), 1.96 (s, 3H), 1.68 (s, 4H), 1.25-1.26 (d, 12H), 1.06-1.11 (m, 1H), 0.44-0.47 (m, 2H), 0.20-0.22 (m, 2H) | 398.1 (M − 22)⁺ |

TABLE 1-continued

| NO | Structure | ¹HNMR | m/z |
|---|---|---|---|
| 13 | 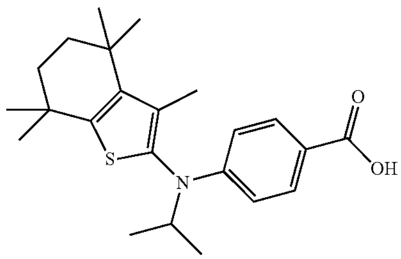 [SMILES: Cc1c(N(c2ccc(C(=O)O)cc2)C(C)C)sc2c1C(C)(C)CCC2(C)C] | δ 7.82-7.85 (d, 2H), 6.47-6.50 (d, 2H), 4.24-4.33 (m, 1H), 1.89 (s, 3H), 1.64 (s, 4H), 1.22-1.24 (d, 12H), 1.86 (s, 6H) | 384 (M − H)⁺ |
| 14 | 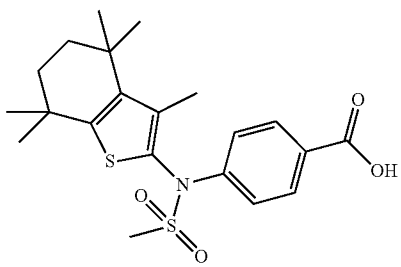 [SMILES: Cc1c(N(c2ccc(C(=O)O)cc2)S(C)(=O)=O)sc2c1C(C)(C)CCC2(C)C] | δ 8.00-8.03 (d, 2H), 7.37-7.40 (d, 2H), 3.13 (s, 3H), 2.15 (s, 3H), 1.62 (s, 4H), 1.20-1.24 (d, 12H) | 422.1 (M + H)⁺ |
| 15 | 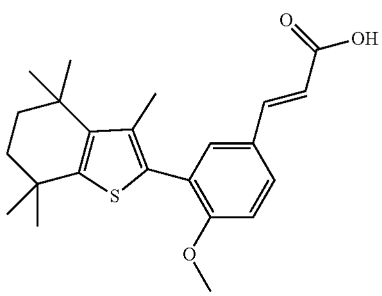 [SMILES: COc1ccc(/C=C/C(=O)O)cc1-c1sc2c(c1C)C(C)(C)CCC2(C)C] | δ 12.21 (s, 1H), 7.69-7.72 (dd, 1H), 7.53-7.58 (d, 1H), 7.50-7.51 (d, 1H), 7.12-7.15 (d, 1H), 6.40-6.45 (d, 1H), 3.81 (s, 3H), 2.03 (s, 3H), 1.68 (s, 4H), 1.28 (s, 12H) | 385.2 (M + H)⁺ |
| 16 | 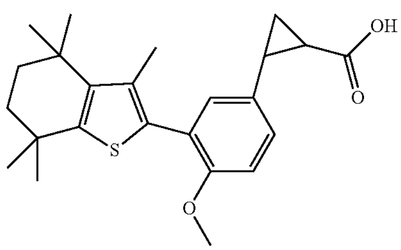 [SMILES: COc1ccc(C2CC2C(=O)O)cc1-c1sc2c(c1C)C(C)(C)CCC2(C)C] | δ 6.98-7.01 (d, 1H), 6.92 (s, 1H), 6.76-6.79 (d, 1H), 3.71 (s, 3H), 2.48 (br, 1H), 2.01 (s, 3H), 1.76-1.77 (m, 1H), 1.62 (s, 4H), 1.47-1.54 (m, 2H), 1.25-1.26 (d, 12H) | 399.2 (M + H)⁺ |
| 17 | 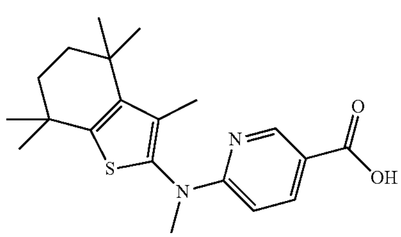 [SMILES: Cc1c(N(C)c2ccc(C(=O)O)cn2)sc2c1C(C)(C)CCC2(C)C] | δ 8.88-8.89 (d, 1H), 7.94-7.96 (d, 1H), 6.27-6.30 (d, 1H), 3.47 (s, 3H), 1.94 (s, 3H), 1.65 (s, 4H), 1.23-1.25 (d, 12H) | 359.1 (M + H)⁺ |
| 18 | 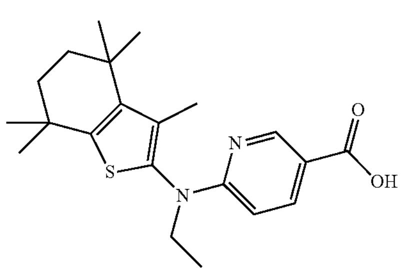 [SMILES: CCN(c1ccc(C(=O)O)cn1)c1sc2c(c1C)C(C)(C)CCC2(C)C] | δ 8.85-8.86 (d, 1H), 7.85-7.89 (dd, 1H), 6.10-6.13 (d, 1H), 3.80-3.85 (q, 2H), 1.92 (s, 3H), 1.65 (s, 4H), 1.23-1.25 (d, 12H), 076-0.83 (t, 3H) | 373.2 (M + H)⁺ |

TABLE 1-continued

| NO | Structure | ¹HNMR | m/z |
|---|---|---|---|
| 19 | 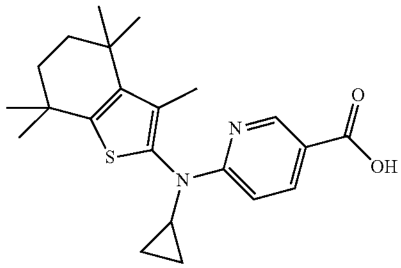 [SMILES: Cc1c(N(c2ccc(C(=O)O)cn2)C2CC2)sc2c1C(C)(C)CCC2(C)C] | δ 12.69 (s, 1H), 8.70 (s, 1H), 7.99-8.03 (dd, 1H), 6.58-6.61 (d, 1H), 3.08-3.12 (m, 1H), 1.88 (s, 3H), 1.68 (s, 4H), 1.26 (d, 12H), 0.86-0.88 (m, 2H), 0.52 (br, 2H) | 385.1 (M + H)⁺ |
| 20 | 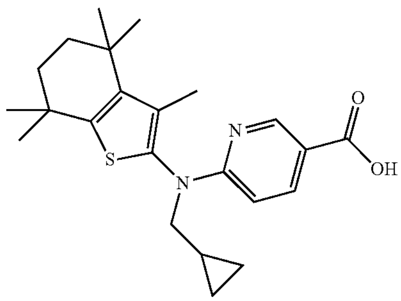 [SMILES: Cc1c(N(CC2CC2)c2ccc(C(=O)O)cn2)sc2c1C(C)(C)CCC2(C)C] | δ 8.82-8.83 (d, 1H), 7.85-7.89 (dd, 1H), 6.11-6.14 (d, 1H), 3.62-3.89 (m, 2H), 1.94 (s, 3H), 1.64 (s, 4H), 1.24-1.25 (d, 12H), 0.76-0.81 (m, 1H), 0.38-0.41 (m, 2H), 0.17-0.24 (m, 2H) | 397.1 (M − H)⁺ |
| 21 | 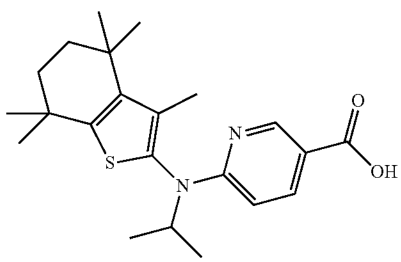 [SMILES: Cc1c(N(c2ccc(C(=O)O)cn2)C(C)C)sc2c1C(C)(C)CCC2(C)C] | δ 12.62 (s, 1H), 8.71 (s, 1H), 7.89-7.92 (d, 1H), 5.96-5.99 (d, 1H), 5.18-5.22 (m, 1H), 1.93 (s, 3H), 1.70 (s, 4H), 1.27-1.28 (d, 12H), 1.22-1.24 (d, 3H), 0.99-1.01 (d, 3H) | 385.2 (M − H)⁺ |
| 22 | 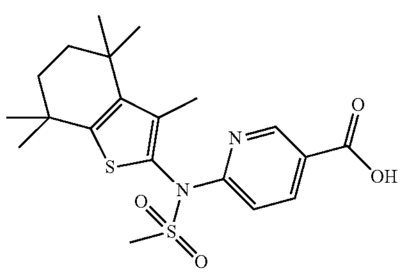 [SMILES: Cc1c(N(c2ccc(C(=O)O)cn2)S(C)(=O)=O)sc2c1C(C)(C)CCC2(C)C] | δ 9.03 (s, 1H), 8.14-8.17 (d, 1H), 6.54-6.56 (d, 1H), 3.56 (s, 3H), 2.15 (s, 3H), 1.64 (s, 4H), 1.24 (s, 12H) | 423.1 (M + H)⁺ |
| 23 | 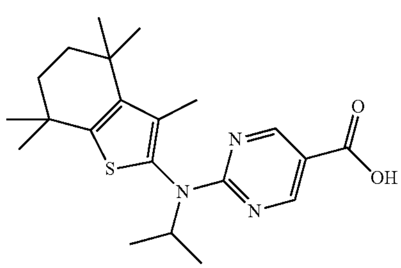 | δ 8.88 (s, 2H), 3.42 (s, 3H), 1.92 (s, 3H), 1.63 (s, 4H), 1.23-1.25 (d, 12H) | 360.1 (M + H)⁺ |

TABLE 1-continued
| NO | Structure | ¹HNMR | m/z |
|---|---|---|---|
| 24 | 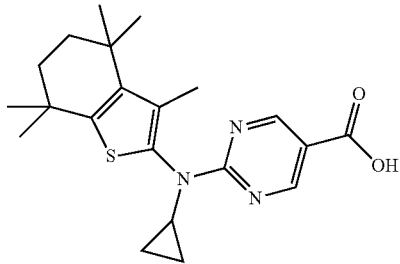 [SMILES: Cc1c(N(c2ncc(C(=O)O)cn2)C2CC2)sc2c1C(C)(C)CCC2(C)C] | δ 8.94 (s, 2H), 3.24-3.27 (m, 1H), 1.87 (s, 3H), 1.63 (s, 4H), 1.22-1.24 (d, 12H), 0.79-0.91 (m, 2H), 0.55 (br, 2H) | 386.2 (M + H)⁺ |
| 25 | 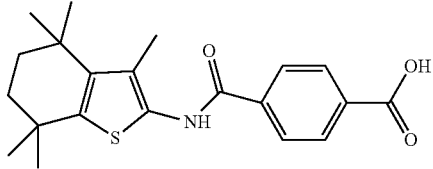 [SMILES: Cc1c(NC(=O)c2ccc(C(=O)O)cc2)sc2c1C(C)(C)CCC2(C)C] | δ 8.13-8.16 (d, 2H), 7.87-7.89 (d, 2H), 2.18 (s, 3H), 1.62 (s, 4H), 1.23-1.26 (d, 12H) | 372.2 (M + H)⁺ |
| 26 | 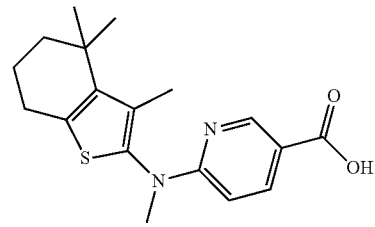 [SMILES: Cc1c(N(C)c2ccc(C(=O)O)cn2)sc2c1C(C)(C)CCC2] | δ 8.91 (s, 1H), 8.09-8.11 (d, 1H), 6.31-6.34 (d, 1H), 3.46 (s, 3H), 2.67-2.71 (t, 2H), 2.29-2.34 (t, 2H), 2.01 (s, 3H), 1.84-1.86 (m, 2H), 1.30 (s, 6H) | 331.1 (M + H)⁺ |
| 27 | 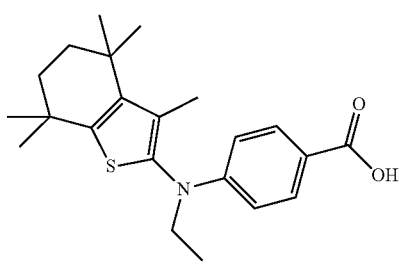 | δ 7.83-7.86 (d, 2H), 6.66-6.69 (d, 2H), 2.18 (s, 1H), 3.63-3.70 (q, 2H), 1.61-1.68 (m, 4H), 1.24 (s, 6H), 1.19-1.22 (t, 3H), 1.13 (s, 6H) | 358.2 (M + H)⁺ |
| 28 | 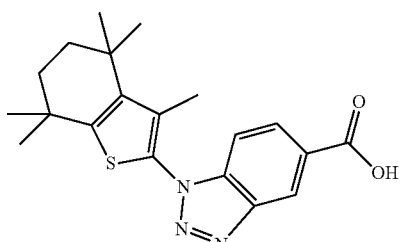 | δ 8.91 (s, 1H), 8.20-8.23 (d, 1H), 7.48-7.51 (d, 1H), 199 (s, 3H), 1.70 (s, 4H), 1.29-1.31 (d, 12H) | 370.1 (M + H)⁺ |
| 29 | 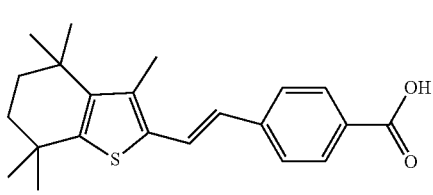 [SMILES: Cc1c(/C=C/c2ccc(C(=O)O)cc2)sc2c1C(C)(C)CCC2(C)C] | δ 7.96-7.99 (d, 2H), 6 7.43-7.45 (d, 2H), 7.31-7.36 (d, 1H, J = 15.9 Hz ), 6.71-6.75 (d, 1H J = 15.6 Hz), 2.30 (s, 3H), 1.61 (s, 4H), 1.24-1.26 (S, 12H) | 353.0 (M + H)⁺ |

TABLE 1-continued
| NO | Structure | ¹HNMR | m/z |
|---|---|---|---|
| 30 | 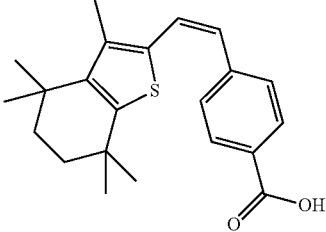 [SMILES: Cc1c(/C=C\c2ccc(C(=O)O)cc2)sc2c1C(C)(C)CCC2(C)C] | δ 7.91-7.93 (d, 2H), 6 7.31-7.34 (d, 2H), 6.61-6.65 (d, 1H, J = 12 Hz), 6.43-6.47 (d, 1H J = 12 Hz ), 2.07 (s, 3H), 1.57 (s, 4H), 1.15-1.19 (S, 12H) | 353.1 (M − H)+ |
| 31 | 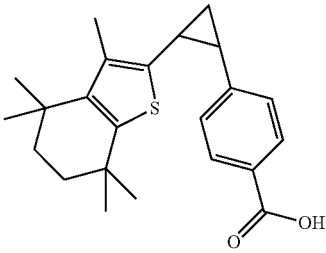 [SMILES: Cc1c(C2CC2c2ccc(C(=O)O)cc2)sc2c1C(C)(C)CCC2(C)C] | δ 12.80 (br, 1H), 7.83-7.86 (d, 2H), 7.29-7.31 (d, 2H), 2.27 (br, 1H), 2.16 (s, 3H), 1.98 (br, 1H), 1.61 (s, 4H), 1.50-1.52 (m, 2H), 1.22 (s, 12H), | 367.1 (M − H)+ |
| 32 | 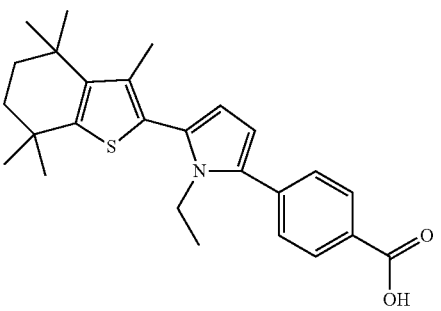 [SMILES: CCn1c(-c2ccc(C(=O)O)cc2)ccc1-c1sc2c(c1C)C(C)(C)CCC2(C)C] | δ 8.06-8.09 (d, 2H), 7.47-7.50 (d, 2H), 6.30-6.31 (d, 1H), 6.17-6.18 (d, 1H), 3.89-3.96 (q, 2H), 2.13 (s, 3H), 1.65 (s, 4H), 1.26-1.28 (d, 12H), 1.17-1.21 (t, 3H) | 420.2 (M − H)+ |
| 33 | 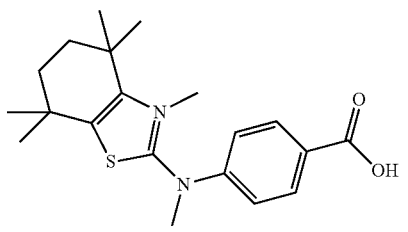 | δ 7.97-8.00 (d, 2H), 7.40-7.43 (d, 2H), 3.49 (s, 3H), 1.63 (s, 4H), 1.86 (s, 12H) | 345.2 (M + H)+ |
| 34 | 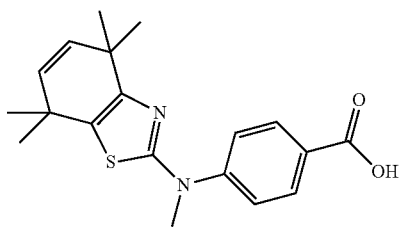 [SMILES: CN(c1ccc(C(=O)O)cc1)c1nc2c(s1)C(C)(C)C=CC2(C)C] | δ 7.99-8.02 (d, 2H), 7.43-7.46 (d, 2H), 5.39-5.49 (m, 2H), 3.52 (s, 3H), 1.25-1.26 (d, 12H) | 343.2 (M + H) |
| 35 | 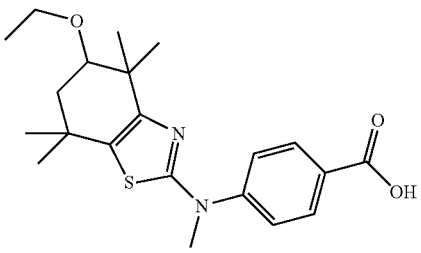 [SMILES: CCOC1CC(C)(C)c2sc(N(C)c3ccc(C(=O)O)cc3)nc2C1(C)C] | δ 7.98-8.01 (d, 2H), 7.41-7.44 (d, 2H), 3.63-3.68 (m, 2H), 3.49 (s, 3H), 3.32-3.44 (m, 1H), 1.75-1.76 (m, 2H), 1.86-1.22 (d, 12H), 1.14-1.18 (t, 3H) | 389.1 (M + H)+ |

TABLE 1-continued

| NO | Structure | ¹HNMR | m/z |
|---|---|---|---|
| 36 | 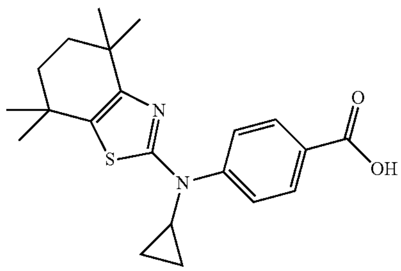 [SMILES: CC1(C)CCC(C)(C)c2sc(N(c3ccc(C(=O)O)cc3)C3CC3)nc21] | δ 7.95-7.98 (d, 2H), 7.59-7.62 (d, 2H), 2.88-2.95 (m, 1H), 1.63 (s, 4H), 1.23 (s, 6H), 1.17 (s, 6H), 1.02-1.04 (m, 2H), 0.79-0.81 (m, 2H) | 371.2 (M + H)+ |
| 37 | 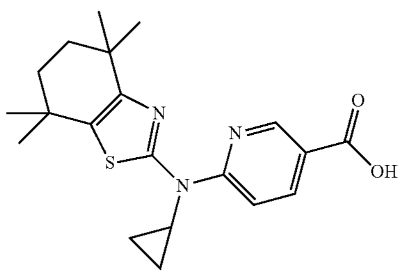 [SMILES: CC1(C)CCC(C)(C)c2sc(N(c3ccc(C(=O)O)cn3)C3CC3)nc21] | δ 13.01 (s, 1H), 8.82-8.83 (d, 1H), 8.21-8.25 (dd, 1H), 7.55-7.58 (d, 1H), 3.13-3.16 (m, 1H), 1.67 (s, 4H), 1.22-1.27 (d, 12H), 1.17-1.23 (m, 2H), 0.60-0.71 (m, 2H) | 372.1 (M + H)+ |
| 38 | 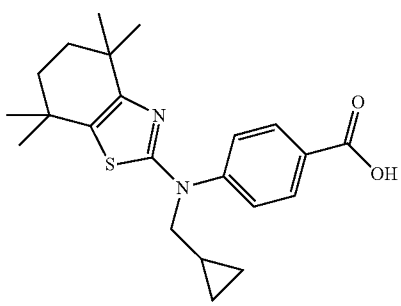 [SMILES: CC1(C)CCC(C)(C)c2sc(N(CC3CC3)c3ccc(C(=O)O)cc3)nc21] | δ 8.01-8.03 (d, 2H), δ 7.38-7.40 (d, 2H), 3.84-3.86 (d, 2H ), 1.61 (s, 4H), 1.19-1.21 (d, 12H), 0.79-0.83 (m, 1H), 0.40-0.43 (m, 2H), 0.17-0.19 (m, 2H) | 385.1 (M + H)+ |
| 39 | 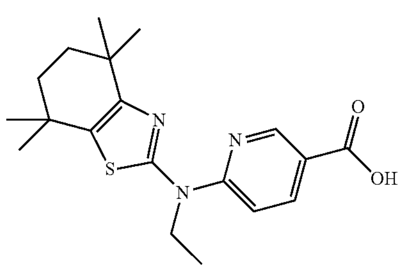 [SMILES: CCN(c1ccc(C(=O)O)cn1)c1nc2c(s1)C(C)(C)CCC2(C)C] | δ 9.01-9.02 (d, 1H), 8.14-8.18 (dd, 1H), 7.05-7.08 (d, 1H), 4.32-4.39 (q, 2H), 1.64 (s, 4H), 1.32-1.34 (t, 3H), 1.27 (s, 6H), 1.20 (s, 6H) | 360.1 (M + H)+ |
| 40 | 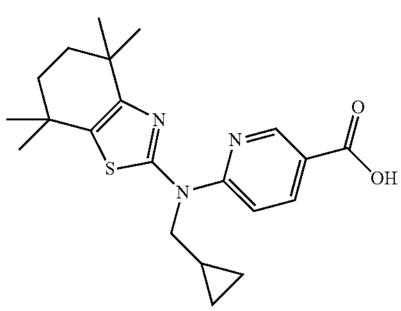 [SMILES: CC1(C)CCC(C)(C)c2sc(N(CC3CC3)c3ccc(C(=O)O)cn3)nc21] | δ 9.01-9.02 (d, 1H), 8.14-8.18 (dd, 1H), 7.11-7.14 (d, 1H), 4.26-4.28 (d, 2H), 1.64 (s, 4H), 1.27 (s, 6H), 1.18 (s, 6H), 0.78-0.87 (m, 1H), 0.48-0.49 (m, 2H), 0.46-0.47 (m, 2H) | 386.1 (M + H)+ |

TABLE 1-continued

| NO | Structure | $^1$HNMR | m/z |
|---|---|---|---|
| 41 | 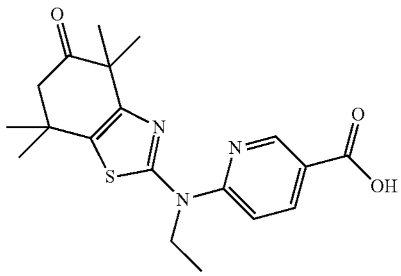 [SMILES: CCN(c1ccc(C(=O)O)cn1)c1nc2c(s1)C(C)(C)CC(=O)C2(C)C] | δ 9.06 (s, 1H), 8.22-8.25 (d, 1H), 7.02-7.05 (d, 1H), 4.39-4.46 (q, 2H), 2.61 (s, 2H), 1.39 (s, 6H), 1.32 (s, 6H), 1.17-1.19 (t, 3H) | 374.2 (M + H)$^+$ |
| 42 | 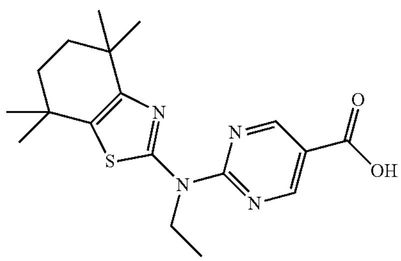 [SMILES: CCN(c1ncc(C(=O)O)cn1)c1nc2c(s1)C(C)(C)CCC2(C)C] | δ 9.10 (s, 2H), 4.60-4.67 (q, 2H), 1.64 (s, 4H), 1.30-1.35 (t, 3H), 1.28 (s, 6H), 1.21 (s, 6H) | 361.1 (M + H)$^+$ |
| 43 | 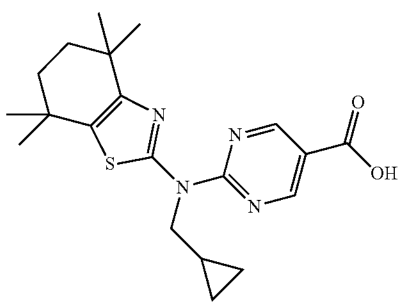 [SMILES: CC1(C)CCC(C)(C)c2sc(N(CC3CC3)c3ncc(C(=O)O)cn3)nc21] | δ 9.10 (s, 2H), 4.50-4.53 (d, 2H), 1.64 (s, 4H), 1.28 (s, 6H), 1.19 (s, 6H), 0.79-0.81 (m, 1H), 0.49-0.50 (m, 2H), 0.37-0.41 (m, 2H) | 385.1 (M − H)$^+$ |
| 44 | 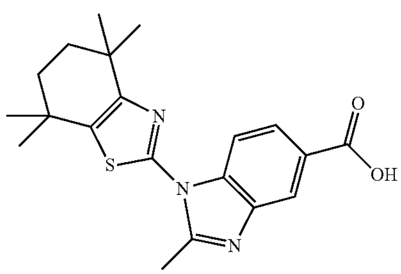 [SMILES: Cc1nc2cc(C(=O)O)ccc2n1-c1nc2c(s1)C(C)(C)CCC2(C)C] | δ 8.49 (s, 1H), 8.03-8.05 (d, 1H), 7.67-7.70 (d, 1H), 2.78 (s, 3H), 1.74 (s, 4H), 1.28-1.33 (d, 12H) | 370.1 (M + H)$^+$ |
| 45 | 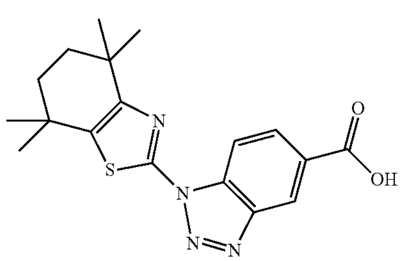 [SMILES: CC1(C)CCC(C)(C)c2sc(-n3nnc4cc(C(=O)O)ccc43)nc21] | δ 8.87 (s, 1H), 8.46-8.49 (d, 1H), 8.30-8.33 (d, 1H), 1.74 (s, 4H), 1.40 (s, 12H) | 357.0 (M + H)$^+$ |
| 46 | 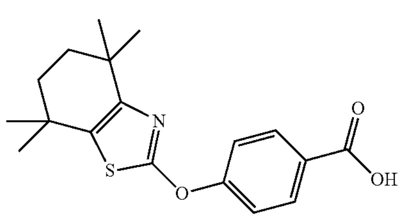 [SMILES: CC1(C)CCC(C)(C)c2sc(Oc3ccc(C(=O)O)cc3)nc21] | δ 8.27 (s, 1H), 7.92-7.96 (d, 2H), 6.99-7.02 (d, 2H), 1.71 (s, 4H), 1.27-1.30 (d, 12H) | 332.1 (M + H)$^+$ |

TABLE 1-continued

| NO | Structure | ¹HNMR | m/z |
|---|---|---|---|
| 47 | 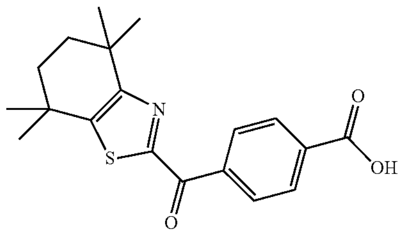 [SMILES: CC1(C)CCC(C)(C)c2sc(C(=O)c3ccc(C(=O)O)cc3)nc21] | δ 8.57-8.60 (d, 2H), 8.23-8.26 (d, 2H), 1.79 (s, 4H), 1.36-1.39 (d, 12H | 344.1 (M + H)⁺ |
| 48 | 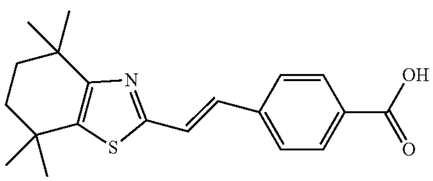 [SMILES: CC1(C)CCC(C)(C)c2sc(/C=C/c3ccc(C(=O)O)cc3)nc21] | δ 7.90-7.93 (d, 2H), 7.76-7.79 (d, 2H), 7.52-7.57 (d, 1H, J = 15 hz), 7.34-7.39 (d, 1H, J = 15 hz), 1.71 (s, 4H), 1.26-1.30 (d, 12H) | 342.1 (M + H)⁺ |
| 49 | 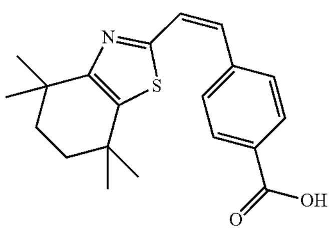 [SMILES: CC1(C)CCC(C)(C)c2sc(/C=C\c3ccc(C(=O)O)cc3)nc21] | δ 7.92-7.94 (d, 2H), 7.85-7.88 (d, 2H), 6.82 (s, 2H), 1.67 (s, 4H), 1.21-1.22 (d, 12H) | 340.1 (M − H)⁺ |
| 50 | 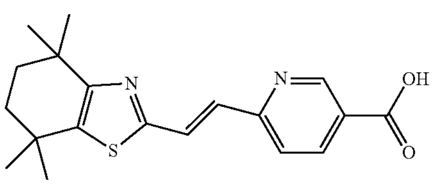 [SMILES: CC1(C)CCC(C)(C)c2sc(/C=C/c3ccc(C(=O)O)cn3)nc21] | δ 9.01 (s, 1H), 8.15-8.18 (d, 1H), 7.74-7.79 (d, 1H, J = 15 hz), 7.66-7.69 (d, 1H) 7.38-7.43 (d, 1H, J = 15.9 hz), 1.71 (s, 4H), 1.27-1.30 (d, 12H) | 343.1 (M + H)⁺ |
| 51 | 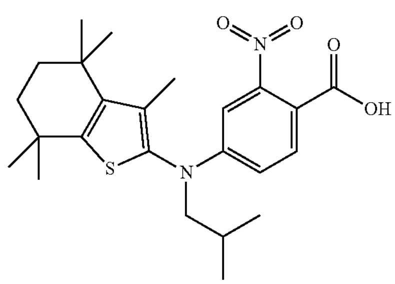 [SMILES: Cc1c(N(CC(C)C)c2ccc(C(=O)O)c([N+](=O)[O-])c2)sc2c1C(C)(C)CCC2(C)C] | δ 7.72-7.75-(d, 1H), 6.57-6.59 (d, 2H), 3.29-3.45 (m, 2H), 2.04-2.08 (m, 1H), 1.86 (s, 3H), 1.63 (s, 5H), 1.24 (s, 6H), 1.20 (s, 6H), 0.91-0.93 (d, 6H). | 445.3 (M + H)⁺ |
| 52 | 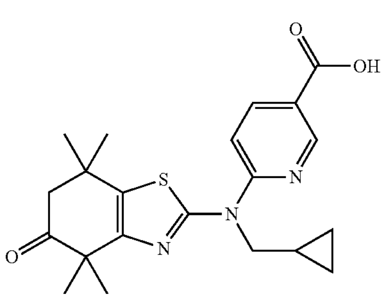 [SMILES: CC1(C)CC(=O)C(C)(C)c2nc(N(CC3CC3)c3ccc(C(=O)O)cn3)sc21] | — | 400.3 (M + H)⁺ |

TABLE 1-continued

| NO | Structure | ¹HNMR | m/z |
|----|-----------|-------|-----|
| 53 | 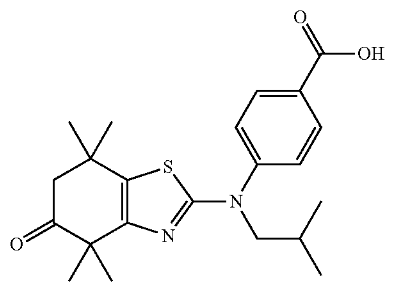 [SMILES: CC(C)CN(c1ccc(C(=O)O)cc1)c1nc2c(s1)C(C)(C)CC(=O)C2(C)C] | δ 12.94 (s, 1H), 7.96-7.99 (d, 2H), 7.57-7.60 (d, 2H), 3.82-3.84 (d, 2H), 2.64 (s, 2H), 1.92-2.01 (m, 1H), 1.28 (s, 6H), 1.17 (s, 6H), 0.87-.0.89 (d, 6H). | 401.3 (M + H)⁺ |
| 54 | 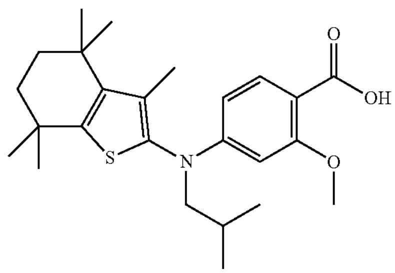 [SMILES: COc1cc(N(CC(C)C)c2sc3c(c2C)C(C)(C)CCC3(C)C)ccc1C(=O)O] | δ 8.61 (s, 1H), 7.57-7.60 (d, 1H), 6.54 (s, 1H), 6.18-6.20 (d, 1H), 6.06 (s, 1H), 3.64 (s, 3H), 2.00-2.04 (m, 5H), 1.92 (s, 6H), 1.67 (s, 6H), 1.43-1.50 (m, 4H), 0.91-0.93 (d, 6H). | 430.2 (M + H)⁺ |
| 55 | 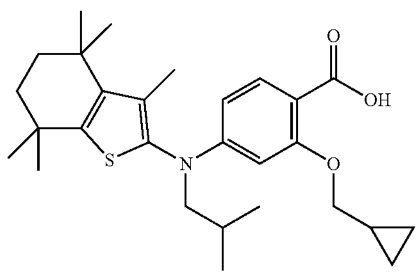 [SMILES: Cc1c(N(CC(C)C)c2ccc(C(=O)O)c(OCC3CC3)c2)sc2c1C(C)(C)CCC2(C)C] | — | 470.2 (M + H)⁺ |
| 56 | 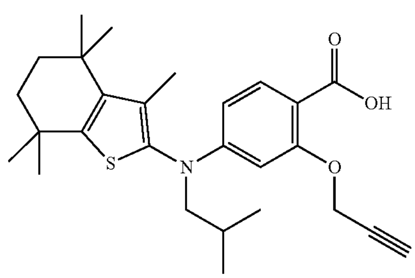 [SMILES: C#CCOc1cc(N(CC(C)C)c2sc3c(c2C)C(C)(C)CCC3(C)C)ccc1C(=O)O] | — | 454.2 (M + H)⁺ |
| 57 | 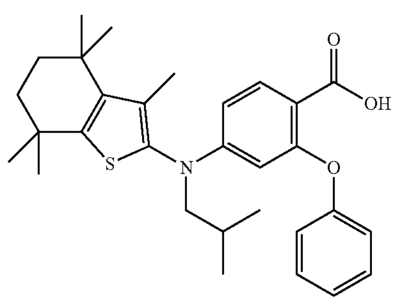 [SMILES: Cc1c(N(CC(C)C)c2ccc(C(=O)O)c(Oc3ccccc3)c2)sc2c1C(C)(C)CCC2(C)C] | — | 492.3 (M + H)⁺ |

| NO | Structure | ¹HNMR | m/z |
|---|---|---|---|
| 58 | 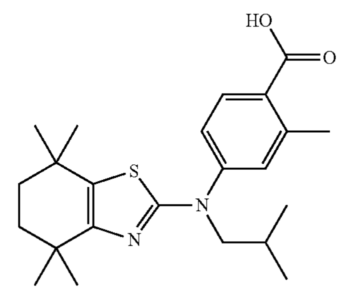 [SMILES: Cc1cc(N(CC(C)C)c2nc3c(s2)C(C)(C)CCC3(C)C)ccc1C(=O)O] | δ 12.73 (s, 1H), 7.83-7.86 (d, 1H), 7.39 (s, 1H), 7.32-7.35 (d, 1H), 3.76-3.79 (d, 2H), 1.62 (s, 4h), 1.15-1.16 (m, 15H), 0.86-.0.88 (d, 6H). | 401.4 (M + H)⁺ |
| 59 | 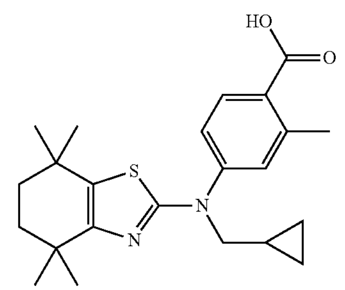 [SMILES: Cc1cc(N(CC2CC2)c2nc3c(s2)C(C)(C)CCC3(C)C)ccc1C(=O)O] | δ 12.75 (s, 1H), 7.84-7.87 (d, 1H), 7.32-7.38 (t, 2H), 3.79-3.82 (d, 2H), 1.62 (s, 6H), 1.17-1.15 (m, 15H), 0.40-0.42 (d, 2H), 0.21-0.22 (d, 2H). | 399.4 (M + H)⁺ |
| 60 | 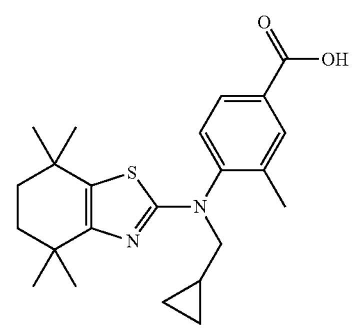 [SMILES: Cc1cc(C(=O)O)ccc1N(CC1CC1)c1nc2c(s1)C(C)(C)CCC2(C)C] | δ 13.02 (s, 1H), 7.82-7.86 (dd, 1H), 7.44-7.47 (d, 1H), 3.64-3.66 (d, 2H), 2.43-2.44 (m, 1H), 2.25 (s, 3H), 1.59 (s, 4H), 1.16 (s, 6H), 1.09 (s, 6H), 0.39-0.42 (d, 2H), 0.36-0.38 (d, 2H). | 399.4 (M + H)⁺ |
| 61 | 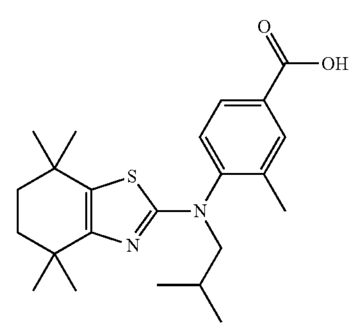 [SMILES: Cc1cc(C(=O)O)ccc1N(CC(C)C)c1nc2c(s1)C(C)(C)CCC2(C)C] | δ 13.01 (s, 1H), 7.91-7.92 (d, 1H), 7.82-7.85 (dd, 1H), 7.43-7.46 (d, 1H), 3.61-3.63 (d, 2H), 2.22 (s, 3H), 1.86-1.95 (m, 1H), 1.59 (s, 4H), 1.15 (s, 6H), 1.10 (s, 6H), 0.88-0.91 (d, 6H). | 401.4 (M + H)⁺ |
| 62 | 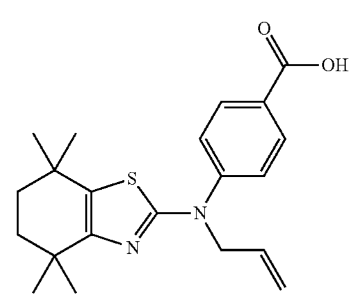 [SMILES: C=CCN(c1ccc(C(=O)O)cc1)c1nc2c(s1)C(C)(C)CCC2(C)C] | δ 12.79 (s, 1H), 7.89-7.92 (d, 2H), 7.51-7.54 (d, 2H), 5.88-5.99 (m, 1H), 5.14-5.22 (m, 2H), 4.57-4.59 (d, 2H), 1.64 (s, 4H), 1.18 (s, 12H). | 371.1 (M + H)⁺ |

| NO | Structure | ¹HNMR | m/z |
|---|---|---|---|
| 63 | 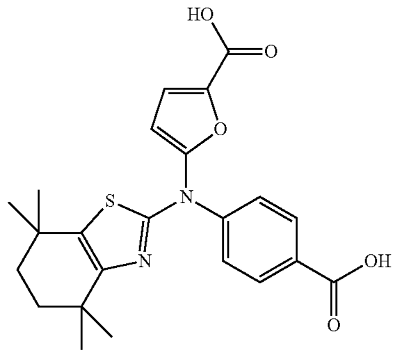 [SMILES: CC1(C)CCC(C)(C)c2sc(N(c3ccc(C(=O)O)cc3)c3ccc(C(=O)O)o3)nc21] | δ 12.97-13.01 (s, 2H), 7.97-8.00 (d, 2H), 7.43-7.46 (d, 2H), 7.34-7.35 (d, 1H), 6.75-6.76 (d, 1H), 1.67 (s, 4H), 1.19 (s, 12H). | 441.1 (M + H)+ |
| 64 | 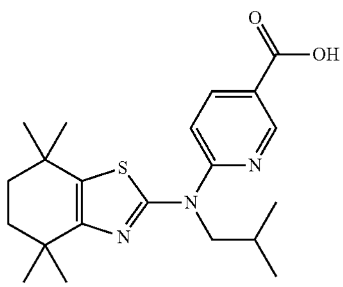 [SMILES: CC(C)CN(c1ccc(C(=O)O)cn1)c1nc2c(s1)C(C)(C)CCC2(C)C] | δ 12.95 (s, 1H), 8.83-8.84 (d, 1H), 8.15-8.19 (dd, 1H), 7.34-7.37 (d, 1H), 4.27-4.29 (d, 2H), 2.17-2.24 (m, 1H), 1.66 (s, 1H), 1.28 (s, 6H), 1.20 (s, 6H), 0.89-0.92 (d, 6H). | 388.3 (M + H)+ |
| 65 | 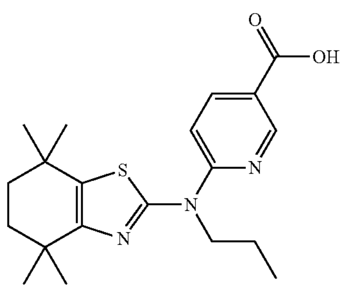 [SMILES: CCCN(c1ccc(C(=O)O)cn1)c1nc2c(s1)C(C)(C)CCC2(C)C] | δ 13.07 (s, 1H), 8.85 (s, 1H), 8.18-8.21 (d, 1H), 7.32-7.35 (d, 1H), 4.28-4.33 (t, 2H), 1.71-1.73 (m, 2H), 1.66 (s, 4H), 1.27 (s, 6H), 1.21 (s, 6H), 0.93-0.98 (t, 3H). | 374.2 (M + H)+ |
| 66 | 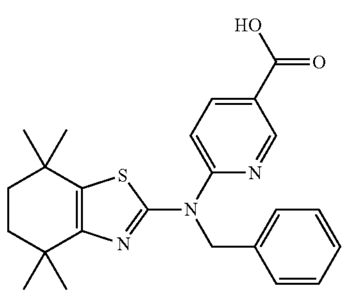 [SMILES: CC1(C)CCC(C)(C)c2sc(N(Cc3ccccc3)c3ccc(C(=O)O)cn3)nc21] | δ 12.98 (s, 1H), 8.862-8.868 (d, 1H), 8.12-8.15 (dd, 1H), 7.21-7.29 (m, 6H), 5.67 (s, 2H), 1.66 (s, 4h), 1.29 (s, 6H), 1.15 (s, 6H). | 422.2 (M + H)+ |
| 67 | 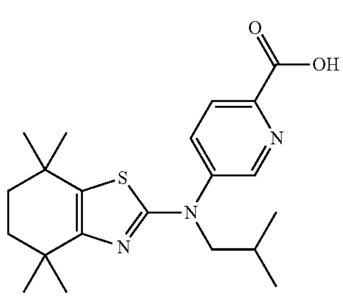 | — | 388.2 (M + H)+ |

TABLE 1-continued

| NO | Structure | ¹HNMR | m/z |
|---|---|---|---|
| 68 | 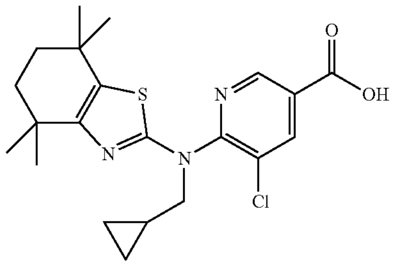 [SMILES: CC1(C)CCC(C)(C)c2sc(N(CC3CC3)c3ncc(C(=O)O)cc3Cl)nc21] | δ 12.93 (s, 1H), 8.75 (s, 1H), 8.06 (s, 1H), 4.28-4.30 (d, 2H), 1.67-1.75 (d, 5H), 1.40 (s, 6H), 1.27 (s, 6H), 0.74-0.75 (d, 2H), 0.47-0.49 (d, 2H). | 420.1 (M + H)⁺ |
| 69 | 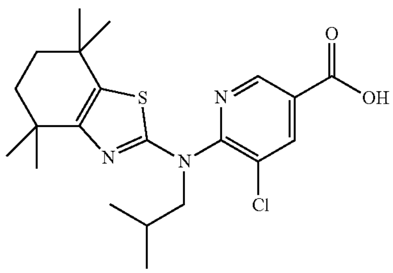 [SMILES: CC(C)CN(c1nc2c(s1)C(C)(C)CCC2(C)C)c1ncc(C(=O)O)cc1Cl] | δ 12.93 (s, 1H), 8.74 (s, 1H), 8.06 (s, 1H), 4.14-4.17 (d, 2H), 1.66-1.72 (d, 4H), 1.36 (s, 6H), 1.26 (s, 7H), 0.88-0.90 (d, 6H). | 422.2 (M + H)⁺ |
| 70 | 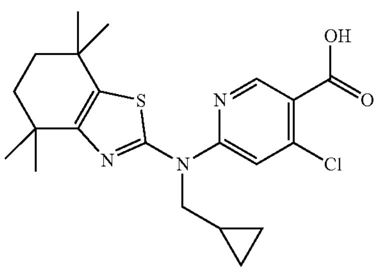 [SMILES: CC1(C)CCC(C)(C)c2sc(N(CC3CC3)c3cc(Cl)c(C(=O)O)cn3)nc21] | δ 13.30 (s, 1H), 8.82 (s, 1H), 7.53 (s, 1H), 4.33-4.35 (d, 2H), 1.67 (d, 4H), 1.28 (s, 6H), 1.23 (s, 1H), 1.20 (s, 6H), 0.45-0.48 (d, 4H). | 420.1 (M + H)⁺ |
| 71 | 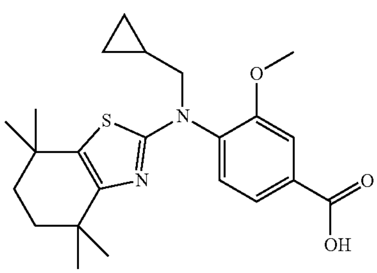 [SMILES: COc1cc(C(=O)O)ccc1N(CC1CC1)c1nc2c(s1)C(C)(C)CCC2(C)C] | δ 13.13 (s, 1H), 7.58-7.64 (t, 2H), 7.50-7.53 (d, 1H), 3.84 (s, 3H), 3.61-3.63 (d, 2H), 1.59 (s, 4H), 1.17 (s, 6H), 1.09 (s, 6H), 0.33-0.35 (d, 2H), 0.08-010 (d, 2H). | 415.9 (M + H)⁺ |
| 72 | 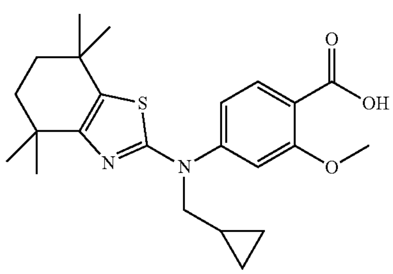 | δ 12.50 (s, 1H), 7.68-7.71 (d, 1H), 7.24-7.25 (s, 1H), 7.02-7.04 (d, 1H)3.85-3.81 (m, 5H), 1.63 (s, 4H), 1.16-1.17 (m, 13H), 0.42-0.46 (d, 2H), 0.23-0.25 (d, 2H). | 415.4 (M + H)⁺ |

TABLE 1-continued

| NO | Structure | ¹HNMR | m/z |
|---|---|---|---|
| 73 | 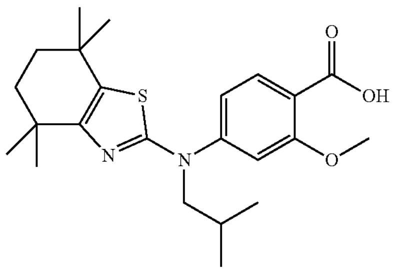 | δ 12.49 (s, 1H), 7.67-7.69 (d, 1H), 7.25 (s, 1H), 7.01-7.04 (d, 1H)3.85-3.80 (s, 5H), 1.62 (s, 4H), 1.16 (s, 13H), 0.87-0.89 (d, 6H). | 417.4 (M + H)⁺ |
| 74 | 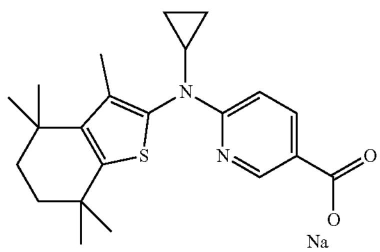 | δ 8.52-8.56 (d, 1H), 7.88-7.92 (d, 1H), 6.41-6.44 (d, 1H), 2.97 (m, 1H), 1.87 (s, 3H), 1.67 (s, 4H), 1.25 (s, 12H), 0.81-0.83 (m, 2H), 0.47 (m, 2H). | 385.1 (M + H)⁺ |
| 75 | 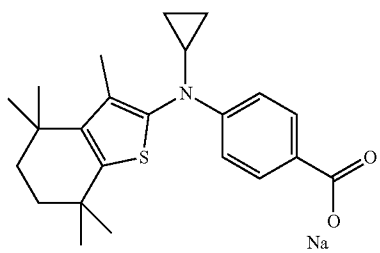 | δ 7.65-7.68 (d, 2H), 6.59-6.62 (d, 2H), 2.27s, 1H), 1.90 (s, 3H), 1.67 (s, 4H), 1.25 (s, 12H), 0.83-.085 (m 2H), 0.51 (m, 2H). | 384.2 (M + H)⁺ |
| 76 | 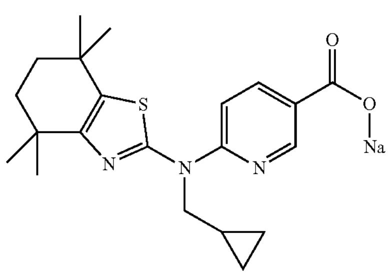 | δ 8.75 (s, 1H), 8.13-8.16 (d, 1H), 7.20-7.22 (d, 1H), 4.26-4.28 (d, 2H), 1.65 (s, 4H), 1.53-1.58 (m, 1H), 1.27 (s, 6H), 1.19 (s, 6H), 0.50-0.51 (m, 2H), 0.43-0.45 (m, 2H). | 386.1 (M + H)⁺ |
| 77 | 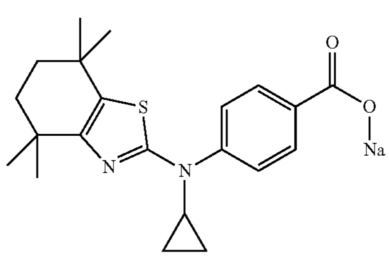 | δ 8.51-8.52 (s, 1H), 7.79-7.81 (d, 1H), 7.34-7.37 (d, 1H), 3.06-3.07 (m, 2H), 1.62 (s, 4H), 1.21 (s, 6H), 1.12 (s, 6H), 0.96-0.98 (d, 2H), 0.60 (m, 2H). | 371.1 (M + H)⁺ |
| 78 | 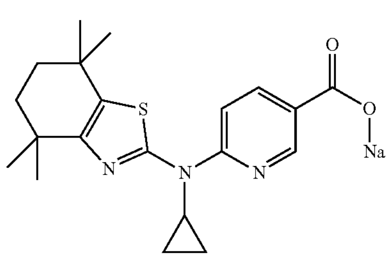 | δ 8.94 (s, 1H), 8.33-8.36 (d, 1H), 7.56-7.59 (d, 1H), 3.28 (s, 1H), 1.88 (s, 4H), 1.48 (s, 6H), 1.38 (s, 6H), 1.08 (m, 2H), 0.84 (m, 2H). | 370.49 (M − 23)⁺ |

TABLE 1-continued

| NO | Structure | ¹HNMR | m/z |
|---|---|---|---|
| 79 | 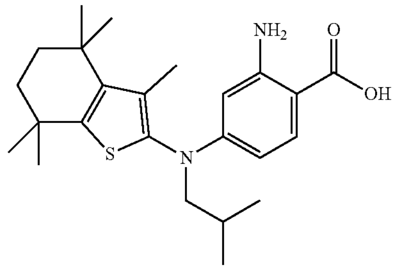 [SMILES: Cc1c(N(CC(C)C)c2ccc(C(=O)O)c(N)c2)sc2c1C(C)(C)CCC2(C)C] | δ 7.62-7.65-(d, 1H), 5.89-5.92 (d, 1H), 5.67-5.67 (d, 1H), 3.31 (bs, 2H), 2.01-2.06 (m, 1H), 1.86 (s, 3H), 1.62 (s, 5H), 1.23 (s, 6H), 1.20 (s, 6H), 0.89-0.91 (d, 6H). | 415.4 (M + H)⁺ |
| 80 | 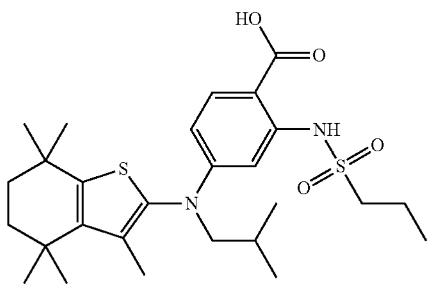 [SMILES: CCCS(=O)(=O)Nc1cc(N(CC(C)C)c2sc3c(c2C)C(C)(C)CCC3(C)C)ccc1C(=O)O] | δ 10.30 (s, 1H), 7.78-7.81-(d, 1H), 6.77 (s, 1H), 6.64 (s, 1H), 6.20-6.23 (d, 1H), 2.92-2.97 (m, 2H), 2.03-2.29 (m, 3H), 1.89 (s, 4H), 1.63-1.72 (m, 6H), 1.24 (s, 6H), 1.22 (s, 6H), 0.94-.090 (m, 4H), 0.76-0.81 (m, 6H). | 521.3 (M + H)⁺ |
| 81 | 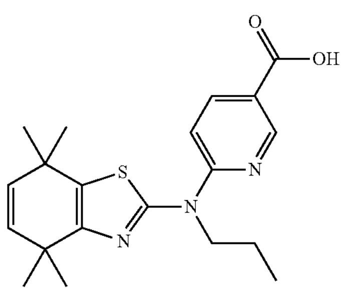 | δ 12.98 (s, 1H), 8.87 (s, 1H), 8.20-8.23 (d, 1H), 7.35-7.38 (d, 1H), 5.52-5.61 (q, 2H), 4.32-4.37 (t, 2H), 1.71-1.78 (q, 2H), 1.34 (s, 6H), 1.28 (s, 6H), 0.94-0.99 (t, 3H). | 372.2 (M + H)⁺ |
| 82 | 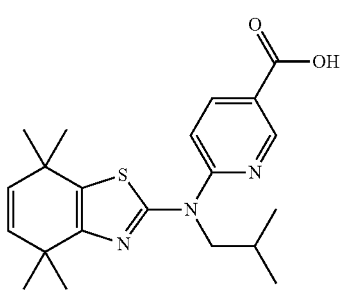 | δ 12.98 (s, 1H), 8.86 (s, 1H), 8.17-8.21 (dd, 1H), 7.34-7.47 (d, 1H), 5.55-5.61 (q, 2H), 4.25-4.41 (d, 2H), 2.18-2.23 (m, 2H), 1.38 (s, 6H), 1.21 (s, 6H), 0.91-0.93 (d, 6H). | 386.2 (M + H)⁺ |
| 83 | 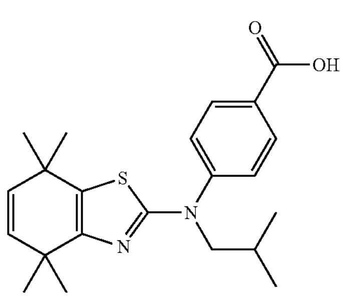 [SMILES: CC(C)CN(c1ccc(C(=O)O)cc1)c1nc2c(s1)C(C)(C)C=CC2(C)C] | — | 385.3 (M + H)⁺ |

TABLE 1-continued
| NO | Structure | ¹HNMR | m/z |
|---|---|---|---|
| 84 | 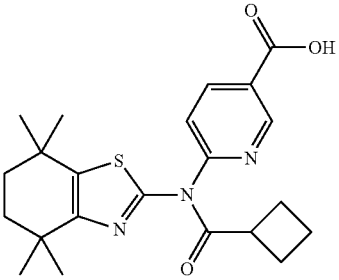 [SMILES: CC1(C)CCC(C)(C)c2sc(N(C(=O)C3CCC3)c3ccc(C(=O)O)cn3)nc21] | — | 414.3 (M + H)⁺ |
| 85 | 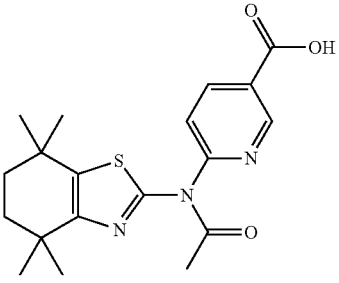 [SMILES: CC(=O)N(c1ccc(C(=O)O)cn1)c1nc2c(s1)C(C)(C)CCC2(C)C] | δ 13.66 (s, 1H), 9.06-9.063 (d, 1H), 8.45-8.49 (dd, 1H), 7.72--7.75 (d, 1H), 1.97 (s, 3H), 1.62 (s, 4H), 1.27 (s, 6H), 0.97 (s, 6H). | 374.3 (M + H)⁺ |
| 86 | 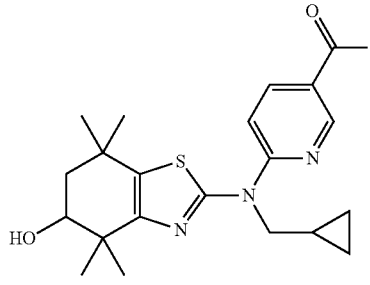 | — | 402.3 (M + H)⁺ |
| 87 | 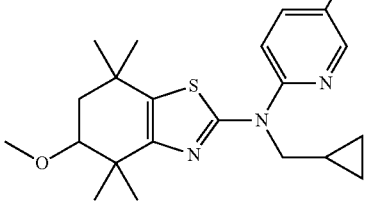 | δ 9.08-9.09 (d, 1H)8.22-8.26 (dd, 1H), 7.17-7.20 (d, 1H), 4.34-4.36 (d, 2H), 3.46 (s, 3H), 3.32-3.39 (dd, 1H), 1.88-1.93 (dd, 1H), 1.69-1.77 (t, 2H), 1.38 (s, 6H), 1.25s, 6H), 0.85-.0.90 (m, 1H), 0.51-.058 (m, 4H). | 416.3 (M + H)⁺ |
| 88 | 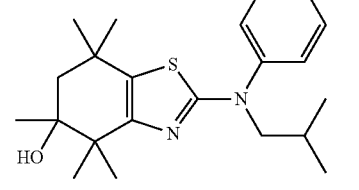 | δ 12.83 (s, 1H), 7.92-7.95 (d, 2H), 7.55-7.25 (d, 2H), 4.13 (s, 1H), 3.78-3.82 (m, 2H), 1.97-2.01 (m, 1H), 1.68-1.80 (q, 2H), 1.28 (s, 6H), 1.20 (s, 6H), 1.06 (s, 3H), 0.86-.0.88 (d, 6H). | 417.2 (M + H)⁺ |

TABLE 1-continued

| NO | Structure | ¹HNMR | m/z |
|---|---|---|---|
| 89 | 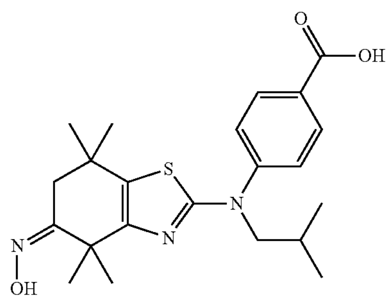 [SMILES: CC(C)CN(c1ccc(C(=O)O)cc1)c1nc2c(s1)C(C)(C)C/C(=N/O)C2(C)C] | δ 12.90 (s, 1H), 10.61 (s, 1H), 7.94-7.97 (d, 2H), 7.55-7.58 (d, 2H), 3.81-3.83 (d, 2H), 2.68 (s, 2H), 1.92-2.01 (m, 1H), 1.35 (s, 6H), 1.14 (s, 6H), 0.87-.0.89 (d, 6H). | 416.4 (M + H)⁺ |
| 90 | 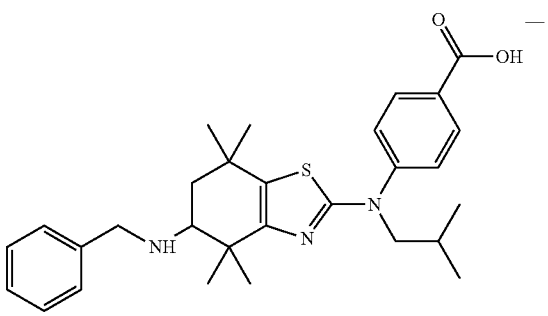 | — | 492.3 (M + H)⁺ |
| 91 | 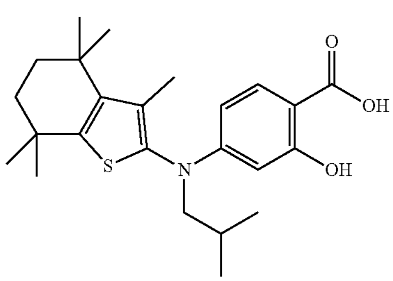 [SMILES: Cc1c(N(CC(C)C)c2ccc(C(=O)O)c(O)c2)sc2c1C(C)(C)CCC2(C)C] | — | 416.3 (M + H)⁺ |
| 92 | 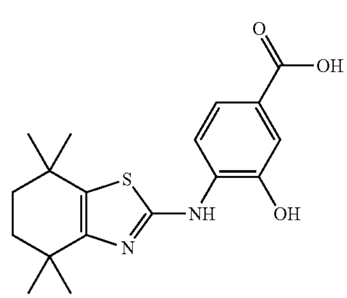 [SMILES: CC1(C)CCC(C)(C)c2sc(Nc3ccc(C(=O)O)cc3O)nc21] | δ 12.39 (s, 1H), 10.31 (s, 1H), 9.49 (s, 1H), 8.27-8.30 (d, 1H), 7.38-7.40 (d, 2H), 1.65 (s, 4H), 1.21 (s, 12H). | 347.1 (M + H)⁺ |
| 93 | 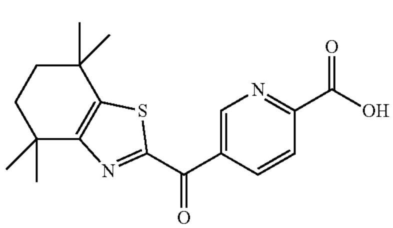 [SMILES: CC1(C)CCC(C)(C)c2sc(C(=O)c3ccc(C(=O)O)nc3)nc21] | — | 345.2 (M + H)⁺ |

TABLE 1-continued

| NO | Structure | ¹HNMR | m/z |
|---|---|---|---|
| 94 | 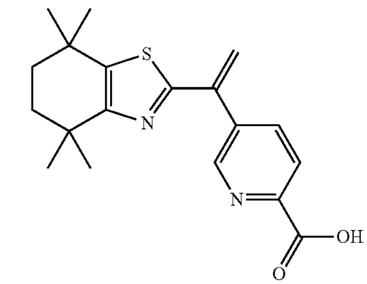 [SMILES: C=C(c1ccc(C(=O)O)nc1)c1nc2c(s1)C(C)(C)CCC2(C)C] | — | 343.2 (M + H)⁺ |
| 95 | 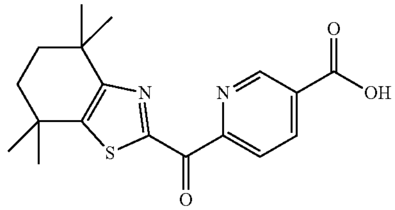 [SMILES: CC1(C)CCC(C)(C)c2sc(C(=O)c3ccc(C(=O)O)cn3)nc21] | — | 345.1 (M + H)⁺ |
| 96 | 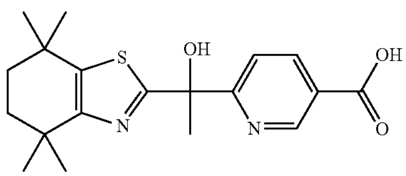 [SMILES: CC1(C)CCC(C)(C)c2sc(C(C)(O)c3ccc(C(=O)O)cn3)nc21] | — | 361.2 (M + H)⁺ |
| 97 | 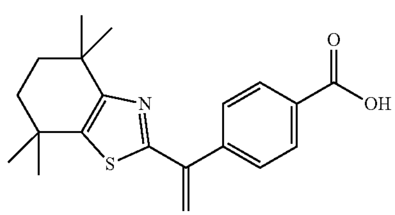 [SMILES: C=C(c1ccc(C(=O)O)cc1)c1nc2c(s1)C(C)(C)CCC2(C)C] | δ 13.03 (s, 1H), 7.95-7.98 (d, 2H), 7.60-7.62 (d, 2H), 6.04 (s, 1H), 5.65 (s, 1H), 1.70 (s, 4H), 1.27 (s, 6H), 1.22 (s, 6H). | 342.2 (M + H)⁺ |
| 98 | 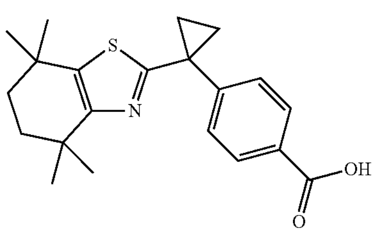 [SMILES: CC1(C)CCC(C)(C)c2sc(C3(c4ccc(C(=O)O)cc4)CC3)nc21] | — | 356.1 (M + H)⁺ |
| 99 | 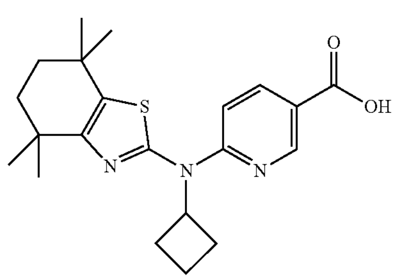 [SMILES: CC1(C)CCC(C)(C)c2sc(N(c3ccc(C(=O)O)cn3)C3CCC3)nc21] | 12.92 (s, 1H), 8.78 (s, 1H), 8.07-8.101 (d, 1H), 6.78-6.811 (d, 1H), 4.86-4.98 (t, 1H), 2.404 (s, 4H), 2.02-2.08 (t, 2H), 1.69 (s, 4H), 1.27 (s, 6H), 1.218 (s, 6H). | 386.1 (M + H)⁺ |

TABLE 1-continued

| NO | Structure | ¹HNMR | m/z |
|---|---|---|---|
| 100 | 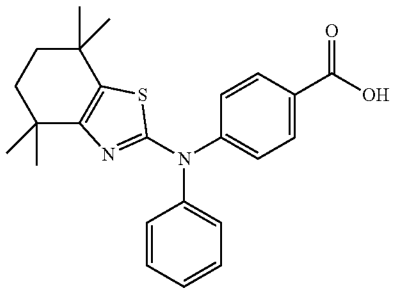 [SMILES: CC1(C)CCC(C)(C)c2sc(N(c3ccccc3)c3ccc(C(=O)O)cc3)nc21] | 12.712 (s, 1H), 7.85-7.88 (d, 2H), 7.521-7.57 (t, 2H), 7.38-7.45 (m, 5H), 1.65 (s, 4H), 1.207 (s, 6H), 1.156 (s, 6H). | 407.2 (M + H)⁺ |
| 101 | 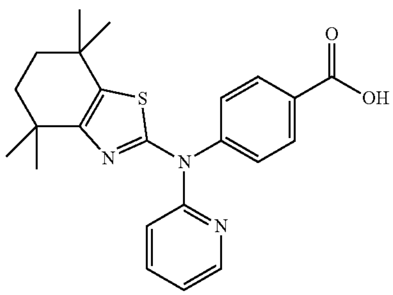 [SMILES: CC1(C)CCC(C)(C)c2sc(N(c3ccc(C(=O)O)cc3)c3ccccn3)nc21] | — | 408.1 (M + H)⁺ |
| 102 | 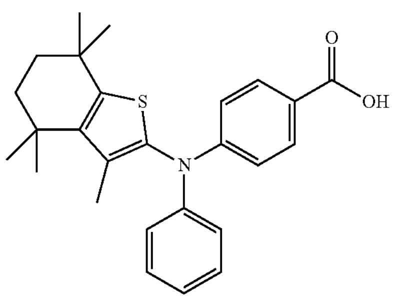 [SMILES: Cc1c(N(c2ccccc2)c2ccc(C(=O)O)cc2)sc2c1C(C)(C)CCC2(C)C] | — | 420.2 (M + H)⁺ |
| 103 | 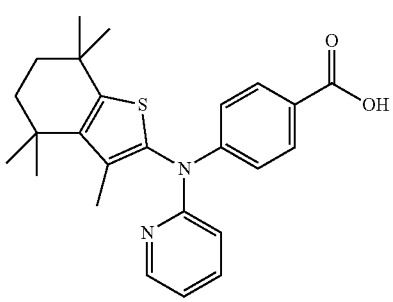 [SMILES: Cc1c(N(c2ccc(C(=O)O)cc2)c2ccccn2)sc2c1C(C)(C)CCC2(C)C] | — | 421.3 (M + H)⁺ |
| 104 | 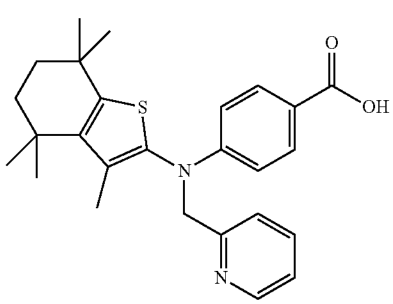 [SMILES: Cc1c(N(Cc2ccccn2)c2ccc(C(=O)O)cc2)sc2c1C(C)(C)CCC2(C)C] | — | 435.1 (M + H)⁺ |

TABLE 1-continued

| NO | Structure | ¹HNMR | m/z |
|---|---|---|---|
| 105 | 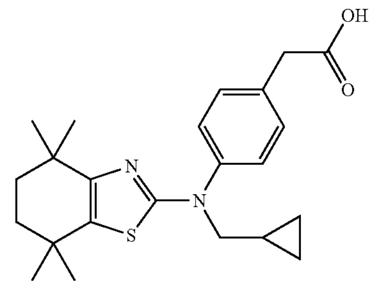 [SMILES: CC1(C)CCC(C)(C)c2sc(N(CC3CC3)c3ccc(CC(=O)O)cc3)nc21] | δ 12.37 (s, 1H), 7.31-7.35 (m, 4H), 3.70-3.72 (d, 2H), 3.60 (s, 2H), 1.60 (s, 4H), 1.17 (s, 6H), 1.10 (s, 6H), 0.38-0.41 (d, 2H), 0.17-0.18 (d, 2H). | 399.2 (M + H)⁺ |
| 106 | 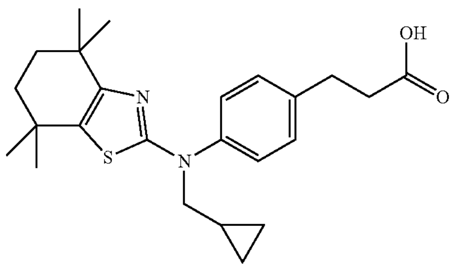 [SMILES: CC1(C)CCC(C)(C)c2sc(N(CC3CC3)c3ccc(CCC(=O)O)cc3)nc21] | δ 12.15 (s, 1H), 7.31- (s, 4H), 3.68-3.71 (d, 2H), 2.82-2.87 (t, 2H), 1.59 (s, 4H), 1.23-1.25 (m, 4H), 1.23 (s, 6H), 1.10 (s, 6H), 0.85 (m, 1H), 0.37-0.40 (d, 2H), 0.16-0.17 (d, 2H). | 413.3 (M + H)⁺ |
| 107 | 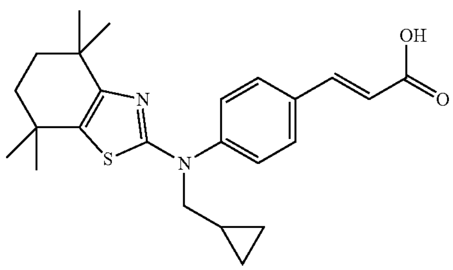 [SMILES: CC1(C)CCC(C)(C)c2sc(N(CC3CC3)c3ccc(/C=C/C(=O)O)cc3)nc21] | δ 12.36 (s, 1H), 7.72-7.75 (d, 2H), 7.56-7.62 (d, 1H), 7.46-7.48 (d, 2H), 6.47-6.53d, 1H), 3.79-3.81 (d, 3H), 1.62 (s, 4H), 1.14-1.17 (m, 12H), 0.39-0.42 (d, 2H), 0.19-0.21 (d, 2H). | 411.3 (M + H)⁺ |
| 108 | 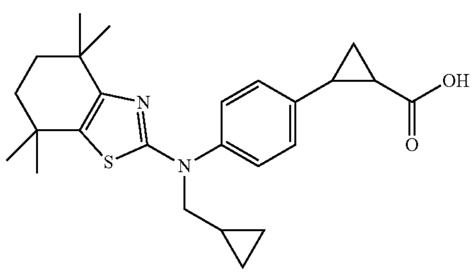 [SMILES: CC1(C)CCC(C)(C)c2sc(N(CC3CC3)c3ccc(C4CC4C(=O)O)cc3)nc21] | δ 12.16 (s, 1H), 7.14-7.16 (d, 2H), 7.05-7.08 (d, 2H), 3.52-3.54 (d, 2H), 1.64-1.69 (m, 1H), 1.42 (s, 4H), 1.21-1.30 (m, 4H), 0.99 (s, 6H), 0.93 (s, 6H), 0.21-0.23 (d, 2H), −0.01-0.00 (d, 2H). | 425.4 (M + H)⁺ |

Biological Activity

The ability of the compounds of the invention to act as agonists of RXR and thus upregulate gene expression in a number of organs such as liver, skeletal muscle and adipose tissue was thus tested as follows:

Liver (HepG2 Cells) Gene Expression Data:

HepG2 cells (Source ATCC-cat no: HB-8065) were seeded in MEM media (6.9 mM glucose) containing 10% FBS (Fetal Bovine Serum) and cultured for 36 h. After 36 h of culture, cells were treated with 1 μM of candidate RXRa agonists in fresh MEM media (6.9 mM glucose and 10% FBS-Fetal Bovine Serum). After 24 h of treatment, supernatant was discarded and added Tri-reagent (Sigma, St. Louis, Mo., USA) to the cells. Total RNA was extracted from HepG2 cells using Tri-reagent (Sigma, St. Louis, Mo., USA), followed by chloroform extraction and isopropyl alcohol precipitation. cDNA was synthesized by reverse transcription (ABI, Foster City, Calif., USA). The level of gene expression was measured for AcoX1, ApoA1, ApoC3, THRSP, Sult2A1, SREBP-1c, CYP3A4 using primer sequence known in the prior art. The cDNA was amplified using SYBR Green PCR Master Mix (Eurogenetic, Belgium).

Muscle (C2C12 Cells) Gene Expression Data:

C2C12 cells (Myoblast cells—Source ATCC—cat no: CRL-1772) were seeded in DMEM media (25 mM glucose) containing 10% FBS and cultured (day 0) after 24 h give a media change (day 1). After media change cells treated changed to differentiated media (25 mM glucose and 2% FBS) (day 3 to day 7). Differentiated cells (Myofibers) were treated with 1 μM of candidate RXRa agonists. After 24 h of treatment, supernatant was discarded and added Tri-reagent (Sigma, St. Louis, Mo., USA) to the cells. Total RNA was extracted from C2C12 cells using Tri-reagent (Sigma, St. Louis, Mo., USA), followed by chloroform extraction and isopropyl alcohol precipitation. cDNA was synthesized by reverse transcription (ABI, Foster City, Calif., USA). The level of gene expression was measured for CPT1, UCP3, ABCA1, SREBP-1c, PDK4 using primer sequence known in the prior art. The cDNA was amplified using SYBR Green PCR Master Mix (Eurogenetic, Belgium).

Adipose (3T3 L1 Cells) Gene Expression Data:

3T3L1 cells (Pre-adipocytes, Source ATCC— cat no: CL-173) were seeded in DMEM media (25 mM glucose) containing 10% BCS and cultured (day 0), after 24 h given a media change (day 1). 48 h after media change, cells were treated with RXRa agonists along with differentiation media (25 mM glucose, 10% FBS, 500 µM IBMX, 1 µM Dexamethasone and 100 nM Insulin) (day 3 to day 5). Till termination cells (Adipocytes) were maintained in maintenance media (25 mM glucose, 10% FBS, 100 nM Insulin). Supernatant was discarded, added Tri-reagent (Sigma, St. Louis, Mo., USA) to the cells. Total RNA was extracted from cells using Tri-reagent (Sigma, St. Louis, Mo., USA), followed by chloroform extraction and isopropyl alcohol precipitation. cDNA was synthesized by reverse transcription (ABI, Foster City, Calif., USA). The level of gene expression was measured for FABP4, SCD1, PCK1, UCP1, ABCA1, CPT1b, PPARg, SREBP-1c using primer sequence known in the prior art. The cDNA was amplified using SYBR Green PCR Master Mix (Eurogenetic, Belgium).

Biological Activity

Transactivation Assay for Evaluating the Activity.

HEK-293 cells (ATCC) were seeded one day prior to transfection. For assessing EC50 of activation of RXR isoforms 2 µg of hRXR α, β, or γ (OriGENE, USA) over-expressing vector, 1 µg of plasmid expressing firefly luciferase under RARE element (RARE-Luc) and 25 ng of renilla luciferase vector (QIAGEN, USA) were co-transfected using lipofectamine reagent. Post 24 h of transfection, cells were treated with different concentrations of RXR agonists (100 nM, 300 nM and 1 uM) for 24 h followed by estimation of luciferase activity using Dual Luciferase Reporter Assay System (Promega). Luciferase activity was normalized to that of renilla luciferase. The activities of the RXR compounds were expressed relative to LG268, a known RXR agonist.

The results were as follow:

TABLE 2

Activity of compounds tested at Activity at 1 □M

| Cmpd | Activity at 1 □M |
|---|---|
| 1 | ***** |
| 2 | ***** |
| 3 | ***** |
| 4 | **** |
| 5 | ** |
| 6 | *** |
| 7 | ***** |
| 8 | ***** |
| 9 | *** |
| 10 | ***** |
| 11 | **** |
| 13 | ** |
| 14 | **** |
| 15 | ** |
| 16 | * |
| 17 | ***** |
| 18 | ***** |
| 19 | ***** |
| 20 | ***** |
| 21 | ***** |
| 22 | ***** |
| 23 | *** |

TABLE 2-continued

Activity of compounds tested at Activity at 1 □M

| | |
|---|---|
| 24 | *** |
| 25 | * |
| 26 | * |
| 27 | ***** |
| 28 | * |
| 29 | ***** |
| 30 | ***** |
| 31 | ** |
| 32 | * |
| 33 | *** |
| 34 | ** |
| 35 | *** |
| 36 | ***** |
| 37 | ***** |
| 38 | *** |
| 39 | ***** |
| 40 | **** |
| 41 | * |
| 42 | ** |
| 43 | * |
| 44 | * |
| 45 | * |
| 46 | * |
| 47 | * |
| 48 | * |
| 49 | ***** |
| 50 | * |
| 75 | ***** |

| | |
|---|---|
| <0.7 | * |
| >0.7 and <0.8 | ** |
| >0.8 and <0.9 | *** |
| >0.9 to <1 | **** |
| >1 | ***** |

TABLE 3

Activity of compounds tested at Activity at Activity at 300 nM

| Compound | Activity at 300 nM |
|---|---|
| 40 | ***** |
| 46 | ** |
| 51 | ***** |
| 52 | ***** |
| 53 | ***** |
| 54 | *** |
| 55 | *** |
| 56 | *** |
| 57 | ***** |
| 58 | *** |
| 59 | ** |
| 60 | ** |
| 61 | **** |
| 62 | ***** |
| 63 | *** |
| 64 | ***** |
| 65 | ***** |
| 66 | ***** |
| 67 | * |
| 68 | * |
| 69 | * |
| 70 | ***** |
| 71 | * |
| 72 | * |
| 73 | ** |
| 79 | ***** |
| 80 | *** |
| 81 | ***** |
| 82 | ***** |
| 83 | * |
| 84 | ** |
| 85 | ** |
| 86 | ***** |
| 87 | ***** |

TABLE 3-continued

Activity of compounds tested at Activity at Activity at 300 nM

| | |
|---|---|
| 88 | ** |
| 89 | ** |
| 90 | ** |
| 91 | ***** |
| 92 | * |
| 93 | * |
| 94 | ** |
| 95 | ** |
| 96 | ** |
| 97 | ** |
| 98 | **** |
| 99 | ***** |
| 100 | ***** |
| 101 | *** |
| 102 | ***** |
| 103 | ***** |
| 104 | * |
| 105 | ***** |
| 106 | ***** |
| 107 | ***** |
| 108 | ***** |

| | |
|---|---|
| <0.3 | * |
| >0.3 and <0.4 | ** |
| >0.4 and <0.5 | *** |
| >0.5 to <0.6 | **** |
| >0.6 | ***** |

In Vitro Data for Alzheimer's Disease

Several In vitro assays were carried out on Compound 40 to study its impact on N2A cells and Astrocytes. Several measurements were taken to support its use in treatment of Alzheimer's disease Alzheimer's disease (AD) is a chronic, progressive, neurodegenerative disorder. A wide array of anti-amyloid and neuroprotective therapeutic approaches are under investigation on the basis of the hypothesis that amyloid beta (Aβ) protein plays a pivotal role in disease onset and progression and that secondary consequences including tau hyperphosphorylation and neurofibrillary tangle formation, oxidation and inflammation contribute to the disease process. Interventions in these processes with agents that reduce amyloid production, limit aggregation, or increase removal will stop the cascade of events comprising AD pathogenesis. Reducing tau hyperphosphorylation, limiting oxidation and excitotoxicity, and controlling inflammation might be beneficial disease modifying strategies.

In order to study the impact of Compound 40 on Alzheimer's Disease, cultured mouse neuronal cells (N2A cells) were treated with 320 uM cholesterol alone or with test molecule for 24 h. Cholesterol was removed and treatment is continued for 24 h. Cholesterol content in the cells was measured by biochemical methods, normalized to total protein. For gene expression studies, cells were treated with 320 uM cholesterol alone or with test molecule for 48 h. RNA was made and later converted to cDNA and the gene expression was measured. It was seen that Compound 40 reduced cholesterol accumulation (FIG. 1 A), reduced oxidative stress (ROS levels) (FIG. 1 B), decreased apoptosis (Caspase activity) (FIG. 1 C) and increased the cholesterol efflux (ABCA1 and ABCG1 expression) (FIG. 1 D). These cellular events lead to reduced plaque formation and improvement in the health of neuronal cells.

Furthermore, cultured astrocytes were treated with phorbol-12-myristate-13-acetate (PMA) and Lipopolysaccharides (LPS) alone or with test molecule for 48 h to measure ROS levels. To evaluate the effect on inflammation markers, astrocytes were treated with PMA and test molecule for 48 h. Data from astrocytes revealed the potential of compound-40 to reduce both oxidative stress (ROS levels) (FIG. 2 A) and inflammation (IL6 secretion and expression, expression of IL1b, COX2 and MCP1) (FIGS. 2 B, C, D, E and F). Since compound-40 has the potential to reduce inflammation, we expect it will have significant impact remyelination of neurons and hence it can be positioned for multiple sclerosis.

Impact of RXR Agonist on Pancreatic Cancer Cell Lines

Figure 3A:
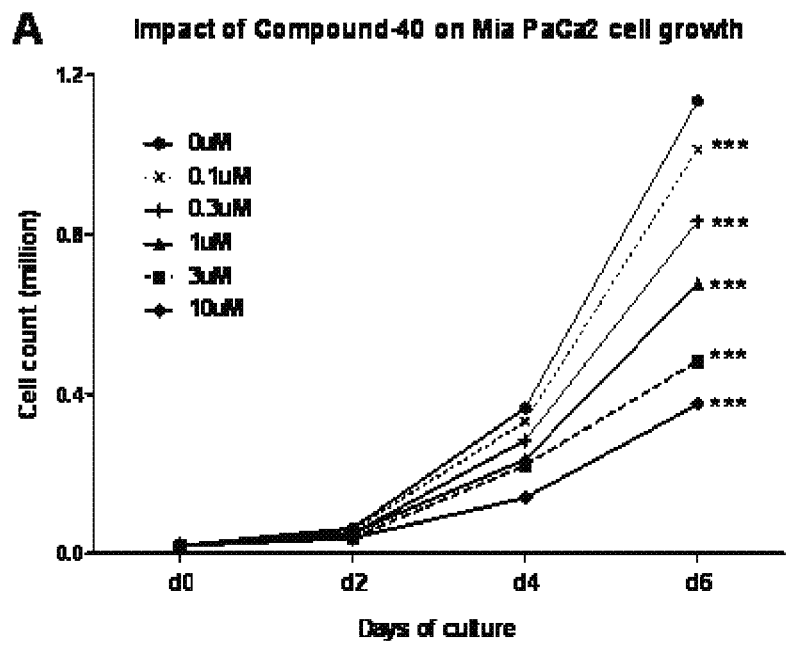
FIG. 3A shows MiA PaCa2 cell line growth on cells treated with compound 40.

Cancer is characterized by uncontrolled cell growth. Any agent which can reduce the cellular growth will have high therapeutic potentials. Hence, the impact of RXR agonist compound-40 on MIA PaCa-2 cell growth was assessed. MIA PaCa-2 cells (ATCC) were seeded in a 6-well plate (20,000 cells per well) in DMEM containing 25 mM glucose, 10% FBS, 2.5% horse serum in presence or absence of different concentrations of compound-40 as mentioned. Cells were harvested on day 2, day 4 and day 6, and cell numbers were measured. MIA PaCa-2 cells were grown with or without different concentrations of compound-40 (0.0, 0.1, 0.3, 1.0, 3.0 and 10.0 uM) and cell growth was measured by cell count at different time points (day 2, 4 and 6). Untreated MIA PaCa-2 cells showed an exponential rate of cell growth which was reduced by compound-40 treatment. Even 0.1 uM compound-40 showed a significant reduction in cell growth which was further reduced by increasing compound-40 concentration (FIG. 3A).

Figure 3B:
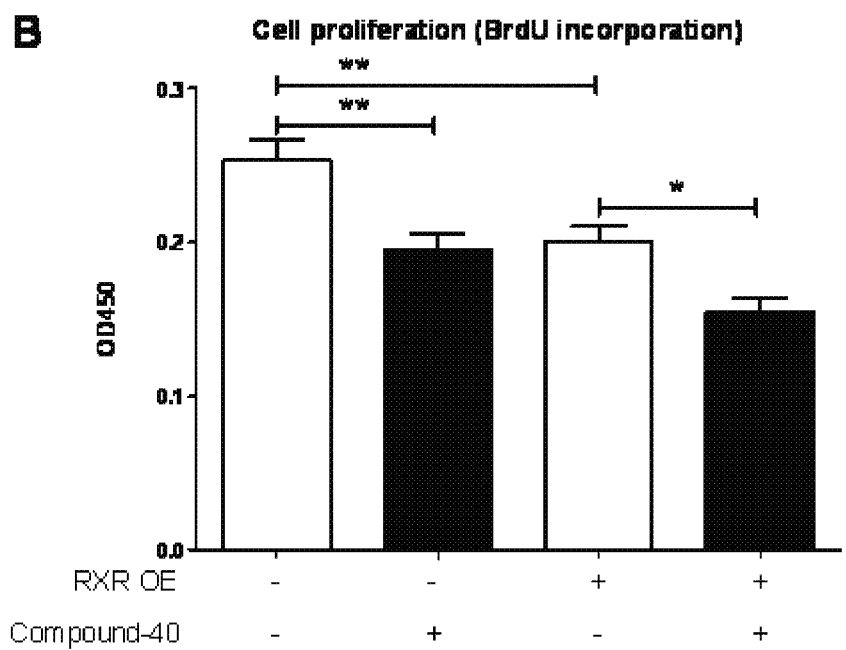
FIG. 3B shows the results of a cell proliferation assay (BrdU incorporation) of MiA PaCa2 cell line growth on cells treated with compound 40.

Impact of compound-40 on cell proliferation was further evaluated by BrdU incorporation assay. MIA PaCa-2 cells were grown for 4 days in presence or absence of compound-40 (3 uM). After treatment with vehicle control or compound-40 (3 uM), cells were exposed to BrdU. BrdU incorporation was measured using a commercially available kit (Roche) as per manufacturer's protocol. The BrdU incorporation was significantly reduced by compound-40 treatment indicating its potency to reduce cell growth (FIG. 3B). Over-expression of RXRa also reduced the BrdU incorporation suggesting a pivotal role of RXR pathway in reducing cancer cell growth. compound-40 treatment further reduced the BrdU incorporation in RXRa over-expressing MIA PaCa-2 pancreatic cancer cell line. Hence the data indicate that compound-40 mediated RXR signalling pathway reduces cell growth in pancreatic cancer cells.

Figure 4A:
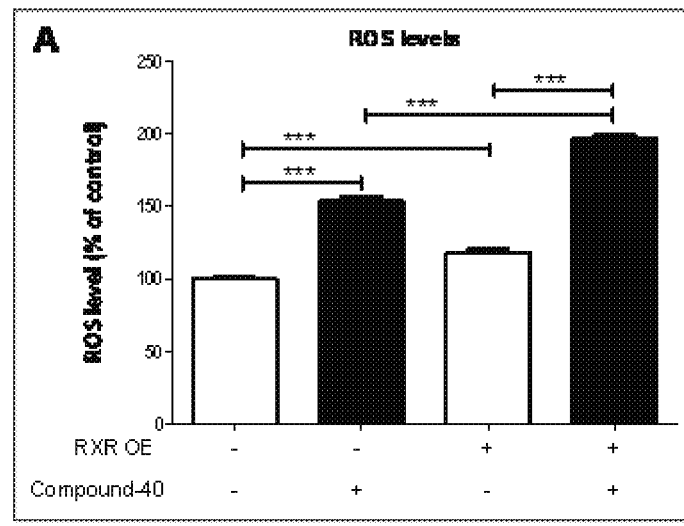
FIG. 4A shows reduced oxidative stress (ROS) levels in MiA PaCa2 treated with compound 40.

To assess the impact of Compound 40 on ROS level, the cells were exposed to ROS indicator probe (DCFH-DA) for 1 h. ROS induced increase in DCF fluorescence was estimated at 485 nm excitation and 528 nm emission. ROS levels were normalized to cellular DNA levels which were measured by using bis-benzamide fluorescence at 360 nm excitation and 460 nm emission. The ROS levels are represented at % of control. Treatment of compound-40 for 4 days resulted in significant augmentation of stress levels in MIA PaCa-2 cells as measured by increased reactive oxygen species (ROS) levels (FIG. 4A). Over-expression of RXRa further augmented the ROS levels. Hence, compound-40 mediated RXR signalling pathway increased ROS levels in pancreatic cancer cells.

Figure 4B:
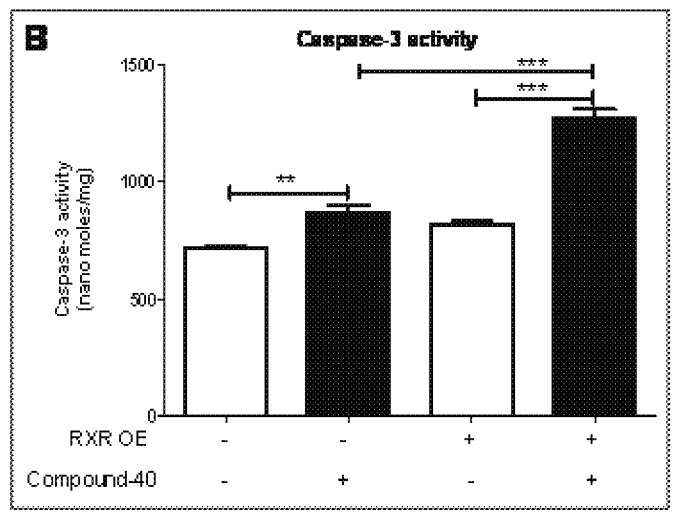
FIG. 4B shows caspase levels in MiA PaCa2 treated with compound 40.
Figure 4C:
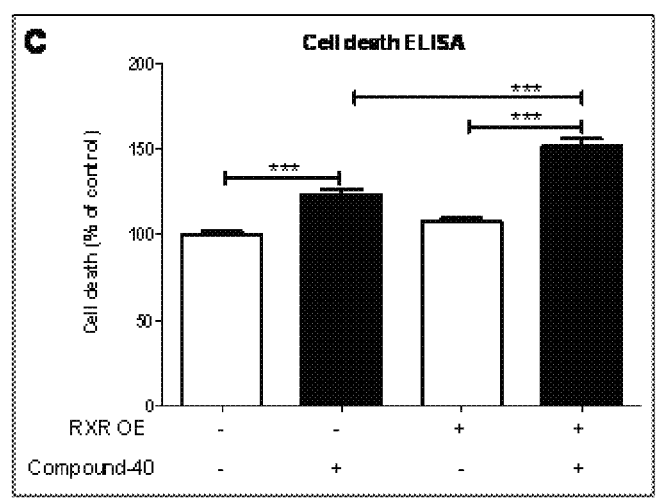
FIG. 4C shows a cell death ELISA in MiA PaCa2 treated with compound 40.

In order to assess whether this increased stress resulted in apoptosis, caspase-3 activity and cell death were measured. Caspase-3 activity was measured using its ability to cleave its substrate (Ac-DEVD-R110). Increased Caspase-3 activity would lead to higher release of fluorescent R110 which was measured at 485 nm excitation and 530 nm emission. Activity of caspase-3 (as nano-moles of R110 released) was normalized to total cellular protein. Caspase-3 activity, a measurement of the terminal stage of apoptosis, was significantly increased by compound-40 treatment and was further enhanced by RXRa over-expression (FIG. 4B). Similarly, increased cell death, as measured by increase in DNA fragmentation, was also observed in MIA PaCa-2 cell line upon compound-40 treatment and RXRa over-expression further increased the cell death. Cell death was measured by increased levels of DNA fragments as per manufacturer's protocol (Roche) and was normalized to total cellular DNA. Data are represented as % of control. However, over-expression of RXRa alone, without compound-40 did not result in increased cell death (FIG. 4C).

Taken together, these data indicate that RXR agonist compound-40 increases apoptosis in MIA PaCa-2 pancreatic cancer cells.

Impact of RXR Agonist on Breast Cancer Cell Lines

Culture of MCF7 breast cancer cell line in presence of compound-40 (3 uM) resulted in reduced cell growth (FIG. 5A). This impact of compound-40 was maintained for long-term as revealed by the data obtained for 15 passages. Furthermore, BrdU incorporation was also significantly reduced in MCF7 cells treated with compound-40 (FIG. 5B). Reduction in cell proliferation was attendant with a significant increase in cellular stress, as measured by increased ROS levels (FIG. 5C). Finally, increased levels of apoptosis, as measured by increased DNA fragmentation was also increased in MCF7 cells by culturing them with compound-40 (FIG. 5D). In conclusion, the data indicates that compound-40 has a potency to reduce breast cancer cell growth and induce apoptosis in them.

Impact of RXR Agonist on Leukemia Cell Lines

Figure 6:
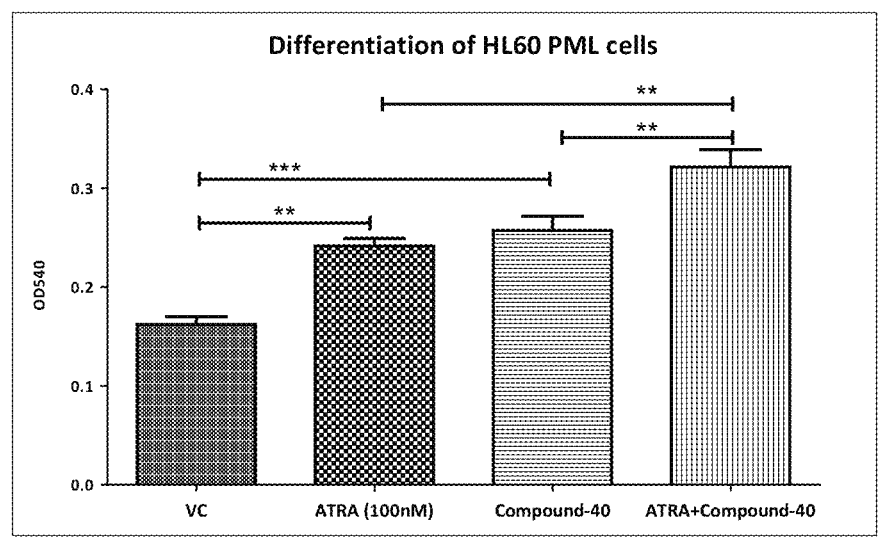
FIG. 6 shows differentiation of HL60 PML cells treated with compound 40.

Progression of promyelocytic leukemia can be abrogated by their differentiation. Hence, an agent causing differentiation can be of therapeutic values. In order to estimate the differentiating ability of compound-40, HL-60 promyelocytic leukemia cell line was used as an in vitro model of the disease. HL-60 cells were cultured for 72 h as either control or under treatment as mentioned. After 72 h of culture, cells were exposed to nitro blue tetrazolium (NBT) solution containing phorbol myristate acetate (PMA) for 1 h at 37° C. Differentiated cells have increased oxidative burst potential which reduces NBT. Levels of reduced NBT were measured at 540 nm absorption. HL-60 cells differentiation was significantly increased by compound-40 treatment (FIG. 6). Similarly, all transretinoic acid (ATRA), a known differentiating agent being used for therapy, also induced differentiation in HL-60 cells. Interestingly, compound-40 treatment showed an additive effect with ATRA on differentiation. In conclusion, compound-40 can cause differentiation in promyelocytic leukemia cell line and has an additive effect with ATRA.

In Vivo Experimental Data

I. Evaluation of Effect of RXR Agonist on DIO Mice

Six week old male C57BL/6J mice were selected, acclimatized for a period of 1 week, Animals were assigned to either chow (10% kcal from fat) or high fat diet (HFD) (D12492; 60% kcal from fat), Research Diets, Inc., New Jersey, USA. Animals were housed in polypropylene cages and maintained at 23±1° C. at 60±10% humidity and 12 hour cycles of light and dark with free access to feed and water (ad libitum). After 11 weeks of the diet intervention, the HFD fed animals were assigned to specific treatment groups based upon body weight, glucose AUC during OGTT, fasting and fed blood glucose and fasting TG. The lean control mice (n=10) were fed with normal chow diet while the treatment group (n=10) and HFD Control (n=10) with high fat diet throughout the experimental period. Treatment group received Compound 40 at a dose of 5-20 mg/kg b.wt, once daily, po as suspension in 1% MC (methyl cellulose) as vehicle. Lean control and HFD controls animals were administered with vehicle.

Figure 7A:
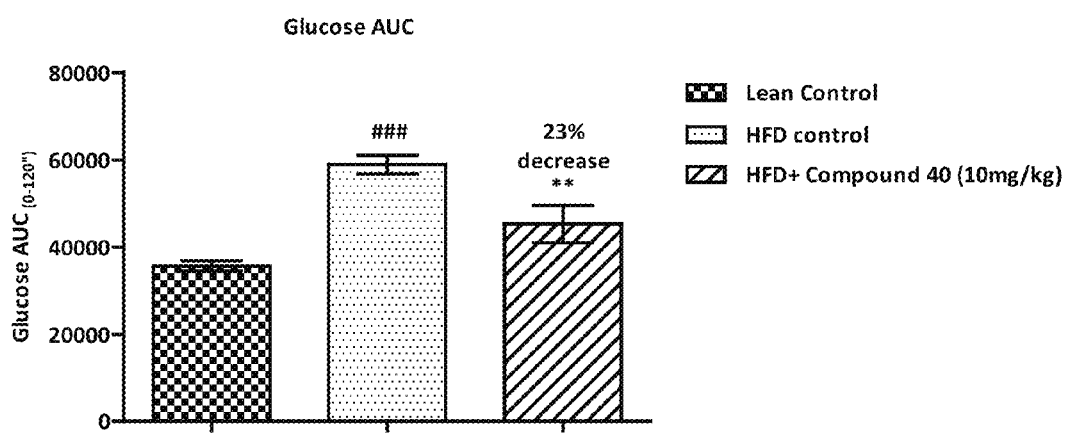
FIG. 7A shows effect of compound 40 on Glucose in DIO mice.
Figure 7B:
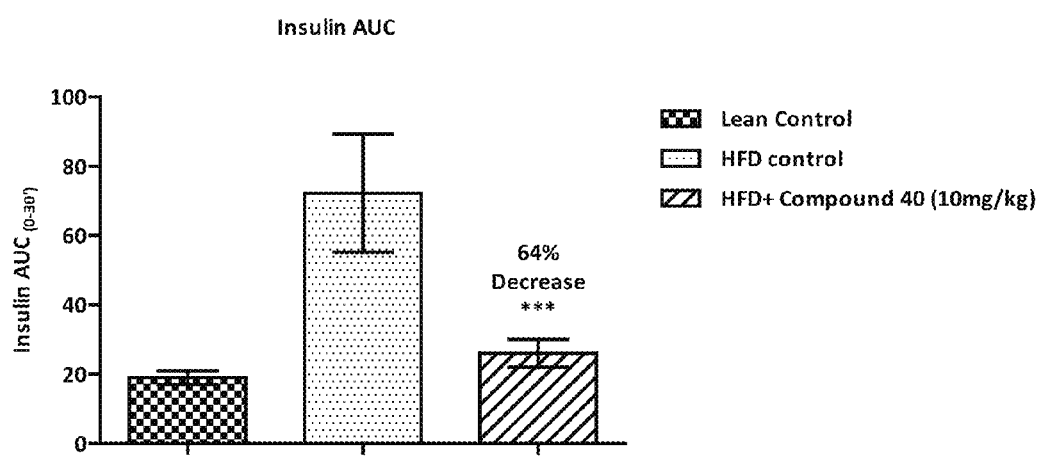
FIG. 7B shows effect of compound 40 on insulin levels in DIO mice.
Figure 8:
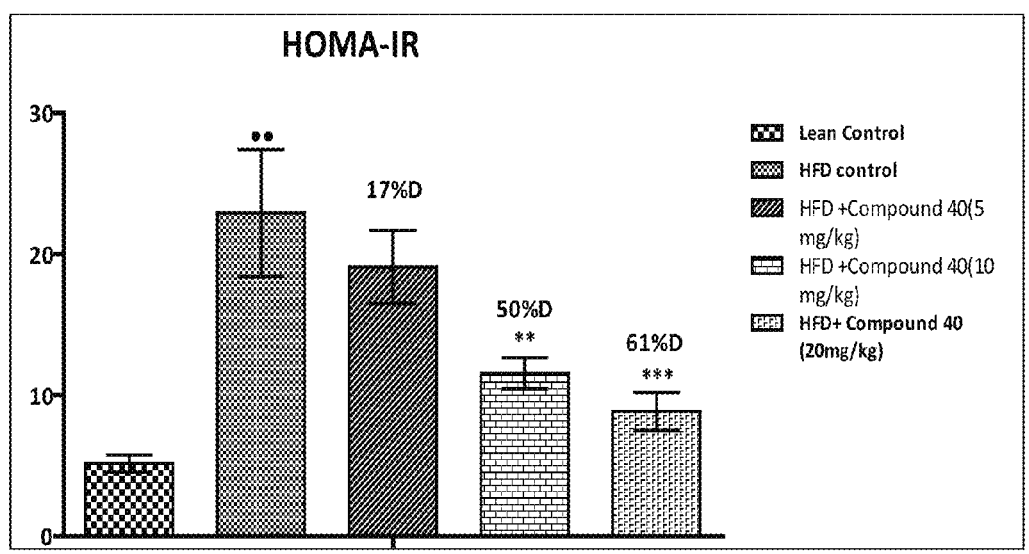
FIG. 8 shows effect of compound 40 on HOMA IR in DIO mice.

Weekly body weight & daily feed consumption was recorded. The blood collected from tail vein was subjected for estimation of glucose and TG using Co-agucheck TG strip. OGTT was performed in 6 h fasted mice with 2 g/kg, of oral glucose challenge after 9 weeks of treatment. It was observed that Compound 40 significantly reduces hyperinsulinemia and improves glucose disposal (FIG. 7). It was also seen that Compound 40 improves HOMA-IR indicating improvement in whole body insulin sensitivity (FIG. 8).

Figure 12A:
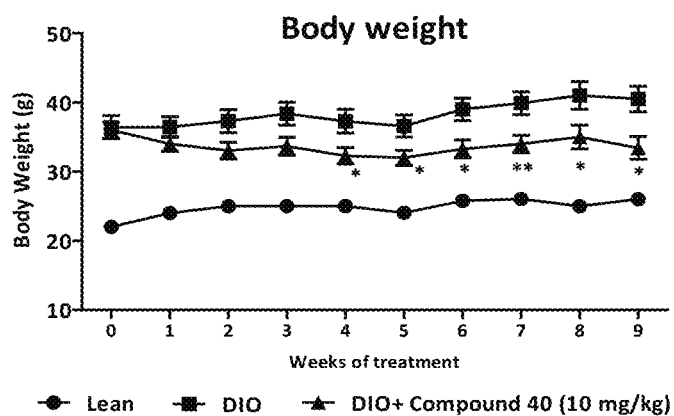
FIG. 12A shows effect of compound 40 on bodyweight in DIO mice.
Figure 12B:
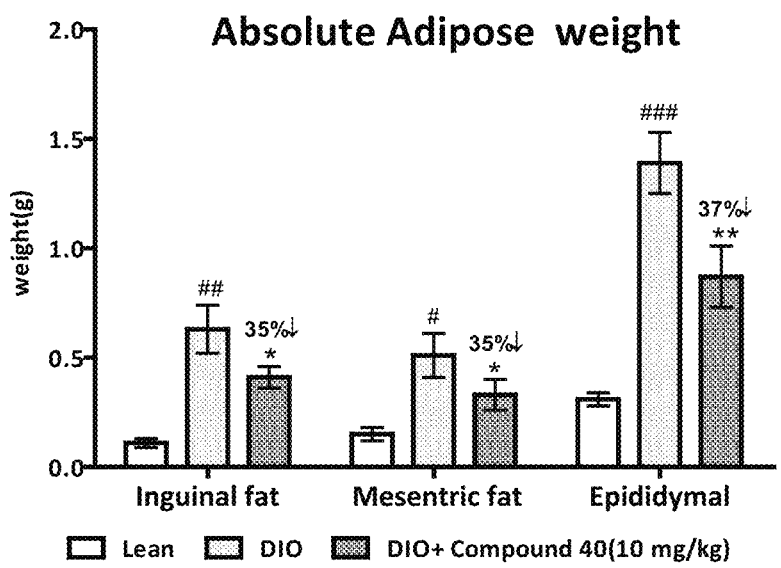
FIG. 12B shows effect of compound 40 on absolute adipose weight in DIO mice.
Figure 13A:
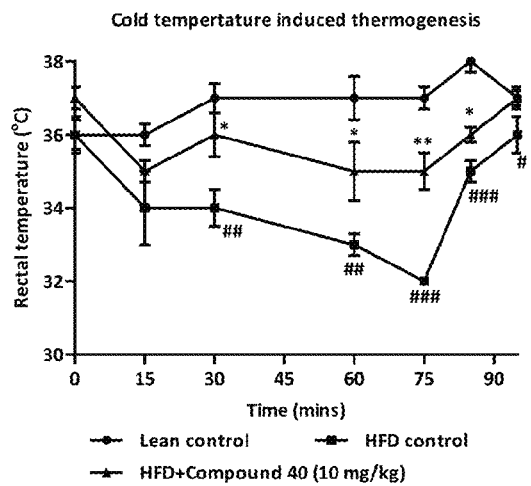
FIG. 13A shows effect of compound 40 on thermogenesis in DIO mice.
Figure 13B:
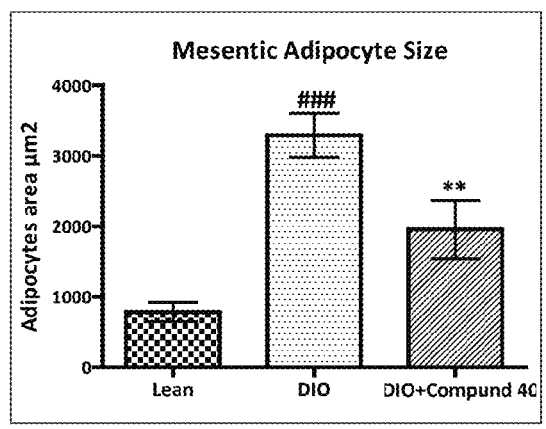
FIG. 13B shows effect of compound 40 on mesentic adipocyte size in DIO mice.
Figure 13C:
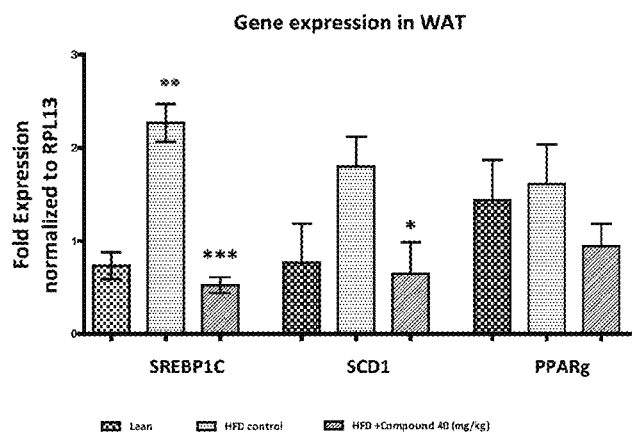
FIG. 13C shows effect of compound 40 on gene expression in WAT.

Measurement of Thermogenesis: Body temperatures were assessed at the end of treatment period using a rectal probe. For the cold exposure experiment, mice were housed individually and transferred to a cold environment with an ambient temperature of 4° C. Temperature was measured every 15 min for 75 min and then brought to room temperature, then rectal temperature was measured for further 20 min with 10 min interval. After 10 weeks of treatment, blood was collected, from retro-orbital bleeding, for biochemical measurements. Then animals were euthanized and necropsied, the liver was excised immediately, weighed and taken to estimate liver triglyceride (TG). Different adipose depots were separated and weighed. It was observed that Compound 40 significantly reduced body weight gain with decrease in various adipose depot weights (FIG. 12). Furthermore, it also significantly enhances non-shivering thermogenesis and UCP1 expression levels in inguinal white adipose tissues indicating browning of WAT (FIG. 13).

Figure 9:
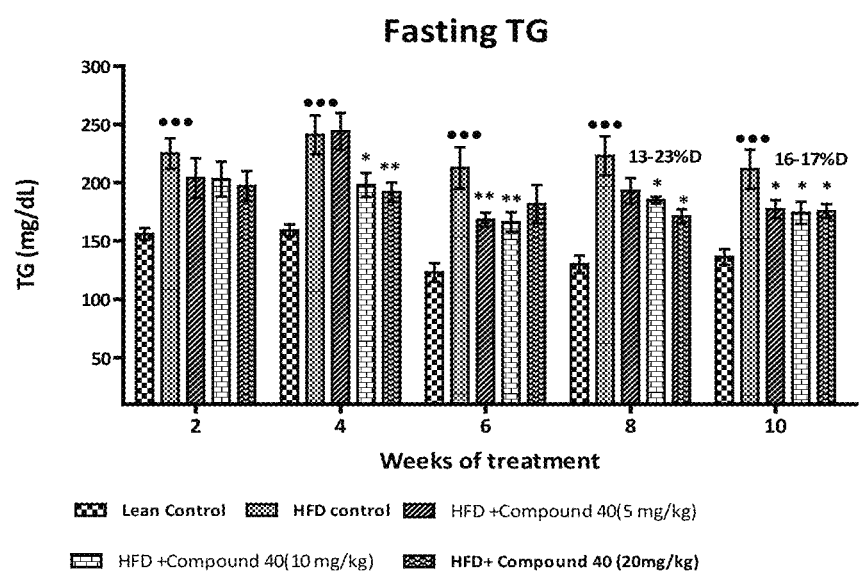
FIG. 9 shows effect of compound 40 on Fasting TG in DIO mice.
Figure 10A:
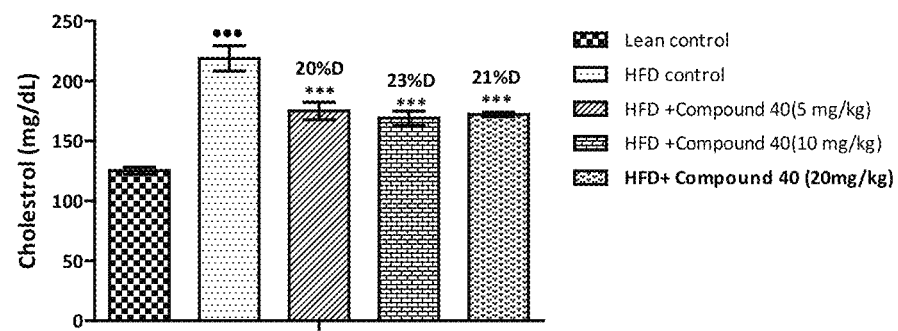
FIG. 10A shows effect of compound 40 on total cholesterol in DIO mice.
Figure 10B:
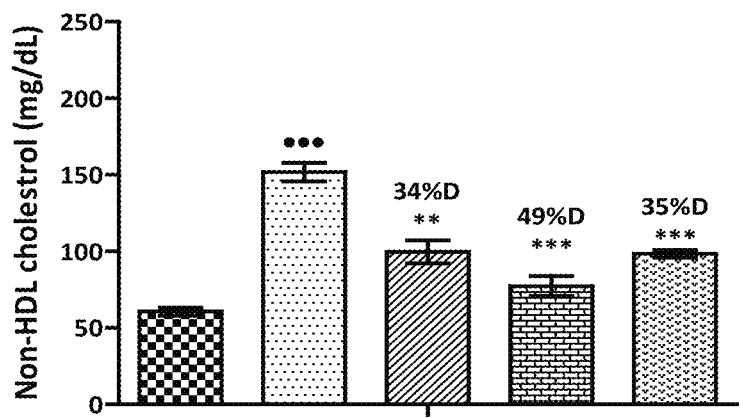
FIG. 10B shows effect of compound 40 on non-HDL cholesterol in DIO mice.
Figure 11A:
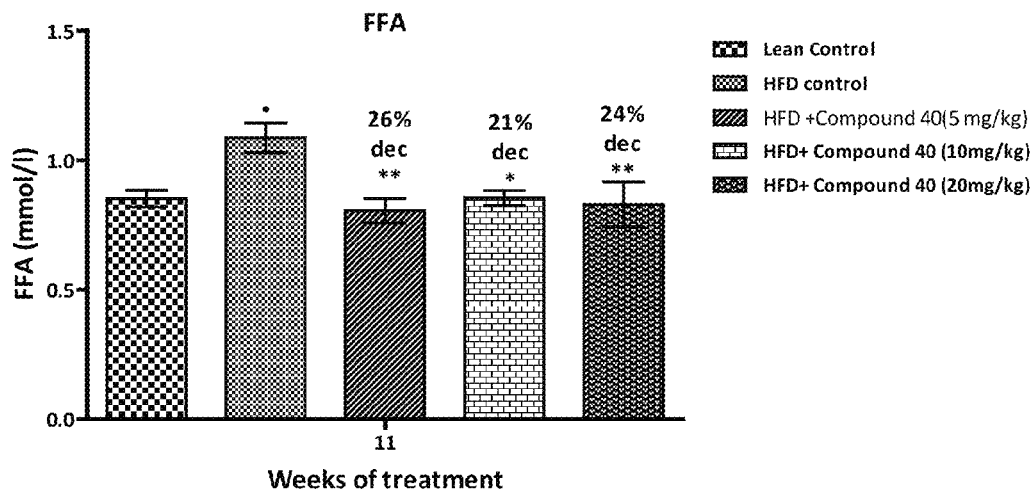
FIG. 11A shows effect of compound 40 on FFA in DIO mice.
Figure 11B:
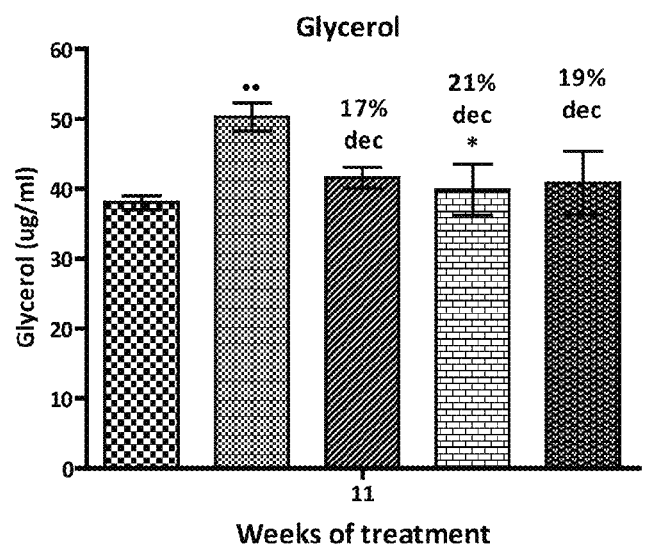
FIG. 11B shows effect of compound 40 on glycerol levels in DIO mice.

Animals were sacrificed after terminal measurement of fasting glycerol, free fatty acid, cholesterol, LDL levels. It was observed that treatment with Compound 40 significantly reduces fasting TG without increasing ectopic fat accumulation (FIG. 9). Furthermore, it was also observed that Compound 40 significantly reduces fed cholesterol levels (FIG. 10). Also, significant decrease in the circulating free fatty acid and glycerol levels were observed post treatment (FIG. 11).

Exercise endurance test or tread mill test (TMT): Exercise endurance test was accomplished on a motor treadmill at a low to moderate intensity of 5-20 cm/sec as maximal running speed with an intensity of 0.2 mA shock and one degree of inclination. The animals were subjected for TMT till exhaustion and different observations like distance traveled (cm), time spent on shock zone (sec), number of shocks, total time (min) were measured for all the mice in different groups.

Synergistic Effect of Compound 40 with Exercise on Metabolic Profile in DIO Mice Six week old male C57BL/6J mice were selected, acclimatized for a period of 1 week, Animals were assigned to either chow (10% kcal from fat) or high fat diet (HFD) (D12492; 60% kcal from fat), Research Diets, Inc., New Jersey, USA. After 11 weeks of the diet intervention, the HFD fed animals were assigned to specific treatment groups based upon body weight, glucose AUC during OGTT, fasting and fed blood glucose and fasting TG. The lean control mice (n=10) were fed with normal chow diet while the treatment group (n=10) and HFD Control (n=10), with and without exercise training, with high fat diet throughout the experimental period. Treatment group received Compound 40 with and without exercise training, at a dose of 10 mg/kg b.wt, once daily, po as suspension in 1% MC (methyl cellulose) as vehicle. Lean control and HFD controls animals were administered with vehicle. Exercise training was accomplished on a motor treadmill at a low to moderate intensity of 5-20 cm/sec as maximal running speed with an intensity of 0.2 mA shock and one degree of inclination. The animals were adapted to this procedure 5 days a week and different observations like distance traveled (cm), time spent on shock zone (sec), number of shocks, total time (min) will be measured for all the mice in different groups. Weekly body weight & daily feed consumption was recorded. The blood collected from tail vein was subjected for estimation of glucose and TG. OGTT was performed in 6 h fasted mice with 2 g/kg, of oral glucose challenge after 4 and 8 weeks of treatment. Then animals were euthanized and necropsied, the liver was excised immediately, weighed and taken to estimate liver triglyceride (TG). Different adipose depots were separated and weighed.

Figure 14A:
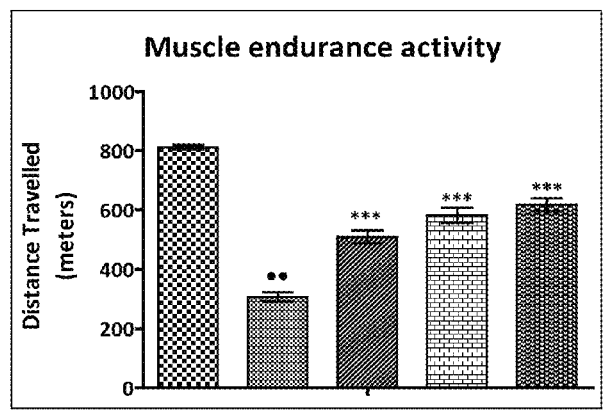
FIG. 14A shows effect of compound 40 on muscle endurance activity (distance) in DIO mice.
Figure 14B:
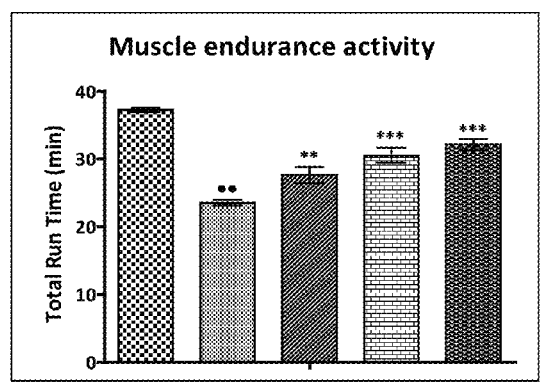
FIG. 14B shows effect of compound 40 on muscle endurance activity (total run time) in DIO mice.
Figure 29A:
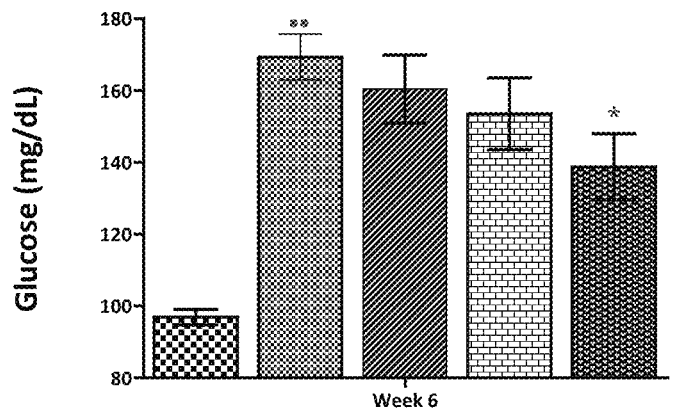
FIG. 29A shows effect of compound 40 on fasting glucose in Wistar rats.
Figure 29B:
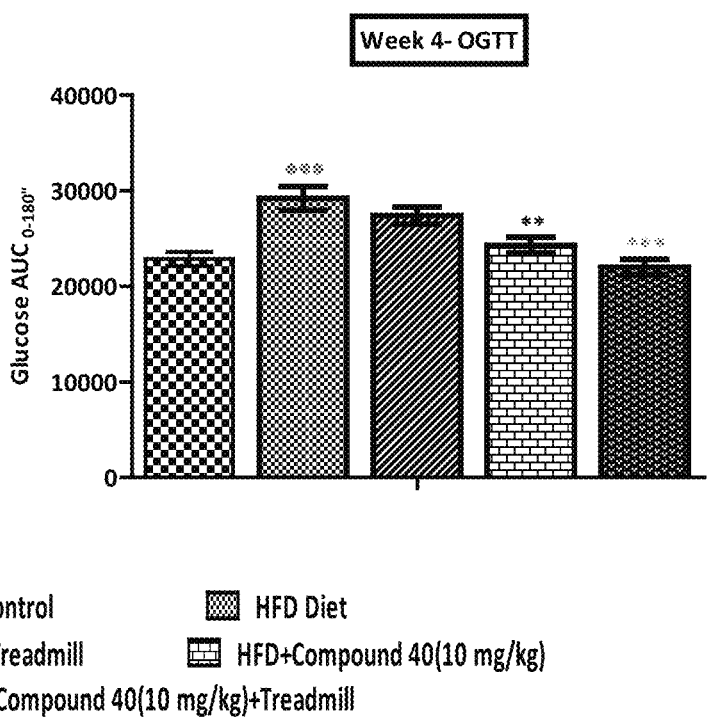
FIG. 29B shows effect of compound 40 on glucose in Wistar rats.
Figure 30A:
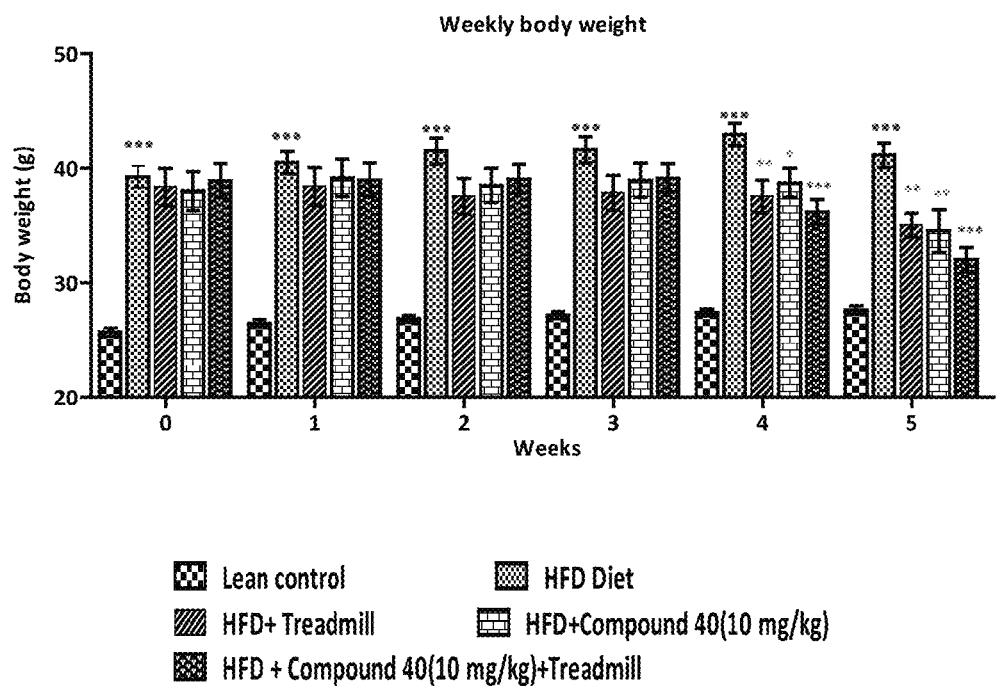
FIG. 30A shows effect of compound 40 on weekly body weight in Wistar rats.
Figure 30B:
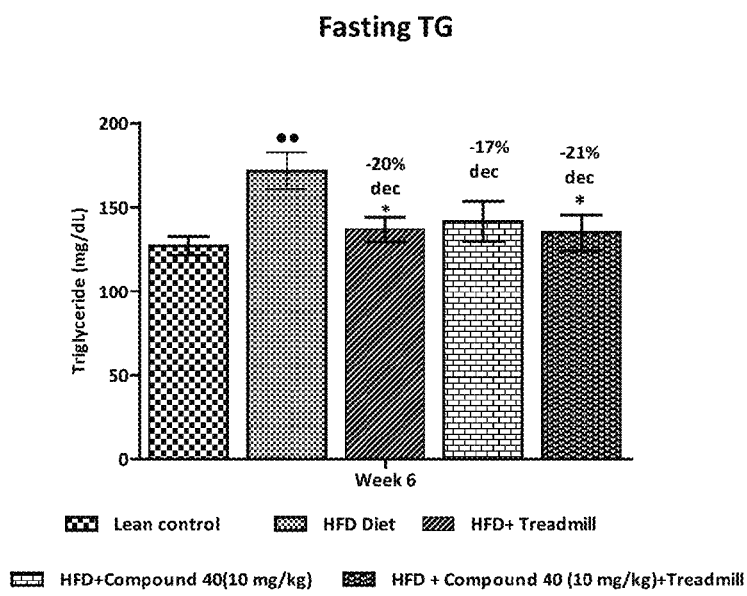
FIG. 30b shows effect of compound 40 on fasting TG in Wistar rats.

On treatment with Compound 40 it was seen that it significantly improves muscle endurance (FIG. 14). Also, in the treatment group a significant improvement in the fasting glucose and OGTT levels were observed. (FIG. 29). Furthermore improvement was also observed in Body weight and fasting TG levels (FIG. 30) of the treatment group.

II. Evaluation of Effect of RXR Agonist on Ob/Ob Mice

Figure 15:
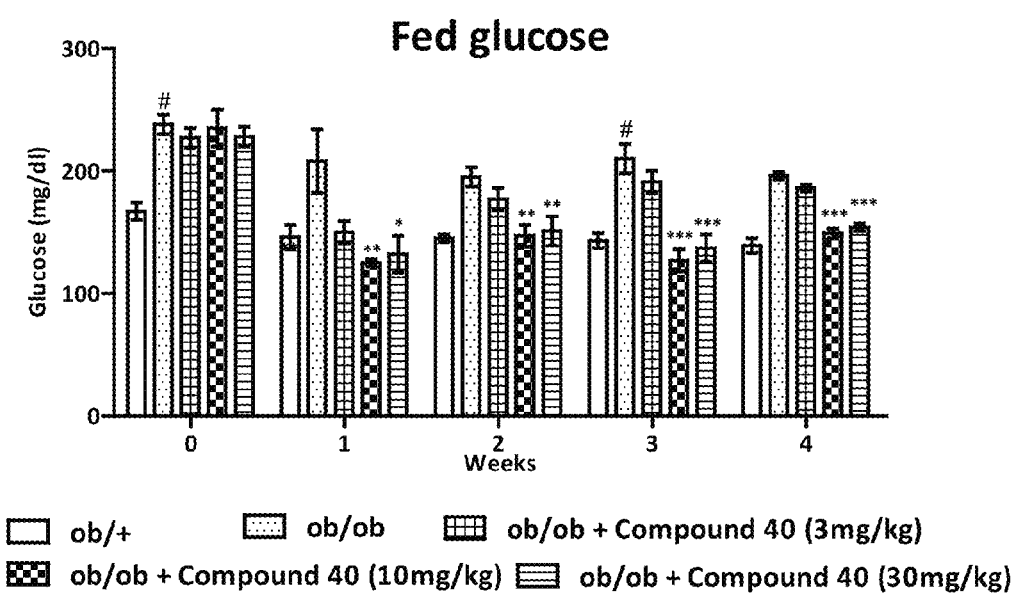
FIG. 15 shows effect of compound 40 on ob/ob mice.
Figure 16A:
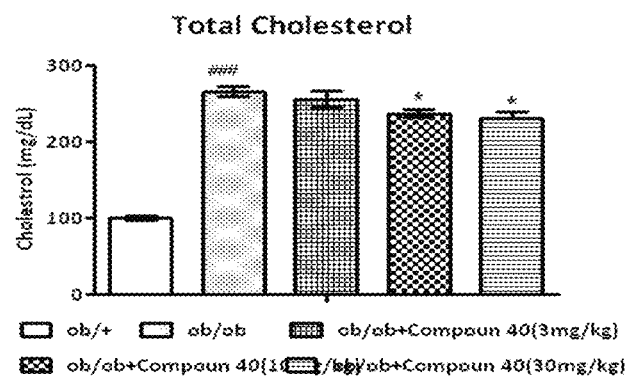
FIG. 16A shows effect of compound 40 on total cholesterol in ob/ob mice.
Figure 16B:
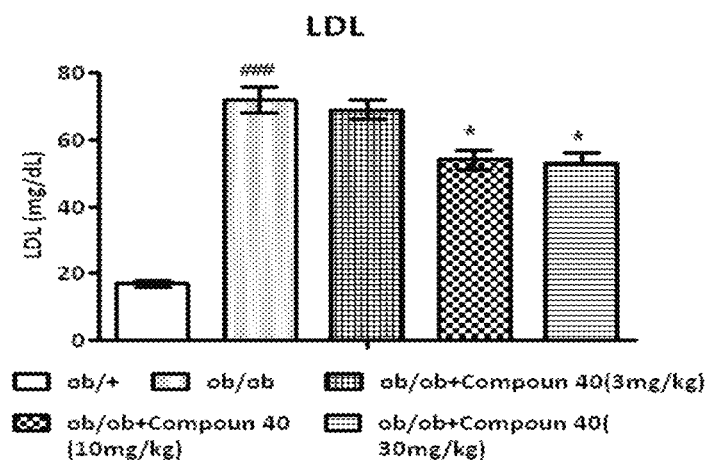
FIG. 16B shows effect of compound 40 on LDL cholesterol in ob/ob mice.

The male ob/ob and lean mice were procured from Harlon laboratories, acclimatized for a week, were fed a standard laboratory diet. The lean control and the ob/ob mice were 16 weeks old at the start of the study and were randomized to either vehicle or drug (Compound 40, 3, 10 and 30 mg/kg, BID, po) treatment groups by body weight, fed glucose and glucose AUC during an oral glucose tolerance test. The treatment was continued for 4 weeks. Fed glucose and fast triglycerides (tail snip) were monitored weekly. At the end of week 4 of the treatment, Animals were sacrificed before terminal measurement of fasting glycerol, free fatty acid, cholesterol, LDL levels. It was observed that the treated animals displayed both an early onset and sustained control of prandial hyperglycemia (FIG. 15). Furthermore, it was also seen that treatment with Compound 40 significantly decreased total cholesterol accounted for primarily by decreasing LDL-c (FIG. 16).

III. Evaluation of Effect of RXR Agonist on Db/Db Mice

The male db/db and lean mice were procured from Jackson Laboratory, US laboratories, acclimatized for a week, were fed a standard laboratory diet. The lean control and the db/db mice were 8 weeks old at the start of the study and were randomized to either vehicle or drug (Compound 40, 2.5, 5, 10 and 15 mg/kg, BID, po) treatment groups by body weight, fed glucose and glucose AUC during an oral glucose tolerance test. The treatment was continued for 8 weeks. Body weight, fasting and fed glucose and fast triglycerides (tail snip) were monitored weekly. At the end of week 8 of the treatment, glucose and insulin HbA1c levels were followed at different time intervals. Blood samples collected from tail nipping method were subjected at the end of week 7 of treatment period measured for HbA1c levels by DCA vantage (SIEMENS).

Assessment of 24 h glucose profile: Fed state blood samples were collected by tail nipping method and measured for glucose levels at every 2 h time intervals up to 8 h and then followed by 4 h intervals at the end of week 7 of treatment.

Figure 17:
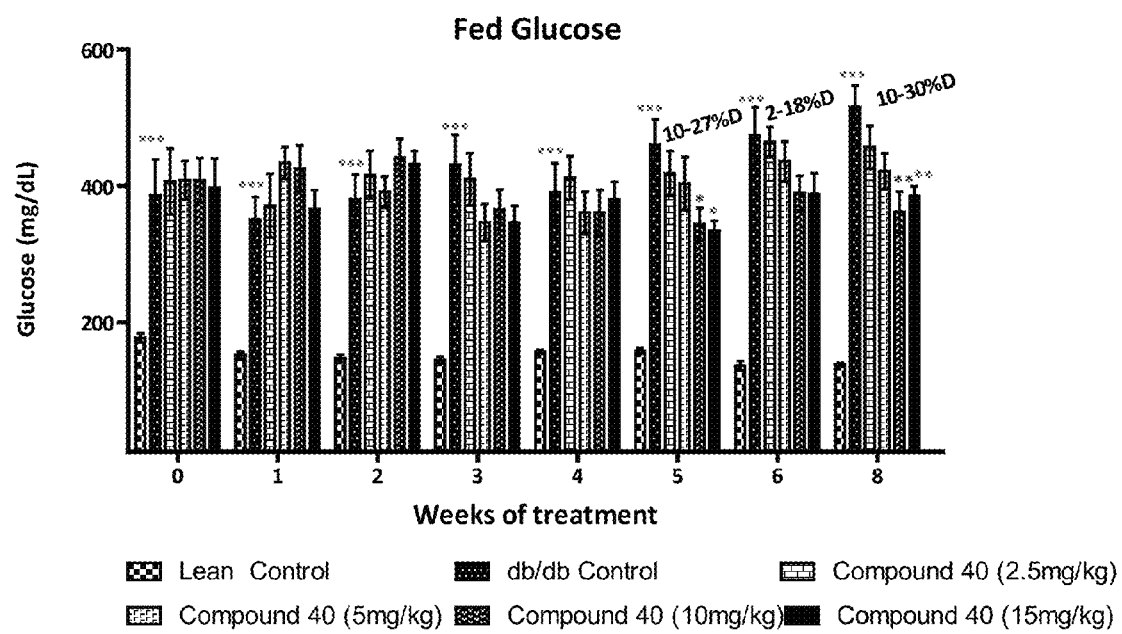
FIG. 17 shows effect of compound 40 on db/db mice.
Figure 18:
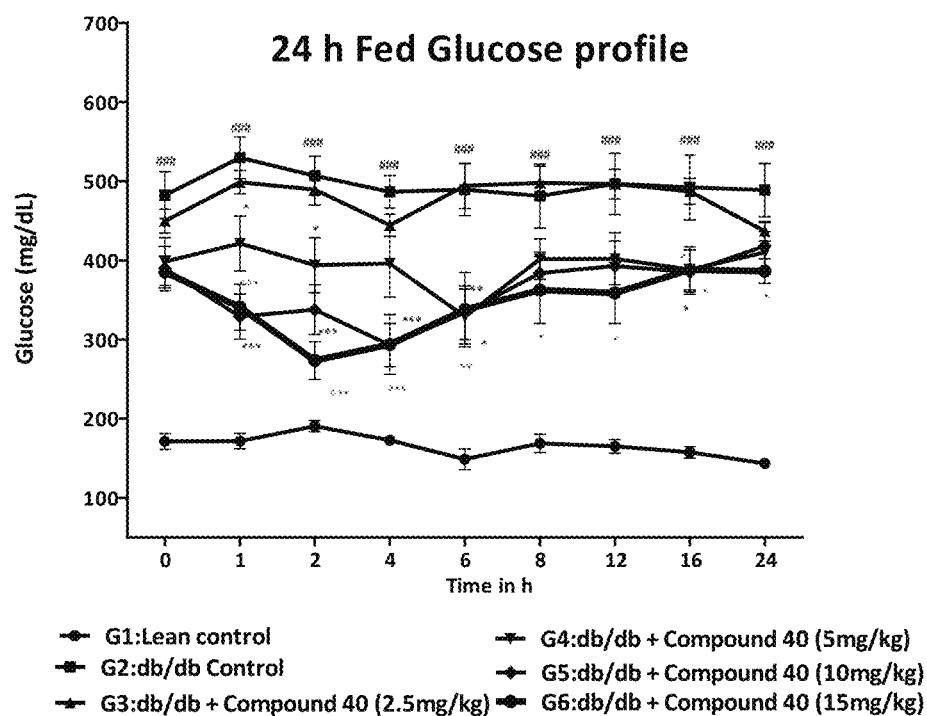
FIG. 18 shows effect of compound 40 on fed glucose profile of db/db mice.
Figure 19:
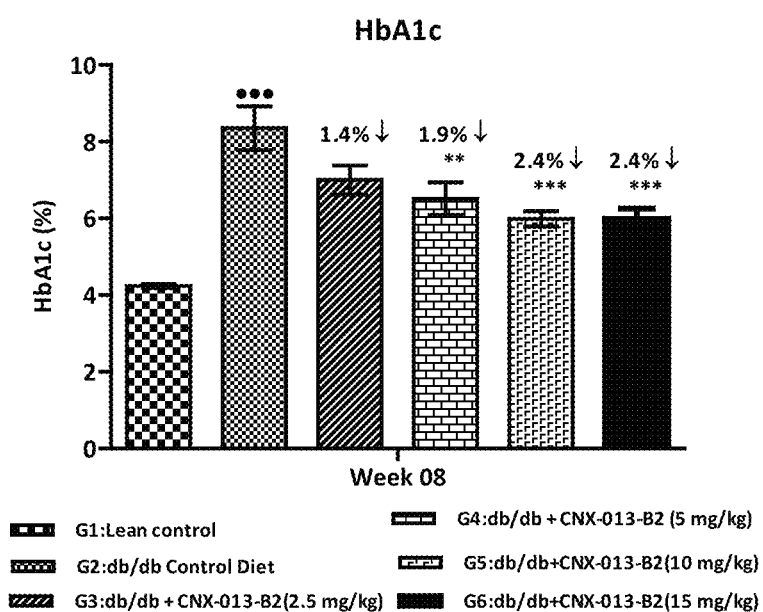
FIG. 19 shows effect of compound 40 on HbA1c levels of db/db mice.

It was observed that treatment with Compound 40 significantly reduced post-prandial blood glucose levels (FIG. 17). The treatment also significantly reduced glucose excursion during the prandial phase (FIG. 18). It was also observed that the treatment with Compound 40 resulted in a steep and dose dependent reduction in HbA1c levels (FIG. 19).

IV. Evaluation of Effect of RXR Agonist on Male ZDF Rats

Figure 20A:
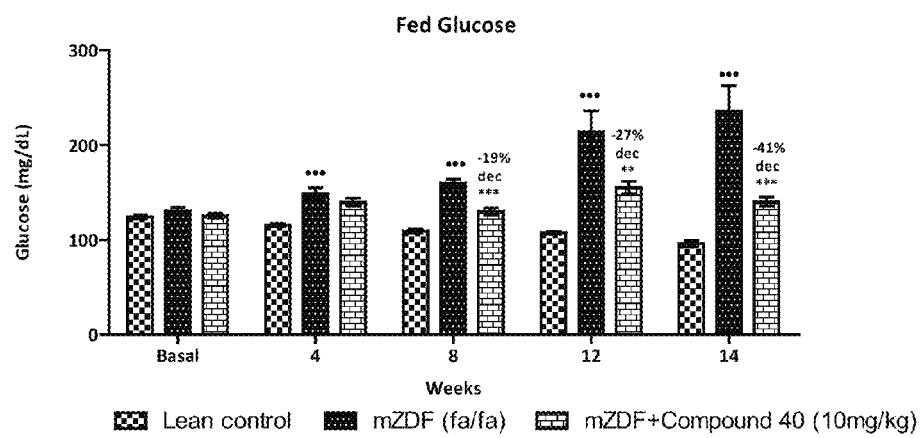
FIG. 20A shows effect of compound 40 on glucose levels in fed glucose ZDF rats.
Figure 20B:
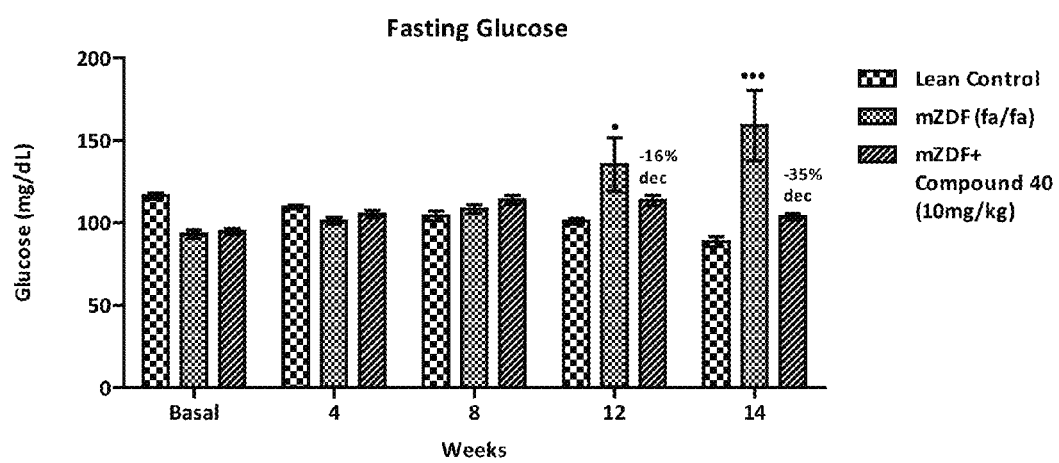
FIG. 20B shows effect of compound 40 on glucose levels in fasting ZDF rats.
Figure 21A:
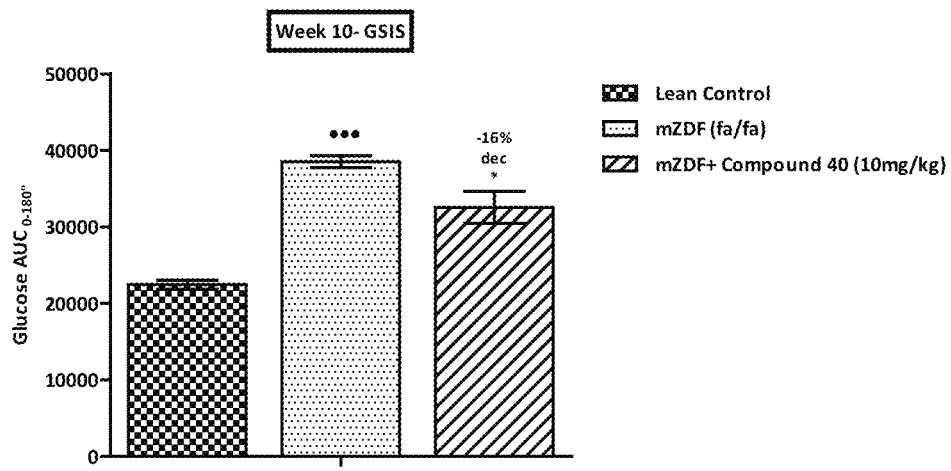
FIG. 21A shows effect of compound 40 on glucose levels in ZDF rats.
Figure 21B:
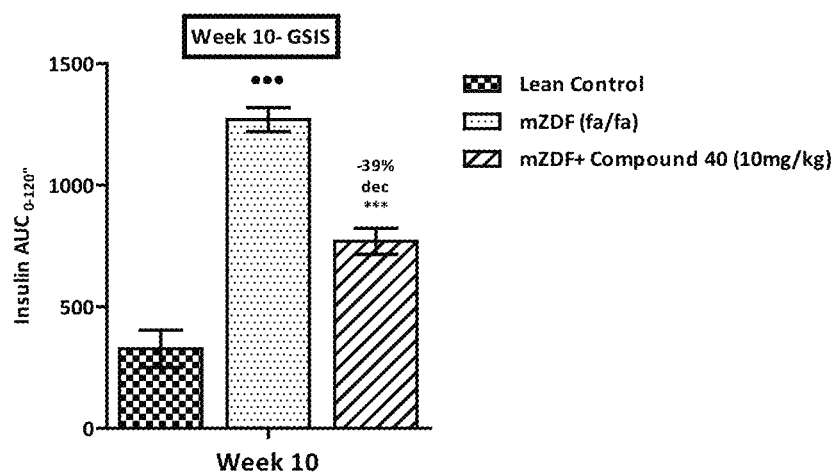
FIG. 21B shows effect of compound 40 on insulin levels in ZDF rats.
Figure 22:
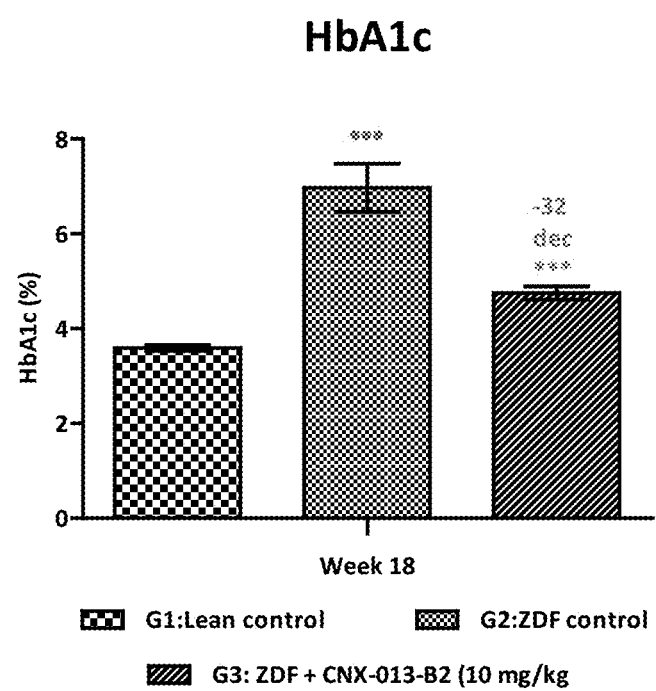
FIG. 22 shows effect of compound 40 on HbA1c levels in ZDF rats.
Figure 23:
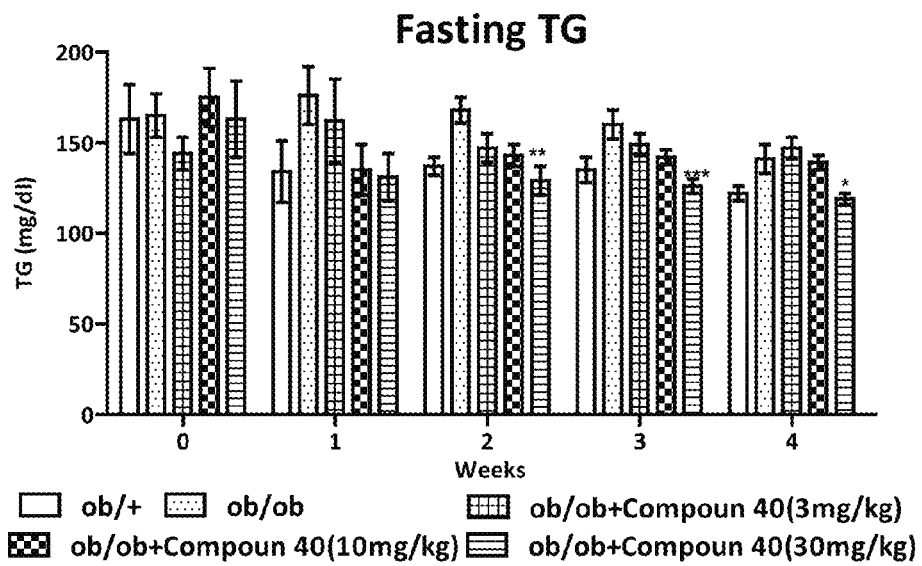
FIG. 23 shows effect of compound 40 on fasting TG levels in ZDF rats.
Figure 24:
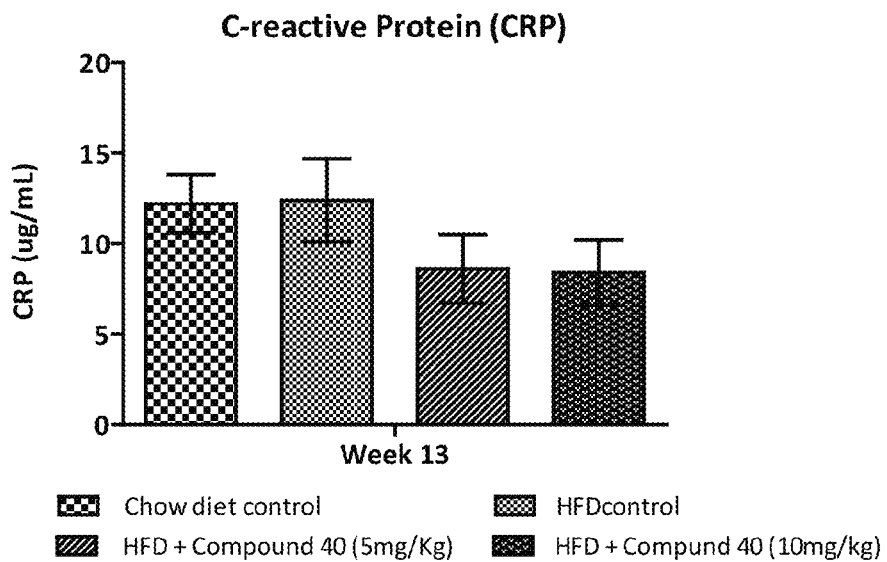
FIG. 24 shows effect of compound 40 on CRP levels in ZDF rats.
Figure 25A:
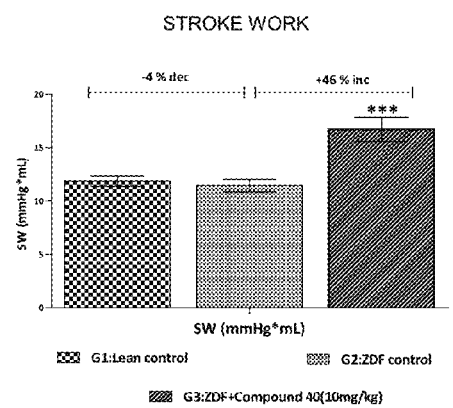
FIGS. 25A-D shows effect of compound 40 on cardiac function ZDF rats.
Figure 25B:
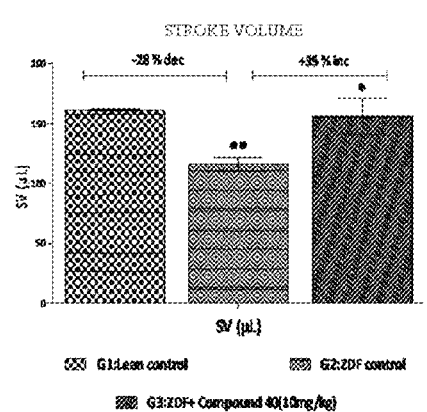
Figure 25C:
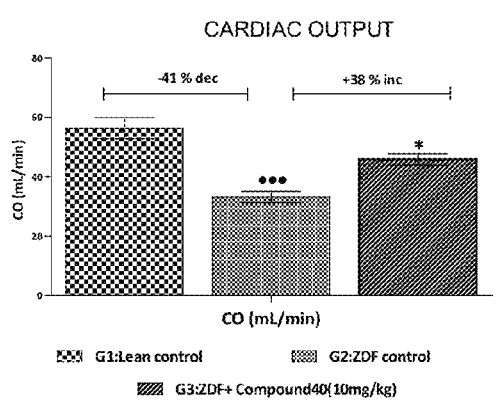
Figure 25D:
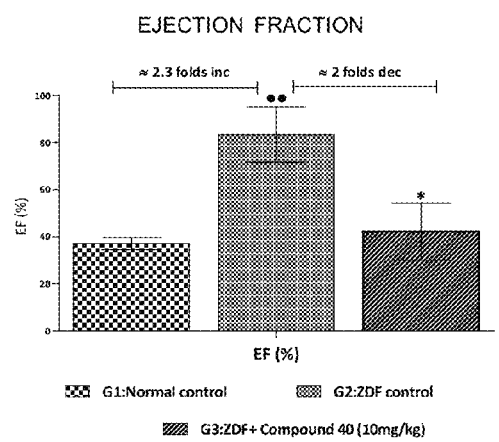
Figure 26A:
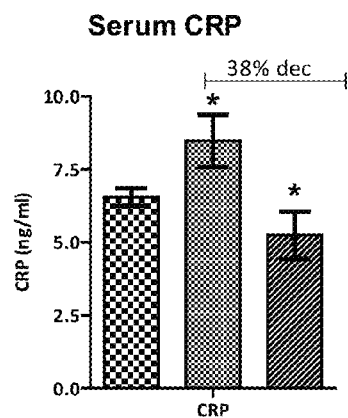
FIGS. 26A-D shows effect of compound 40 on levels of biomarkers for cardiovascular risk in ZDF rats.
Figure 26B:
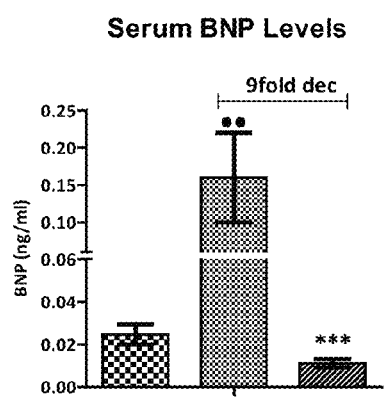
Figure 26C:
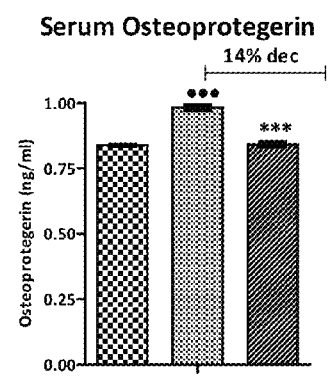
Figure 26D:
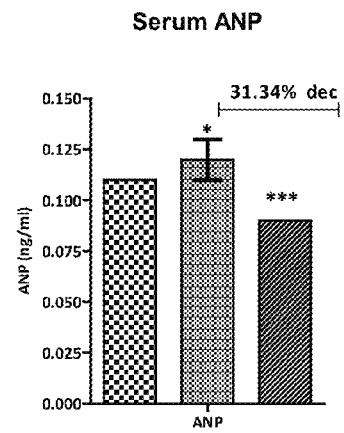

Five week old male ZDF rats from Charles River & age matched control rats were housed under temperature 22±3° C., relative humidity 50-70%, 12 hour light and 12 hour dark cycle with artificial fluorescent tubes. The animals were housed in a group of 3 in standard polypropylene cages with stainless steel top grill having facilities for pelleted food and drinking water in bottle. The animals were fed with normal chow diet (Provomi), Bisleri, commercially available mineral drinking water was provided ad libitum. The lean control and the male XDF rats were randomized to either vehicle or drug (Compound 40, 10 mg/kg, BID, po) treatment groups by body weight, fed glucose and glucose. The treatment was continued for 8 weeks. Body weight, fasting and fed glucose and fast triglycerides (tail snip) were monitored weekly. At the end of week 8 of the treatment, glucose and insulin HbA1c levels were followed at different time intervals. Blood samples collected from tail nipping method HbA1c levels by DCA vantage (SIEMENS). It was observed that treatment with Compound 40 significantly increased the activity of SDH indicating improvement in glucose oxidation in muscle. Furthermore, treatment displayed both an early onset and sustained control of prandial hyperglycemia and also showed significant control of Fasting glucose (FIG. 20). Furthermore, it was seen that the treatment significantly reduced hyperinsulinemia and improves glucose disposal (FIG. 21). The treatment also showed very significant improvement in the HbA1c levels (FIG. 22). On measurement of fasting TG during treatment and there after, it was observed that Compound 40 does not cause hypertriglyceridemia. Moreover it significantly reduces fasting TG levels (FIG. 23). Also, it was observed that Compound 40 also aides in decreasing CRP levels indicating potential cardio vascular benefit (FIG. 24). Substantial improvement in the Cardiac function (FIG. 25) and improvement in levels of biomarkers of Cardio vascular risk was also noted (FIG. 26).

Measurement of Nerve conduction velocity: Nerve conduction velocity was measured using Electronic stimulator connected to AD Power Lab 8/30, AD instruments. Briefly animals were anaesthetized and three different electrodes (+ve, −ve and neutral) were connected from Bio amp to animal. +ve electrode was placed on front side of fourth finger on hind paw, −ve electrode was placed just above +ve electrode at a distance of 10 mm and neutral electrode was placed on abdomen region. Voltage at a rate of 5 mv with pulse width of 0.001 sec was provided on two different regions at a distance of 1 cm on sciatic nerve. Nerve conduction was recorded using Lab chart software in scope view panel. Latencies at two different points were measured by taking the mouse cursor at the beginning of peaks. Nerve conduction velocity was measured using the following formulae $$NCV \text{ (m/s)} = \text{Latency at point } B \text{ (ms)} - \text{Latency at point } A \text{ (ms) Distance between } A \text{ and } B \text{ (mm)}$$

Figure 27:
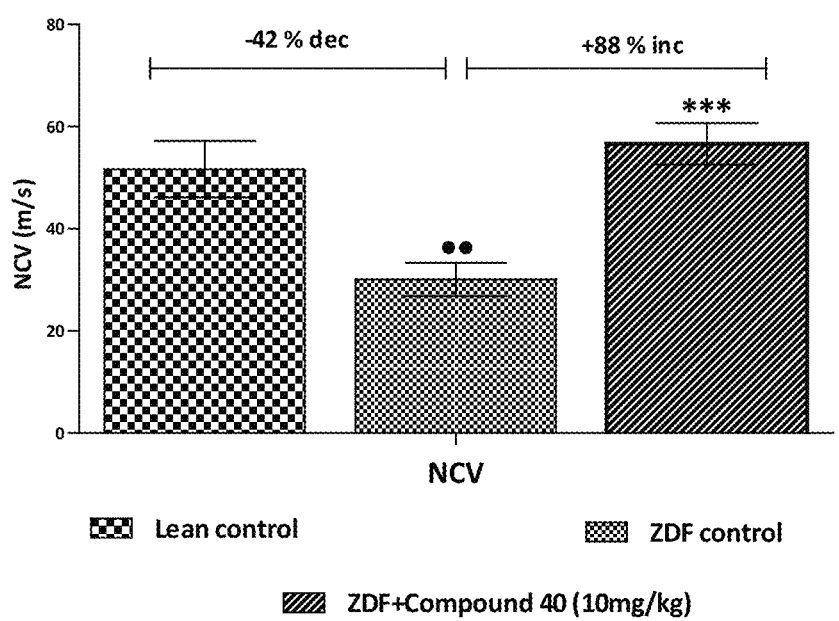
FIG. 27 shows effect of compound 40 on nerve conduction velocity in ZDF rats.

Significant improvement in the NCV was noted in the treatment group (FIG. 27).

Figure 28A:
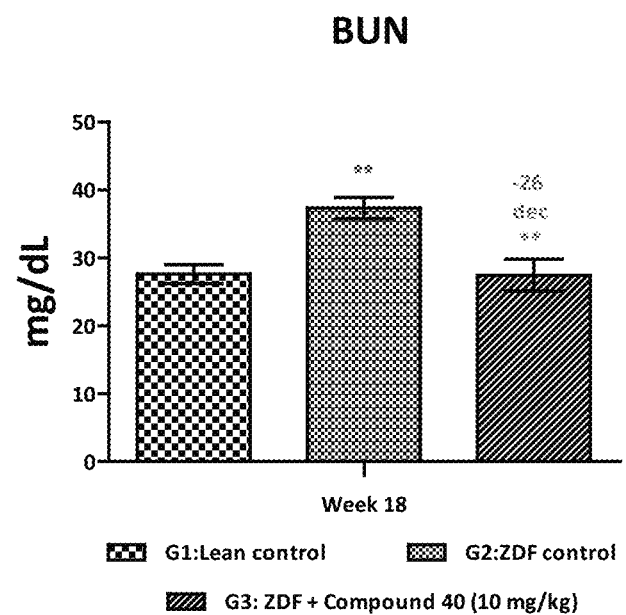
FIG. 28A shows effect of compound 40 on BUN levels ZDF rats.
Figure 28B:
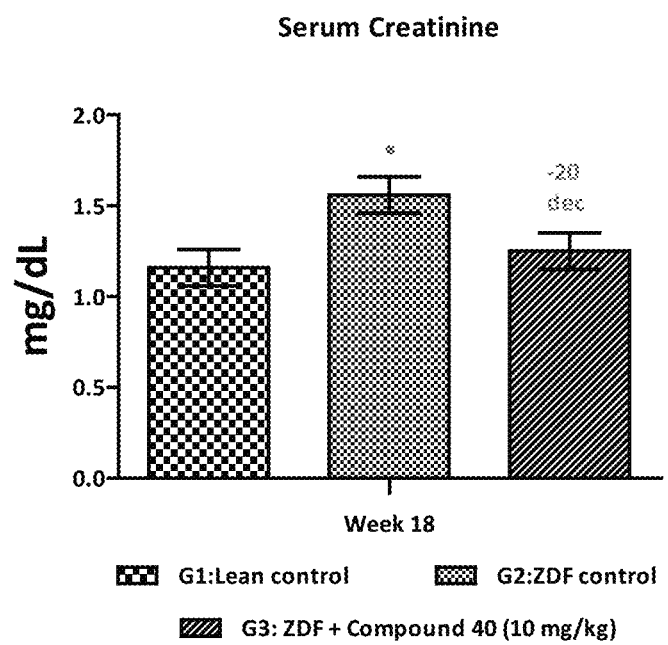
FIG. 28B shows effect of compound 40 on serum creatinine levels in ZDF rats.

Measurement of Hemodynamic Parameters by Using Millar MPVS System:

At the end of 22 weeks of treatment period animal were subjected to hemodynamic measurement using Millar MPVS system, briefly animal was anesthetized using urethane and all surgical procedure was done on thermal plate, both jugular vein and carotid artery was cannulated in which jugular vein was used for saline calibration whereas rat millar Cather was introduced into left ventricle through carotid artery was be used for recording the Pressure volume loop. Blood was withdrawn from the tail vein puncture by pricking with needle into pre-filled EDTA tubes, mix and placed on ice immediately, centrifuge at 10000 rpm for 10 minutes using cold centrifuge. The plasma separated was subjected for estimation of ANP, BNP, Osteprotegerin Using USCN kit and Serum urea and BUN using Robonik kit. Substantial decrease in BUN and Serum Creatinine levels were observed in diseased animals treated with Compound 40 (FIG. 28).

Figure 31:
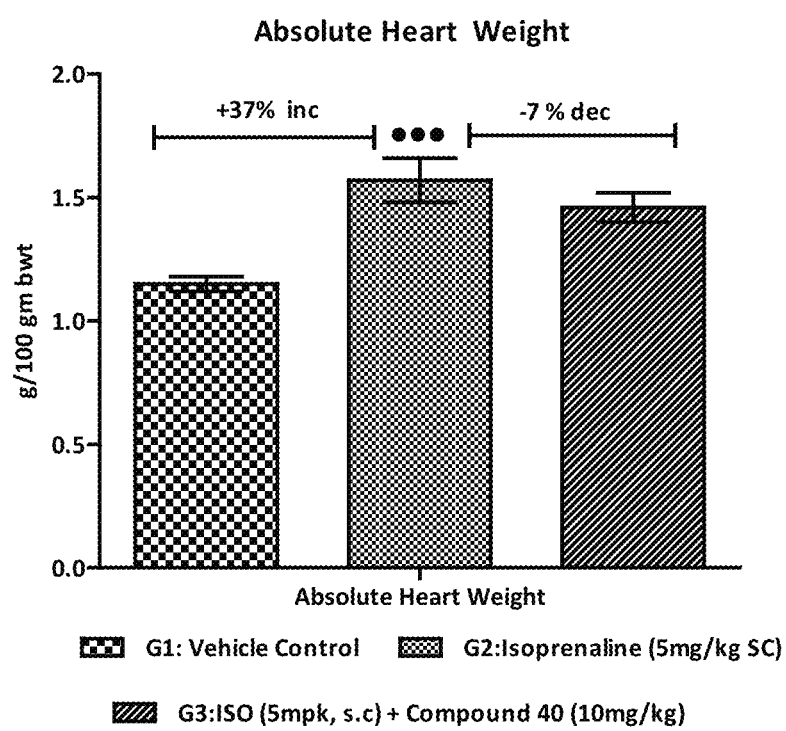
FIG. 31 shows effect of compound 40 on absolute heart weight in Wistar rats.
Figure 32A:
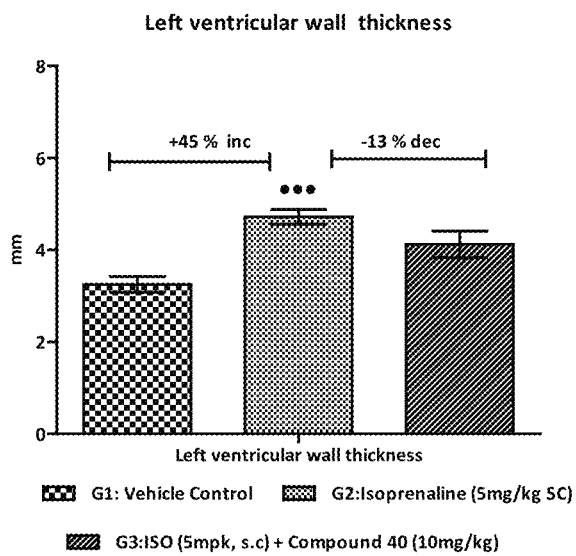
FIG. 32A shows effect of compound 40 on left ventricular wall thickness in Wistar rats.
Figure 32B:
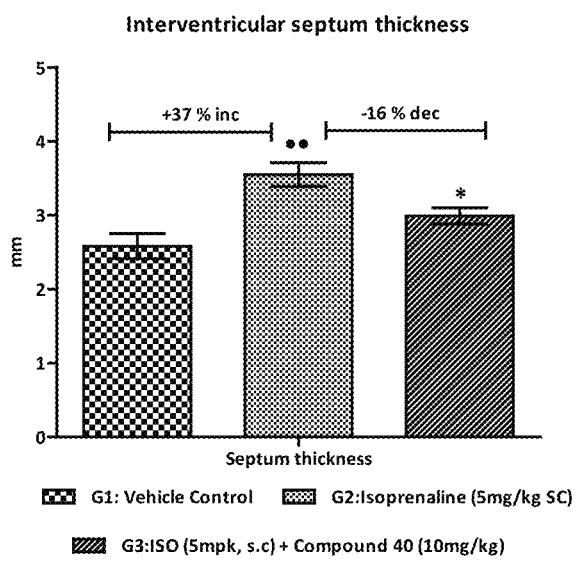
FIG. 32B shows effect of compound 40 on intraventricular septum thickness in Wistar rats.
Figure 33A:
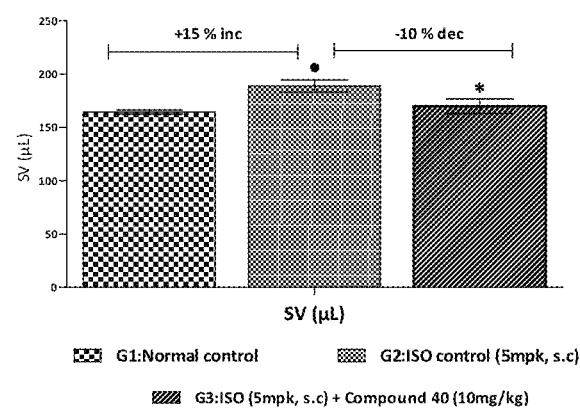
FIG. 33A shows effect of compound 40 on heart stroke volume in Wistar rats.
Figure 33B:
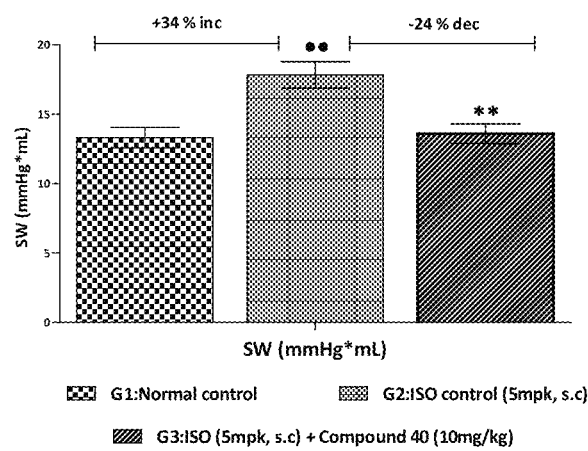
FIG. 33B shows effect of compound 40 on heart stroke work in Wistar rats.
Figure 34A:
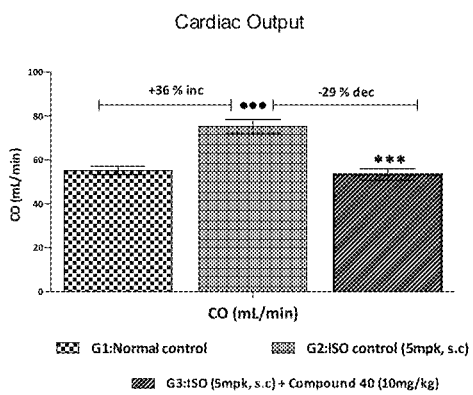
FIGS. 34A-C shows effect of compound 40 on various cardiac factors in Wistar rats.
Figure 34B:
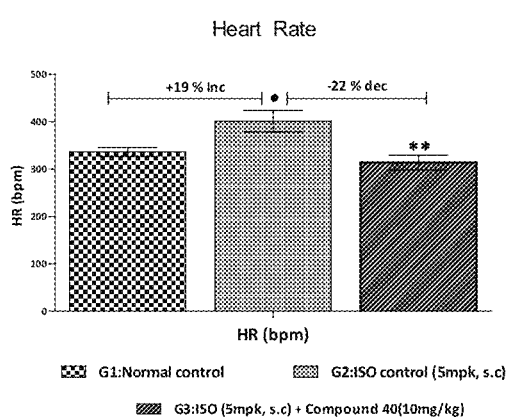
Figure 34C:
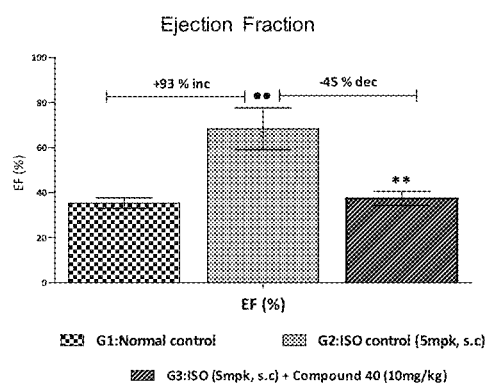
Figure 35A:
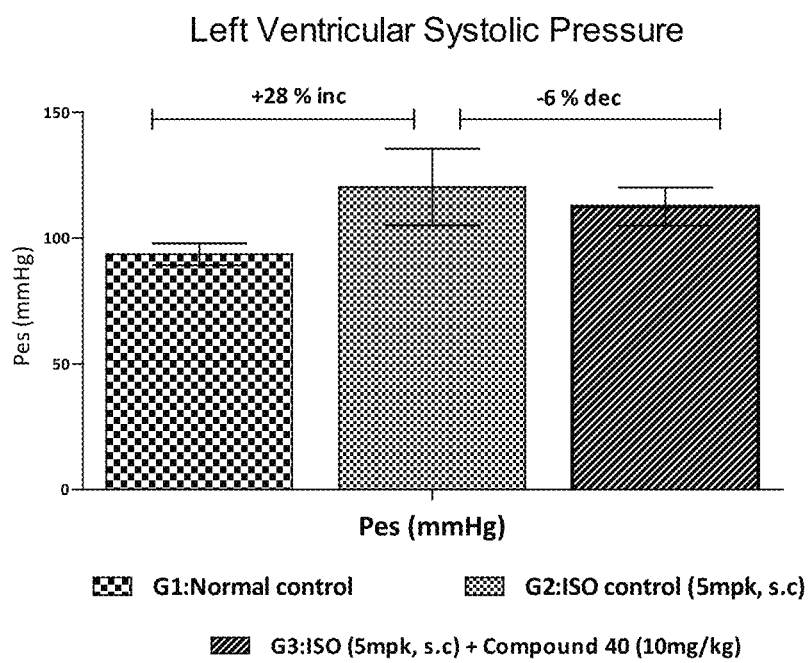
FIGS. 35A-B shows effect of compound 40 on various cardiac factors in Wistar rats.
Figure 35B:
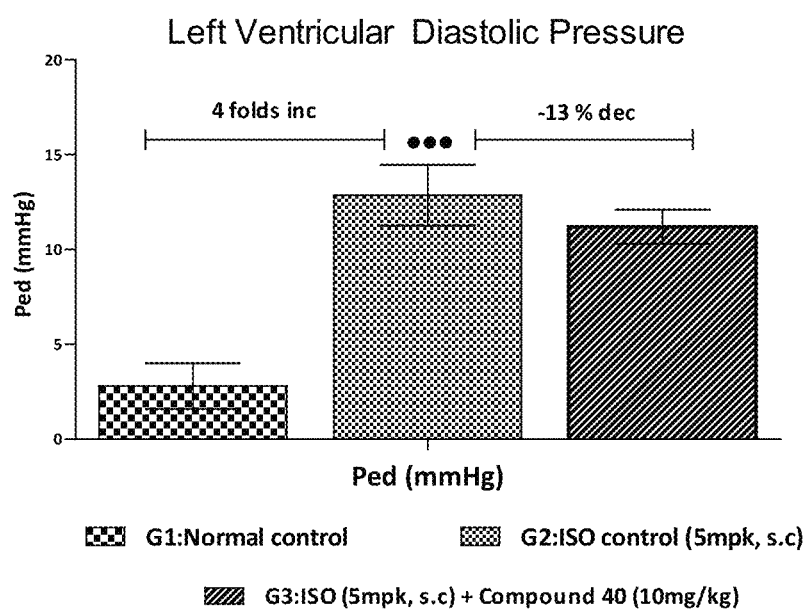
Figure 36:
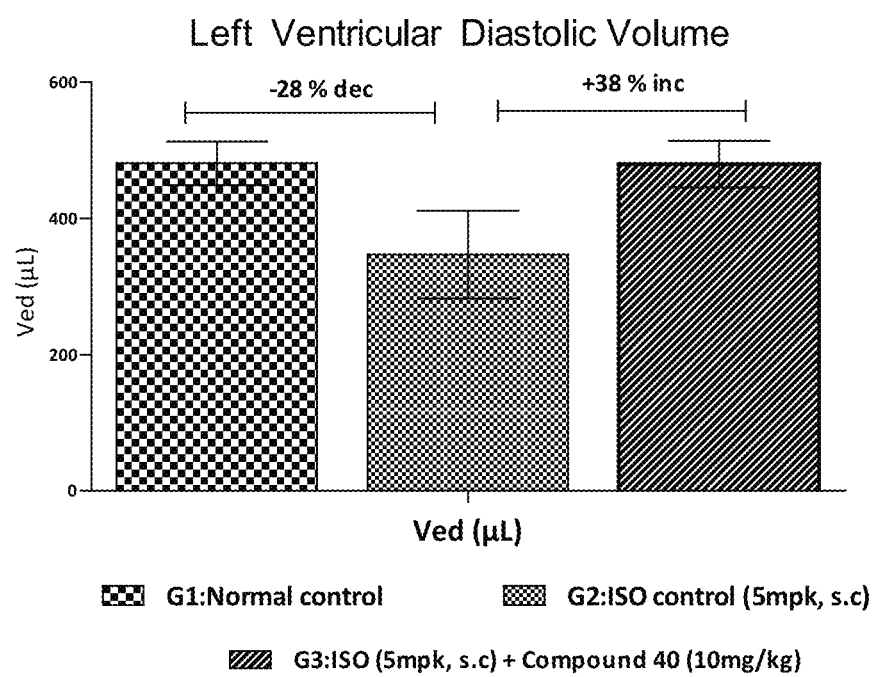
FIG. 36 shows effect of compound 40 on left ventricular diastolic volume in Wistar rats.
Figure 37A:
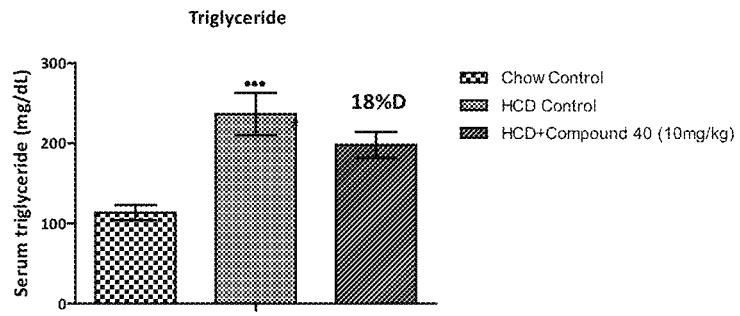
FIGS. 37A-D shows effect of compound 40 on various TG levels in hamsters.
Figure 37B:
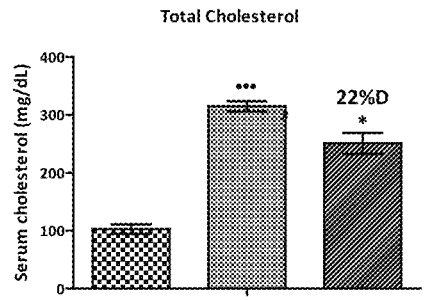
Figure 37C:
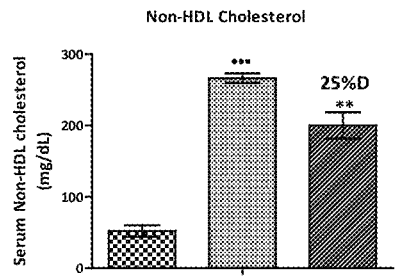
Figure 37D:
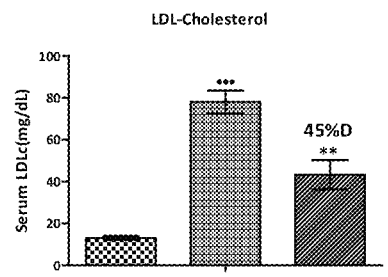

V. Evaluation of Effect of RXR Agonist on Isoprenaline Induced Cardiac Hypertrophy in Rats Male Wistar rats of fourteen weeks age were housed under controlled temperature 22±3° C., relative humidity 50-70%, 12 hour light and 12 hour dark cycle with artificial fluorescent tubes. Animals were acclimatized for seven days. On eight day animals were randomized based on their body weights and allotted into nine animals/group. Different groups into which animals allotted were G1: Vehicle control, G2: Isoprenaline control (5 mg/kg, s.c. twice a week) and G3: Isoprenaline (5 mg/kg, s.c. twice a week)+Compound 40 (10 mg/kg, p.o., q.d.). Treatment with Compound 40 (10 mpk) for G3 group was started one week prior to isoprenaline administration and both the treatments were continued for eleven weeks. The animals were monitored for daily feed consumption and weekly body weight throughout the study. At the end of treatment period (Week 11) five animals from each group were subjected to Cardiovascular hemodynamic assessment by Millar catheter using MPVS Ultra control interface connected to AD power lab, AD instruments. Different parameters measured were heart rate, stroke work, stroke volume, cardiac output, left ventricular systolic pressure, left ventricular diastolic pressure, left ventricular diastolic volume Immediately after hemodynamic estimation terminal blood from all the animals were collected followed by the collection of hearts. All the separated serum samples were used for estimation of several cardiac markers like ANP, BNP, CRP, LDH, CKN, CKMB and SGOT. Collected hearts were examined for histopathological changes and gene expression studies. All the numerical output was expressed as Mean±SEM, one way ANOVA followed by Dunnets' test using Graph pad prism software. A substantial reduction in the absolute heart weight was observed in the treatment group (FIG. 31). A significant reduction in the thickness of the ventricular wall and septum was observed making Compound 40 a potential line of treatment of ventricular hypertrophy and cardiac failure (FIG. 32). The treatment group showed significant improvement in Stroke work (SW) and Stroke volume (SV) (FIG. 33), improved cardiac output, heart rate and ejection fraction (FIG. 34), improvement in ventricular refilling (FIG. 35) and (FIG. 36) thus showing that Compound 40 can play a significant role in improvement of Cardiac function.

VI. Evaluation of Effect of RXR Agonist on High Cholesterol Diet Induced Hyperlipidaemia in Hamsters Eight to ten week old male Syrian Hamsters were housed in polypropylene cages provided with sterile paddy husk as bedding material. The animals were maintained at temperature 22±3° C., relative humidity 50-70%, 15-18 air cycle changes with 12 h dark and light cycle. The animals were provided with rodent feed (ad libitum) supplied by harlan laboratories to normal control animals and treatment groups were fed with High Cholesterol diet, prepared in-house by mixing 11.5% coconut oil, 11.5% corn oil, 0.5% cholesterol, and 0.25% deoxycholate in chow diet. Bisleri water (ad libitum) was provided. The animals were randomized based on body weight and divided into control and treatment groups. Compound 40 was administered, at a dose of 10 mg/kg b.wt, for a period of 8-12 weeks to the treatment group. Daily feed consumption, weekly body weight, total cholesterol and triglyceride levels were estimated. The treated animals show significant reduction in total cholesterol, Non-HDL cholesterol and LDL-c (FIG. 37).

The invention claimed is:
1. A compound of formula (I):

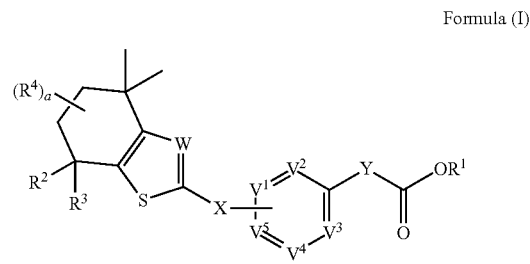

Formula (I)

wherein:
$R^1$ is selected from the group consisting of H, $C_1$-$C_6$alkyl and a carboxylic acid protecting group;
$R^2$ and $R^3$ are independently selected from the group consisting of H and $C_1$-$C_6$alkyl;
each $R^4$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^5$, $SO_3H$, $SO_2NR^5R^5$, $SO_2R^5$, $SONR^5R^5$, $SOR^5$, $COR^5$, COOH, $COOR^5$, $CONR^5R^5$, $NR^5COR^5$, $NR^5COOR^5$, $NR^5SO_2R^5$, $NR^5CONR^5R^5$, $NR^5R^5$, and acyl, or two $R^4$ on the same carbon atom when taken together form a =O substituent or a group of formula =NOH, or two $R^4$ on adjacent carbon atoms when taken together form a double bond;
wherein each $R^5$ is independently selected from the group consisting of H, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl;
a is an integer selected from the group consisting of 0, 1, 2, 3, and 4;
wherein X is —$NR^{10}$—;
wherein $R^{10}$ is selected from the group consisting of H, optionally substituted $C_1$-$C_{12}$alkyl, optionally substituted $C_2$-$C_{12}$ alkenyl, optionally substituted $C_2$-$C_{12}$ alkynyl, optionally substituted $C_1$-$C_{12}$haloalkyl, optionally substituted $C_2$-$C_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{18}$aryl, optionally substituted C$_1$-C$_{18}$heteroaryl, optionally substituted C$_3$-C$_{12}$cycloalkylC$_1$-C$_{12}$alkyl, optionally substituted C$_2$-C$_{12}$heterocycloalkylC$_1$-C$_{12}$alkyl, optionally substituted C$_6$-C$_{18}$aryl C$_1$-C$_{12}$alkyl, optionally substituted C$_1$-C$_{18}$heteroarylC$_1$-C$_{12}$alkyl, SO$_3$H, SO$_2$NR$^5$R$^5$, SO$_2$R$^5$, SONR$^5$R$^5$, SOR$^5$, COR$^5$, COOH, COOR$^5$, CONR$^5$R$^5$ and acyl;

V$^2$, V$^3$ and V$^4$ are each independently CR$^6$;

each R$^6$ is independently selected from the group consisting of H, halogen, OH, NO$_2$, CN, SH, NH$_2$, CF$_3$, OCF$_3$, optionally substituted C$_1$-C$_{12}$alkyl, optionally substituted C$_1$-C$_{12}$haloalkyl optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{18}$aryl, optionally substituted C$_1$-C$_{18}$heteroaryl, optionally substituted C$_1$-C$_{12}$alkyloxy, optionally substituted C$_2$-C$_{12}$alkenyloxy, optionally substituted C$_2$-C$_{12}$alkynyloxy, optionally substituted C$_2$-C$_{10}$heteroalkyloxy, optionally substituted C$_3$-C$_{12}$cycloalkyloxy, optionally substituted C$_3$-C$_{12}$cycloalkenyloxy, optionally substituted C$_2$-C$_{12}$heterocycloalkyloxy, optionally substituted C$_2$-C$_{12}$heterocycloalkenyloxy, optionally substituted C$_6$-C$_{18}$aryloxy, optionally substituted C$_1$-C$_{18}$heteroaryloxy, optionally substituted C$_1$-C$_{12}$alkylamino, SR$^5$, SO$_3$H, SO$_2$NR$^5$R$^5$, SO$_2$R$^5$, SONR$^5$R$^5$, SOR$^5$, COR$^5$, COOH, COOR$^5$, CONR$^5$R$^5$, NR$^5$COR$^5$, NR$^5$COOR$^5$, NR$^5$SO$_2$R$^5$, NR$^5$CONR$^5$R$^5$, NR$^5$R$^5$, and acyl;

V$^1$ is N;

V$^5$ is CR$^8$;

R$^8$ is a bond to X,

Y is a bond;

W is selected from the group consisting of N and CR$^9$;

R$^9$ is selected from H and C$_1$-C$_6$alkyl;

or a pharmaceutically acceptable salt thereof.

2. A compound according to claim 1 wherein R$^1$ is H.

3. A compound according to claim 1 wherein a is 0.

4. A compound according to claim 1 wherein R$^2$ and R$^3$ are methyl.

5. A compound according to claim 1 wherein W is N.

6. A compound according to claim 1 wherein W is CR$^9$.

7. A compound according to claim 6 where R$^9$ is methyl.

8. A compound according to claim 1 wherein R$^{10}$ is selected from the group consisting of H, C$_1$-C$_{12}$alkyl, and C$_3$-C$_{12}$cycloalkylC$_1$-C$_{12}$alkyl.

9. A compound according to claim 1 wherein each R$^6$ is independently selected from the group consisting of H, CH$_3$, CH$_2$CH$_3$, CH$_2$CH$_2$CH$_3$, CH(CH$_3$)$_2$, (CH$_2$)$_3$CH$_3$, Cl, Br, F, I, OH, NO$_2$, NH$_2$, CN, OCH$_3$, OCH$_2$CH$_2$CH$_3$, CF$_3$, and OCF$_3$.

10. A compound according to claim 1 wherein each optional substituent is independently selected from the group consisting of H, CH$_3$, CH$_2$CH$_3$, CH$_2$CH$_2$CH$_3$, CH(CH$_3$)$_2$, (CH$_2$)$_3$CH$_3$, Cl, Br, F, I, OH, NO$_2$, NH$_2$, CN, OCH$_3$, OCH$_2$CH$_2$CH$_3$, CF$_3$, and OCF$_3$.

11. A compound according to claim 1 selected from the group consisting of

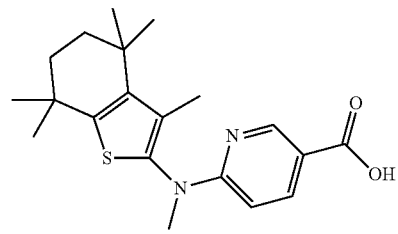

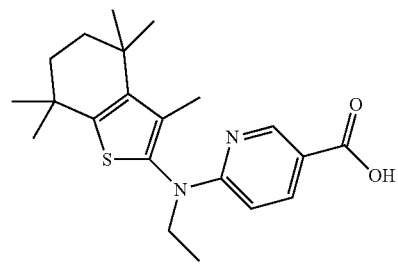

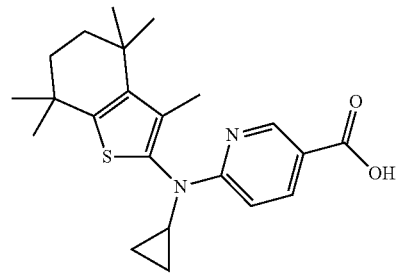

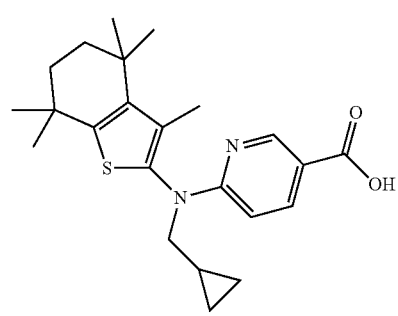

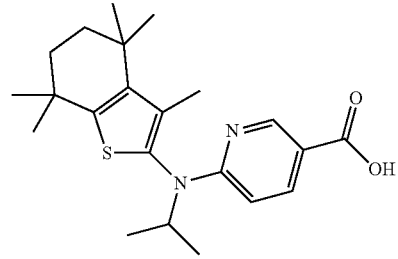

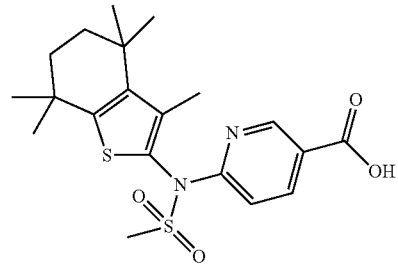

207
-continued
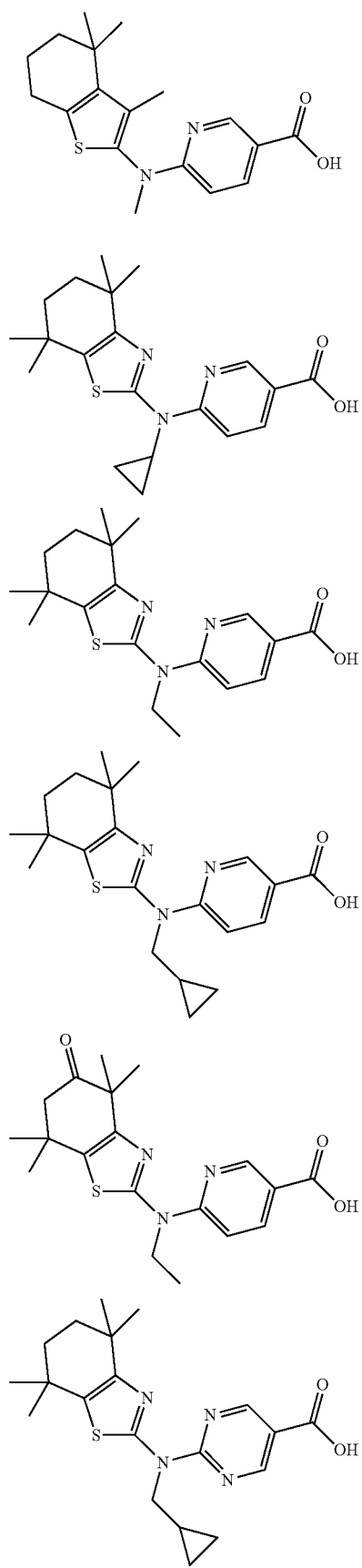
208
-continued
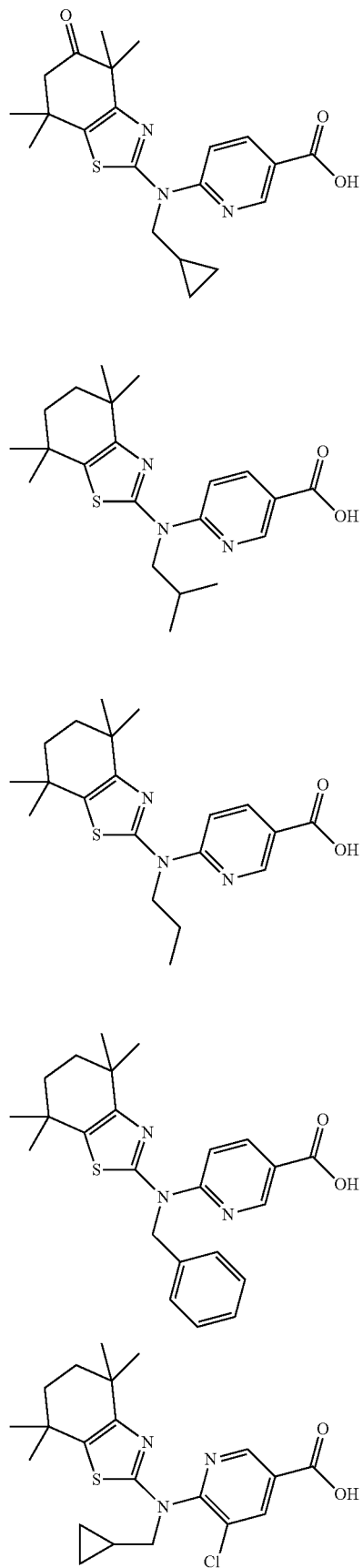

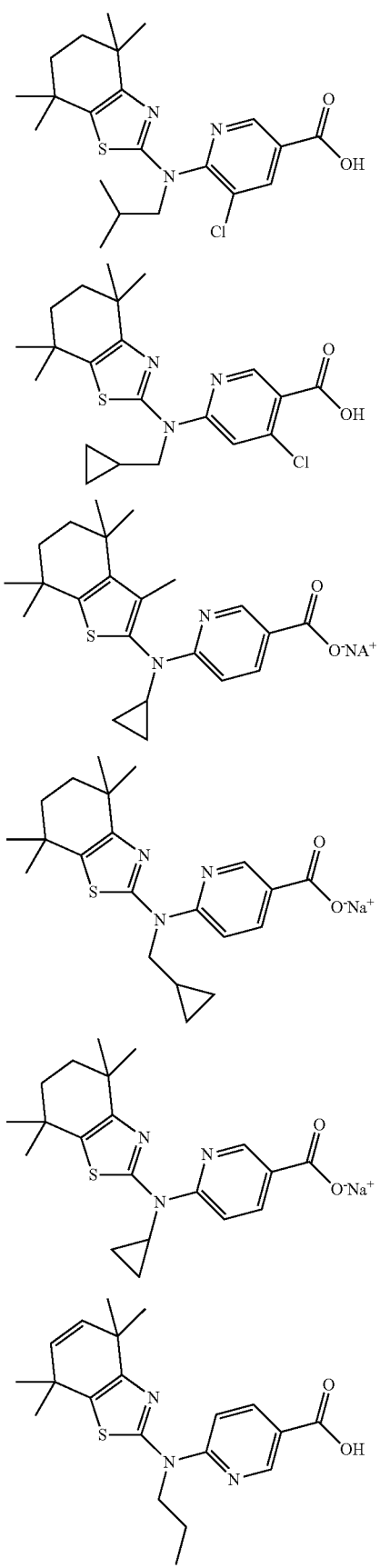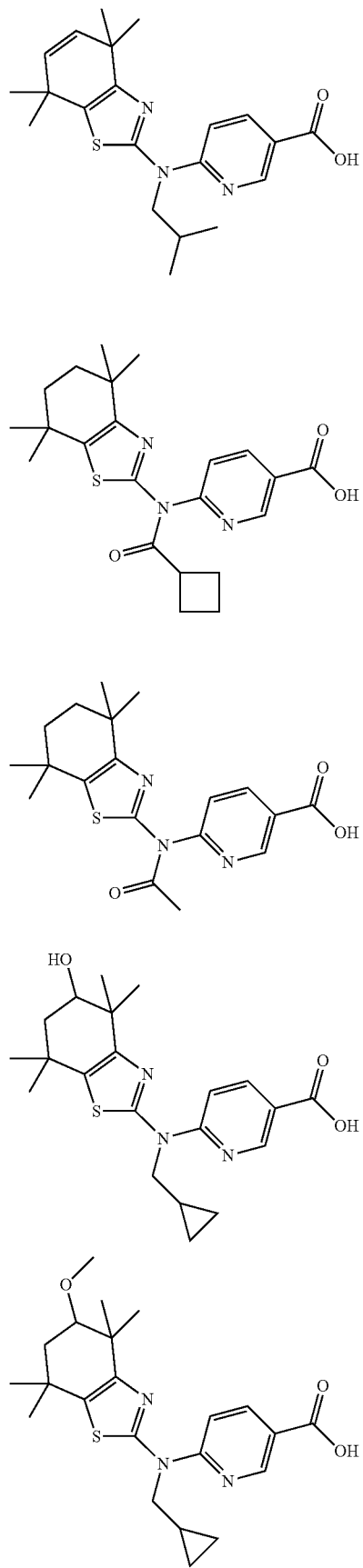

211
-continued
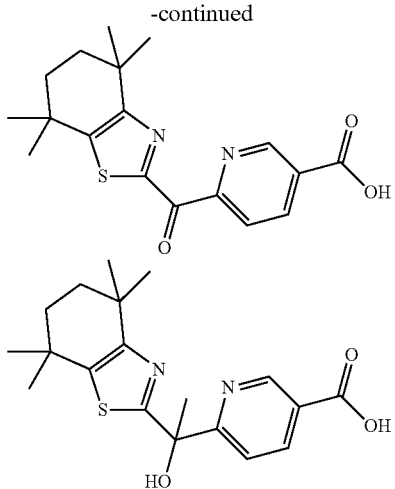
212
-continued
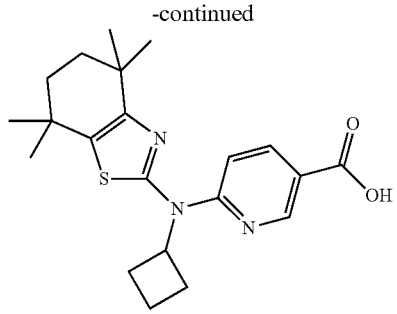
or pharmaceutically acceptable salt thereof.
12. A pharmaceutical composition including a compound according to claim 1 and a pharmaceutically acceptable diluent, excipient or carrier.
* * * * *